US012760317B2

(12) United States Patent
Frederick et al.

(10) Patent No.: US 12,760,317 B2
(45) Date of Patent: Oct. 13, 2026

(54) TOBACCO PLANTS COMPRISING IMPROVED NITROGEN USE EFFICIENCY AND BURLEY CHARACTERISTICS AND PRODUCTS THEREOF

(71) Applicant: ALTRIA CLIENT SERVICES LLC, Richmond, VA (US)

(72) Inventors: Jesse Frederick, Richmond, VA (US); Andrew Carl Adams, Midlothian, VA (US); Dongmei Xu, Glen Allen, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 406 days.

(21) Appl. No.: 17/150,704

(22) Filed: Jan. 15, 2021

(65) Prior Publication Data

US 2021/0230627 A1 Jul. 29, 2021

Related U.S. Application Data

(60) Provisional application No. 62/962,380, filed on Jan. 17, 2020.

(51) Int. Cl.
*C12N 15/82* (2006.01)
*A01H 6/82* (2018.01)

(52) U.S. Cl.
CPC ......... *C12N 15/8262* (2013.01); *A01H 6/823* (2018.05); *C12Q 2600/13* (2013.01)

(58) Field of Classification Search
None
See application file for complete search history.

(56) References Cited

U.S. PATENT DOCUMENTS

| | | | | |
|---|---|---|---|---|
| 4,732,856 | A | 3/1988 | Federoff | |
| 4,762,785 | A | 8/1988 | Comai | |
| 4,945,050 | A | 7/1990 | Sanford et al. | |
| 5,004,863 | A | 4/1991 | Umbeck | |
| 5,013,658 | A | 5/1991 | Dooner et al. | |
| 5,104,310 | A | 4/1992 | Saltin | |
| 5,141,131 | A | 8/1992 | Miller, Jr. et al. | |
| 5,149,645 | A | 9/1992 | Hoekema et al. | |
| 5,159,135 | A | 10/1992 | Umbeck | |
| 5,177,010 | A | 1/1993 | Goldman et al. | |
| 5,231,019 | A | 7/1993 | Paszkowski et al. | |
| 5,316,931 | A | 5/1994 | Donson et al. | |
| 5,463,174 | A | 10/1995 | Moloney et al. | |
| 5,464,763 | A | 11/1995 | Schilperoort et al. | |
| 5,469,976 | A | 11/1995 | Burchell | |
| 5,563,055 | A | 10/1996 | Townsend et al. | |
| 5,589,367 | A | 12/1996 | Donson et al. | |
| 5,659,026 | A | 8/1997 | Baszczynski et al. | |
| 5,789,156 | A | 8/1998 | Bujard et al. | |
| 5,814,618 | A | 9/1998 | Bujard et al. | |
| 5,866,785 | A | 2/1999 | Donson et al. | |
| 5,879,918 | A | 3/1999 | Tomes et al. | |
| 5,886,244 | A | 3/1999 | Tomes et al. | |
| 5,889,190 | A | 3/1999 | Donson et al. | |
| 5,889,191 | A | 3/1999 | Turpen | |
| 5,932,782 | A | 8/1999 | Bidney | |
| 5,981,840 | A | 11/1999 | Zhao et al. | |
| 6,072,050 | A | 6/2000 | Bowen et al. | |
| 8,124,851 | B2 | 2/2012 | Dewey et al. | |
| 8,319,011 | B2 | 11/2012 | Xu et al. | |
| 9,137,958 | B2 * | 9/2015 | Elliott et al. | A01H 5/12 |
| 9,187,759 | B2 | 11/2015 | Dewey et al. | |
| 9,228,194 | B2 | 1/2016 | Dewey et al. | |
| 9,228,195 | B2 | 1/2016 | Dewey et al. | |
| 9,247,706 | B2 | 2/2016 | Dewey et al. | |
| 10,888,064 | B2 * | 1/2021 | Frederick et al. | C12N 9/88 |
| 11,602,118 | B2 * | 3/2023 | Frederick et al. | C12N 9/90 |
| 2007/0240728 | A1 | 10/2007 | Hashimoto et al. | |
| 2008/0120737 | A1 | 5/2008 | Hashimoto et al. | |
| 2009/0119791 | A1 * | 5/2009 | Mallmann et al. | A01H 5/12 800/317.3 |
| 2017/0233756 | A1 | 8/2017 | Begemann et al. | |
| 2017/0303582 | A1 * | 10/2017 | Lu et al. | C12Y 107/01001 |
| 2018/0119163 | A1 | 5/2018 | Kudithipudi et al. | |
| 2019/0069506 | A1 * | 3/2019 | Frederick et al. | A01H 5/12 |
| 2019/0216037 | A1 | 7/2019 | Pramod et al. | |
| 2019/0246596 | A1 | 8/2019 | Pramod et al. | |
| 2019/0271000 | A1 * | 9/2019 | Godoy et al. | C12N 15/8243 |

FOREIGN PATENT DOCUMENTS

| | | | |
|---|---|---|---|
| WO | WO 2004/041006 | A1 | 5/2004 |
| WO | WO 2011/027315 | A1 | 2/2011 |
| WO | WO 2018/067985 | A1 | 3/2018 |

(Continued)

OTHER PUBLICATIONS

Pathak et al. (2008) Curr Sct 94(11) 1394-403.*
Edwards et al. (2017) BMC Genomics 18:448.*
Henicka (1932) J Ag Res 44(6): 477-93.*
Pathak et al. (2008) Curr Sci 94(11) 1394-40.*
Allister et al. (2012) Plant Biotech J 10(9):1011-25.*
Wang et al. (2013) Plant Mol Biol Rep 31:886-900.*
Edwards KX507181 (2017).*
He et al. (2020) BMC Plant Biol 20:378.*
UPOV (2002) Tobacco Guidelines.*
Gao et al. (2016) Mitochond DNA Pt. B1:867-68.*
Aycock & McKee (1979) Tob Sci 23:107-11.*

(Continued)

*Primary Examiner* — Russell T Boggs

(74) *Attorney, Agent, or Firm* — Arnold & Porter Kaye Scholer LLP

(57) ABSTRACT

The present disclosure provides tobacco products and compositions with improved nitrogen use efficiency while retaining commercial characteristics of Burley tobacco. This disclosure further provides methods for making and producing tobacco products and compositions with improved nitrogen use efficiency while retaining commercial characteristics of Burley tobacco.

8 Claims, 11 Drawing Sheets

Specification includes a Sequence Listing.

(56) References Cited

FOREIGN PATENT DOCUMENTS

WO WO 2019/046756 A1 3/2019
WO WO/2019/140297 A1 7/2019

OTHER PUBLICATIONS

International Search Report dated Mar. 18, 2021 in Int'l Appln. PCT/US2021/013678.
Ladha et al., "Efficiency of Fertilizer Nitrogen in Cereal Production: Retrospects and Prospects," *Advances in Agronomy,* 87, pp. 85-156 (2005).
Allen et al., "MicroRNA-Directed Phasing during Trans-Acting siRNA Biogenesis in Plants," *Cell,* 121(2):207-221 (2005).
Altschul et al., "Basic local alignment search tool," *Journal of Molecular Biology,* 215:403-410 (1990).
Altschul et al., "Gapped BLAST and PSI-BLAST: a new generation of protein database search programs," *Nucleic Acids Research,* 25(17):3389-3402 (1997).
Anzalone et al., "Search-and-replace genome editing without double-strand breaks or donor DNA," *Nature,* 576:149-157 (2019).
Bartel, "MicroRNAs: Genomics, Biogenesis, Mechanism, and Function," *Cell,* 116(2):281-297 (2004).
Bowman et al., "Revised North Carolina grade index for flue-cured tobacco," *Tobacco Science,* 32:39-40 (1988).
Canevascini et al., "Tissue-Specific Expression and Promoter Analysis of the Tobacco ltp1 Gene," *Plant Physiology,* 112(2):513-524(1996).
Centers for Disease Control and Prevention, "Protocol for Analysis of Nicotine, Total Moisture and pH in Smokeless Tobacco Products," *Federal Register,* 7(4):712-719 (2009).
Cermak et al., "Efficient design and assembly of custom TALEN and other TAL effector-based constructs for DNA targeting," *Nucleic Acids Research,* 39(12):e82 (2011).
Christensen et al., "Sequence analysis and transcriptional regulation by heat shock of polyubiquitin transcripts from maize," *Plant Molecular Biology,* 12:619-632 (1989).
Christensen et al., "Maize polyubiquitin genes: structure, thermal perturbation of expression and transcript splicing, and promoter activity following transfer to protoplasts by electroporation," *Plant Molecular Biology,* 18:675-689 (1992).
Christou et al. "Stable Transformation of Soybean Callus by DNA-Coated Gold Particles," *Plant Physiology.* 87(3):671-674 (1988).
Collins et al., "Determination of nicotine alkaloids in tobacco using the autoanalyzer," *Tobacco Science* 13:79-81 (1969).
CORESTA Method No. 62, "Determination of Nicotine in Tobacco and Tobacco Products by Gas Chromatographic Analysis," (2005).
Crossway et al., "Micromanipulation techniques in plant biotechnology," *BioTechniques,* 4(4):320-334 (1986).
Davis, "A combined automated procedure for the determination of reducing sugars and nicotine alkaloids in tobacco product using a new reducing sugar method," *Tobacco Science* 20:139-144 (1976).
Davis et al., "Chapters 4B and 4C of Tobacco, Production, Chemistry and Technology," $7^{th}$ Edition, Blackwell Publishing, Oxford, MA, pp. 70-103 (1999).
De Wet et al., "Exogenous DNA transfer in maize (*Zea mays*) using DNA-treated pollen. in Experimental Manipulation of Ovule Tissue," Longman, London, pp. 197-209 (1985).
D'Halluin et al., "Transgenic maize plants by tissue electroporation.," *The Plant Cell,* 4(12):1495-1505 (1992).
Doyle et al., "TAL Effector-Nucleotide Targeter (TALE-NT) 2.0: tools for TAL effector design and target prediction," *Nucleic Acids Research,* 40(W1): W117-W122 (2012).
Edwards et al. "A reference genome for Nicotiana tabacum enables map-based cloning of homeologous loci implicated in nitrogen utilization efficiency," *BMC Genomics,* 18:448 (2017).
Fedoroff et al., "Cloning of the bronze locus in maize by a simple and generalizable procedure using the transposable controlling element Activator (Ac)," *PNAS,* 81 (12) 3825-3829 (1984).
Finer et al., "Transformation of soybean via particle bombardment of embryogenic suspension culture tissue," *In Vitro Cellular & Developmental Biology—Plant,* 27: 175-182 (1991).
Gaj et al., "ZFN, TALEN, and CRISPR/Cas-based methods for genome engineering," *Trends in Biotechnology,* 31(7):397-405 (2013).
Gatz et al., "Regulation of a modified CaMV 35S promoter by the Tn10-encoded Tet repressor in transgenic tobacco," *Molecular and General Genetics,* 227:229-237 (1991).
Goldman et al., "Female sterile tobacco plants are produced by stigma-specific cell ablation," *The EMBO Journal* 13:2976-2984 (1994).
Griffiths-Jones et al., "Rfam: an RNA family database," *Nucleic Acids Research,* 31(1):439-441 (2003).
Guevara-Garcia et al., "Tissue-specific and wound-inducible pattern of expression of the mannopine synthase promoter is determined by the interaction between positive and negative cis-regulatory elements," *The Plant Journal,* 4(3):495-505 (1993).
Hansen et al., "Wound-inducible and organ-specific expression of ORF13 from *Agrobacterium rhizogenes* 8196 T-DNA in transgenic tobacco plants," *Molecular and General Genetics,* 254(3):337-343 (1997).
Hibi et al., "Putrescine N-Methyltransferase in Cultured Roots of Hyoscyamus albus[1]: n-Butylamine as a Potent Inhibitor of the Transferase both in Vitro and in Vivo," *Plant Physiology* 100(2): 826-35 (1992).
Hildering et al., "Chimeric structure of tomato plants after seed treatment with EMS and X-rays. The use of induced mutations in plant breeding," Pergamon Press, Oxford, pp. 317-320 (1965).
Hoekema et al., "A binary plant vector strategy based on separation of vir- and T-region of the Agrobacterium tumefaciens Ti-plasmid," *Nature,* 303:179-180 (1983).
Horsch et al., "A simple and general method for transferring genes into plants," *Science* 227:1229-1231 (1985).
Kaeppler et al., "Silicon carbide fiber-mediated DNA delivery into plant cells," *Plant Cell Reports,* 9:415-418 (1990).
Kaeppler et al., "Silicon carbide fiber-mediated stable transformation of plant cells," *Theoretical and Applied Genetics,* 84:560-566 (1992).
Kawamata et al., "Temporal and Spatial Pattern of Expression of the Pea Phenylalanine Ammonia-Lyase Genel Promoter in Transgenic Tobacco," *Plant and Cell Physiology,* 38(7):792-803 (1997).
Lam, "Analysis of Tissue-Specific Elements in the CaMV 35S Promoter," *Results and Problems in Cell Differentiation,* 20:181-196 (1994).
Last et al., "pEmu: an improved promoter for gene expression in cereal cells," *Theoretical and Applied Genetics,* 81:581-588 (1991).
Lewis et al. "Impact of Alleles at the Yellow Burley (Yb) Loci and Nitrogen Fertilization Rate on Nitrogen Utilization Efficiency and Tobacco-Specific Nitrosamine (TSNA) Formation in Air-Cured Tobacco," *J. Agric. Food Chem.,* 60, 6454-6461 (2012).
Li et al., "Metabolome and molecular basis for carbohydrate increase and nitrate reduction in burley tobacco seedlings by glycerol through upregulating carbon and nitrogen metabolism," *Scientific Report,* 8:13300 (2018).
Matsuoka et al., "Tissue-specific light-regulated expression directed by the promoter of a C4 gene, maize pyruvate, orthophosphate dikinase, in a C3 plant, rice," *PNAS,* 90(20):9586-9590 (1993).
Mayo et al., "Genetic transformation of tobacco NT1 cells with Agrobacterium tumefaciens," *Nature Protocols,* 1:1105-1111 (2006).
McCabe et al., "Stable Transformation of Soybean (*Glycine max*) by Particle Acceleration," *Biotechnology,* 6:923-926 (1988).
McCallum et al. "Targeted screening for induced mutations," *Nature Biotechnology,* 18:455-457 (2000).
McNellis et al., "Glucocorticoid-inducible expression of a bacterial a virulence gene in transgenic *Arabidopsis* induces hypersensitive cell death," *The Plant Journal,* 14(2):247-257 (1998).
Miller et al., "A grade index for type 22 and 23 fire-cured tobacco," *Tobacco International,* 192(22):55-57 (1990).
Miller, "Memorandum on the Proposed Burley Tobacco Grade Index," Legacy Tobacco Document Library, Bates Nos. 523267826-523267833 (1988).

(56) References Cited

OTHER PUBLICATIONS

Morita et al., "Vacuolar transport of nicotine is mediated by a multidrug and toxic compound extrusion (MATE) transporter in Nicotiana tabacum," *PNAS,* 106:2447-2452 (2009).
Odell et al., "Identification of DNA sequences required for activity of the cauliflower mosaic virus 35S promoter," *Nature,* 313: 810-812, (1985).
Official Standard Grades for Burley Tobacco (U.S. Type 31 and Foreign Type 93), effective Nov. 5, 1990 (55 F.R. 40645).
Official Standard Grades for Flue-Cured Tobacco (U.S. Types 11, 12, 13, 14 and Foreign Type 92), effective Mar. 27, 1989 (54 F.R. 7925).
Official Standard Grades for Georgia and Florida Shade-Grown Cigar-Wrapper Tobacco (U.S. Type 62), Effective Apr. 1971. A USDA grade index value can be determined according to an industry accepted grade index.
Official Standard Grades for Ohio Cigar-Leaf Tobacco (U.S. Types 42, 43, and 44), effective Dec. 8, 1963 (28 F.R. 11719 and 28 F.R. 11926).
Official Standard Grades for Pennsylvania Seedleaf Tobacco (U.S. Type 41), effective Jan. 8, 1965 (29 F.R. 16854).
Official Standard Grades for Wisconsin Cigar-Binder Tobacco (U.S. Types 54 and 55), effective Nov. 20, 1969 (34 F.R. 17061).
Orozco et al., "Localization of light-inducible and tissue-specific regions of the spinach ribulose bisphosphate carboxylase/oxygenase (rubisco) activase promoter in transgenic tobacco plants," *Plant Molecular Biology,* 23(6):1129-1138 (1993).
Parizotto et al., "In vivo investigation of the transcription, processing, endonucleolytic activity, and functional relevance of the spatial distribution of a plant miRNA," *Genes & Development,* 18:2237-2242 (2004).
Paszkowski et al., "Direct gene transfer to plants," *The EMBO Journal,* 3:2717-2722 (1984).
Porta et al., "Use of viral replicons for the expression of genes in plants," *Molecular Biotechnology,* 5:209-221 (1996).
Reynolds et al., "Rational siRNA design for RNA interference," *Nature Biotechnology,* 22:326-330 (2004).
Riggs et al., "Stable transformation of tobacco by electroporation: evidence for plasmid concatenation," *Proc. Natl. Acad. Sci. USA* 83(15):5602-5606 (1986).
Rinehart et al., "Tissue-Specific and Developmental Regulation of Cotton Gene FbL2A (Demonstration of Promoter Activity in Transgenic Plants)," *Plant Physiology,* 112(3):1331-1341 (1996).
Russell et al., "Tissue-specific expression in transgenic maize of four endosperm promoters from maize and rice," *Transgenic Research,* 6(2) :157-168 (1997).
Schena et al., "A steroid-inducible gene expression system for plant cells," *Proc. Natl. Acad. Sci. USA* 88(23):10421-10425 (1991).
Shillito et al., "[19] Direct gene transfer to protoplasts of dicotyledonous and monocotyledonous plants by a number of methods, including electroporation," *Methods in Enzymology,* 153 :313-336 (1987).
Singh et al., "Cytological characterization of transgenic soybean," *Theoretical and Applied Genetics,* 96:319-324 (1998).
Sood et al., "Improving androgenesis-mediated doubled haploid production efficiency of FCV tobacco (*Nicotiana tabacum* L.) through in vitro colchicine application," *Plant Breeding,* 132.6, 764-771 (2013).
Thompson et al., "Clustal W: Improving the sensitivity of progressive multiple sequence alignment through sequence weighting, position-specific gap penalties and weight matrix choice," *Nucleic Acids Research,* 22:4673-4680 (1994).
Tomes et al., "Chapter 16: Direct DNA Transfer into Intact Plant Cells via Microprojectile Bombardment, in Plant Cell, Tissue, and Organ Culture Fundamental Methods" Springer-Verlag Berlin Heidelberg, pp. 197-213 (1995).
Touraev et al., "Microspore Embryogenesis and In Vitro Pollen Maturation in Tobacco, in Plant Cell Culture Protocols. Methods In Molecular Biology," Humana Press, 111:281-291 (1999).
Van Camp et al., "Enhancement of Oxidative Stress Tolerance in Transgenic Tobacco Plants Overproducing Fe-Superoxide Dismutase in Chloroplasts," *Plant Physiology,* 112(2):525-535 (1996).
Velten et al., "Isolation of a dual plant promoter fragment from the Ti plasmid of Agrobacterium tumefaciens," The EMBO Journal, 3(12):2723-2730 (1984).
Verkerk, "Chimerism of the tomato plant after seed irradiation with fast neutrons," *Netherlands Journal of Agricultural Science,* 19(4):197-203 (1971).
Weising et al., "Foreign Genes in Plants: Transfer, Structure, Expressions and Applications," *Annual Review of Genetics,* 22:421-477 (1988).
Wernsman et al., "Tobacco," *Principles of Cultivar Development: Crop Species,* MacMillan Publishing Co., 2(17):669-698 (1987).
Yamamoto et al., "The Promoter of a Pine Photosynthetic Gene Allows Expression of a β-Glucuronidase Reporter Gene in Transgenic Rice Plants in a Light-Independent but Tissue-Specific Manner," *Plant & Cell Physiology,* 35(5): 773-778 (1994).
Yamamoto et al., "Light-responsive elements of the tobacco PSI-D gene are located both upstream and within the transcribed region," *The Plant Journal,* 12(2):255-265 (1997).
"Receipt in the Case of an Original Deposit (BP/4): dS1532 (PTA-126901) and dS1563 (PTA-126902)," American Type Culture Collection (ATCC®), Nov. 19, 2020, 1 page.
"Viability Statement (BP/9): PTA-126901 and PTA-126902," American Type Culture Collection (ATCC®), Nov. 19, 2020, 1 page.
"Codes Used in Sequence Description: Nucleotide—Nucleotide Base Codes," *DDBJ Annotated/Assembled Sequences,* accessed and printed on Sep. 12, 2023 (5 pages), available online: https://www.ddbj.nig.ac.jp/ddbj/code-e.html.
"CORESTA Recommended Method No. 7: Determination of Nicotine in the Mainstream Smoke of Cigarettes by Gas Chromatographic Analysis," pp. 1-5, (1987) (updated Aug. 1991) (Paris, France).
"Draft for Diplomatic Conference for the Revision of the International Convention for the Protection of New Varieties of Plants," (of Dec. 2, 1961, as revised at Geneva on Nov. 10, 1972; on Oct. 23, 1978; and on Mar. 19, 1991), 54 pages, Mar. 4-19, 1991 (Geneva, Switzerland).
"Nomenclature for Incompletely Specified Bases in Nucleic Acid Sequences: Recommendation 1984," *Nomenclature Committee of the International Union of Biochemistry* (*NC-IUB*), accessed and printed on Sep. 12, 2023 (9 pages), available online: https://iubmb.qmul.ac.uk/misc/naseq.html.
"Nucleotide Codes, Amino Acid Codes, and Genetic Codes," *KEGG,* accessed and printed on Sep. 12, 2023 (2 pages), available online: https://www.genome.jp/kegg/catalog/codes1.html.
UIPAC Nucleotide Code listing, accessed and printed on Sep. 12, 2023, (1 page), available online: https://www.bioinformatics.org/sms/iupac.html.
Van Camp et al., "Tissue-Specific Activity of Two Manganese Superoxide Dismutase Promoters in Transgenic Tobacco1," Plant Physiology, 112(2), pp. 525-535 (Oct. 1996), available online: DOI: 10.1104/pp.112.2.525.
Search Report issued in Chinese Application No. 202180014428X, dated May 30, 2025; 4 pages with machine translation.
GenBank Accession No. KX507181.1, "Nicotiana tabacum cultivar K326 EGY1 mRNA, complete cds," dated May 7, 2017 (2 pages).
GenBank Accession No. KX507182.1, "Nicotiana tabacum cultivar TN90 truncated EGY1 mRNA, complete cds," dated May 7, 2017 (2 pages).
GenBank Accession No. KX507183.1, "Nicotiana tabacum cultivar K326 EGY2 mRNA, complete cds," dated May 7, 2017 (2 pages).
GenBank Accession No. KX507184.1, "Nicotiana tabacum cultivar TN90 truncated EGY2 mRNA, complete cds," dated May 7, 2017 (2 pages).

* cited by examiner

Ds1532 Ds1563 TN90 MD609

SEQUENCE LISTING

```
<160> NUMBER OF SEQ ID NOS: 65

<210> SEQ ID NO 1
<211> LENGTH: 128
<212> TYPE: PRT
<213> ORGANISM: Nicotiana tabacum

<400> SEQUENCE: 1

Met Gly Leu Lys Gly Lys Leu Ile Ser Gln Met Glu Met Lys Cys Ala
1               5                   10                  15

Gly Asp Leu Leu His Glu His Phe Lys Ser Asn Pro His Gln Thr Ser
            20                  25                  30

Thr Met Ser Pro Asp Lys Ile Thr Asn Phe Thr Leu His Glu Gly Gln
        35                  40                  45

Leu Gly Asn Thr Gly Ser Val Val Ser Trp Lys Tyr Val Leu Gly Gly
    50                  55                  60

Lys Glu Arg His Ala Lys Gln Ala Leu His Ile Asp Asp Ala Lys Lys
65                  70                  75                  80

Ser Ile Thr Phe Asn Phe Leu Glu Gly Tyr Met Asn Glu Leu Tyr Lys
                85                  90                  95

Ser Met Thr Pro Gln Tyr Arg Ile Asn Asn Asn Leu Glu Cys His Lys
            100                 105                 110

Ser Arg Asn His Pro Met Gln Val Thr Ser Pro Asn His Thr Gln Ile
```

115 120 125

<210> SEQ ID NO 2
<211> LENGTH: 540
<212> TYPE: PRT
<213> ORGANISM: Nicotiana tabacum

<400> SEQUENCE: 2

```
Met Lys Ala Glu Gly Ser Ala Leu Ser Ser Ala Gly Ser Tyr His Arg
1               5                   10                  15

Leu Ala Tyr His Glu Val Ile Asn Asp Asp Asn Gln Asn Lys Ile Phe
            20                  25                  30

Thr Ser Asp Asp Ser Arg Leu Arg Gln Leu Gly Tyr Lys Gln Glu Leu
        35                  40                  45

Tyr Arg Gly Leu Ser Phe Ile Ala Asn Phe Ser Phe Thr Phe Ala Ile
    50                  55                  60

Val Ser Val Leu Thr Gly Ile Ser Thr Leu Tyr Asn Gln Ala Leu Thr
65                  70                  75                  80

Phe Gly Gly Pro Ile Thr Leu Val Tyr Gly Trp Pro Ile Val Ser Leu
                85                  90                  95

Met Thr Leu Ile Val Gly Leu Ala Met Ala Glu Ile Cys Ser Ala Tyr
            100                 105                 110

Pro Thr Ser Ala Gly Leu Tyr Tyr Trp Ser Ala Lys Leu Ser Gly Asn
        115                 120                 125

Tyr Phe Gly Pro Phe Ala Ser Trp Ile Thr Gly Trp Phe Asn Ile Val
    130                 135                 140

Gly Gln Trp Ala Val Thr Ala Ser Ile Asp Phe Ser Leu Ala Gln Leu
145                 150                 155                 160

Val Gln Val Met Ile Leu Leu Ser Thr Gly Gly Leu Asn Gly Gly Gly
                165                 170                 175

Tyr Gln Ala Ser Lys Tyr Val Val Ile Ala Leu His Gly Gly Ile Leu
            180                 185                 190

Leu Leu His Ala Ile Leu Asn Ser Leu Pro Ile Ser Trp Leu Ser Phe
        195                 200                 205

Phe Gly Gln Leu Ala Ala Ala Trp Asn Val Leu Gly Val Phe Leu Leu
    210                 215                 220

Met Ile Leu Ile Pro Met Val Ser Thr Glu Arg Ala Ser Ala Lys Phe
225                 230                 235                 240

Val Phe Thr Asn Phe Asn Thr Asp Asn Gly Asp Gly Ile Asn Asn Asn
                245                 250                 255

Leu Tyr Ile Phe Val Leu Gly Leu Leu Met Ser Gln Tyr Thr Leu Thr
            260                 265                 270

Gly Tyr Asp Ala Ser Ala His Met Thr Glu Glu Thr Lys Asn Ala Asp
        275                 280                 285

Lys Asn Gly Pro Lys Gly Ile Val Ser Ala Ile Gly Ile Ser Val Leu
    290                 295                 300

Ala Gly Trp Ala Tyr Ile Leu Gly Ile Thr Phe Ala Val Thr Asp Ile
305                 310                 315                 320

Pro His Leu Leu Asn Lys Asn Asn Asp Ser Gly Gly Tyr Ala Ile Ala
                325                 330                 335

Gln Ile Phe Tyr Asp Ala Phe Lys Asn Arg Tyr Gly Ser Gly Val Gly
            340                 345                 350

Gly Ile Ile Cys Leu Gly Val Ile Ala Ile Ala Val Phe Phe Cys Gly
        355                 360                 365
```

Met Ser Ser Leu Thr Ser Asn Ser Arg Met Ala Tyr Ala Phe Ser Arg
    370                 375                 380

Asp Gly Ala Met Pro Tyr Ser Ser Phe Trp His Lys Val Asn Lys Gln
385                 390                 395                 400

Glu Val Pro Leu Asn Ala Val Trp Met Ser Ala Phe Ile Ala Phe Cys
                405                 410                 415

Met Ala Leu Thr Ser Leu Gly Ser Leu Val Ala Phe Gln Ala Met Thr
            420                 425                 430

Ser Ile Ala Thr Ile Gly Leu Tyr Ile Ala Tyr Ala Leu Pro Ile Leu
        435                 440                 445

Phe Arg Val Thr Leu Ala Arg Lys Ser Phe Thr Pro Gly Pro Phe Asn
    450                 455                 460

Leu Gly Ser Tyr Gly Leu Val Val Gly Trp Val Ala Ile Phe Trp Val
465                 470                 475                 480

Ala Leu Ile Ser Val Leu Phe Ser Leu Pro Val Ala Tyr Pro Ile Thr
                485                 490                 495

Asp Gln Thr Leu Asn Tyr Thr Pro Val Ala Val Gly Gly Leu Leu Ile
            500                 505                 510

Leu Val Val Ser Ser Trp Ile Phe Ser Ala Ile His Trp Phe Lys Gly
        515                 520                 525

Pro Ile Thr Asn Leu Gly Asn Ser Ser Glu Glu Ala
    530                 535                 540

<210> SEQ ID NO 3
<211> LENGTH: 145
<212> TYPE: PRT
<213> ORGANISM: Nicotiana tabacum

<400> SEQUENCE: 3

Met Ala Ser Thr Gln Gln Ala Val Ser Ser Gly Ser Asp Ala Asp Gln
1               5                   10                  15

Arg Tyr Ala Lys Phe Asp Glu Arg Lys Arg Lys Arg Met Glu Ser Asn
            20                  25                  30

Arg Glu Ser Ala Arg Arg Ser Arg Met Arg Lys Gln Gln Arg Leu Gly
        35                  40                  45

Glu Leu Met Ser Glu Thr Thr Gln Leu Gln Asn Gln Asn Ser Ile Cys
    50                  55                  60

Arg Glu Arg Ile Asp Ser Val Glu Arg Asn Tyr Cys Ala Ile Asp Ala
65                  70                  75                  80

Glu Asn Asn Val Leu Arg Ala Gln Ile Ala Glu Leu Thr Glu Arg Leu
                85                  90                  95

Asn Ser Leu Asn Ser Leu Thr Gln Phe Trp Ala Asp Ala Thr Gly Phe
            100                 105                 110

Pro Val Asp Leu Pro Glu Ile Pro Asp Thr Leu Leu Glu Pro Trp Gln
        115                 120                 125

Leu Pro Cys Pro Ile Gln Pro Ile Asp Ala Ser Ser Asp Met Leu Leu
    130                 135                 140

Phe
145

<210> SEQ ID NO 4
<211> LENGTH: 654
<212> TYPE: PRT
<213> ORGANISM: Nicotiana tabacum

<400> SEQUENCE: 4

```
Met Pro Gly Val Tyr Leu Glu Thr Ala Ser Leu Pro Lys Gly Arg Gly
1               5                   10                  15

Leu Glu Cys Gln Glu Ser Gln Ala Val Arg Tyr Phe Phe Arg Gly Arg
            20                  25                  30

Asn Lys Val Asp Asp Ser Leu Thr Ile Glu Ile Phe Asn Leu Phe Pro
        35                  40                  45

Trp Ile Phe Phe Thr Ile Leu Ala Met Asp Lys His His His Gln Leu
    50                  55                  60

Pro Leu Thr Lys Ser Thr Ser Arg Gln Arg Tyr Asn Glu Trp Val Phe
65                  70                  75                  80

Arg Asp Val Pro Ser Asp Ile Thr Ile Glu Val Asp Gly Gly Ile Phe
                85                  90                  95

Ser Leu His Lys Phe Pro Leu Val Ser Arg Ser Gly Arg Ile Arg Arg
            100                 105                 110

Leu Val Ala Glu His Arg Asp Ser Asp Ile Ser Arg Ile Glu Leu Val
        115                 120                 125

Ser Leu Pro Gly Gly Thr Glu Ser Phe Glu Leu Ala Ala Lys Phe Cys
    130                 135                 140

Tyr Gly Val Asn Phe Glu Ile Thr Ala Ala Asn Val Ala Gln Leu Cys
145                 150                 155                 160

Cys Val Ser Asp Tyr Leu Glu Met Ser Glu Asp Tyr Ser Lys Asn Asn
                165                 170                 175

Leu Gly Ser Arg Ala Glu Glu Tyr Leu Asp Ser Ile Val Cys Lys Asn
            180                 185                 190

Leu Glu Met Cys Val Glu Val Leu Arg Gln Cys Glu Asn Leu Leu Pro
        195                 200                 205

Leu Ala Asp Glu Leu Lys Val Val Ser Arg Cys Ile Asp Ala Val Ala
    210                 215                 220

Ser Lys Ala Cys Val Glu Gln Ile Ala Ser Ser Phe Ser Arg Leu Glu
225                 230                 235                 240

Tyr Ser Ile Ser Gly Gly Arg Leu His Met Ser Lys Gln Ala Asn Cys
                245                 250                 255

Glu Leu Asp Trp Trp Ile Glu Asp Ile Ser Met Leu Arg Ile Asp Leu
            260                 265                 270

Tyr Gln Arg Val Ile Thr Ala Met Lys Phe Arg Gly Val Arg Pro Glu
        275                 280                 285

Ser Ile Ala Ala Ser Leu Val Asn Tyr Ala Gln Lys Glu Leu Ile Gln
    290                 295                 300

Lys Thr Leu Ser Gly Ser Asn Ile Gln Glu Lys Leu Val Val Glu Thr
305                 310                 315                 320

Ile Val Ser Leu Met Pro Val Glu Lys Phe Val Val Pro Leu Thr Phe
                325                 330                 335

Leu Phe Gly Leu Leu Arg Ser Ala Val Met Leu Asp Cys Thr Val Ala
            340                 345                 350

Cys Arg Leu Asp Leu Glu Arg Arg Ile Gly Ser Gln Leu Asp Thr Ala
        355                 360                 365

Thr Leu Asp Asp Ile Leu Ile Pro Ser Phe Arg His Ala Gly Asp Thr
    370                 375                 380

Leu Phe Asp Val Asp Thr Val His Arg Ile Leu Val Asn Phe Ser Gln
385                 390                 395                 400

Gln Glu Gly Asp Ser Asp Asp Asp Met Glu Asp Val Ser Val Phe Glu
                405                 410                 415

Ser Asp Ser Pro Thr Thr Thr Pro Ser Gln Thr Ala Leu Phe Lys Val
```

420 425 430

Ser Lys Leu Val Asp Asn Tyr Leu Ala Glu Ile Ala Leu Asp Ala Asn
435 440 445

Leu Lys Leu Asn Lys Phe Ile Ala Val Ala Glu Thr Leu Pro Ala His
450 455 460

Ala Arg Thr Val His Asp Gly Leu Tyr Arg Ala Ile Asp Leu Tyr Leu
465 470 475 480

Lys Ala His Gln Thr Leu Ser Asp Pro Asp Lys Arg Arg Leu Cys Lys
485 490 495

Leu Ile Asp Phe Gln Lys Leu Ser Gln Glu Ala Gly Ala Gln Ala Ala
500 505 510

Gln Asn Glu Arg Leu Pro Leu Gln Ser Ile Val Gln Val Leu Tyr Phe
515 520 525

Glu Gln Leu Arg Leu Arg Asn Ala Leu Phe Cys Ser Tyr Pro Asp Asp
530 535 540

Asp Ile Lys Pro Thr His Gln Ser Trp Arg Ile Asn Ser Gly Ala Leu
545 550 555 560

Ser Ala Ala Met Ser Pro Lys Asp Asn Tyr Ala Ser Leu Arg Arg Glu
565 570 575

Asn Arg Glu Leu Lys Leu Glu Leu Ala Arg Met Arg Met Arg Leu Asn
580 585 590

Asp Leu Glu Lys Asp His Val Cys Met Lys Arg Asn Met Gln Lys Ser
595 600 605

Ser Ser Arg Arg Phe Met Lys Ser Phe Ser Lys Arg Ile Gly Lys Lys
610 615 620

Phe Asn Ile Phe Gly His Asn Phe Ser Arg Asp Cys Ser Ser Pro Ser
625 630 635 640

Ser Gln Ser Glu Arg Thr Glu Ser Lys Ile Thr Glu Arg Thr
645 650

<210> SEQ ID NO 5
<211> LENGTH: 303
<212> TYPE: PRT
<213> ORGANISM: Nicotiana tabacum

<400> SEQUENCE: 5

Met Glu His Ser Ala Ala Asp Arg Asp Pro Lys Ala Val Glu Phe Ala
1 5 10 15

Lys Asp Lys Asn Gly Val Gly Gln Val Leu Leu Arg Asn Pro Arg Gly
20 25 30

Ala Ser Val Arg Val Ser Leu His Gly Gly Gln Val Leu Ser Trp Lys
35 40 45

Asn Asp His Gly Glu Glu Leu Leu Phe Ile Ser Ser Lys Ala Thr Phe
50 55 60

Lys Pro Pro Thr Ala Val Arg Gly Gly Ile Pro Ile Cys Phe Pro Gln
65 70 75 80

Phe Gly Asn Arg Gly Ser Leu Glu Gln His Gly Phe Ala Arg Asn Arg
85 90 95

Met Trp Ile Ile Asp Asp Asn Pro Pro Pro Leu His Pro Asn Asp Ser
100 105 110

Asn Gly Lys Ala Phe Thr Asp Leu Leu Leu Lys Ser Ser Asp Asp Asp
115 120 125

Leu Lys Val Trp Pro His Gly Phe Glu Phe Arg Leu Arg Val Thr Leu
130 135 140

Ala Val Asp Gly Ser Leu Thr Leu Ile Ser Arg Ile Arg Asn Val Asn
145 150 155 160

Cys Lys Pro Phe Ser Phe Ser Ile Ala Tyr His Thr Tyr Phe Ala Leu
165 170 175

Ser Asp Ile Ser Glu Val Arg Val Glu Gly Leu Glu Thr Leu Asp Tyr
180 185 190

Leu Asp Asn Leu Cys Asn Arg Glu Arg Phe Thr Glu Gln Gly Asp Ala
195 200 205

Leu Thr Phe Glu Thr Glu Val Asp Arg Val Tyr Leu Ser Ser Ser Asp
210 215 220

Val Ile Ala Ile Phe Asp His Glu Lys Lys Arg Thr Phe Val Ile Lys
225 230 235 240

Arg Glu Gly Leu Pro Asp Val Val Val Trp Asn Pro Trp Glu Lys Lys
245 250 255

Ser Lys Thr Ile Ala Asp Phe Gly Asp Asp Glu Tyr Arg His Met Leu
260 265 270

Cys Val Asp Gly Ala Ala Ile Glu Lys Pro Ile Thr Leu Lys Pro Gly
275 280 285

Glu Glu Trp Thr Gly Arg Leu Glu Leu Ser Val Met Pro Ser Ser
290 295 300

<210> SEQ ID NO 6
<211> LENGTH: 578
<212> TYPE: PRT
<213> ORGANISM: Nicotiana tabacum

<400> SEQUENCE: 6

Met Glu Val Met Lys Lys Lys Glu Asn Thr Ser Arg Lys Met Lys Gly
1 5 10 15

Gly Met Ile Thr Met Pro Phe Ile Phe Ala Asn Glu Ile Cys Glu Lys
20 25 30

Leu Ala Val Val Gly Phe Gly Ala Asn Met Ile Ile Tyr Leu Thr Asn
35 40 45

Glu Leu His Leu Pro Leu Thr Lys Ala Ala Asn Thr Leu Thr Asn Phe
50 55 60

Gly Gly Thr Ala Ser Leu Thr Pro Leu Leu Gly Ala Phe Ile Ala Asp
65 70 75 80

Thr Phe Ala Gly Arg Phe Trp Thr Ile Thr Ile Ala Ser Ile Ile Tyr
85 90 95

Gln Ile Gly Met Ile Ile Leu Thr Val Ser Ala Ile Leu Pro Gln Leu
100 105 110

Arg Pro Pro Ser Cys Lys Gly Asp Glu Phe Cys Lys Glu Ala Asn Ser
115 120 125

Gly Gln Leu Ala Ile Leu Tyr Ile Ser Leu Leu Leu Thr Ala Phe Gly
130 135 140

Ser Gly Gly Ile Arg Pro Cys Val Val Ala Phe Gly Ala Glu Gln Phe
145 150 155 160

Asp Glu Thr Asp Pro Asn Gln Lys Thr Gln Thr Trp Lys Phe Phe Asn
165 170 175

Trp Tyr Tyr Phe Ser Met Gly Phe Ser Met Leu Ile Ala Val Thr Val
180 185 190

Ile Val Tyr Ile Gln Asp Asn Ile Gly Trp Gly Ile Gly Phe Gly Val
195 200 205

Pro Thr Ile Ala Met Leu Ile Ser Ile Ile Val Phe Ile Phe Gly Tyr
210 215 220

Pro Leu Tyr Arg Asn Leu Asp Pro Ala Gly Ser Pro Phe Thr Arg Leu
225 230 235 240

Leu Gln Val Cys Val Ala Ala Tyr Lys Lys Arg Lys Leu Asp Met Val
245 250 255

Ser Asp Pro Ser Phe Leu Tyr Gln Asn Glu Glu Leu Asp Ser Ala Ile
260 265 270

Ser Thr Ala Gly Lys Leu Val His Thr Lys Gln Met Lys Phe Leu Asp
275 280 285

Arg Ala Ala Ile Val Thr Glu Glu Asp Asn Arg Lys Ser Pro Asn Leu
290 295 300

Trp Arg Leu Asn Thr Val His Arg Val Glu Glu Leu Lys Ser Ile Ile
305 310 315 320

Arg Met Gly Pro Ile Trp Ala Ser Gly Ile Ile Leu Ile Thr Ala Tyr
325 330 335

Ala Gln Gln His Thr Phe Ser Val Gln Gln Ala Lys Thr Met Asp Arg
340 345 350

His Leu Ile Asn Ser Phe Glu Ile Pro Ala Ala Ser Met Thr Val Phe
355 360 365

Thr Leu Thr Ala Met Leu Cys Thr Ile Cys Phe Tyr Asp Arg Val Phe
370 375 380

Val Pro Ile Ala Arg Lys Phe Thr Gly Leu Glu Arg Gly Ile Ser Phe
385 390 395 400

Leu Ser Arg Met Ala Ile Gly Phe Ser Ile Ser Val Leu Ala Thr Leu
405 410 415

Val Ala Gly Phe Ile Glu Val Lys Arg Lys Glu Ala Ala Leu Thr His
420 425 430

Gly Leu Ile Asp Lys Gly Lys Ala Ile Val Pro Ile Ser Val Phe Trp
435 440 445

Leu Val Pro Gln Tyr Cys Leu His Gly Val Val Ala Phe Met Ser Ile
450 455 460

Gly His Leu Glu Phe Phe Tyr Asp Gln Ala Pro Glu Ser Met Arg Ser
465 470 475 480

Thr Ala Thr Ala Leu Phe Trp Thr Ser Ile Ser Ala Gly Asn Tyr Leu
485 490 495

Ser Thr Leu Leu Val Ser Leu Val His Lys Phe Thr Ser Gly Ser Gly
500 505 510

Gly Ser Asn Trp Leu Pro Asp Asn Asn Leu Asn Lys Gly Lys Leu Glu
515 520 525

Tyr Phe Tyr Trp Leu Ile Thr Ile Leu Gln Val Val Asn Leu Ile Tyr
530 535 540

Tyr Leu Phe Cys Ala Lys Phe Tyr Thr Phe Lys Pro Ile Gln Val His
545 550 555 560

Lys Thr Glu Asp Leu Asp Ser Lys Lys Asp Ser Ile Glu Leu Val Asn
565 570 575

Asn Val

<210> SEQ ID NO 7
<211> LENGTH: 517
<212> TYPE: PRT
<213> ORGANISM: Nicotiana tabacum

<400> SEQUENCE: 7

Met Ala Leu Ser Asn Thr Leu Ser Leu Ser Ser Ser Lys Ser Leu Val
1 5 10 15

-continued

```
Gln Ser His Leu Leu His Asn Pro Ser Leu Pro Gln Pro Arg Ile Pro
            20                  25                  30

Val Phe His Asn Pro Gln His Gly Arg Arg His Pro Ile Ser Ala Val
        35                  40                  45

His Ala Ala Glu Pro Ala Lys Thr Ala Thr Ala Ser Gln Pro Leu Lys
    50                  55                  60

Lys Thr Gln Trp Ser Leu Asp Ser Trp Lys Ser Lys Lys Ala Leu Gln
65                  70                  75                  80

Leu Pro Glu Tyr Pro Asp Glu Lys Glu Leu Glu Ser Val Leu Glu Thr
                85                  90                  95

Leu Glu Ser Asn Pro Pro Leu Val Phe Ala Gly Glu Ala Arg Asn Leu
            100                 105                 110

Glu Glu Arg Leu Gly Glu Ala Ala Leu Gly Lys Ala Phe Leu Leu Gln
        115                 120                 125

Gly Gly Asp Cys Ala Glu Ser Phe Lys Glu Phe Asn Ala Asn Asn Ile
    130                 135                 140

Arg Asp Thr Phe Arg Ile Leu Leu Gln Met Ser Val Val Leu Met Phe
145                 150                 155                 160

Gly Gly Gln Val Pro Val Ile Lys Val Gly Arg Met Ala Gly Gln Phe
                165                 170                 175

Ala Lys Pro Arg Ser Asp Pro Phe Glu Glu Ile Asp Gly Val Lys Leu
            180                 185                 190

Pro Ser Tyr Lys Gly Asp Asn Ile Asn Gly Asp Thr Phe Asp Glu Lys
        195                 200                 205

Ser Arg Ile Pro Asp Pro His Arg Leu Ile Arg Ala Tyr Met Gln Ser
    210                 215                 220

Ala Ala Thr Leu Asn Leu Leu Arg Ala Phe Ala Thr Gly Gly Tyr Ala
225                 230                 235                 240

Ala Met Gln Arg Val Thr Glu Trp Asn Leu Asp Phe Val Glu Asn Ser
                245                 250                 255

Glu Gln Gly Asp Arg Tyr Gln Glu Leu Ala His Arg Val Asp Glu Ala
            260                 265                 270

Leu Gly Phe Met Ala Ala Ala Gly Leu Thr Val Asp His Pro Ile Met
        275                 280                 285

Ala Thr Thr Asp Phe Trp Thr Ser His Glu Cys Leu Leu Leu Pro Tyr
    290                 295                 300

Glu Gln Ala Leu Thr Arg Glu Asp Ser Thr Ser Gly Leu Phe Tyr Asp
305                 310                 315                 320

Cys Ser Ala His Met Ile Trp Val Gly Glu Arg Thr Arg Gln Leu Asp
                325                 330                 335

Gly Ala His Val Glu Phe Leu Arg Gly Val Ala Asn Pro Leu Gly Ile
            340                 345                 350

Lys Val Ser Gln Lys Met Asp Pro Asn Glu Leu Val Lys Leu Ile Asp
        355                 360                 365

Ile Leu Asn Pro Thr Asn Lys Pro Gly Arg Ile Thr Val Ile Val Arg
    370                 375                 380

Met Gly Ala Glu Asn Met Arg Val Lys Leu Cys His Leu Ile Arg Ala
385                 390                 395                 400

Val Arg Gly Ala Gly Gln Ile Val Thr Trp Val Cys Asp Pro Met His
                405                 410                 415

Gly Asn Thr Ile Lys Ala Pro Cys Gly Leu Lys Thr Arg Ala Phe Asp
            420                 425                 430
```

```
Ser Ile Leu Ala Glu Val Arg Ala Phe Phe Asp Val His Glu Gln Glu
        435                 440                 445

Gly Ser His Pro Gly Gly Ile His Leu Glu Met Thr Gly Gln Asn Val
    450                 455                 460

Thr Glu Cys Ile Gly Gly Ser Arg Thr Val Thr Tyr Asp Asp Leu Gly
465                 470                 475                 480

Ser Arg Tyr His Thr His Cys Asp Pro Arg Leu Asn Ala Ser Gln Ser
                485                 490                 495

Leu Glu Leu Ser Phe Ile Val Ala Glu Arg Leu Arg Lys Arg Arg Met
            500                 505                 510

Ala Ser Gln Arg Leu
        515


<210> SEQ ID NO 8
<211> LENGTH: 254
<212> TYPE: PRT
<213> ORGANISM: Nicotiana tabacum

<400> SEQUENCE: 8

Met Ala Ala Ser Ser Thr Leu Ser Ser Ser Ile Thr Thr Phe Lys Leu
1               5                   10                  15

Ser Pro Cys Gln Pro Arg Ala Ser Ser Thr Thr Ala Ser Val Lys Ile
            20                  25                  30

Pro Ser Ile Pro Pro Ile Thr Leu Ser Ile Leu Leu Ile Ser His Phe
        35                  40                  45

Gly Pro Thr Pro Lys Asn Pro Thr Val Ala Pro Leu Arg Cys Ser Ala
    50                  55                  60

Thr Ser Thr Thr Pro Glu Thr Thr Thr Thr Thr Ser Thr Pro Phe His
65                  70                  75                  80

Asp Leu Cys Tyr Val Val Gly Asp Asn Ile Asp Asn Asp Gln Ile Ile
                85                  90                  95

Pro Ala Lys Tyr Leu Thr Leu Val Ser Ser Asn Pro Asp Glu Tyr Lys
            100                 105                 110

Lys Leu Gly Ser Tyr Ala Leu Cys Gly Leu Pro Leu Ser Tyr Gln Thr
        115                 120                 125

Arg Phe Val Asp Pro Asp Glu Phe Ser Ser Lys Tyr Ser Ile Ile Ile
    130                 135                 140

Gly Gly Glu Asn Phe Gly Cys Gly Ser Ser Arg Glu His Ala Pro Val
145                 150                 155                 160

Ala Leu Gly Ala Ala Gly Val Ala Glu Ser Tyr Ala Arg Ile Phe Phe
                165                 170                 175

Arg Asn Ser Val Ala Thr Gly Glu Val Tyr Pro Leu Glu Ser Glu Val
            180                 185                 190

Arg Ile Cys Glu Glu Cys Lys Thr Gly Asp Val Val Ala Val Glu Leu
        195                 200                 205

Ala Glu Ser Arg Leu Ile Asn His Met Thr Gly Lys Glu Tyr Lys Leu
    210                 215                 220

Lys Ser Ile Gly Asp Val Gly Pro Val Ile Glu Ala Gly Gly Ile Phe
225                 230                 235                 240

Ala Tyr Ala Arg Lys Ala Gly Met Ile Pro Ser Arg Glu Ala
                245                 250


<210> SEQ ID NO 9
<211> LENGTH: 386
<212> TYPE: DNA
<213> ORGANISM: Nicotiana tabacum
```

<400> SEQUENCE: 9
atgggtctca aaggcaagtt gatctctcaa atggagatga agtgtgctgg agatttgctt 60
catgaacact tcaaatcaaa tccacaccaa acctccacca tgtctcctga taagataaca 120
aatttcacgt tacatgaggg tcagttgggt aatactggtt ctgttgtcag ctggaagtat 180
gttctcggag gaaaagagag gcatgcgaag caggccctac acatagatga tgcaaaaaaa 240
tcaatcacct tcaattttct tgaaggttat atgaatgaat tatacaagtc catgacacca 300
caatatagaa tcaataataa tctagaatgc cataagtctc gaaaccatcc aatgcaagtt 360
acaagtccta accatacgca aatctg 386

<210> SEQ ID NO 10
<211> LENGTH: 1622
<212> TYPE: DNA
<213> ORGANISM: Nicotiana tabacum

<400> SEQUENCE: 10
atgaaagcag aaggctcagc attatcatca gctggttctt atcatcgact tgcttatcat 60
gaagttatta atgatgataa tcaaaacaaa atttttacaa gtgatgactc tcgtctcaga 120
caattgggtt acaaacaaga actctatcgt ggcctttcgt tcattgcgaa cttctcattt 180
acattcgcca ttgtatcagt tcttacgggc atatccacat tgtataatca ggccttaact 240
tttggtgggc ctataactct tgtttacggt tggcccatag ttagcttaat gacacttatt 300
gtgggcctgg ccatggctga aatatgttca gcttatccaa cttcagctgg gctttactat 360
tggagtgcta aattgtctgg aaattacttc ggcccatttg cttcttggat tactggctgg 420
tttaacattg ttggtcagtg ggctgtcacg gcaagtatag atttttcctt ggcgcagtta 480
gttcaggtga tgattctcct tagcactggt ggattaaatg gaggtggata ccaagcctct 540
aaatacgttg ttatcgcact ccacggtgga attctgcttt tacatgctat attaaacagt 600
cttcctatct catggttgtc cttctttgga caactagccg ctgcatggaa tgttttaggt 660
gtctttcttc ttatgatttt gatcccaatg gtctcaacag aaagagccag cgctaaattt 720
gtgtttacta atttcaatac tgacaatggg gatggaatta acaataacct ctacatcttc 780
gtcctcggac ttcttatgag ccagtatacg ttgacaggtt atgacgcttc tgctcatatg 840
acagaagaaa cgaaaaatgc agataagaat gggccaaaag gaatagtaag tgctattggc 900
atatcagttc ttgctggctg ggcttatata cttggtataa ccttcgcagt tacagatatc 960
ccgcatctat tgaataaaaa caatgattct gggggttatg ctattgctca aatcttttac 1020
gatgcattca agaatagata cggcagtggt gttggtggaa tcatttgctt aggtgtaatt 1080
gctattgccg tattcttttg tggtatgagc tcactaacta gcaactcgag gatggcttat 1140
gcattctcca gagatggagc gatgccatat tcgtcgttct ggcataaagt aaacaagcaa 1200
gaggttccac taaatgcagt ctggatgtcg gcctttatag cattttgcat ggcattgacg 1260
tctcttggaa gcttggtagc atttcaagcc atgacatcga tagcaacaat tgggctctat 1320
attgcttatg ccttgccaat cctatttcga gtgactctag ctcgaaagtc tttcactcca 1380
ggtcctttta acttgggaag ctatgggctc gttgtaggtt gggttgcaat attttgggtt 1440
gcactcattt ctgtactctt ctctttgcct gttgcatacc ctattacaga tcaaactctc 1500
aactatactc ctgtcgcggt cggtggcctt ctcattcttg ttgtttcttc ttggatcttc 1560
agtgctatac attggtttaa aggtcctatt accaatttag gaaactctag tgaggaagca 1620
ta 1622

<210> SEQ ID NO 11
<211> LENGTH: 437
<212> TYPE: DNA
<213> ORGANISM: Nicotiana tabacum

<400> SEQUENCE: 11
atggcttcta ctcagcaagc ggtgagttct ggttctgatg cagaccagcg gtatgcaaag 60
tttgatgaac ggaaaaggaa gagaatggaa tccaaccgtg agtctgctcg taggtcacgg 120
atgaggaagc agcagcgatt gggggagttg atgagcgaaa caacacagct acagaaccag 180
aacagtatct gccgcgagag gattgattct gttgaaagaa attattgtgc catcgatgca 240
gagaacaatg tgttgagggc tcagattgct gaattgactg aacgtttgaa ttcactgaac 300
tcgctcactc aattttgggc tgatgctact ggatttcctg ttgacctccc tgaaattccc 360
gacactttgc ttgagccatg gcagctgcct tgccctattc aacctatcga tgcttcttct 420
gatatgttgc tgttttg 437

<210> SEQ ID NO 12
<211> LENGTH: 1965
<212> TYPE: DNA
<213> ORGANISM: Nicotiana tabacum

<400> SEQUENCE: 12
atgccggggg tctatttgga aacagcctct ctacccaagg gtaggggtct ggaatgtcaa 60
gaatcacaag ctgttaggta tttctttcga gggagaaata aagtcgatga ttcattgact 120
attgagattt tcaatctttt cccttggatt ttcttcacca tattggccat ggacaagcac 180
caccatcaac tacctctaac caagtctact tcgcgccagc gttataacga atgggtattt 240
cgagatgttc ctagtgatat aacaatagaa gtggatggtg gcatattttc actccacaag 300
tttccccttg tttcgagaag cggacgaatc cggaggctag tagcagagca cagagattct 360
gatatatcaa gaattgagct tgttagttta ccaggtggaa cagaatcatt cgagctagca 420
gccaaattct gttatggtgt caactttgag atcacagcag caaatgttgc tcagctttgt 480
tgcgtatccg attatctcga gatgtcagag gactactcga aaaacaatct cggttcaaga 540
gctgaagaat atcttgacag cattgtttgc aagaatcttg aaatgtgtgt tgaagtcttg 600
agacaatgtg aaaacttact tccacttgct gatgagctga aagttgttag ccggtgtatc 660
gatgctgtag catcgaaagc ttgtgtcgag caaatcgcct caagtttctc gcgattggag 720
tatagtatct caggtggaag actacatatg agtaaacaag ccaattgcga attggactgg 780
tggattgagg atatttcaat gcttcgtatc gacttgtacc aacgtgtcat aaccgcgatg 840
aagtttcgtg gggttaggcc tgagagtatt gctgcatcac tagtgaacta tgcacagaag 900
gaattgatac aaaagaccct ttctggttca aatatccaag aaaaactagt ggttgagacg 960
atcgtgagcc tgatgccagt tgaaaaattc gtcgtgccct tgacctttct ttttggattg 1020
ttgcgaagtg cagtgatgtt agattgcacg gttgcttgta ggcttgatct cgagaggcgg 1080
ataggatctc aattggatac ggctaccctg gacgatatac tgattccttc ctttcgacat 1140
gctggtgata cattgtttga tgttgacaca gtgcatcgaa tattggttaa cttttcacag 1200
caagagggcg atagcgatga tgatatggaa gatgtatcgg tttttgaatc cgatagccct 1260
actacgacgc catcacaaac tgcattgttc aaagtatcaa agttggttga caattaccta 1320
gctgaaattg cactagatgc aaatctaaag ctgaacaagt tcattgctgt tgcagaaaca 1380

```
ttaccagcac atgcgcgtac tgtccacgat ggactttatc gagcaatcga cctttacctc   1440

aaggctcatc aaactttatc agatccagac aagaggagac tatgcaaatt gattgatttc   1500

caaaagctct cacaggaagc tggtgcacag gctgcacaaa atgagcgcct tcccctccaa   1560

tcaatcgttc aagttcttta tttcgagcaa ttgaggctac gaaacgcctt gttttgttcg   1620

taccctgatg atgacattaa gccaacgcac cagtcttgga ggatcaatag tggtgctctt   1680

agtgctgcaa tgtctcccaa ggacaattat gcttcgttga gacgagaaaa tagagagcta   1740

aaacttgaac tagcgcggat gaggatgaga ttaaatgacc tggaaaaaga tcatgtttgt   1800

atgaagagga atatgcaaaa atctagctcg agacgattca tgaaatcctt ctccaaaagg   1860

attggcaaaa agttcaatat tttcggacat aatttttcca gggattgtag ttctccctca   1920

agtcagtcag aaagaactga atctaaaata actgaaagaa cttga                   1965
```

```
<210> SEQ ID NO 13
<211> LENGTH: 911
<212> TYPE: DNA
<213> ORGANISM: Nicotiana tabacum

<400> SEQUENCE: 13

atggagcatt ctgcagcaga tagggatcct aaagctgtag aatttgcaaa ggataagaat     60

ggagttggtc aagttttgct tcgaaatcca cgtggcgcct ctgttcgagt tagcctgcat    120

ggaggacagg ttctttcttg gaagaatgac catggtgaag aattactttt tataagcagt    180

aaggcaactt ttaagccgcc aacagctgtg agaggaggaa ttccaatttg ttttccacag    240

tttggaaacc ggggctccct cgagcaacat ggatttgcca gaaataggat gtggatcatt    300

gatgataatc ctcctcctct acaccctaat gattccaatg gcaaagcatt caccgattta    360

ctacttaaat catctgatga tgatcttaaa gtctggcctc atggttttga atttcggctg    420

agagtaactt tggctgttga tggatctctt accctgatat cacgcatcag aaatgtcaac    480

tgcaagccgt ttagtttctc cattgcatac catacatatt ttgctctctc agatatcagt    540

gaagtgagag tggaaggctt ggagactctt gactaccttg acaacttgtg caacagagaa    600

cgtttcactg agcaaggaga tgccttaaca tttgaaaccg aggtggatcg agtttatctt    660

agttcatcag atgtgatagc aatttttgat cacgagaaaa agcggacttt tgtgataaag    720

agggaagggc ttcctgatgt tgtggtttgg aatccatggg agaagaaatc taaaaccata    780

gcagattttg gagatgacga gtacagacat atgctttgtg tagacggagc agcaattgag    840

aaaccaatca ccttgaagcc aggtgaagaa tggactggaa ggttggaact gtccgtcatg    900

ccttcaagtt g                                                         911
```

```
<210> SEQ ID NO 14
<211> LENGTH: 1736
<212> TYPE: DNA
<213> ORGANISM: Nicotiana tabacum

<400> SEQUENCE: 14

atggaagtaa tgaagaagaa agaaaacacc tctagaaaaa tgaagggtgg aatgattacc     60

atgcccttca tatttgcaaa tgagatatgt gagaagttgg cagtggtggg atttggtgca    120

aatatgataa tatacttgac aaatgagctc catcttccat tgactaaagc agctaatact    180

cttacaaact ttggtggcac tgcaagtttg actccattac ttggagcttt cattgctgat    240

acctttgcag gaaggttttg gaccataaca attgcttcta tcatctacca aatcggtatg    300
```

```
atcattttaa cagtatcagc aatacttcct caactaaggc caccttcttg caaaggtgat    360
gaattttgca aagaagcaaa ttctggccaa ctagccattc tctatatatc attactccta    420
acagcatttg gatcaggagg aattaggcct tgtgttgtag catttggagc agaacaattt    480
gatgaaactg atccaaatca aaaaacacaa acatggaaat tcttcaattg gtattatttc    540
agtatgggat tttccatgct aatagctgtg acagtaattg tttatatcca agataatatt    600
ggatggggta taggatttgg agtcccaact attgctatgc ttatttcaat tattgttttc    660
atatttggat accctttata tagaaacttg gatcctgctg gtagtccttt tactaggcta    720
ttgcaagttt gtgttgctgc ttacaagaaa agaaaattgg acatggtttc tgatcctagt    780
ttcttgtacc aaaatgaaga gcttgattct gctatttcta ctgctggcaa gcttgttcac    840
actaagcaaa tgaagttctt ggacagagca gcaatagtga cagaggaaga caatcgaaaa    900
tctccgaatc tatggaggct aaacacagtt catcgcgtag aagagctaaa atcgatcata    960
agaatgggac caatatgggc atctggaata attctaatca cagcatatgc tcaacaacac   1020
acattctcag ttcaacaggc aaaaaacaatg gacagacact taataaattc cttcgaaatc  1080
ccagctgcat caatgacagt cttcacatta acagcaatgt tatgcaccat ttgcttctat   1140
gaccgcgtat ttgtgcctat agcacgtaaa ttcactggtc tagaacgagg catatcgttt   1200
cttagcagaa tggctattgg gttctctatt tcagttctag ccacattagt agctggattt   1260
atagaagtta aacgaaaaga agcagcctta actcatggac tgatcgataa aggtaaggcg   1320
attgttccca tttcagtatt ttggcttgtg cctcagtatt gtttacatgg tgtggtggca   1380
tttatgtcaa ttggacatct tgaatttttc tatgatcaag caccagagag tatgagaagt   1440
acagctactg cattattttg gacatcaatt tcagctggga attatttgag tacacttttg   1500
gtttcattag tgcataaatt tacttcagga tctggaggat caaattggtt acctgataat   1560
aatttgaata agggaaaatt agagtatttt tattggttaa tcacaattct acaagtggtt   1620
aacttgattt actatctgtt ttgtgcaaaa ttctatactt ttaagcctat tcaggtacac   1680
aagacagaag atttggactc taaaaaagat agtattgaac ttgtaaataa tgttta       1736
```

<210> SEQ ID NO 15
<211> LENGTH: 1553
<212> TYPE: DNA
<213> ORGANISM: Nicotiana tabacum

<400> SEQUENCE: 15

```
atggctttat caaacacctt atcattgtca tcatcaaaat cccttgttca atctcacctt     60
ctccacaatc cctccttacc ccagcctcgt attcccgttt ttcacaaccc ccaacatggg    120
cggcgccacc ccatctccgc cgtacacgcg gcggagcccg ccaaaacagc aactgcttca    180
cagccgttga aaaaaaccca atggagtctt gattcttgga aaagcaaaaa ggctttgcaa    240
ttacctgaat acccagatga aaaagaactt gaatctgtgc ttgaaactct tgaatctaat    300
cctccacttg tgtttgctgg tgaagctagg aatttagaag agagacttgg tgaagctgct    360
ttaggaaaag ctttttttatt acaaggtggt gattgtgctg agagttttaa ggaatttaat    420
gctaataata ttcgtgatac ttttaggatt cttcttcaga tgagtgttgt tcttatgttt    480
ggtggtcaag ttcctgtgat taaggttgga agaatggcgg gtcagtttgc gaaaccaaga    540
tcagatccgt ttgaggagat tgatggagtg aagctgccaa gttacaaggg tgataacatt    600
aatggcgata catttgatga gaagtcaaga attccagacc ctcataggct tattagggct    660
tacatgcaat ctgctgcgac tcttaacctt cttagggctt ttgctactgg aggttatgct    720
```

gcaatgcaga gggtcaccga atggaatctt gattttgtgg agaacagtga gcaaggagat 780
aggtatcaag aactagctca cagagtcgat gaagccttgg gattcatggc tgctgctgga 840
ctcacagtag accaccctat catggcaaca actgattttt ggacatctca cgagtgcttg 900
cttcttcctt atgaacaagc acttacaagg gaggattcaa cttctggtct tttctatgat 960
tgttccgctc acatgatttg ggttggggaa cgaaccaggc aacttgacgg tgctcatgtt 1020
gagttcttga gaggagtagc aaacccactt ggcataaagg tgagccaaaa gatggatcca 1080
aatgagctcg ttaaactcat tgacatcctg aacccaacca ataagcccgg aagaattact 1140
gtaattgtga gaatgggtgc tgagaatatg agagtgaagc tttgccactt gatcagggca 1200
gttcgaggag ctggacagat tgttacctgg gtttgtgacc cgatgcacgg caacaccata 1260
aaggcaccat gcggactcaa aacccgtgct ttcgattcaa tcctggctga ggtccgagct 1320
ttcttcgatg tgcatgagca agaagggagc caccctggtg gtatccatct agaaatgaca 1380
gggcaaaatg tgactgaatg cattggcgga tcacgaacag taacctacga cgatttgggc 1440
tctcgctacc acacacattg tgacccaaga ttgaacgctt ctcaatctct agaactttcc 1500
ttcatcgtag ctgaacgact aagaaaacga agaatggcct ctcaacgtct gta 1553

<210> SEQ ID NO 16
<211> LENGTH: 764
<212> TYPE: DNA
<213> ORGANISM: Nicotiana tabacum

<400> SEQUENCE: 16
atggcggctt catcaactct ttccagttcc atcaccacct tcaaactgtc tccgtgccaa 60
ccacgcgcct cctctactac cgcctccgtc aaaatccctt caattcctcc aataaccctt 120
tcaatccttt taatttctca ttttggccca actcccaaaa accctaccgt cgcaccactc 180
cgttgttccg ctacctccac cacaccagaa actaccacaa cgacttccac accattccac 240
gacctttgct acgtcgtcgg ggacaacatc gacaatgacc aaatcatccc tgcaaaatac 300
ctaaccctag tttcgtcaaa cccagacgag tacaaaaaac tcgggtccta cgcgctgtgc 360
ggactccctt tatcatacca aacccgtttc gtcgacccag atgaattctc atccaagtac 420
tccatcatca taggcggtga aaacttcggg tgcgggtcgt cgcgggagca cgcgccggtt 480
gctttaggag ctgcgggtgt ggcggagtcg tacgcgagga tattcttcag gaactcggtt 540
gcgactggcg aagtttatcc ccttgaatca gaagtgagga tttgtgagga gtgtaagacg 600
ggtgatgtgg tggctgttga actagcagag agtaggttga ttaatcatat gactgggaaa 660
gagtataaat tgaagtcaat tggtgatgtt ggtcctgtca ttgaagctgg tggcattttt 720
gcttatgcaa gaaaggctgg aatgattcct tcccgagaag ctta 764

<210> SEQ ID NO 17
<211> LENGTH: 2500
<212> TYPE: DNA
<213> ORGANISM: Nicotiana tabacum

<400> SEQUENCE: 17
tctgacatat ctatagcatt tcatttcact acaagtcact tcatgtcgtc accgtttaat 60
gtgcttaata tgtcgaaacc atgactagtg atatagacat tctcaaattt cttaaagagg 120
cataaggaac ttttgcatgg attgaaagag agcatatata atttatttct agcatccatt 180
gcctaaaatg agatgactct ctctccactt taatttccat acaatctcaa ggaagacatt 240

-continued

```
ggatagtaga tatataagct ccattttgtg aactcctgta agatcattgc ctcatgtgct    300
atattgcacg gactttccga aatgctgttg tattcatgtc agatcctcta aaaatatatt    360
acttttggag aatctgacac acatctagag acattttcgg aaaatctgag caatgtagct    420
ctagtgtgcc ggagaaagca taggtcaatt agtcttgcaa ttgactaatt gcaatctgct    480
aatagaagta tatatgtaag agtacatcga catggtaagc actaaactat cagataggct    540
atcttttttc atataccaa gtcttggtgc acaaactcgg tacttatgct ggtgagaagt    600
aatacctatc cagtgaaata gtcgaggtgc cggaaaatca gtctacgcac tacttagtta    660
aaaaagttct aaatcatcta aaaggagcag gagcttttgg gaaagaaaca ggtataaggc    720
aatgtgcaat ggtgactgtc gacaacatta attatgcaaa ggtgagaaat atcatctctt    780
tattgtaaat ataaagtgac acacacgagc agtatggaaa atctaataaa gttgatgctt    840
gtgcaacaaa ttcatttgga atttctttgg tgaattattc ttttggttgt caatgtgtaa    900
gtgtttagag tagacatgaa ttgataactg aagaaaagtt tgagtaactt gttggaccct    960
gccaaattat tgtgaatgtg taagtatttc cacaatgtca ctgatcatac tgttgcagat   1020
acacatacgg ccagaattca ataatagcaa taactaaaaa tttctaccaa actgaaaatg   1080
caaaattgag gcagataaaa tttgtaagat tgtggtatgg ggcgtgaagt tgttgactta   1140
tagccactgg tgcaattgat ttaagatagg accttatctc ttctcatcca ctaccttttt   1200
cgtttgcctt tcatttacct tgctccattc attttcttta tgtatatcca gatttttttaa   1260
tttgaatttg cagttcgttt aagtataact tcagcagctg ctgacacatg tcacgttagt   1320
tacctctttt atttgtggga tgtggcgagc agtgatctga taagggatat ttgaccttta   1380
tcgaacacat gacatgaaaa aaaaaaggtt aattgattta gttgaagata agtgaagctc   1440
taaaggcaat tgaaggaatt taaatttact aaaatccaaa aacacgatat taattatatg   1500
ttccgtgcat gcttaactca cgcgtactag agattttaat ccttctaatt ctattacgtt   1560
tattctaata cttgcattgg atttttacta gccaaaactc gacgcagatt gatctcctta   1620
ttctcactaa agataagagg agccaaaagt ggagtaagaa atctttacaa actaaagggg   1680
ttagatgaaa aggaagaatc caatacttcg gattcaacat gttaacaaaa gcaatttttt   1740
aaccgacttt gtcactacag ggaaaaaaaa tatttttaca ctattcaggc agtctaaatt   1800
ttcaacgaac ggaattcaat taaactctct acgtcacatg tacatctgtg atcagcaata   1860
attgttgagt tgatttggaa ttaagtaaat tagttctgat cactccggaa gtgaaactgc   1920
aaatgtgcaa taacacgaac aaaagactat gattccatgg tttcaacata gcccacaaac   1980
aagctaattg agattatggc gattaataga agatcattag gtttaatttg gcgaggcgaa   2040
tagccattgc atgtatagtc caaaccatga aaatgacaca acaaaccata cgacaaccta   2100
aaaaagaatg caaatatagg tggaacttga tattgaggat taaataactg ccccacaaga   2160
aaaaacaaca tgccccatat tcaaccataa cgatcactcg tatttaatta ttctctcctt   2220
taattcaaat aaaaaaaaat cttaggttct tggcttctta gccatatgct tttagttcca   2280
ggcaaaagta ctgcaacatt caatctccaa cgtacaaact ctcatctaca atggattgaa   2340
gctctcattt gcttagcaat cactttcaac tctgttataa tactgttata tgtaagagac   2400
ccgacccatg atcaagaccc attccacaac tatataatat atactagtga gtgaggagta   2460
ataaaagcaa gcaaaagcta aaaggaagtt cttgagccaa                          2500
```

<210> SEQ ID NO 18
<211> LENGTH: 1406

<212> TYPE: DNA
<213> ORGANISM: Nicotiana tabacum

<400> SEQUENCE: 18
ccttatagaa attgtctgct tctttcttct cgaaactcaa aaccccgatc gaaaaattag 60
tttttggggt tagaacatgg atgggattga gtttaaaaac gtaaagatca tagagcctag 120
agggaaaaga atctgatgtc atgtcgtaaa ggaaaaggaa agcaaataac agtgtccagc 180
ctcgaggcaa aggaagaaaa gatgccccgg aaacaggaag gctttaggct caaattaagc 240
acactcaatt cactcctctg tttaattaga atttccatgt ttcctccttc cgcggacacc 300
cccatcttag tttcttccac aacatttata attcaatgtc ctaaatttgg aagcgacata 360
ttgcattata cctctagtaa tcagttggat tagccgatta ggtaaacgta agagatacac 420
tatgtaagta tattcttcaa ggtatatgag aatatgttta cgtaacagaa tgatttaaat 480
gaactgatta ttgattctgt attatcatgc ttatgctttc gatgattaat tagccacatc 540
tagctaaact ttttcttcca tatctttttt tttttttttg tgatttacaa gaatagatcg 600
tgtcatttgt tttcttaaag tacctatgtc aacatcatgg atgacatgga ataacaagtg 660
catggaggtc gataagaaaa aaacaagcag ctccttggat ttttcgaagt ttggactttt 720
tagagcctca attttgctga aatatcgaaa tttggagacg tgagattcac ccagtcaccg 780
cttacgattt aatttatata cactgacaag tataaataaa ttataatatt ataaatttaa 840
tttgacagtt atatcatgtt atatgcttta tttttcgagt aactccttca acttattgtg 900
agcattacct atggttattt tgaatttaag gtattacatt gacgctttaa agttctatta 960
cacagtagtg tatagaagtt aaactcagac tgttttcacc ctttgttcac actccaattt 1020
tgaaaaactg attaacaagg actatccaac ttctatttaa gaagaaacta atccttgttt 1080
gatttaatca atcttgaatt tctgtgaacg gtacaaattc cgtgaccaaa ctggaccatc 1140
atctaaactc caactaacgc acggaataat atcaagcttt atgctttaga ttttgtattt 1200
tctaacataa agatcctaga gaaacagacc acataaaaga cattttacga cgtgcatgtc 1260
cagcagtggc tataaaaatg ataagaaatg tgcgctcaat agtcgttcca tgctctgttt 1320
atatatatgt accttctcat acattaaaca tcatatcata caaaagatca ctaaaacaga 1380
aggaaaaaag aaaagatctt cagaat 1406

<210> SEQ ID NO 19
<211> LENGTH: 2500
<212> TYPE: DNA
<213> ORGANISM: Nicotiana tabacum

<400> SEQUENCE: 19
gcgcaatatc caggacggtg gtcttgcacc gcatcccacc cgggagggat caactcgacg 60
tgatcgggaa ggccgtattt agccttaagc tctaataaat cagcctcctt cattgccgac 120
ttaaaggttt cgggttcgac ttcaggcaat tttgagaaat cggacctgga tcgtacgagg 180
aactatctct tccatcgtca ggaagcttct gtcctcaaca gcagtgggaa tgctctcagc 240
atgaggagga aaaactatcg ctagagggac cgggtcactt ccctcgctgg actcagaagg 300
tacattagac atgttttaaa cgaaagagag gaaggtatca aacaacggag gattaaaaac 360
gatgaggatc gctggaacaa agggaaaaga tgcacaacaa tggaaaagga agaagaagat 420
ataaggtttc gatgtaggaa gtctgtaaag tttgggatta caccctcata tccctattta 480
taggaattca ggcgccagaa ccaagaaatt ggctcatcat tacctagcat cggaattgaa 540
gtggcaggac caatcaggag ccccatgcaa aataaagcga cgcatcggga atacgcatca 600
tgatgatgca cgaggtcatg acgtcacctt gattcatgga caacacaact ccaaaatttg 660
cagctcacga agggccactt ttctagctcg cctcaatcat cacgagccga tcagctcgtc 720
taatcgtttt gaccgtaatg aacataattc gctcatcagg cccgcctgag gtcggcctca 780
ataagcggag gggctaactg tatgggtcaa aatctgtcct aaaatattta agataagata 840
atactaaaga aagaattctc gagccgtcgt tagtcgaggt ggactaggaa ggagcgaaac 900
ttatagtcga agaatcgacg agagccatgg tcgagatgtc aataatggtc gaagtcgagc 960
accgttgata aagctgtaac aactagtttt cgaaatagga tattaaagag aatattctag 1020
tggattctct gcacttgtac tattaaggtt tactaggaat atgtctcata taaatagaaa 1080
aagagacaat gatatgaggc atgtgatatt catttgtaac aagatacttt gacaaaaaag 1140
attctctctc tctctctctc tctcactaag atacaaacac caccttttca ctaagattct 1200
tgtctgtatt attccatact ttttcatcag atccgagaat aattcaagca ttcaaggatt 1260
tgtgtgtcac tcatcattgt caagaggaac aaccatcccg ttcatccttt attgggtgaa 1320
tcattcctcc tatttactta agtgtcattt attgttattc attgccatta aatgccacat 1380
tattattcat gatttttgga atagttattg catactgtta tcactattcg accaaatcta 1440
tgtgacttta tcacaccctt ggaagctacg tctagaaata ttattgttaa ctaattttaa 1500
cccataatca cataaatttg attatttgaa ccgagagtca tatttttggt caaacatata 1560
ctttattaat aagttatcat aatcgctttg tttttaaagg attgcacgcc gaaatttgtc 1620
gctaataatt gacatatcta aaacgttgtg tccccgttgc actcaaattc cgggtccgcc 1680
tctagaccta ctaacatttt taccactata gtgagtatct tgcatgtttc acgtacattt 1740
tgtgcatctg cacactcact aatctttctt aaaatatgtg acgacaaata cattctttct 1800
tagaagcttg aagacagcag gatttctctg agataaaatg aaactaaaga aaaagaaaaa 1860
gcaatgcttt gggcttaggc tcattcagaa tatagagtca gtaaattcaa aatgaatatg 1920
atcttaatac atttattatt ttaattattt tagaacatac gtaaacaata tatataataa 1980
gttcaattga actaagaaaa cttgtctctc tatttgtgta tgccaatatt gaacgagact 2040
accatcatga aataaaaaaa tccagtccac tcgtatgtcg tatgactatt taactctaat 2100
gcttcttttc atagatattc atatgattca tgtcgaaaat ataatgttcg atcggttgaa 2160
ttcttagctg acaatagcag acatttgaaa atgtatactc cccttagtta ttccaacttc 2220
caaaagtcac taaactctaa tagcatgaca ggaagcgtaa caatgccatg ccaaaatcca 2280
aattgcctag taggagtaaa aacaaaatga aatgggtcac cattcatcgg caattaggta 2340
accatatctc ttttgatatt tgagccacaa atatacgagt gatactcatt attttaatct 2400
catccacgtg gcaccatccc attaactgct tatctcaggc tgaaacctta gtatcttgca 2460
tattttcttc ttcctcagtg taaaacctta attcacaata 2500

<210> SEQ ID NO 20
<211> LENGTH: 2500
<212> TYPE: DNA
<213> ORGANISM: Nicotiana tabacum

<400> SEQUENCE: 20
gaacacatct aaacaacttg gaatcacctc aaatatcgca cagaagttgc aaatgacata 60
acaaacctat tttaactcct agaacaataa tccaaactcg ataacatcaa agtcaactcc 120
cgatcaaacc tatgaacttt tcaaaccttc aaattgccaa cttttaccaa ttatagccaa 180

```
aaccttctag aaatattcaa atgtaaatct gggcatacat ccaagtccaa aattgccata    240
cggacctacc agaaccatca aaactcagat ccatggtcaa atacataaaa gtcaaacttg    300
gtcaattctt ccgacttaaa actttctatc taagaatcat tctctcgaat caattccgaa    360
ccgcttaaaa actaaaatcg acgatatccg taggtcataa taaatcatac gaagctactc    420
gtgccctcaa accaccgaac gaagcacaaa tgctcaaaat cactacttgg gtcgttacat    480
ttttgagttg gtcacactat ttatttttgt acttgttgaa ttgatgaaac tatataggtt    540
atagcaagtt ttacttatat ttgttgcctc ttttacctcg ccgagggtag ttatgatact    600
tgctgagtac gttgggtcgg ttgtactgat actacactct gcacttaatt gtacaaatcc    660
aggtgtcaga cccagacatt agtagctgag gctagcagaa gagttgattg ctgagcgacg    720
aggtagaact gcattcttga tcgcagtctt ggcgtctctt ttcttaatta ctgttgtctt    780
tatttcagac agtattgtac ttggtcattt cagactttat ttccgtatta gagcttatga    840
ctctgtattt accagtttct acgggatata tcatgtatta gcggtatttt gctatattga    900
agttttagac atatgttatt tctataaatt atgttatttt ggttctttat tgttatgtcc    960
ggcttgccta gcaaatgtgt taggcgtcat catgactggt tgggattttg ggtcgtgaca   1020
catatcttct ctaaatgcta tcaccgtaat gtatacatgt cttttattca tatcttctct   1080
atatgttgct ttacatgatg aaataattca cggtatatat cttctctata tattaatctg   1140
tattacctga cttatttatc catgcatatc ttttctatat gcaactgttg actggttctt   1200
tgaactgtta gtttgtttac aatgcttgtg catgtcttgt ctatatatat cgatggcctt   1260
acttgtactt catgcttaga ttttgttatt gttcttgtgc acatgtacat tcatgaacat   1320
ttcaggtttc ataaaattag tatcttttga cttaaattct cattactact tcactgagat   1380
tagtcaagag atttactaag tacatgtggt tagttatact catactatac ttttgcacct   1440
tgcgtgcaga tttcagagtt gagctgctgt gatgatgaag gccagcattg aagaggtacc   1500
ggtgttctag atacaagttg tcacttgttc atggttgttt acgttttata ttatatttat   1560
gtaaatttta aatagatgct gtaatctctg ttcatattag agttgcactc gtaatcttgt   1620
tcttaatcgt tcatgacttg tactaccagt ccttgggata attatgtgaa ttttctcaat   1680
cttatttatt atttattgat aatctttcat tcgagttgtg ttatttgttg tttggcttac   1740
ctagcatacc atagttaggt gccagtactc gtaacatttg ttcttacttt ctagactttt   1800
agtgtatatt aaaaatattt atttttatgt actgctttgc attagtaaga ggatctttta   1860
ggtataatgc tctttcttac ttttaataac tatcgtcttg tattaataaa attttcttgc   1920
aaattttaaa agcaatgaca tattaatgga gaaattatac acaatataaa gatataatca   1980
atttaaaaaa gcaacatgta aaaagttgta gacgagataa gatgcctatt atttatattt   2040
ggtacatgaa tgtcattttc catgaaagtt tttcaaaacc aataatttgt atatgttagt   2100
tgaaatgtca cttttgtttt gttcaatcag aaccagtaat ttgtatttaa taatactaat   2160
gtcattttta tccgactcaa ttaactactc cctcttttac aacaaggaaa gaaaagcttg   2220
ttactctccc tataagtttt tcacgaaggc aatacaattg ttgcaacttc tttttcataa   2280
tcgtagtttt tcttcattga tcataatggg tggaaagagt tctccaacga tgttttgttt   2340
ggttctagcc ttcttacttt atgcatctat ttagtataat tttattatat ataaatgttc   2400
ggatttttct ctcactactt tctcccccctt acttcaaccc aactatcaaa agagattatt   2460
tttagatatc aaaataatta acacaaactt tattacaaat                          2500
```

<210> SEQ ID NO 21
<211> LENGTH: 2500
<212> TYPE: DNA
<213> ORGANISM: Nicotiana tabacum

<400> SEQUENCE: 21
caaaatactc tataatgaaa taaatgagga gaaagaaaga gaagagtgaa aagtcttgaa 60
ttggtgtgtt tactaatgag gagaaactcc tctatttata gcaagaaatc cttagcctaa 120
taatggatat tatgtcatgc aaatgtcatg atctacaaat ttgttataat ggatattatg 180
tcatggcaaa tgtcatggac caaaatttgt tataatggat attatgtcat ggcaaatgtc 240
atgaaccaca aatttgttat aatggtatta tatcatggca aatgtcatga aaatttggcc 300
atattacata ggatcacttt tcgaagacaa acacaattat atggataata caaatgatgt 360
aaattcatcg tgtttaaagc atattccatt tcggatgcct ccaaatctga aaatatgtaa 420
cgccaaatat tgtttatttt aaaaaatgcc aattatacaa ggctctatcc atgcaaagta 480
acttatccac acgtaaaagc aatacaacgt taattaggcc aagaattagc ataagttagt 540
gcaattttaa agttttgtac tcacctttta tgcctcaaat atctgtccaa ataaagtagt 600
aaaatttaac aaattgatat cacagagaaa caaagaaatt atttggaatc attctagtgt 660
actttcaaat attcactaaa tttatctcga agttatgcat aatttgcgca ccttgagcta 720
aaataattga tttgtttcta ttatatacgt ttatacatta ccagtgcttt ttgttttttt 780
ggtctacttg ttcggcacaa ttattacact taacaatgca ataataattg agaatacggt 840
aaagggccaa aattatccct agactattcg atttggtata aaattgtcct ccgttcatct 900
attgagtcaa aaatgtctat attgttattt tagtggctca ataatgcctt tattactaac 960
cgacttattt gaaaaaaata attaataaat atccacgtgt caccgtccat tggctaaata 1020
aaatacttac taaactttta aaaaagaatc accataacct aggttttgat tggcgccgca 1080
cgattataaa cctgtaatcc aaatctttta ttcttaatag acaatgtaac ttattcttct 1140
tcctctttta attaagttca gttctgcaaa tgggagaatt tatgtcacca caacaacaag 1200
aaaagtaaca atttaagcaa gaaaatgttg attttgggaa taaatgaagt gggtatggga 1260
ataaaatttc ggatcttgac ttaggaagta attcaattaa atgagagtaa attcattaat 1320
gaaaacaaat gggtatgaca tgggtgaaaa taattcatta tctcctcctc taattcgatt 1380
tcatggagat gggagaagaa agagggagtt ggcagctagg cgggtccttt ttggggccgg 1440
tccgatgaaa acccaggtta tggttttctt ctttttaaa aaaatataaa ttggtaagga 1500
tttatattta gaccaatggg acggtgatat gtggatatta attaattttt ttagataagt 1560
tcgttggtaa taaggacata attgaaccac taaataacgg taaggacatt tctagctcaa 1620
taggtagacg gggatatttt tgcaccaaat cgaatagtgt agggtagttt tgacccttct 1680
ccgtactaga agcaaggaga ttagtaacat agcaaaatta ttttgttaat accaaatcaa 1740
acaaagcgac caacatcaca gttgaggacc acggcgcctt agttcatcat attctatgat 1800
gataactgtt ttaatactaa taaataagta tgattataat tgtttaaaca ataaagaaaa 1860
ccaagaatat gtccagttac gttataatga taagactcta ccaaacaaca catgtcaact 1920
tcatcgctaa tttgaattgc tcatagctaa caaaattttt gataatttat cgtaaatcta 1980
taactaattt ggattagcga cgattttgtt cagctacaaa atttgtccgt agctaattcc 2040 tgtttttttag tagtaaaact agcctagtac aactttgttg gttgtgtgac ataaaaaata 2100
aaatttctcg tattcaacta attaatcaca ttccaaattc ttcataaata ctaaatagat 2160
tctctttttc cataactgaa gcaccaatta ctcgagaaaa gaaaattaaa gtaaatatgg 2220
gttccgaaac tatcaagctt cctaatatag acttctccaa tgtgacctaa agccaggcac 2280
acttgtatgg aaccaagtga aaagccaagt ccacaaagct ctagtaaact atggcgtttt 2340
gaagcatcat ttgataaaat cctatacacc ttcgaaaatc ctttttgaat ccttaaaaga 2400
gcttttcgat ctccctttac aaaccaaaat aagaaacatt tcaaccaaac ctttccatgg 2460
ctacgttgga cagtatccag cagttccact ctatgaaagt 2500

<210> SEQ ID NO 22
<211> LENGTH: 2500
<212> TYPE: DNA
<213> ORGANISM: Nicotiana tabacum

<400> SEQUENCE: 22
ttaaggatat gttttaaata attccttaaa aaaaatactc tgagcattat tggtacttta 60
agcttacaaa aaattatact tttatttttc atcaaatatt taacaaacgc tatttgtcga 120
aattgtgggg ggaaaaaaag aatttaacta gtaacgctag aaaagttcca taaaatttca 180
gaaactacag tgcaaaattg cactagacac aaaaaggtaa actaaaaata gcaaaacttg 240
catctcataa attgcaccaa attctagaaa atagaccaaa aatagaagaa ctgtaaaaat 300
tgtaccttta aatgtgagtt ctagctaaat tctttgtatt tcacagttcc ctcaaagacg 360
gagtttgttt actatttgac aatgaaagaa aatagtaaaa atagtacgat atagtcagtt 420
ttcggactgg tcattcaaaa atagtcagcg tttaccaagt caataaaaat agccactatt 480
ttgctgcaaa agagaccgat ccagcataat atactggagt tcggtgcacc tgtgtatgaa 540
ctccagcata ttatgctgga ccgatatact ttgctggctc cagtataata tactggagac 600
tggagcaccg gtgctccaaa ctccagtata ttatgatgga ccggtatact tgctggaact 660
ccagtatatt atgctggagt tctagtgtac ttatgttgga actccatcat attatgctgg 720
agttccggca tacttatctc ggaactccag tataatatgc tggagttcaa gtatacttat 780
gctggaactc cagcataata tactgacgta ttttccgggt tttgaacagt attttcgctc 840
agatttatct ttacatgaaa agtggctaaa tttcgattac ttttgaaact gggctatttt 900
tgaacgacca gttgtaaatc tggctatttt tgaatttctc ccaagaaaat atcctaactt 960
aaataacaaa aaatgctcga aaggtatatt tgaagtacta cttttttgaa cctattccaa 1020
acttacaagt aggggtgtac aaacggaacc ggaaaatcgc accaaactga aaagtcaaac 1080
caaaccgatt aaaagacccg actaggtttg gtttgatttg gtttggtatt gagtaaaaaa 1140
atcataacca aactgacata taaatatata atttttatat atacttttaa gattttatat 1200
aaaattttct ttaaagaata tctaaaatat ttgggattct cttgtgggat ataatattta 1260
atatgatcca taattattaa ccttaaataa tgggttatat gatcgcgttc tcatcaagtg 1320
ttactgaaat gcgtcaatct ctatgtccgt ccatattcat atcatatgtt aagatctatt 1380
atattcttat atctttttc gaatgtgaag tgataattag tattatttag gtatcatatt 1440
ggtttttata tttaattact aattcggtta accttgaaaa tatatatcaa caaaaaatta 1500
ttgtcaaacg aataaaaaaa ataactatta tgtgttacta agaaaattct cccttaaaaa 1560
tattttaata gataatttgt caattttttta tatttttact aaacatatat ttacttatca 1620
aaaatttaat aaagtaaaat taaaataata tttaattaac aaaaaacctg aaaaatcgaa 1680
aaaatccgac aaaacaaaat caatccaaac cgatagggtt gggttggtac acccctactt 1740

```
acaagctcat ctctattatt ttctcaagtt tgtattgaag gttcaaattt caaggattat   1800

aattataatg attgcaaaac gacaatctta atataggtga ttaattctga tatggacaaa   1860

attttgcgtc gtatccatga tcgaccaact accaataatt ttcaaatgct caagggtttc   1920

aagtgcgtgt ttatgttctg aaattgtagc tagttggata tattccatca aatcttgtaa   1980

agctaataat gtttcttgac ctttttaaat atactagtga tcctttcatg agatattgag   2040

atcagttttt tctatctgct tggaattgaa taatatagaa tataaacata tgatatattg   2100

ggggcaaata cggacataaa atttaaagtg agtcacttac tttatatgtt aaactatgtc   2160

aagattaatg accacaatcc gaagccgaag gaatataata cgaacgatga attttgttta   2220

cgattaggtg gaatgattga tattaaaaaa gaatgtaaaa gcaaataaga aaaggtgaat   2280

aatgcatatt aacaatctat attttatacg attaggtagg aagataatat gattgatatt   2340

taaacgtaaa tattttaaag tacgttgctg tctttgtgac ccctctggcc ataccattac   2400

ccattattta tattccctcg tatcaacatt cagtagcaag taaaaagaga taatttttgt   2460

tgattatttg ttgttgaact tgataaattt tgctgaaaaa                         2500
```

<210> SEQ ID NO 23
<211> LENGTH: 2500
<212> TYPE: DNA
<213> ORGANISM: Nicotiana tabacum

<400> SEQUENCE: 23

```
gagacgcata ttgtaagaag aagaaagagg ggataagata ggtgggtcga ggaccgggag     60

actgcatatg taagctttca atttcttta agtattataa tttactttta taaaatttta    120

aatactattt aatttaaaat aatatagggt cgctaccaaa gtaacgtgga ggaattcatc    180

gtagtcacca gctggtgaat cgggtgagcc aacccaacct tcggacgagg atgctgaaag    240

aatatggttg gagtctgttg gcggtccaaa atggggaagg tatacgggct tcctactaaa    300

aattccatcg ctataagtgt ggaatgcagg aatagggact tcctgcaggc gagaacttaa    360

tagggagagc ctctcgctat gcgggagaca gtacaaagct acatcgagct agaagcggcc    420

aaggaaagag aaaggcttag agatgctcaa ttccttggca tgcaagctca gatcagaact    480

ctcctatcta tggagctttt ccgttgcccg tctcgtgagt catcccaggg tcgactccac    540

gtgatcgttc ctcctccttg tgatcgttcc tccgtcctcc ccgtgatcgt ttcccgtcct    600

ccacaagaat tctctatacg tcttgtagat gaaagttcat cagatggtga tgatgttgta    660

gaaaataccc cttgaccaat actttgatat actttgaact agactaatag aactgttttg    720

aattagattg aacaattttg aacttgttgt aattagtttt tgcttggttt tggattgtga    780

ggttcaagtg aactttaatt tgttagtttt aaggtattaa ttggatgttt ggttgttgtt    840

gttggatatt tagttagatt tgtggtgaat taggggttgt atatggtgaa ttaggggtta    900

ttagatgtga attgggggta ttggtatgct gtttttattt gacaggtggt atagctacca    960

aaacaggcat tttctgccaa aattaaaccc agaaaaccga ccaacatttg tcagtaacta   1020

aaaaaaaaaa attaaattgc acattcacaa ccaatgttgg ttggttaatg tacaatgaat   1080

ttccagaaat tcaacattac cgaccgaatt tagtcggctt gttgcctgcc ctgtccagtt   1140

taccgaccaa ttttggtcgg tatttttaaa ttttaattat ttataaaaaa aatatatttt   1200

ccaataccga ccaaagttgg tcggtatttt taaattttaa ttatttataa aaataatata   1260

ttttccaata ctgaccaaag gcaaaattaa taaatttaat acaccgacca agtttggttg   1320

gtaaaattaa attaataaat aatattccga ctaattttga tcggtaagtc aattaaattg   1380
```

```
tcagatagtc gtgtagagca taccgaccaa cattggtcgg taatttccga gtaactttgg   1440
tcgctatgcc cttccgatct tcaaaatact gttcacacgt gaatgatcgc gttttgaacg   1500
gttattgacc tttaccgact tactttgatc gttttttgg acgatatttt tcgaatttct   1560
aatagtgact gtcatctatt tctttttgaa aaaagaaaaa aagaatcaaa cttgagcttg   1620
gaagcacggg ggaaataaca tggcgatttc ttttgtcata aaagaagaca acaaacaact   1680
cctcgaattc tgcttttaac tttttaagtt gacttcccaa atcccaacta ctcaggaaac   1740
agttgagctt gtttgcctag atctaacaca atatataatg catacgaccc cataacaaaa   1800
tctgtatttt cacgtttatt acactgaaaa aaaaaagata aaacattata tagcagacaa   1860
gataaaacct tctttgtcaa aacaaaatac aaaatatgta ctaagagaaa atcaccaaca   1920
tatcgttacg gattcacttg tttgataaag atgatcttct tttgtggata tttacataaa   1980
taattgatcg aatttattgt ttatacataa attatacact gattatataa gggtatataa   2040
ctattataca tccgtcgact agttcgtttc agcaattagt tgaacaacta cttaaattaa   2100
ttcttttttt aatataagta ttgaaattca attgtcttca ttcttttata acagtaaaat   2160
taatgctcat aattttgtga gccttacatt aattaaggac cgcgtagtcg taaaccaact   2220
ataaaatgaa tataataagc tgtaaattta tctacagcat ttttagttag cgtgcgtacg   2280
taaaaattca aatcgagaga caaacttata acttactaca acctaattat atacgaaatg   2340
aactaacact aaccttcgtc cccactaatt aaaaatcgtg gatcatgttt tatactagct   2400
ttgcatacag ctaattaaaa tctatataga ctacaacttt tgaacatttt ctcacaccac   2460
tttcttttca caacttttag ctactccgaa aaaagtaatt                         2500
```

<210> SEQ ID NO 24
<211> LENGTH: 2500
<212> TYPE: DNA
<213> ORGANISM: Nicotiana tabacum

<400> SEQUENCE: 24

```
ctgaccataa aagttttcta atgacactat tccaataact caagaccaga accaacttaa     60
attacattgt aattttacgg atgattattc aacttttact ttgttacatc gaagtcacta    120
aatttttgaa actttgctac tttcttcctc ctttattcga ggtagaagaa gacagtgcaa    180
tagttgactt attagacagc tttactcata tcacgagagc ttaaaggagc tttgtctaat    240
tccatgatct taatctgtcc atatgtcctt gtatttgatt ttcaagaaag gaattctttt    300
tatttcagag gcggatccag aattttaatt ttatggattc aggattatat tagagcctat    360
tttagtaata cagttagagt ctgcagtacc atttgaaaag tctcatttta aggcttttca    420
ctttgaaatt ccttatccca tttttcaagt ttttgcttct ggagccactc cttttctgag    480
cctgcaagtt caagtgagcg ttactgcagt tcaagaatga caaaaaaggg ttgtgataag    540
ctgcaatgga ttgaagtgaa cgtcaaataa ttaatgctgt gactattgca acttttgcag    600
cttctttagg ctttgtctga agtgaatgtc ttcattcgaa atgaatagac ttcagcaagc    660
tatgttgcta agattctccg aaaatgtcac gaggtccatg tcagatcctt caaaagtaat    720
gcatttttga aggatctgat acgggtgcgg caacattttg gagagtacgc gcaacatagc    780
cagccaacaa gtcgatactt acggtctaat agtttgaaga tctcctatcc aaccaagatt    840
attgaacatg tttcgattgc catttagctc aaatgacaaa atgaatgaat atttcctttt    900
taagtacacg tctctaatac atttatatag tcactccgga aaccctgtta catatattag    960
```

```
tatctacata taggttaatt ggaagccact gaaacaacct taatacttta aaagctaata   1020

aatctacaga aaagagctaa aactacccct aacctattcg cttaggttta aaaatatcct   1080

tcgtccacct attttgtaaa aattgcccct aacatcaact tttcggccca ctcataccct   1140

agaaactaac gaccccattt tgattaagat aattttttta ttacttatta tgtgtcaatt   1200

tcctaatggc ttaaattaaa acctcattcc acatcctatt agcccgctcc ataacccaaa   1260

atatccatac tcgacccatg accggctttt taaaatgcct taacttcacc tctcatcttc   1320

tcctctttca tccctaccct cccactctat attttctcta atcatcctcc tccatggcca   1380

aagtacaata actcgccatt ggtaactgag gactaccgtc ggcttcaact ttaagatctt   1440

cacccttcaa cacccacgga tcttcctctc ccactcagat tttcggcct taatttaatt    1500

tttaaattaa tatttttttg ttaaatcaat tttttgagtg aaatctggta ttctttggaa   1560

ttaaattaat ggttcattta aagattttat ggtttaataa gttatgtttc cgccaaagtt   1620

atatttttg taccaccatg tagctttttt ggagttcgac ggcggtgatt tggttaggaa    1680

actgttggcg gagattaagt tggaaagaa aaacagggaa agggataagg taccaaataa    1740

taaattaata aaaagaaaaa tatgaaattt tgatatatga aaccaaaata acgattggat   1800

catgagtccg gtatggaatc gggtgtttga ggggctaaaa agggattaac gagttggaac   1860

gactaagatg gattgcgagt ggcttattta cggatcagtt ctgggttaga gtgagatttt   1920

taattttgac caataagcaa ttgccacatc atatataacc aaaaaaattt tattcagcaa   1980

aggtccgtca gaaataaggg catgaatgag ccaaattttt aacgatgaag acagttttta   2040

caaaataggt ggacagatgg tatttttaaa cccaaacgaa taggttaggg gcagttttgg   2100

ccctttttg ataaatctaa tatcactcca gtaatgacaa agctagaatc tacatatatc    2160

tgtctttatt ttcaacatat agattcctta cacatcattg tcacaaatct tgcttaaatg   2220

gaatctcaga gttaaataga gatagatttc actcaattat cagatcataa ctaaactacc   2280

taaagatgga tttaggagga attatcttaa tcttcctttt cagtaccctc tgcctctatc   2340

tcctttggac aatcattaaa ctcctttatt taatatggtg gatgccactt caaatacaaa   2400

atagaatgag ttttcaggga atcaaaggcc ccccttatag ctttccccat gggaatacca   2460

aagaaatctc actaatgaga agccaaacta tggacaacct                         2500

<210> SEQ ID NO 25
<211> LENGTH: 318
<212> TYPE: PRT
<213> ORGANISM: Nicotiana tabacum

<400> SEQUENCE: 25

Met Cys Val Tyr Ser Asn Cys Asn Lys Lys Arg Gly Arg Gly Arg Glu
1               5                   10                  15

Arg Gly Val Val Ile Gln Gly Lys Thr Ala Val Gly Asn Asn Lys Thr
            20                  25                  30

Thr Asn Tyr Tyr Leu Tyr Phe Leu Ile Phe Ala Pro Ser Leu Thr Ser
        35                  40                  45

Thr Ala His Arg Phe Ser Asp Pro Lys Lys Val Ala Lys Met Asn Asp
    50                  55                  60

Ala Asp Val Ser Lys Gln Ile Gln Gln Met Val Arg Phe Ile Arg Gln
65                  70                  75                  80

Glu Ala Glu Glu Lys Ala Tyr Gly Phe Pro Ser Pro Pro Lys Lys Tyr
                85                  90                  95

Trp Pro Ile Ser Tyr Ser Ile Asp Gln Leu Ala Leu Val Arg Leu Ile
```

```
            100                 105                 110

Leu Ser Asn Asn Val Arg Ile Glu Glu Glu Phe Asn Ile Glu Lys Leu
        115                 120                 125

Gln Leu Val Glu Leu Glu Lys Lys Lys Ile Arg Gln Glu Tyr Glu Arg
    130                 135                 140

Lys Glu Lys Gln Val Asp Val Arg Lys Lys Ile Glu Tyr Ser Met Gln
145                 150                 155                 160

Leu Asn Ala Ser Arg Ile Lys Val Leu Gln Ala Gln Asp Asp Leu Val
                165                 170                 175

Asn Ser Met Lys Glu Ala Ala Ser Lys Glu Leu Leu Asn Val Ser His
            180                 185                 190

His Gln Asn His His Ile Tyr Lys Lys Leu Leu Gln Asp Leu Ile Val
        195                 200                 205

Gln Ser Leu Leu Arg Leu Lys Glu Pro Cys Val Leu Leu Arg Cys Arg
    210                 215                 220

Glu Asp Asp Val Ser Leu Val Glu Gly Val Leu Asp Ala Ala Lys Glu
225                 230                 235                 240

Glu Tyr Ala Glu Lys Ala Gln Val His Ser Pro Glu Val Ile Ile Asp
                245                 250                 255

Gln Ile Tyr Leu Pro Ser Ala Pro Ser His His Asn Ala His Gly Ser
            260                 265                 270

Ser Cys Tyr Gly Gly Val Val Leu Ala Ser Arg Asp Gly Lys Ile Val
        275                 280                 285

Cys Glu Asn Thr Leu Asp Ala Arg Leu Glu Val Val Phe Arg Lys Lys
    290                 295                 300

Leu Pro Glu Ile Arg Lys Cys Leu Phe Gly Gln Val Ala Ala
305                 310                 315


<210> SEQ ID NO 26
<211> LENGTH: 659
<212> TYPE: PRT
<213> ORGANISM: Nicotiana tabacum

<400> SEQUENCE: 26

Met Ile Thr Pro Lys Leu Ser Leu Leu Cys Ile Gln Asn Pro Gly Thr
1               5                   10                  15

Gln Thr Arg Ser Pro Ser Gly Tyr Ala Asn Glu Ser His Thr Thr Gly
            20                  25                  30

Ser Glu Asn Leu Thr Gln Leu Arg Leu Leu Leu Ser Gly Met Gly Lys
        35                  40                  45

Pro Arg Ile Met His Asn Ser Arg Glu Gly Asn Glu Val Ala His Leu
    50                  55                  60

Leu Ala Lys Lys Thr Ile Asn Gln Ser Asn Met Asp His Leu Val Tyr
65                  70                  75                  80

Leu Ala Ile Ser Pro Ser Leu Val Glu Thr Lys Val Leu Ser Asp Lys
                85                  90                  95

Asp Gly Glu Ser Ser Leu Lys Phe Val Val Asp Asp Ala Cys Arg Met
            100                 105                 110

Ser Asn Met Asp Phe Met Lys Val Phe Asp Gln Thr Val Arg Glu Ile
        115                 120                 125

Lys Arg Glu Val Asn Leu Lys Val Leu Lys Val Pro Glu Ile Glu Gln
    130                 135                 140

Lys Val Leu Asp Ala Thr Asp Asp Glu Pro Trp Gly Pro His Gly Thr
145                 150                 155                 160
```

```
Ala Leu Ala Glu Ile Ala Gln Ala Thr Lys Lys Phe Ser Glu Cys Gln
                165                 170                 175

Met Val Met Asn Val Leu Trp Thr Arg Leu Thr Glu Thr Gly Lys Asn
            180                 185                 190

Trp Arg Tyr Val Tyr Lys Ser Leu Ala Val Val Glu Tyr Leu Val Ala
        195                 200                 205

His Gly Ser Glu Arg Ala Val Asp Glu Ile Val Glu His Thr Tyr Gln
    210                 215                 220

Ile Ser Ser Leu Thr Ser Phe Glu Tyr Val Glu Pro Asn Gly Lys Asp
225                 230                 235                 240

Met Gly Ile Asn Val Arg Lys Lys Ala Glu Asn Ile Val Ala Leu Leu
                245                 250                 255

Asn Asn Lys Glu Lys Ile Glu Asp Ala Arg Asn Lys Ala Ala Ala Asn
            260                 265                 270

Arg Asp Lys Tyr Phe Gly Leu Ser Ser Ser Gly Val Thr Phe Lys Ser
        275                 280                 285

Ser Ser Ala Ser Leu Asn Ser Ser Ser Asn Phe Gln Ser Gly Asp Arg
    290                 295                 300

Tyr Gly Gly Phe Gly Asn Lys Ser Asp Gly Asp Ser Phe Lys Asp Ser
305                 310                 315                 320

Tyr Arg Glu Lys Asp Arg Tyr Gly Glu Asp Lys Phe Asp Gln Phe Lys
                325                 330                 335

Ser Lys Lys Gly Ser Ser Arg Tyr Gly Ser Asn Val Gln Asp Thr Val
            340                 345                 350

Ser Ser Ser Gly Ser Lys Thr Ser Lys Arg Val Gly Lys Pro Asp Lys
        355                 360                 365

Ala Thr Ser Asn Pro Pro His Ser Ala Ala Val Ser Ser Ser Lys Tyr
    370                 375                 380

Glu Glu Asp Phe Asp Asp Phe Asp Pro Arg Gly Thr Ser Ser Thr Lys
385                 390                 395                 400

Pro Ser Thr Glu Lys Ser Asp Gln Val Asp Leu Phe Gly Gln Asn Leu
                405                 410                 415

Ile Gly Asp Leu Leu Asp Val Pro Thr Pro Val Pro Ala Asp Asn Ser
            420                 425                 430

Thr Val Ser Ser His Pro Ser Glu Val Asp Leu Phe Ala Asp Ala Asn
        435                 440                 445

Phe Ala Leu Ala Lys Pro Gln Ser Glu Ile Ser Val Asp Leu Phe Ala
    450                 455                 460

Ser Gln Pro Ala Ser Ser Ser Ala Ala Pro Ser Thr Ile Asp Phe Phe
465                 470                 475                 480

Ser Ala Pro Asp Pro Val Val Gln Ser Asp Ile Arg Ser Pro Lys Ser
                485                 490                 495

Asp Lys Ile Asn Ala Thr Thr Val Asp Pro Phe Ala Ala Val Pro Leu
            500                 505                 510

Asn Thr Phe Asp Ser Ser Asp Pro Phe Gly Thr Phe Val Ser His Ala
        515                 520                 525

Asp Pro Val Ser Val Ala Ser Glu Asn Ala Asn Arg Gly Gly Asn Gln
    530                 535                 540

Glu Glu Thr Pro Ser Lys Leu Asp Lys Ser Ser Val Glu Ala Lys Pro
545                 550                 555                 560

Ala Pro Lys Lys Asp Asp Phe Gln Val Arg Ser Gly Ile Trp Ala Asp
                565                 570                 575

Ser Leu Ser Arg Gly Leu Ile Asp Leu Asn Ile Ser Ala Pro Lys Lys
```

580 585 590

Val Asn Leu Ala Asp Ile Gly Ile Val Gly Gly Leu Thr Asp Gly Ser
595 600 605

Asp Val Lys Glu Lys Gly Pro Thr Thr Phe Tyr Met Gly Arg Ala Met
610 615 620

Gly Gln Gly Thr Gly Leu Gly Gln Ser Gly Phe Thr Ser Thr Ser Thr
625 630 635 640

Gly Gly Asp Asp Phe Phe Ser Ser His Gln Asn Tyr Gln Phe Gly Ser
645 650 655

Phe Gln Lys

<210> SEQ ID NO 27
<211> LENGTH: 284
<212> TYPE: PRT
<213> ORGANISM: Nicotiana tabacum

<400> SEQUENCE: 27

Met Ala Met Asp Asp Asn Phe His Arg Gln Arg Leu Gly Ala His Ala
1 5 10 15

Pro Pro Gly Tyr Phe Val Arg Leu Glu Asn Gly Arg Ala Lys Asp Asp
20 25 30

Leu Tyr Leu Arg Lys Gly Gly Arg Met Arg Lys Trp Leu Cys Cys Thr
35 40 45

Cys Gln Val Glu Glu Ser Asp Pro Ser His Glu Asn Glu Leu His Lys
50 55 60

Ser Pro Lys Asn Asn Phe Asp Gly Tyr Gln Lys Gly Ser Lys Ala Ser
65 70 75 80

Val Pro Ala Lys Ala Glu Val Gln Lys Ala Ile Pro Thr Ile Glu Val
85 90 95

Pro Ala Leu Ser Leu Asp Glu Leu Lys Glu Glu Thr Asp Asn Phe Gly
100 105 110

Ser Lys Ala Leu Ile Gly Glu Gly Ser Tyr Gly Arg Val Tyr Tyr Ala
115 120 125

Asn Leu Asn Asn Gly Lys Ala Val Ala Val Lys Lys Leu Asp Val Ser
130 135 140

Ser Glu Pro Glu Thr Asn Val Asp Phe Leu Ser Gln Val Ser Met Val
145 150 155 160

Ser Arg Leu Lys His Val Asn Leu Val Asp Leu Leu Gly Tyr Cys Val
165 170 175

Glu Gly Asn Leu Arg Val Leu Ala Tyr Glu Lys Gly Val Gln Gly Ala
180 185 190

Gln Pro Gly Pro Thr Leu Asp Trp Met Gln Arg Val Lys Ile Ala Val
195 200 205

Asp Ala Ala Arg Gly Leu Glu Tyr Leu His Glu Lys Val Gln Pro Pro
210 215 220

Ile Ile His Arg Asp Ile Arg Ser Ser Asn Val Leu Leu Phe Glu Asp
225 230 235 240

Tyr Lys Ala Lys Leu Leu Ile Leu Ile Cys Gln Ile Ser Leu Leu Thr
245 250 255

Trp Leu Leu Ala Phe Ile Leu His Glu Phe Trp Glu His Leu Val Ile
260 265 270

Met His Gln Ser Asn Val Leu His Leu Thr Leu Leu
275 280

<210> SEQ ID NO 28
<211> LENGTH: 485
<212> TYPE: PRT
<213> ORGANISM: Nicotiana tabacum

<400> SEQUENCE: 28

```
Met Pro Pro Pro Pro Ser Thr Ile Ser Asp Asp Asp Ser Ser Tyr Phe
1               5                   10                  15

His Val Ser Thr Leu Leu Pro Leu Tyr Arg Ala Arg Leu Arg Lys Lys
            20                  25                  30

Leu Asn Leu Arg Arg Leu Arg Asn Gly Thr Cys Arg Ala Glu Phe Ala
        35                  40                  45

Asn Asp Ala Pro Ile Ala Val Ala Ile Gly Ala Cys Ile Phe Ser Ser
    50                  55                  60

Leu Val Phe Pro Thr Thr Tyr Thr Glu Asp Asp Asp Gly Asp Ser Val
65                  70                  75                  80

Ile Asp Ser Ala Asp Ala Arg Phe Ala Val Met Gly Ile Ile Ser Phe
                85                  90                  95

Ile Pro Tyr Phe Asn Trp Met Ser Trp Val Phe Ala Trp Leu Asp Thr
            100                 105                 110

Gly Lys Gln Arg Tyr Ala Val Tyr Ala Leu Val Tyr Leu Ala Pro Tyr
        115                 120                 125

Leu Arg Thr Asn Leu Ser Leu Ser Pro Glu Asp Ser Trp Leu Pro Ile
    130                 135                 140

Ala Ser Ile Leu Leu Cys Ile Phe His Ile Gln Leu Glu Val Ser Ile
145                 150                 155                 160

Lys Asn Gly Asp Phe Gln Ala Leu Asn Lys Phe Thr Gly Thr Gly Glu
                165                 170                 175

Glu Leu Ser Ser Val Ser Arg Lys Lys Asp Asp Ser Ile Ser Glu Glu
            180                 185                 190

Asp Met Ile Ala Gly Asp Val Val Asn Pro Asp His Ile Asp Val Gly
        195                 200                 205

Phe Asp Ser Ile Gly Gly Leu Gly Gly Ile Lys Asp Thr Leu Phe Gln
    210                 215                 220

Leu Ala Ile Leu Pro Leu Arg Arg Pro Glu Leu Phe Cys His Gly Lys
225                 230                 235                 240

Leu Leu Gly Pro Met Lys Gly Val Leu Leu Tyr Gly Pro Pro Gly Thr
                245                 250                 255

Gly Lys Thr Met Leu Ala Lys Ala Ile Ala Lys Glu Ser Gly Ala Val
            260                 265                 270

Phe Ile Asn Val Lys Val Ser Thr Leu Met Ser Lys Trp Phe Gly Asp
        275                 280                 285

Ala Gln Lys Leu Val Ala Ala Ile Phe Gly Leu Ala Tyr Lys Leu Gln
    290                 295                 300

Pro Ala Ile Ile Phe Ile Asp Glu Val Asp Ser Phe Leu Gly Gln Arg
305                 310                 315                 320

Arg Ala Ser Glu Thr Glu Met Leu Thr Ser Met Lys Thr Glu Phe Met
                325                 330                 335

Ala Leu Trp Asp Gly Phe Thr Thr Asp Gln Asn Ala Arg Val Met Val
            340                 345                 350

Leu Ala Ala Thr Asn Arg Pro Thr Asp Leu Asp Glu Ala Ile Leu Arg
        355                 360                 365

Arg Phe Ser Gln Ser Phe Glu Ile Gly Lys Pro Ser Leu Ser Asp Arg
    370                 375                 380
```

Thr Lys Ile Phe Lys Val Val Leu Lys Gly Glu Arg Ile Glu Asp Asn
385 390 395 400

Val Asp Phe Asp Arg Leu Ala Gly Leu Cys Glu Gly Tyr Thr Gly Ser
405 410 415

Asp Ile Leu Glu Ala Cys Lys Leu Ala Ala Phe Ile Pro Leu Arg Glu
420 425 430

Tyr Leu Gln Asp Glu Lys Lys Gly Lys Gln Ser Gln Ala Pro Arg Pro
435 440 445

Leu Ser Gln Ser Asp Leu Glu Thr Ala Leu Ala Gln Ser Lys Lys Thr
450 455 460

Lys Ile Thr Ala Arg Lys Pro Ala Val Val Ser Phe Arg Leu Asp Asp
465 470 475 480

Tyr Glu Asp Leu Asp
485

<210> SEQ ID NO 29
<211> LENGTH: 444
<212> TYPE: PRT
<213> ORGANISM: Nicotiana tabacum

<400> SEQUENCE: 29

Met Ser Ser His Asp Ile Arg Arg Pro Phe Lys Arg Pro Ala Ile Ser
1 5 10 15

Asp Gln Gln Arg Arg Arg Glu Leu Ser Leu Leu Arg Gln Cys Gln Asn
20 25 30

Arg Arg Asp Ala Gln Leu Gln Ala Arg Arg Leu Ala Ser Thr Val Leu
35 40 45

Ser Leu Gln Pro Thr Gln Asp Asp Asp Tyr Lys Ser Ala Ser Glu Glu
50 55 60

Gln Gln Leu Asp Ile Glu Val Ala Ser Val Pro Glu Val Asp Ser Phe
65 70 75 80

Pro Asp Glu Thr Asp Ala Asp Phe Gly His Pro Arg Asp Ala His Asp
85 90 95

Ile Arg Gln Ala Thr Lys Leu Arg Gly Pro Glu Ala Arg Gln Trp Phe
100 105 110

Ala Lys Gln Leu Met Leu Pro Glu Trp Met Ile Asp Val Pro Asp Asn
115 120 125

Leu Asn Thr Asp Trp Tyr Val Phe Ala Arg Pro Ala Gly Lys Arg Cys
130 135 140

Phe Val Val Ser Ser Asn Gly Thr Thr Ile Ser Arg Leu Arg Asn Gly
145 150 155 160

Ile Arg Leu His Arg Phe Pro Ser Ala Leu Pro Asn Gly Ala Arg Ile
165 170 175

Asn Asn Ser Lys Ser Ala Gln Ser Tyr Cys Ile Leu Asp Cys Ile Phe
180 185 190

His Glu Ser Asp Glu Thr Tyr Tyr Val Ile Asp Gly Val Cys Trp Ala
195 200 205

Gly Leu Ser Leu Tyr Glu Cys Thr Ala Glu Phe Arg Phe Phe Trp Leu
210 215 220

Asn Ser Lys Leu Ala Glu Thr Gly Ala Cys Asp Ala Pro Ser Thr Tyr
225 230 235 240

His Arg Tyr Lys Phe Ser Thr Leu Pro Val Tyr Asn Cys Asp Lys Glu
245 250 255

Gly Leu His Thr Ala Tyr Val Gly Gln Val Pro Tyr Val Lys Asp Gly
260 265 270

Leu Leu Phe Tyr Asn Lys His Ala His Tyr Gln Thr Gly Asn Thr Pro
275 280 285

Leu Thr Leu Val Trp Lys Asp Glu Asn Cys Ser Gln Tyr Val Ile Asp
290 295 300

Thr Asp Asn Arg Gly Gln Val Pro Ser Gln Gln Gln Val Val Leu Glu
305 310 315 320

Leu Leu Asp Asp Ser Arg Leu Ala Thr Ser Asp Asp Pro Pro Val Ile
325 330 335

Phe Gly Cys Leu Leu Gly Glu Phe Ile Gln Lys Thr Glu Leu Gln Arg
340 345 350

Gly Asp Leu Ile Lys Phe Ala Ile Gly Glu Gly Gly Leu Val Phe Val
355 360 365

Asp Ser Lys Leu Glu Lys Ala Asp Leu Gln Tyr Leu Gly Lys Ser Asn
370 375 380

Arg Ala Arg Ala Phe Ala Asp Ser Tyr Ser Lys Val Leu Phe Gln Tyr
385 390 395 400

Ala Ala Arg His Ser Pro Leu Arg Ile Glu His Leu Phe Ala Ser Ile
405 410 415

Ser Ser Cys Val Glu Asp Gly Arg Ser Asn Ser Arg Cys Arg Tyr Gly
420 425 430

Trp Leu Lys Cys His Ala Arg Glu Thr Phe Phe Asn
435 440

<210> SEQ ID NO 30
<211> LENGTH: 829
<212> TYPE: PRT
<213> ORGANISM: Nicotiana tabacum

<400> SEQUENCE: 30

Met Ala Gln Pro Leu Leu Lys Lys Asp Asp Asp Arg Asp Asp Glu Ala
1 5 10 15

Glu Tyr Ser Pro Phe Met Gly Ile Glu Lys Gly Ala Val Leu Gln Glu
20 25 30

Ala Arg Val Phe Asn Asp Pro Gln Leu Asp Ala Arg Arg Cys Ser Gln
35 40 45

Val Ile Thr Lys Leu Leu Tyr Leu Leu Asn Gln Gly Glu Thr Phe Thr
50 55 60

Lys Val Glu Ala Thr Glu Val Phe Phe Ala Val Thr Lys Leu Phe Gln
65 70 75 80

Ser Lys Asp Leu Gly Leu Arg Arg Met Val Tyr Leu Met Ile Lys Glu
85 90 95

Leu Ser Pro Ser Ala Asp Glu Val Ile Ile Val Thr Ser Ser Leu Met
100 105 110

Lys Asp Met Asn Ser Ser Thr Asp Met Tyr Arg Ala Asn Ala Ile Arg
115 120 125

Val Leu Cys Arg Ile Thr Asp Gly Thr Leu Leu Thr Gln Ile Glu Arg
130 135 140

Tyr Leu Lys Gln Ala Ile Val Asp Lys Asn Pro Val Val Ala Ser Ala
145 150 155 160

Ala Leu Val Ser Gly Ile His Leu Leu Gln Thr Asn Pro Glu Ile Val
165 170 175

Lys Arg Trp Ser Asn Glu Val Gln Glu Ala Val Gln Ser Arg Ala Ala
180 185 190

Leu Val Gln Phe His Ala Leu Ala Leu Leu His Gln Ile Arg Gln Asn

```
        195                 200                 205

Asp Arg Leu Ala Val Ser Lys Leu Val Thr Ser Leu Thr Arg Gly Thr
    210                 215                 220

Val Arg Ser Pro Leu Ala Gln Cys Leu Leu Ile Arg Tyr Thr Ser Gln
225                 230                 235                 240

Val Ile Arg Glu Ala Ala Met Ser Asn Gln Thr Gly Asp Arg Pro Phe
                245                 250                 255

Tyr Asp Tyr Leu Glu Gly Cys Leu Arg His Lys Ala Glu Met Val Ile
            260                 265                 270

Phe Glu Ala Ala Arg Ala Ile Thr Glu Leu Ser Gly Val Thr Ser Arg
        275                 280                 285

Glu Leu Thr Pro Ala Ile Thr Val Leu Gln Leu Phe Leu Ser Ser Ser
    290                 295                 300

Lys Pro Val Leu Arg Phe Ala Ala Val Arg Thr Leu Asn Lys Val Ala
305                 310                 315                 320

Met Thr His Pro Met Ala Val Thr Asn Cys Asn Ile Asp Met Glu Ser
                325                 330                 335

Leu Ile Ser Asp Gln Asn Arg Ser Ile Ala Thr Leu Ala Ile Thr Thr
            340                 345                 350

Leu Leu Lys Thr Gly Asn Glu Ser Ser Val Asp Arg Leu Met Lys Gln
        355                 360                 365

Ile Thr Asn Phe Met Ser Asp Ile Gly Asp Glu Phe Lys Ile Val Val
    370                 375                 380

Val Glu Ala Ile Arg Ser Leu Cys Leu Lys Phe Pro Leu Lys Tyr Arg
385                 390                 395                 400

Ser Leu Met Asn Phe Leu Ser Asn Ile Leu Arg Glu Glu Gly Gly Phe
                405                 410                 415

Glu Tyr Lys Lys Ala Ile Val Asp Ser Ile Val Ile Leu Ile Arg Asp
            420                 425                 430

Ile Pro Asp Ala Lys Glu Ser Gly Leu Leu His Leu Cys Glu Phe Ile
        435                 440                 445

Glu Asp Cys Glu Phe Thr Tyr Leu Ser Thr Gln Ile Leu His Phe Leu
    450                 455                 460

Gly Asn Glu Gly Pro Lys Thr Ser Asp Pro Ser Lys Tyr Ile Arg Tyr
465                 470                 475                 480

Ile Tyr Asn Arg Val Ile Leu Glu Asn Ala Thr Val Arg Ala Ser Ala
                485                 490                 495

Val Ser Thr Leu Ala Lys Phe Gly Ala Leu Val Asp Ser Leu Lys Pro
            500                 505                 510

Arg Ile Phe Val Leu Leu Lys Arg Cys Leu Phe Asp Gly Asp Asp Glu
        515                 520                 525

Val Arg Asp Arg Ala Thr Leu Tyr Leu Asn Thr Leu Gly Gly Asp Gly
    530                 535                 540

Ala Val Val Glu Thr Asp Asp Glu Val Lys Glu Phe Leu Phe Gly Ser
545                 550                 555                 560

Leu Gly Val Pro Leu Thr Asn Leu Glu Thr Ser Leu Lys Asn Tyr Glu
                565                 570                 575

Pro Ser Glu Glu Ala Phe Asp Ile Phe Ser Val Pro Lys Glu Val Lys
            580                 585                 590

Ser Gln Pro Leu Ala Glu Lys Lys Ala Pro Gly Lys Lys Pro Thr Gly
        595                 600                 605

Leu Gly Ala Pro Pro Val Gly Pro Thr Ser Thr Val Asp Ser Tyr Glu
    610                 615                 620
```

Arg Leu Leu Ser Ser Ile Pro Glu Phe Ala Ser Tyr Gly Lys Leu Phe
625 630 635 640

Lys Ser Ser Ala Pro Val Glu Leu Thr Glu Ala Glu Thr Glu Tyr Ala
645 650 655

Val Asn Val Val Lys His Ile Phe Asp Ser His Val Val Phe Gln Tyr
660 665 670

Asn Cys Thr Asn Thr Ile Pro Glu Gln Leu Leu Glu Asn Gly Arg His
675 680 685

Leu Trp Leu Leu Arg Lys Pro Glu Gly Val Pro Ala Val Gly Lys Phe
690 695 700

Ser Asn Thr Leu Arg Phe Ile Val Lys Glu Val Asp Pro Thr Thr Gly
705 710 715 720

Glu Ala Glu Asp Asp Gly Val Glu Asp Glu Tyr Gln Leu Glu Asp Leu
725 730 735

Glu Val Val Thr Ala Asp Tyr Met Leu Lys Leu Gly Val Ser Asn Phe
740 745 750

Arg Asn Ala Trp Glu Ser Leu Gly Pro Asp Cys Glu Arg Gly Thr Glu
755 760 765

Val Val Pro Ser Asn Ser Arg Ser His Thr Cys Leu Leu Ser Gly Val
770 775 780

Tyr Ile Gly Ser Val Lys Val Leu Val Arg Leu Ser Phe Gly Leu Asp
785 790 795 800

Gly Ala Lys Glu Val Ala Met Lys Leu Ala Val Arg Ser Glu Asp Ile
805 810 815

Ser Val Ser Asp Ala Ile His Glu Val Val Ala Ser Gly
820 825

<210> SEQ ID NO 31
<211> LENGTH: 566
<212> TYPE: PRT
<213> ORGANISM: Nicotiana tabacum

<400> SEQUENCE: 31

Met Lys Met Arg Gly Tyr Ser Phe Phe Thr Ala Thr Leu Ile Leu Val
1 5 10 15

Ala Val Ser Ile Phe Leu Ser Ser Ile His Thr Asp Ala Leu Pro Arg
20 25 30

Asp Thr Phe Lys Ser Ile Leu Gly Glu Gly Asn Leu Glu Ser Trp Lys
35 40 45

Asn Gly Val Leu Asp Ser Ala Gly Met Ala Gln Ala Pro Gly Pro Ala
50 55 60

Asp Gly His Val Gly Thr Leu Val Leu Ala Gly Asn Arg Thr Arg Arg
65 70 75 80

Pro Asp Phe Leu Ser Gly Phe His Lys Tyr Arg Gly Gly Trp Asp Ile
85 90 95

Ala Asn Lys His Tyr Trp Ala Ser Val Gly Phe Thr Gly Leu Ala Gly
100 105 110

Ile Ile Leu Ala Leu Leu Trp Phe Ile Ser Phe Gly Leu Ala Leu Val
115 120 125

Val His Tyr Cys Cys Gly Trp Lys Phe Asn Ile Arg Gly Arg Glu Trp
130 135 140

His Phe Ser Gln Asn Ile Cys Leu Gly Val Leu Ile Val Leu Thr Cys
145 150 155 160

Ala Ala Ala Ile Gly Cys Val Leu Leu Ser Val Gly Gln Asp Asp Phe

```
                165                 170                 175

His Ala Glu Ala Leu Asp Thr Leu Lys Tyr Val Val Asn Gln Ser Asp
            180                 185                 190

Tyr Thr Val Gln Thr Leu Arg Asn Val Thr Gln Tyr Leu Leu Leu Ala
        195                 200                 205

Lys Thr Val Asn Val Ala Gln Ile Phe Leu Pro Ser Asp Val Lys Asp
    210                 215                 220

Asp Ile Asp His Leu Asn Gly Asp Leu Asp Ser Ala Ala Asp Lys Leu
225                 230                 235                 240

Glu Asp Lys Thr Asn Glu Asn Ser Gly Lys Ile Arg Arg Val Phe Asn
                245                 250                 255

Ala Val Arg Ser Ala Leu Ile Thr Ile Ala Ile Val Met Leu Leu Ile
            260                 265                 270

Ser Ile Leu Gly Leu Cys Leu Ser Ile Leu Gly His Gln His Ala Ile
        275                 280                 285

His Ile Phe Ile Ile Ser Gly Trp Leu Leu Val Ala Val Thr Phe Val
    290                 295                 300

Leu Tyr Gly Val Phe Val Ile Ile Asn Ser Ala Ile Ser Asp Thr Cys
305                 310                 315                 320

Met Ala Met Gly Glu Trp Val Asp Asn Pro His Ala Glu Ser Ala Leu
                325                 330                 335

Ser Asn Ile Leu Pro Cys Val Asp Pro Arg Thr Thr Asn Arg Thr Leu
            340                 345                 350

Phe Lys Ser Lys Gln Val Thr Val Asp Leu Val Asn Ile Val Asn Gly
        355                 360                 365

Phe Ile Asp Thr Tyr Ala Asn Ser Asn Pro Ser Asn His Ala Asn Ser
    370                 375                 380

Asn Tyr Tyr Asn Gln Ser Gly Pro Val Met Pro His Leu Cys Tyr Pro
385                 390                 395                 400

Tyr Asp Ser Gln Leu Gln Asp Leu Pro Cys Pro Ala Asp Gln Val Ser
                405                 410                 415

Met Ala Asn Ser Ser Met Val Trp Gln Asn Phe Thr Cys Asn Val Ser
            420                 425                 430

Ala Ala Ala Ile Cys Thr Ser Val Gly Arg Leu Thr Pro Asp Met Tyr
        435                 440                 445

Gly Gln Leu Val Ala Thr Val Asn Ile Ser Tyr Ala Leu Glu His Tyr
    450                 455                 460

Ala Pro Pro Leu Leu Asn Leu Gln Asn Cys Asp Phe Val Arg Asp Thr
465                 470                 475                 480

Phe Arg Asn Ile Thr Val Asn His Cys Pro Pro Leu Glu His His Leu
                485                 490                 495

Arg Val Val Asn Ala Gly Leu Ala Val Ile Ser Val Gly Val Met Leu
            500                 505                 510

Ser Leu Ala Leu Trp Ile Val Tyr Ala Asn Arg Pro Gln Arg Glu Glu
        515                 520                 525

Val Phe Ala Lys Leu Ser Ser Arg Ile Lys Ser Ser Cys Asn Gly Lys
    530                 535                 540

Asn Ile Ser Cys Ser Asn Ser Asn Ile Asp Leu Ser Ser Arg Gly Thr
545                 550                 555                 560

Thr Pro Lys Thr Gly Val
                565
```

<210> SEQ ID NO 32

<211> LENGTH: 280
<212> TYPE: PRT
<213> ORGANISM: Nicotiana tabacum

<400> SEQUENCE: 32

Met Leu Asp Ala Ser Ala Val Ala Tyr Ile Gln Ile Ala Ser Ile Ala
1 5 10 15

Ile Ala Asp Gln Val Ala Arg Gly Gln Ile Glu Leu Ala Lys Asn Val
20 25 30

Arg Gln Arg Leu Thr Ser Pro Ser Val Ala Ala Pro Pro Leu Ser Thr
35 40 45

Gly Lys Gln Lys Gly Gly Ser Ser Ser Cys Cys Lys Leu Ala Ala Ser
50 55 60

Thr Ser Ser Ala Gln Met Leu Thr Ser Val Leu Ser Ser Leu Val Ala
65 70 75 80

Glu Glu Ala Ala Ser Leu Ser Ser Gly Leu Lys Ser Ala Gly Phe Ser
85 90 95

Ser Ser Leu Pro Phe Ala Ser Pro Glu Lys Arg Leu Lys Leu Asp Lys
100 105 110

Pro Met Thr Phe Ser Asp Met Asn Ser Ser Glu Gly Gly Asn Ser Thr
115 120 125

Tyr Phe Thr Ser Ser Gln Gln Pro Ile Thr Ser Ile Pro Leu Ala Pro
130 135 140

Ser Ser Gly Leu Gln Ser Ser Asn Gln Ile Gln Ala Pro Phe Pro Pro
145 150 155 160

Pro Pro Pro Pro Pro Pro Pro Leu Pro Pro Ala Asn Ser Pro Gly Ser
165 170 175

Gln Leu Gly Gln Ser Ala Ala Met Met Met Gly Met Met Pro Tyr Gly
180 185 190

Tyr Ser Ala Gly Ser Leu Gln Pro Pro Gln Ile Ala Met Gly Leu Arg
195 200 205

Pro Pro Pro Pro Leu Pro Gln Gln Ala Gln Gln Leu His Leu Gln Thr
210 215 220

Gln Gln Pro Gln Ser Gln Gln Gln Pro Ala Asn Gly Gly Phe Tyr Arg
225 230 235 240

Pro Leu Val Leu Asp Ser Met Asp Arg Pro Ile Ser Arg Gln His Gln
245 250 255

Gln His Pro Gly Ser Lys Ser Leu Trp Asn Arg Glu His Met Leu His
260 265 270

Cys Thr Leu Ile Val Lys Val Asp
275 280

<210> SEQ ID NO 33
<211> LENGTH: 225
<212> TYPE: PRT
<213> ORGANISM: Nicotiana tabacum

<400> SEQUENCE: 33

Met Glu Ser Asp Ala His Phe Leu Ala Lys Glu Asp Gly Ile Ile Ala
1 5 10 15

Gly Ile Ala Leu Ala Glu Met Ile Phe Ala Glu Val Asp Pro Ser Leu
20 25 30

Lys Glu Met Ala Asp Ala Ala His Pro Ala Tyr Ile Leu Glu Thr Arg
35 40 45

Lys Thr Ala Pro Gly Leu Arg Leu Val Asp Lys Trp Ala Val Leu Ile
50 55 60

```
Gly Gly Gly Lys Asn His Arg Met Gly Leu Phe Asp Met Val Met Ile
65                  70                  75                  80

Lys Asp Asn His Ile Ser Ala Ala Gly Gly Val Gly Lys Ala Leu Lys
                85                  90                  95

Ser Val Asp Gln Tyr Leu Glu Gln Asn Lys Leu Gln Ile Gly Val Glu
            100                 105                 110

Val Glu Thr Arg Thr Ile Glu Glu Val Arg Glu Val Leu Asp Tyr Ala
        115                 120                 125

Ser Gln Thr Lys Thr Ser Leu Thr Arg Ile Met Leu Asp Asn Met Val
    130                 135                 140

Val Pro Leu Ser Asn Gly Asp Ile Asp Val Ser Met Leu Lys Glu Ala
145                 150                 155                 160

Val Glu Leu Ile Asn Gly Arg Phe Asp Thr Glu Ala Ser Gly Asn Val
                165                 170                 175

Thr Leu Glu Thr Val His Lys Ile Gly Gln Thr Gly Val Thr Tyr Ile
            180                 185                 190

Ser Ser Gly Ala Leu Thr His Ser Val Lys Ala Leu Asp Ile Ser Leu
        195                 200                 205

Lys Ile Asp Thr Glu Leu Ala Leu Glu Val Gly Arg Arg Thr Lys Arg
    210                 215                 220

Ala
225


<210> SEQ ID NO 34
<211> LENGTH: 717
<212> TYPE: PRT
<213> ORGANISM: Nicotiana tabacum

<400> SEQUENCE: 34

Met Thr Glu Val Ala Thr Ser Asn Val Val His Asp Val Leu Gly Arg
1               5                   10                  15

Arg Ala Glu Asp Val Asp Gln Pro Ile Ile Asp Tyr Ile Ile Asn Val
            20                  25                  30

Leu Ala Asp Glu Asp Phe Asp Phe Gly Leu Asp Gly Glu Gly Ala Phe
        35                  40                  45

Glu Ala Leu Gly Glu Leu Leu Val Asp Ser Gly Cys Val Ala Asp Phe
    50                  55                  60

Pro Glu Cys Arg Ala Val Cys Ser Lys Leu Ser Glu Lys Leu Glu Lys
65                  70                  75                  80

His Gly Leu Val Lys Pro Gln Pro Thr Val Arg Ser Leu Lys Met Pro
                85                  90                  95

Leu Arg Met Tyr Asp Gly Met Asp Glu Glu Glu Ala Pro Lys Asn Lys
            100                 105                 110

Lys Pro Glu Pro Val Asp Gly Pro Leu Leu Thr Glu Arg Asp Lys Ile
        115                 120                 125

Lys Ile Glu Arg Arg Lys Arg Lys Asp Glu Arg Leu Arg Glu Ala Glu
    130                 135                 140

Tyr Gln Ala His Leu Lys Glu Val Glu Glu Val Lys Ala Gly Met Pro
145                 150                 155                 160

Leu Val Cys Val Asn His Asp Gly Gln Gly Asp Gly Pro Thr Val Lys
                165                 170                 175

Asp Ile Arg Met Glu Asn Phe Asn Ile Ser Val Ala Gly Arg Asp Leu
            180                 185                 190

Ile Val Asp Gly Ser Val Thr Leu Ser Phe Gly Arg His Tyr Gly Leu
```

```
        195                 200                 205

Ile Gly Arg Asn Gly Thr Gly Lys Thr Thr Leu Leu Arg His Met Ala
    210                 215                 220

Met His Ala Ile Asp Gly Ile Pro Lys Asn Cys Gln Ile Leu His Val
225                 230                 235                 240

Glu Gln Glu Val Val Gly Asp Asp Thr Ser Val Leu Gln Cys Ile Leu
                245                 250                 255

Asn Thr Asp Met Glu Arg Thr Gln Leu Leu Glu Glu Glu Gly Arg Leu
            260                 265                 270

Leu Glu Leu Gln Arg Glu Ile Asp Leu Glu Gly Glu Ala Gly Lys Ser
        275                 280                 285

Asp Lys Leu Asn Gly Glu Ile Asp Lys Asn Ala Leu Ala Lys Arg Leu
    290                 295                 300

Glu Glu Ile Tyr Lys Arg Leu Asp Phe Ile Asp Ala Tyr Ser Ala Glu
305                 310                 315                 320

Ser Arg Ala Ala Thr Ile Leu Ser Gly Leu Ser Phe Thr Thr Glu Met
                325                 330                 335

Gln Lys Arg Ala Thr Lys Thr Phe Ser Gly Gly Trp Arg Met Arg Ile
            340                 345                 350

Ala Leu Ala Arg Ala Leu Phe Ile Glu Pro Asp Leu Leu Leu Leu Asp
        355                 360                 365

Glu Pro Thr Asn His Leu Asp Leu His Ala Val Leu Trp Leu Glu Thr
    370                 375                 380

Tyr Leu Val Lys Trp Pro Lys Thr Phe Ile Val Val Ser His Ala Arg
385                 390                 395                 400

Glu Phe Leu Asn Thr Val Val Thr Asp Ile Ile His Leu Gln Asn Gln
                405                 410                 415

Lys Leu Ser Thr Tyr Lys Gly Asp Tyr Asp Thr Phe Glu Arg Thr Arg
            420                 425                 430

Asp Glu Gln Val Lys Asn Gln Gln Lys Ala Phe Glu Ala Asn Glu Arg
        435                 440                 445

Thr Arg Ala His Met Gln Thr Phe Ile Asp Lys Phe Arg Tyr Asn Ala
    450                 455                 460

Lys Arg Ala Ser Leu Val Gln Ser Arg Ile Lys Ala Leu Glu Arg Ile
465                 470                 475                 480

Gly Arg Val Asp Glu Val Ile Asn Asp Pro Asp Tyr Lys Phe Glu Phe
                485                 490                 495

Pro Ser Pro Asp Asp Arg Pro Gly Ala Pro Ile Ile Ser Phe Ser Asp
            500                 505                 510

Ala Ser Phe Gly Tyr Pro Gly Gly Pro Leu Leu Phe Lys Asn Leu Asn
        515                 520                 525

Phe Gly Ile Asp Leu Asp Ser Arg Val Ala Met Val Gly Pro Asn Gly
    530                 535                 540

Ile Gly Lys Ser Thr Ile Leu Lys Leu Ile Ser Gly Glu Leu Gln Pro
545                 550                 555                 560

Thr Ser Gly Thr Val Phe Arg Ser Ala Lys Val Arg Ile Ala Val Phe
                565                 570                 575

Ser Gln His His Val Asp Gly Leu Asp Leu Ser Ser Asn Pro Leu Leu
            580                 585                 590

Tyr Met Met Arg Cys Phe Pro Gly Val Pro Glu Gln Lys Leu Arg Gly
        595                 600                 605

His Leu Gly Ser Phe Gly Ile Thr Gly Asn Leu Ala Leu Gln Pro Met
    610                 615                 620
```

Tyr Thr Leu Ser Gly Gly Gln Lys Ser Arg Val Ala Phe Ala Lys Ile
625 630 635 640

Thr Phe Lys Lys Pro His Ile Leu Leu Leu Asp Glu Pro Ser Asn His
645 650 655

Leu Asp Leu Asp Ala Val Glu Ala Leu Ile Gln Gly Leu Val Leu Phe
660 665 670

Gln Gly Gly Val Leu Met Val Ser His Asp Glu His Leu Ile Ser Gly
675 680 685

Ser Val Asp Gln Leu Trp Ala Val Ser Glu Gly Arg Val Thr Pro Phe
690 695 700

Asp Gly Thr Phe Gln Asp Tyr Lys Lys Ile Leu Gln Ser
705 710 715

<210> SEQ ID NO 35
<211> LENGTH: 384
<212> TYPE: PRT
<213> ORGANISM: Nicotiana tabacum

<400> SEQUENCE: 35

Met Gly Ala Gln Ile Ser Val Ser Lys Leu Ala Asn Leu Ser Phe Val
1 5 10 15

Pro Arg Ile Arg Val Pro Val Pro Asn Ile Ser Val Pro Ser Pro Ser
20 25 30

Ile Ser Ser Gly Phe Val Ser Asn Leu Ser Cys Ser Ala Ile Gly Ile
35 40 45

Ser Ser Val Leu Val Asn Phe Tyr Gln Ser Ala Ser Leu Ala Lys Ser
50 55 60

Ala Asn Pro Ser Thr Tyr Thr Tyr Thr Val Pro Ser Ser Pro Ser Glu
65 70 75 80

Val Leu Tyr Arg Trp His Leu Pro Glu Pro Asn Val Val Asp Ile Ser
85 90 95

Gly Asn Tyr Asp Cys Ser Ser Val Lys Ser Arg Thr Val Val Val Leu
100 105 110

Leu Gly Trp Leu Gly Ala Lys Gln Lys His Leu Lys Arg Tyr Ala Glu
115 120 125

Trp Tyr Ala Ser Ala Gly Tyr His Val Ile Thr Phe Thr Phe Pro Met
130 135 140

Ser Glu Ile Leu Ser Tyr Gln Val Gly Gly Lys Ala Glu Gln Asp Ile
145 150 155 160

Glu Leu Leu Val Asn His Leu Val Asp Trp Leu Glu Glu Glu His Gly
165 170 175

Lys Asn Leu Val Phe His Thr Phe Ser Asn Thr Gly Trp Leu Thr Tyr
180 185 190

Gly Val Ile Leu Glu Lys Phe Gln Lys Gln Asp Pro Val Leu Met Thr
195 200 205

Arg Ile Lys Gly Cys Ile Val Asp Ser Ala Pro Val Ala Ala Pro Asp
210 215 220

Pro Gln Val Trp Ala Ser Gly Phe Ser Ala Ala Phe Leu Lys Lys Asn
225 230 235 240

Ser Val Ala Thr Lys His Ile Met Thr Ile Asn Asn Lys Asp Ala Asp
245 250 255

Val Thr Ile Glu Thr Lys Thr Ser Ser Asp Ala Thr Pro Ala Val Thr
260 265 270

Glu Ala Ala Leu Leu Val Val Leu Glu Lys Phe Phe Glu Val Val Leu

```
        275                 280                 285

Ser Leu Pro Ala Val Asn Arg Arg Leu Ser Asp Val Leu Asp Leu Leu
    290                 295                 300

Thr Ser Gln Gln Pro Ser Cys Pro Gln Leu Tyr Ile Tyr Ser Ser Ala
305                 310                 315                 320

Asp Arg Val Ile Pro Ala Ile Ser Val Glu Ser Phe Val Glu Glu Gln
                325                 330                 335

Arg Arg Ile Gly Arg Asn Val Arg Ala Cys Asn Phe Ile Ser Thr Pro
            340                 345                 350

His Val Asp His Phe Arg Asn Asp Pro Glu Leu Tyr Thr Leu Gln Leu
        355                 360                 365

Thr Gln Phe Leu Glu Asp Ser Val Leu Ser Ser Cys Lys Gln Ser Ser
    370                 375                 380


<210> SEQ ID NO 36
<211> LENGTH: 547
<212> TYPE: PRT
<213> ORGANISM: Nicotiana tabacum

<400> SEQUENCE: 36

Met Gly Gly Ala Glu Asp Ala Glu Pro Pro Ser Lys Arg Val Lys Val
1               5                   10                  15

Ser Ser Gly Lys Pro Gly Asp Leu Ser Asn Gly Thr Phe Pro Arg Asp
            20                  25                  30

Pro Ala Ser Cys Ser Leu Asn Asp Leu Met Ala Arg Pro Leu Val Cys
        35                  40                  45

Gln Gly Asp Asp Glu Val Val Gly Thr Lys Gly Val Ile Lys Lys Val
    50                  55                  60

Glu Phe Val Arg Ile Leu Ala Glu Ala Leu Tyr Ser Leu Gly Tyr Asn
65                  70                  75                  80

Lys Thr Gly Ala His Leu Glu Glu Glu Ser Gly Ile Pro Leu Gln Ser
                85                  90                  95

Ala Val Val Lys Leu Phe Met Gln Gln Val Leu Asp Gly Lys Trp Asp
            100                 105                 110

Glu Ser Val Ala Thr Leu Arg Lys Ile Gly Leu Val Asp Glu Lys Val
        115                 120                 125

Val Gln Leu Ala Ser Phe Leu Ile Leu Glu Gln Lys Phe Phe Glu Leu
    130                 135                 140

Leu Asp Glu Lys Lys Val Met Asp Ala Leu Lys Thr Leu Ser Thr Glu
145                 150                 155                 160

Ile Gly Pro Leu Cys Ile Asn Thr Asp Arg Val Arg Glu Leu Ser Leu
                165                 170                 175

Cys Ile Leu Ser Pro Leu Gln Gln Val Arg Ala Val Val Ser Gly Gln
            180                 185                 190

Val Val Val Arg Ala Lys Pro Arg Arg Lys Leu Leu Glu Glu Leu Gln
        195                 200                 205

Lys Leu Leu Pro Pro Thr Val Ile Ile Pro Glu Gln Arg Leu Ile Arg
    210                 215                 220

Leu Val Glu Gln Ala Leu Asp Leu Gln Leu Asp Ala Cys Arg Phe His
225                 230                 235                 240

Asn Ser Leu Val Gly Glu Met Ser Leu Leu Thr Asp His Gln Cys Gly
                245                 250                 255

Arg Asp Gln Ile Pro Ser Gln Thr Leu Gln Val Lys Leu Asp Gly Leu
            260                 265                 270
```

```
Phe Cys Met Lys His Gln Phe Ser Gly His Gln Lys Pro Val Ser Tyr
        275                 280                 285

Met Ser Trp Ser Pro Asp Asp His Gln Leu Leu Thr Cys Gly Val Glu
    290                 295                 300

Glu Val Val Arg Arg Trp Asp Ile Glu Ser Gly Glu Cys Thr His Ile
305                 310                 315                 320

Tyr Glu Lys Asn Gly Leu Gly Leu Ile Ser Cys Gly Trp Ala Pro Asp
                325                 330                 335

Gly Lys Arg Ile Leu Cys Gly Val Thr Asp Lys Ser Ile Ser Met Trp
            340                 345                 350

Asp Leu Glu Gly Lys Glu Leu Glu Cys Trp Lys Gly His Arg Thr Ile
        355                 360                 365

Arg Ile Ser Asp Leu Gly Ile Thr Ser Asp Gly Gln His Ile Val Ser
    370                 375                 380

Val Cys Lys Asp Asn Met Ile Leu Leu Phe Gly Trp Glu Ser Lys Ala
385                 390                 395                 400

Glu Lys Val Ile Gln Glu Asp Gln Thr Ile Thr Ser Phe Val Leu Ser
                405                 410                 415

Met Asp Ser Lys Tyr Leu Leu Val Ser Leu Trp Asn Gln Glu Ile His
            420                 425                 430

Leu Trp Asn Ile Glu Gly Thr Val Lys Leu Ile Ser Lys Tyr Lys Gly
        435                 440                 445

His Lys Arg Ser Arg Phe Val Val Arg Ser Cys Phe Gly Gly Leu Gly
    450                 455                 460

Gln Ala Phe Val Ala Ser Gly Ser Glu Asp Ser Gln Val Tyr Ile Trp
465                 470                 475                 480

His Arg Ser Ser Gly Glu Leu Ile Glu Thr Leu Ala Gly His Ser Gly
                485                 490                 495

Thr Val Asn Cys Val Ser Trp Asn Pro Ala Asn Pro His Met Leu Ala
            500                 505                 510

Ser Ala Ser Asp Asp His Thr Ile Arg Ile Trp Gly Met Asn Gln Val
        515                 520                 525

Asn Met Lys His Tyr Asp Thr Val Ser Asn Gly Val His Tyr Cys Asn
    530                 535                 540

Gly Gly Thr
545


<210> SEQ ID NO 37
<211> LENGTH: 587
<212> TYPE: PRT
<213> ORGANISM: Nicotiana tabacum

<400> SEQUENCE: 37

Met Ala Met Val Asp Glu Pro Leu Tyr Pro Ile Ala Val Leu Ile Asp
1               5                   10                  15

Glu Leu Lys Asn Asp Asp Ile Gln Leu Arg Leu Asn Ser Ile Arg Arg
            20                  25                  30

Leu Ser Thr Ile Ala Arg Ala Leu Gly Glu Glu Arg Thr Arg Lys Glu
        35                  40                  45

Leu Ile Pro Phe Leu Ser Glu Asn Asn Asp Asp Asp Asp Glu Val Leu
    50                  55                  60

Leu Ala Met Ala Glu Glu Leu Gly Val Phe Ile Pro Tyr Val Gly Gly
65                  70                  75                  80

Val Glu His Ala His Val Leu Leu Pro Pro Leu Glu Thr Leu Cys Thr
                85                  90                  95
```

-continued

```
Val Glu Glu Thr Cys Val Arg Asp Lys Ala Val Glu Ser Leu Cys Arg
            100                 105                 110

Ile Gly Ser Gln Met Arg Glu Ser Asp Leu Val Asp Trp Phe Val Pro
        115                 120                 125

Leu Val Lys Arg Leu Ala Ala Gly Glu Trp Phe Thr Ala Arg Val Ser
    130                 135                 140

Ala Cys Gly Leu Phe His Ile Ala Tyr Ser Ser Ala Pro Glu Met Leu
145                 150                 155                 160

Lys Ala Glu Leu Arg Ser Ile Tyr Ser Gln Leu Cys Gln Asp Asp Met
                165                 170                 175

Pro Met Val Arg Arg Ser Ala Ala Thr Asn Leu Gly Lys Phe Ala Ala
            180                 185                 190

Thr Val Glu Ser Thr Tyr Leu Lys Ser Asp Ile Met Ser Ile Phe Asp
        195                 200                 205

Asp Leu Thr Gln Asp Asp Gln Asp Ser Val Arg Leu Leu Ala Val Glu
    210                 215                 220

Gly Cys Ala Ala Leu Gly Lys Leu Leu Glu Pro Gln Asp Cys Val Ala
225                 230                 235                 240

His Ile Leu Pro Val Ile Val Asn Phe Ser Gln Asp Lys Ser Trp Arg
                245                 250                 255

Val Arg Tyr Met Val Ala Asn Gln Leu Tyr Glu Leu Cys Glu Ala Val
            260                 265                 270

Gly Pro Glu Pro Thr Arg Thr Asp Leu Val Pro Ala Tyr Val Arg Leu
        275                 280                 285

Leu Arg Asp Asn Glu Ala Glu Val Arg Ile Ala Ala Ala Gly Lys Val
    290                 295                 300

Thr Lys Phe Cys Arg Ile Leu Ser Pro Glu Leu Ala Ile Gln His Ile
305                 310                 315                 320

Leu Pro Cys Val Lys Glu Leu Ser Ser Asp Ser Ser Gln His Val Arg
                325                 330                 335

Ser Ala Leu Ala Ser Val Ile Met Gly Met Ala Pro Val Leu Gly Lys
            340                 345                 350

Asp Ala Thr Ile Glu His Leu Leu Pro Ile Phe Leu Ser Leu Leu Lys
        355                 360                 365

Asp Glu Phe Pro Asp Val Arg Leu Asn Ile Ile Ser Lys Leu Asp Gln
    370                 375                 380

Val Asn Gln Val Ile Gly Ile Asp Leu Leu Ser Gln Ser Leu Leu Pro
385                 390                 395                 400

Ala Ile Val Glu Leu Ala Glu Asp Arg His Trp Arg Val Arg Leu Ala
                405                 410                 415

Ile Ile Glu Tyr Ile Pro Leu Leu Ala Ser Gln Leu Gly Ile Gly Phe
            420                 425                 430

Phe Asp Asp Lys Leu Gly Ala Leu Cys Met Gln Trp Leu Gln Asp Lys
        435                 440                 445

Val Tyr Ser Ile Arg Asp Ala Ala Ala Asn Asn Leu Lys Arg Leu Ala
    450                 455                 460

Glu Glu Phe Gly Pro Glu Trp Ala Met Gln His Ile Ile Pro Gln Val
465                 470                 475                 480

Leu Asp Met Thr Thr Ser Pro His Tyr Leu Tyr Arg Met Thr Ile Leu
                485                 490                 495

Arg Ala Ile Ser Leu Leu Ala Pro Val Met Gly Ser Glu Ile Thr Cys
            500                 505                 510
```

Ser Lys Leu Leu Pro Val Val Ile Thr Ala Thr Lys Asp Arg Val Pro
515 520 525

Asn Ile Lys Phe Asn Val Ala Lys Val Leu Gln Ser Leu Ile Pro Ile
530 535 540

Val Asp His Ser Val Val Glu Lys Thr Ile Arg Pro Ser Leu Val Glu
545 550 555 560

Leu Ala Glu Asp Pro Asp Val Asp Val Arg Phe Tyr Ala Asn Gln Ala
565 570 575

Leu Gln Ser Ile Asp Asn Val Met Met Ser Gly
580 585

<210> SEQ ID NO 38
<211> LENGTH: 621
<212> TYPE: PRT
<213> ORGANISM: Nicotiana tabacum

<400> SEQUENCE: 38

Met Gly Phe Ile Glu Ser Cys Ser Gln Thr Ala Glu Met Glu Ile Arg
1 5 10 15

Lys Cys Ser Pro Phe Leu Glu Ser Glu Leu Leu Ser Gly Asn Gly Gly
20 25 30

Leu Pro Leu Thr Glu Trp Arg Thr Val Pro Asp Ile Trp Arg Thr Ser
35 40 45

Ala Glu Lys Phe Gly Asp Arg Val Ala Val Val Asp Pro Tyr His Asp
50 55 60

Pro Pro Thr Thr Met Thr Tyr Lys Gln Leu Tyr Gln Glu Ile Val Asp
65 70 75 80

Phe Ser Glu Gly Leu Arg Val Val Gly Leu Asn Pro Asn Glu Lys Ile
85 90 95

Ala Leu Phe Ala Asp Asn Ser Cys Arg Trp Leu Val Ala Asp Gln Gly
100 105 110

Thr Met Ala Ser Gly Ala Ile Asn Val Val Arg Gly Ser Arg Ser Ser
115 120 125

Asn Gln Glu Leu Leu Gln Leu Tyr Ser His Ser Glu Ser Val Ala Leu
130 135 140

Ala Ile Asp Asn Pro Glu Met Tyr Asn Arg Ile Ser Asp Thr Phe Gly
145 150 155 160

Ser His Thr Ala Val Arg Phe Ala Ile Leu Leu Trp Gly Glu Lys Ser
165 170 175

Ser Leu Gly Arg Glu Ala Val Gln Gly Tyr Pro Val Tyr Thr Tyr Lys
180 185 190

Glu Ile Ile Glu Leu Gly His Lys Ser Arg Val Asp Leu Leu Asp Ser
195 200 205

Glu Asp Ala Arg Lys Gln Tyr Ser Phe Glu Ala Ile Asn Ser Asp Asp
210 215 220

Val Ala Thr Ile Val Tyr Thr Ser Gly Thr Thr Gly Asn Pro Lys Gly
225 230 235 240

Val Met Leu Thr His Lys Asn Leu Leu His Gln Ile Leu Asn Leu Gly
245 250 255

Glu Ile Val Pro Ala Val Pro Gly Asp Arg Phe Leu Ser Met Leu Pro
260 265 270

Pro Trp His Ala Tyr Glu Arg Ala Cys Glu Tyr Phe Ile Phe Thr His
275 280 285

Gly Thr Glu Gln Val Tyr Thr Thr Val Lys Asn Leu Lys Pro His Tyr
290 295 300

```
Leu Ile Ser Val Pro Leu Val Tyr Glu Thr Leu Tyr Ser Gly Ile Leu
305                 310                 315                 320

Lys Gln Ile Asn Ser Asn Ser Ala Ala Ser Lys Leu Ile Ala Leu Leu
                325                 330                 335

Phe Leu Arg Ile Ser Met Thr Tyr Met Glu Ala Lys Arg Ile Tyr Glu
            340                 345                 350

Ala Gly Val Ser Gly Gly Gly Ser Leu Ser Ser His Val Asp Lys Phe
        355                 360                 365

Phe Glu Ala Ile Gly Ile Lys Ile Gln Asn Gly Tyr Gly Leu Thr Glu
    370                 375                 380

Ser Ser Pro Val Ile Ser Ala Arg His Leu Ala Cys Asn Val Leu Gly
385                 390                 395                 400

Ser Val Gly His Pro Ile Arg His Val Glu Val Lys Ile Val Asn Ala
                405                 410                 415

Glu Thr Asp Glu Val Leu Pro Pro Gly Ser Arg Gly Ile Val Lys Ala
            420                 425                 430

Arg Gly Pro Leu Val Met Lys Gly Tyr Tyr Lys Asn Pro Leu Ala Thr
        435                 440                 445

Lys His Ala Ile Asp Glu Asn Gly Trp Leu Asn Thr Gly Asp Leu Gly
    450                 455                 460

Trp Ile Ala Pro Asp His Ser Val Gly Arg Ser Arg Lys Ser Gly Gly
465                 470                 475                 480

Val Ile Val Leu Glu Gly Arg Ala Lys Asp Thr Ile Val Leu Ser Thr
                485                 490                 495

Gly Glu Asn Val Glu Pro Ser Glu Ile Glu Glu Ala Ala Met Gly Ser
            500                 505                 510

Ser Leu Ile Gln Gln Ile Val Val Ile Gly Gln Asp Gln Arg Arg Leu
        515                 520                 525

Gly Ala Ile Ile Val Pro Asn Lys Glu Glu Val Leu Leu Ala Ala Lys
    530                 535                 540

Lys Ser Ala Ile Val Asp Ser Glu Thr Thr Glu Val Ser Lys Glu Lys
545                 550                 555                 560

Ala Val Gly Ile Leu Tyr Glu Glu Leu Arg Lys Trp Thr Ser Gly Cys
                565                 570                 575

Ser Phe Gln Val Gly Pro Ile Leu Ile Val Asp Glu Pro Phe Thr Ile
            580                 585                 590

Asp Ser Gly Leu Leu Thr Pro Thr Met Lys Ile Lys Arg Asp Lys Ile
        595                 600                 605

Ala Ala Leu Tyr Lys Glu Gln Ile Glu Asn Leu Tyr Lys
    610                 615                 620
```

<210> SEQ ID NO 39
<211> LENGTH: 869
<212> TYPE: PRT
<213> ORGANISM: Nicotiana tabacum

<400> SEQUENCE: 39

```
Met Gly Gly Asp Glu Thr Lys Lys Thr Thr Ile Met Val Leu Lys Val
1               5                   10                  15

Asp Leu Gln Cys Ser Ser Cys Tyr Lys Lys Val Lys Lys Val Leu Cys
            20                  25                  30

Lys Phe Pro Arg Cys Gly Val Ile Lys Ser Ile Glu Ile Lys Glu Pro
        35                  40                  45

Pro Lys Pro Lys Ala Pro Glu Lys Pro Lys Glu Pro Val Lys Pro Lys
```

```
    50                  55                  60

Glu Pro Glu Lys Pro Lys Gln Pro Glu Lys Pro Lys Glu Pro Glu Lys
65                  70                  75                  80

Pro Lys Gln Pro Glu Lys Thr Thr Val Val Val Ile Glu Lys Pro Lys
                85                  90                  95

Glu Pro Glu Lys Pro Lys Ala Pro Glu Lys Ser Lys Glu Pro Glu Lys
            100                 105                 110

Pro Lys Glu Pro Glu Lys Pro Lys Glu Val Glu Lys Pro Lys Pro Lys
        115                 120                 125

Glu Pro Glu Lys Pro Lys Glu Ala Pro Lys Pro Asn Pro Val Ala Pro
    130                 135                 140

Pro Ser Gln Pro Pro Pro Pro Pro Ala Pro Glu Pro Ile Met Val Gln
145                 150                 155                 160

Gln Tyr Pro Gln Pro Pro Leu Gly Tyr Cys Cys Gly Gln Cys Tyr Glu
                165                 170                 175

Gly His Ile Gly Gly Pro Cys Tyr Gln Trp Tyr Gly Arg Pro Val Leu
            180                 185                 190

Pro Ala Pro Cys Tyr Asp Asn Tyr Gly Tyr Asn Tyr Gly Pro Gly Pro
        195                 200                 205

Gly Pro Gly Pro Tyr Gly Tyr Gly Arg Gly Cys Tyr Val Ser Arg Cys
    210                 215                 220

Asp Gln Tyr Phe Ser Glu Glu Asn Ala Thr Gly Cys Ser Ile Ile Lys
225                 230                 235                 240

Trp Glu Pro Asn Ile Val Ala Ser Lys Ala Lys Glu Val Tyr Ser Ala
                245                 250                 255

Val Trp Val Arg Leu Leu Gln Leu Pro Thr Glu Phe Tyr Asp Arg Ile
            260                 265                 270

Val Leu Ser Arg Ile Gly Asn Ser Ile Gly Arg Leu Leu Arg Ile Asp
        275                 280                 285

Ala Cys Thr Ser Ser Thr Leu Arg Arg Arg Tyr Ala Arg Leu Cys Val
    290                 295                 300

Gln Val Gln Met Asp Gln Leu Val Gln Thr Thr Ile Gln Ile Gly Ser
305                 310                 315                 320

His Ile Gln Gln Leu Val Tyr Glu Gly Glu Lys Phe Leu Cys Lys Ala
                325                 330                 335

Cys Gly Arg Leu Gly Asn Thr Thr Ser Thr Cys Ser His Thr Leu Leu
            340                 345                 350

Asp Phe Gln Lys Gln Gln Gln Glu Glu Pro Cys Pro Asn Ser Thr Gly
        355                 360                 365

Phe Ile Gly Lys Glu Arg Gln Leu Lys Ser Asn Asp Lys Pro Ser Pro
    370                 375                 380

Ser Pro Lys Val Thr Ser Gln Lys Glu Ala Gln Pro Met Asp Leu Lys
385                 390                 395                 400

Ile Lys Leu Lys Arg His Leu Gln Val Ser Met Ser Ile Phe Leu Met
                405                 410                 415

Arg His Gln Pro Ile Leu Thr Ser Asn Lys Phe Glu Ser Leu Leu Asn
            420                 425                 430

Asp Ser Ser Ile Thr Phe Pro Glu Ile Ile Glu Ser Gln Met Glu Leu
        435                 440                 445

Asp Gly Gln Asn Ser Asn Leu Ser Pro Asp Ser Lys Leu Ser Phe Ser
    450                 455                 460

Pro Arg Asn His Ser Ser Ser Leu Leu Pro Pro Leu Ser Pro Arg Gly
465                 470                 475                 480
```

```
Gln Lys Ala Thr Cys Asn Ser Asn Lys Pro His Lys Thr Ala Gly Pro
                485                 490                 495

Ser Thr Asn Pro Leu Pro Cys Thr Pro Leu Pro Thr Leu Met Thr Pro
            500                 505                 510

Ile Thr Thr Glu Asn Pro Ile Thr Asp Leu Ser Leu Thr Thr Cys Gln
        515                 520                 525

Leu Ala Met Gln Leu Asn Ser Pro Ile Leu Ala Ser Leu Arg Leu His
    530                 535                 540

Val Lys Asn Arg Thr Met His Thr Lys Phe Leu Leu Thr Asp Phe Gln
545                 550                 555                 560

Ser Leu Pro His Glu Asn Gln Ser Pro Ser Ser Pro Ser Ser Ser Pro
                565                 570                 575

Thr His Tyr Glu Ser Thr Pro Leu Leu Pro Ser Asn Glu Asn Pro Ser
            580                 585                 590

Lys Ile Thr Leu Thr Pro Pro Ser Phe Leu Asn Thr Val Gln Asn Glu
        595                 600                 605

Pro Pro Thr Pro Gly Tyr Lys Pro Ser Asp Leu His His Gln Cys Pro
    610                 615                 620

Leu Thr Gly Pro Pro Thr Asn Ala Met Val Gly Thr Arg Thr Ser Gly
625                 630                 635                 640

Pro Ser Gly Phe Leu His Ser Gln Tyr Pro Lys Ser Arg Ser Pro Val
                645                 650                 655

Cys Ser Thr Glu Pro Thr Gly Pro Ser Ser Ile Asn Leu Gly Gly Tyr
            660                 665                 670

Glu Ala Ser Asn Val Glu Leu His Gln Pro Pro Leu Val Asp Lys Cys
        675                 680                 685

Ser Arg Ala His Ser Pro Thr Leu Ala Pro Ala Leu Leu His Asn Met
    690                 695                 700

Gln Ala His Trp Asn Pro Pro His His Phe Asn Pro Leu Gln Asn Met
705                 710                 715                 720

Gln Leu Phe Tyr Gln Leu Pro Phe Phe Ala Pro Gln Asp Gln Asn Thr
                725                 730                 735

Pro Pro Leu Ile His Ala Trp Gln Pro Ile Pro Gln His Tyr Pro Ala
            740                 745                 750

Pro Met Asp Phe His His Thr His Ser His Pro His His Ser Ala Pro
        755                 760                 765

Val Pro Gly Glu Gln Glu Met Glu Thr Gln Asn Gln Thr Ile Pro Pro
    770                 775                 780

Leu Asn Ile Thr Ser Tyr Thr Glu Asn Ser Asn Leu His Glu Val Lys
785                 790                 795                 800

Ile Leu Leu Phe Gln Ala Met Glu Glu Lys Lys Tyr Val Arg Lys Cys
                805                 810                 815

Pro Thr Glu Leu Tyr Lys Cys Ser Leu Asp Ile Arg Pro Pro Leu Asn
            820                 825                 830

Ala Ala Val Gly Asn Phe Ala Val Ile Leu Ser Pro Ser Leu Asn Gly
        835                 840                 845

Leu Pro Val Pro Pro Met Gly Ser Gln Phe Asn Val Thr Pro Gln Pro
    850                 855                 860

Thr Pro Ile Asn Asp
865
```

<210> SEQ ID NO 40
<211> LENGTH: 369

<212> TYPE: PRT
<213> ORGANISM: Nicotiana tabacum

<400> SEQUENCE: 40

```
Met His Ile Leu Tyr Thr Cys Pro Leu Ile Leu Phe Met Ala Leu Leu
1               5                   10                  15

Phe Ala Tyr Ala Ala Ala Thr Ala Ala Asp Leu Glu Thr Asn Gly Ala
            20                  25                  30

Glu Lys Ala Gly Ala Asp Ala Gly Ile Leu Ser Ser Asn Ser Ser Val
        35                  40                  45

Asn Glu Asn Leu Asp Leu Ile Asn Met Asn Arg Lys Lys Asp Gly His
    50                  55                  60

Leu Asp Asn Asp Ser Ser Asn Val Gly Asp Gln Asn Lys Ser Asn Asp
65                  70                  75                  80

Ser Ser Ala Lys Lys Gly Asp Asp Arg Glu Gly Leu Lys Glu Ala Glu
                85                  90                  95

Val Glu Lys Lys Arg Ile Asp Ser Gly Ser Lys Arg Asp Asp Arg Lys
            100                 105                 110

Glu Glu Thr Lys Glu Ala Glu Gln Gln Asp Lys Ala Lys Asp Ile Ser
        115                 120                 125

Ser Glu Lys Gln Gly Glu Met Glu Lys Ile Leu Pro Asp Gly Ile Gln
    130                 135                 140

Ser Arg Glu Glu Ile Leu Pro Thr Arg Lys Glu Ser Phe His Gly Glu
145                 150                 155                 160

Glu Cys Asp Ser Ser Tyr Ser Cys Thr Ile Glu Glu Lys Ala Val Val
                165                 170                 175

Ala Cys Leu Arg Val Pro Gly Asn Glu Ser Pro Asp Leu Ser Leu Leu
            180                 185                 190

Val Gln Asn Asn Gly Lys Gly Thr Val Asn Ile Leu Ile Lys Ala Pro
        195                 200                 205

Glu Phe Val Gln Leu Glu Lys Glu Lys Ile Glu Leu Gln Gly Lys Glu
    210                 215                 220

Asn Gln Arg Met Lys Val Ser Ile Arg Asn Ala Gly Asn Asp Asn Asn
225                 230                 235                 240

Ile Ile Leu Lys Ala Gly Asp Gly Gln Cys Thr Leu Asp Phe Arg Gly
                245                 250                 255

Leu Ile Asp Asn Ala Asp Lys Thr Ser Gln Phe Lys Tyr Gly Phe Leu
            260                 265                 270

Ser Phe Ala Ile Met Cys Leu Ala Ala Ile Ala Leu Val Ala Thr Val
        275                 280                 285

Leu Met Tyr Phe Lys Arg Arg Leu Leu Val Ser Ser Gly His Lys Tyr
    290                 295                 300

Gln Lys Leu Asp Met Asp Leu Pro Val Ser Ser Gly Arg Lys Thr Glu
305                 310                 315                 320

Thr Leu Ser Thr Asp Gly Trp Asp Asn Ser Trp Asp Asp Asp Trp Asp
                325                 330                 335

Asp Glu Glu Ala Pro Lys Ala Pro Ser Val Pro Val Thr Pro Ser Phe
            340                 345                 350

Ser Ser Lys Ser Ile Thr Ser Arg Arg Ser Ser Lys Glu Ser Trp Lys
        355                 360                 365

Asp
```

<210> SEQ ID NO 41
<211> LENGTH: 957

<212> TYPE: DNA
<213> ORGANISM: Nicotiana tabacum

<400> SEQUENCE: 41
atgtgtgtgt actccaattg taacaaaaaa cgtgggagag ggagagagag aggagtcgtg 60
attcaaggga agacagcagt tggcaataat aagactacaa attactatct ctactttctg 120
attttcgctc cttcactcac atccacagca catcgcttct ccgatccaaa aaaagttgcg 180
aagatgaacg acgcagatgt atcgaagcag atccagcaga tggtcagatt catccgccag 240
gaagccgaag aaaaagccta tggatttccg tctccgccga agaagtattg gcctatttct 300
tattctattg atcaattagc tttagttaga ctaattttga gtaataatgt gcgcattgaa 360
gaagaattca acatcgagaa gttgcagcta gtggaactgg agaagaagaa gatcaggcag 420
gaatacgagc gtaaggagaa acaagtcgat gttcgcaaga aaattgagta ctccatgcaa 480
ctcaacgcct ctcgaatcaa ggttcttcaa gctcaggatg acttggtcaa ctccatgaag 540
gaggcagcat caaaggagct tttaaacgtc agccatcacc agaaccacca tatttataag 600
aagcttctgc aggatcttat tgttcagagt ttgctcagac ttaaagagcc ttgcgtccta 660
ctacgttgtc gggaagatga tgtttccttg gtagaagggg tcttggatgc agcaaaagag 720
gagtatgcag aaaaagctca ggttcactca ccggaggtca taattgacca aatctacctt 780
ccatcagctc catcacatca caatgctcat ggctcttctt gctatggagg agtagttttg 840
gcttctcgag atgggaaaat tgtatgtgaa aatacacttg atgccagatt ggaagttgtg 900
ttccgtaaga aactaccgga gattcgcaag tgtctatttg gtcaggttgc tgcctaa 957

<210> SEQ ID NO 42
<211> LENGTH: 1980
<212> TYPE: DNA
<213> ORGANISM: Nicotiana tabacum

<400> SEQUENCE: 42
atgattactc caaagctatc tctcctttgc atacaaaatc ctggcactca gacaaggtct 60
ccaagtggct atgcaaatga atctcatacc accggaagtg aaaatttgac tcaactgagg 120
ttattactgt ccggaatggg gaagccaagg attatgcata actccaggga aggaaatgaa 180
gtagcccacc tactggctaa gaagacaatc aatcaatcta acatggatca tctcgtctat 240
ctggcaattt ctccttctct tgttgagacc aaggtgttgt cagacaaaga tggagaatct 300
tctctaaaat ttgttgtaga cgatgcttgt aggatgtcca atatggattt catgaaggta 360
ttcgatcaaa cagttcgcga aataaagagg gaggtgaatt tgaaagtgtt gaaggttcct 420
gagattgagc agaaggtatt ggacgctacg gatgatgaac cttggggccc ccatggtact 480
gcattggctg agatagctca ggctacaaaa aaattctctg agtgtcagat ggttatgaat 540
gtcctgtgga caagattgac tgaaacagga aagaattggc gttatgttta taagtctttg 600
gctgttgttg agtatttggt ggctcacgga tctgaacgcg ctgttgatga gatcgtagaa 660
catacctatc agatatcttc tctcacaagt ttcgagtatg ttgaacccaa tgggaaagat 720
atggggatca atgtgaggaa gaaagcagaa aatattgtgg cactattgaa taacaaggaa 780
aagatcgaag acgctagaaa taaagctgct gcaaatcgcg acaagtactt tggattgtca 840
tcttctggag taacatttaa atcgagctct gcctccctaa atagcagcag caactttcag 900
agtggtgatc gatatggagg ttttggaaat aaaagtgatg gcgattcatt taaggatagt 960
tacagggaaa aggatcggta tggtgaagat aaatttgacc agtttaaatc aaagaagggg 1020
tcttctcgtt atggaagcaa tgttcaagac actgtttcat ctagtggatc aaagacgtca 1080
aagagggtag gtaaacctga taaagctact tctaatcctc cacatagtgc agctgtatca 1140
tcaagcaaat atgaggaaga ttttgatgat tttgatcctc gagggacttc aagtactaag 1200
ccttccaccg aaaaatctga ccaagtagat ctatttggac aaaatttgat tggtgacctc 1260
ttggatgtac caacacctgt tccagctgat aattctactg tctccagtca tccatcagag 1320
gttgatttat ttgctgatgc caattttgca ttggcgaaac cacagtctga gataagtgta 1380
gatctgtttg cttctcagcc tgcctcttca tctgcagctc cttcaaccat agattttttt 1440
tctgcaccag atcctgttgt acaatccgat atcagatctc ctaaatcaga caagataaat 1500
gctactacgg ttgatccgtt tgctgcagtt ccactaaata cctttgatag ttctgatccc 1560
tttggtacat ttgtttctca tgctgatcct gtatcagtag ccagtgaaaa tgctaatcgt 1620
ggtgggaatc aggaggagac tcctagcaaa ttagataaat cttctgtcga agctaagccc 1680
gcaccaaaga aggatgattt tcaagtcagg tctggaatat gggctgattc attgagccgt 1740
ggactgattg atctgaatat ctctgcaccc aaaaaggtca accttgcaga cataggcatc 1800
gtgggtggat tgaccgatgg gtcagatgtg aaagaaaaag ggcctactac attttacatg 1860
ggcagagcca tgggtcaagg aaccgggctt ggccaatccg ggttcacgtc cacatcaacg 1920
ggtggagatg actttttttc aagtcaccag aactatcaat ttggcagctt ccaaaagtga 1980

<210> SEQ ID NO 43
<211> LENGTH: 855
<212> TYPE: DNA
<213> ORGANISM: Nicotiana tabacum

<400> SEQUENCE: 43
atggcgatgg atgacaattt ccataggcaa cgactagggg cacatgcacc tccgggttac 60
tttgtccgct tggagaacgg aagggctaaa gacgatcttt acttgagaaa gggaggaagg 120
atgagaaagt ggctctgctg cacctgccaa gtagaggagt ctgacccatc gcatgaaaac 180
gagctccaca aaagccccaa gaacaatttt gatggatatc agaaagggtc aaaagcatca 240
gttcctgcca aggctgaagt gcaaaaggca ataccaacta tagaggtccc tgcattgtct 300
ttggatgaac tgaaagagga aactgacaat tttggatcga aggcattaat tggtgaagga 360
tcttacggaa gagtatacta tgctaatcta aacaatggca aagccgtggc tgtaaaaaag 420
cttgatgttt catctgagcc tgagactaat gttgacttcc tgagccaggt ctctatggtt 480
tcaagattga agcatgtaaa tctggttgat ttgcttggtt actgtgtgga agggaacctt 540
cgtgtattag cttatgagaa aggagtacaa ggagcacaac ctggacctac acttgattgg 600
atgcaacggg taaaaattgc tgttgatgct gcaaggggcc ttgagtattt gcatgagaag 660
gtccagcctc caataataca cagggatatc agatcaagca atgtccttct ctttgaagac 720
tacaaagcaa aattgctgat tttaatctgt caaatcagtc tcctgacatg gctgctcgcc 780
ttcattctac acgagttttg ggaacatttg gttatcatgc accagagtaa tgtcttgcac 840
cttactcttc tttga 855

<210> SEQ ID NO 44
<211> LENGTH: 1458
<212> TYPE: DNA
<213> ORGANISM: Nicotiana tabacum

<400> SEQUENCE: 44
atgccaccgc cgccgtccac catctccgac gatgattcct cttacttcca cgtcagcact 60

```
cttctacctc tatatcgagc tcgcctccgc aaaaaactta atctgagaag gttgagaaat    120

ggaacttgta gggcagagtt tgcaaacgac gcgccaatcg ccgtcgctat cggtgcttgc    180

attttcagct cgttggtttt tccgactact tacacggagg atgatgacgg ggactccgtg    240

attgattctg ctgatgcgag gtttgctgtt atgggaatta tcagcttcat tccgtatttt    300

aattggatga gttgggtttt cgcgtggttg gatactggga agcagcgtta cgctgtttat    360

gctcttgtgt atttggctcc atatttaaga accaatctgt ctctttctcc tgaagacagc    420

tggctaccaa ttgctagcat cctcttgtgc atcttccaca ttcaactaga agtaagtatc    480

aaaaatggag attttcaggc attgaacaaa tttactggga ctggagagga actatcatca    540

gtttctagga agaaagatga tagcatctct gaagaggata tgattgctgg ggatgtcgtg    600

aatccagacc acatagatgt ggggtttgat tcgattgggg ggcttggtgg gattaaggat    660

actttgtttc agctggccat tttacctctg cgaaggcctg aattgttttg tcatgggaaa    720

ttgcttggtc caatgaaagg ggttctgttg tatggaccac ctgggacagg gaagacaatg    780

cttgctaaag ccattgctaa agagtctggt gctgtgttca ttaatgtgaa ggtttctact    840

ctcatgagca agtggtttgg tgatgcgcaa aagcttgttg ctgctatttt tggtttggcc    900

tataagctcc agcctgctat aatatttatt gatgaagttg acagcttttt gggccagcgt    960

cgtgcaagtg agactgaaat gctgactagc atgaaaactg agttcatggc cttatgggat   1020

ggttttacta ctgatcagaa tgctagagtt atggtcctgg cagcaaccaa tcgcccaact   1080

gaccttgatg aggcaatact taggcgcttt tctcagtcat ttgagattgg gaaaccttcc   1140

cttagtgata gaacaaagat atttaaggta gtattgaagg gtgagagaat tgaagataac   1200

gttgactttg atcgacttgc tggcttgtgt gagggataca ctggttcaga cattctcgag   1260

gcctgcaagc tagctgcctt tattcctctt agggagtatt tgcaagatga gaagaaagga   1320

aagcaatcac aggctccaag gccattgtca cagtctgatc tagagacagc tttggctcaa   1380

tcaaagaaga ccaagattac tgctaggaaa cctgctgtag tgagctttcg gttggatgat   1440

tatgaggatt tagactga                                                 1458
```

```
<210> SEQ ID NO 45
<211> LENGTH: 1335
<212> TYPE: DNA
<213> ORGANISM: Nicotiana tabacum

<400> SEQUENCE: 45

atgagctcac acgatatacg ccgcccgttc aaacggccgg cgatctcaga ccaacaaaga     60

cgccgagaac tttcattgct ccggcagtgc caaaaccgcc gcgacgctca gttacaagcc    120

cgtcgtttag cttccacagt cctctctctt caacccacgc aagacgatga ctacaagtcc    180

gcttccgaag agcaacagct ggatatagaa gttgcttccg tccccgaagt tgattccttt    240

ccggatgaaa ccgacgccga ttttggacat cctagggacg cacatgatat tcgtcaagct    300

actaagctca gaggacctga agctcgtcag tggttcgcca agcagcttat gcttcctgaa    360

tggatgattg atgttcctga taacttgaac acggattggt atgtatttgc taggccagct    420

ggaaagagat gttttgttgt ttcttcaaac ggaacaacaa tcagtagact gcgcaatgga    480

attcgcttgc accgttttcc ttctgctcta cctaacggtg ccagaattaa taacagtaaa    540

tctgctcaat catactgtat tctcgattgc atatttcacg agtctgatga aacatattat    600

gtcattgacg gtgtatgttg ggcgggactt tcgttatatg agtgcacggc ggaattcaga    660
```

ttcttttggt taaacagcaa gcttgctgag acgggggctt gtgatgctcc ctctacttat 720
catagatata aatttagtac acttcctgtc tacaactgtg acaaagaagg actacacaca 780
gcttatgtag gacaagttcc atatgtcaag gatggattac tgttttacaa caagcatgca 840
cattaccaaa caggaaatac accgttaaca ttggtttgga aggatgagaa ctgtagccag 900
tatgtcattg atacagataa tagaggacaa gttccaagtc aacaacaggt agttttggag 960
ctcctagatg atagcagact ggctacatct gatgatcctc ctgtcatatt tggttgcttg 1020
cttggggaat tcatacaaaa gacagaactt cagcgtggag atcttataaa gtttgctata 1080
ggtgaaggcg gattagtttt tgttgacagt aaactggaga aagctgatct acaatacttg 1140
ggcaaatcca atcgtgctcg tgcttttgct gatagttact cgaaggtctt gttccagtac 1200
gctgctcgac attctcctct gagaattgaa catctttttg catcaatcag ttcatgtgtc 1260
gaagatggaa gatcaaactc aagatgcaga tatggctggt taaagtgcca tgcacgggaa 1320 actttttca actaa 1335

<210> SEQ ID NO 46
<211> LENGTH: 2490
<212> TYPE: DNA
<213> ORGANISM: Nicotiana tabacum

<400> SEQUENCE: 46
atggctcagc ctctcctgaa gaaagacgac gatcgcgatg acgaagcgga gtactctccg 60
tttatgggga ttgagaaggg ggctgtgctt caggaagcta gggttttcaa tgatccgcaa 120
ttggatgcac gcagatgctc acaggtcatt acaaagcttc tgtatcttct gaatcagggt 180
gagacgttta caaaggttga agctacagaa gtgttctttg ctgtcacaaa actctttcag 240
tcaaaggatc ttggtctaag gagaatggta tacttgatga taaaagagct ttctccctca 300
gctgatgagg taatcatcgt tactagctct cttatgaagg acatgaatag cagtacagat 360
atgtatcgtg caaatgctat tcgagtcctc tgccgaatca cagatgggac tcttctcaca 420
caaattgaga gatacttgaa acaagcgatt gttgacaaaa accctgttgt tgcaagtgct 480
gcccttgtta gtggaatcca tttgcttcag acaaacccgg agattgtgaa aagatggagc 540
aatgaggtcc aagaagctgt tcagtcaagg gcagctctcg ttcaattcca tgcactggcg 600
ctgctgcacc agataaggca aaatgaccgt ttagctgtga gcaagcttgt taccagtttg 660
acaagaggaa ctgttcgctc acctctagct caatgcctct tgattcgtta tactagtcag 720
gttataagag aggctgccat gagtaatcaa acaggggata ggccattcta tgactatcta 780
gagggttgcc tacgtcacaa agcagaaatg gttatttttg aagctgccag ggcaatcaca 840
gagcttagtg gtgtgactag tcgagaatta actcctgcaa tcactgttct acagctcttt 900
ttaagctctt ccaagccagt tcttaggttt gctgctgttc gaaccttgaa taaggtggca 960
atgacacatc ctatggctgt gacaaactgc aacatagata tggagagctt gatttctgat 1020
cagaatagga gcatagcaac tcttgccata acgactcttc ttaagaccgg caatgaatca 1080
agtgttgatc gtttgatgaa gcagataact aattttatgt ccgacattgg tgatgagttc 1140
aagattgttg tggtggaagc cattagatca ttgtgtttga agtttcccct gaagtacaga 1200
tctttgatga atttcttaag caatattttg agggaagaag gaggatttga gtacaaaaag 1260
gctattgttg actcaattgt gatcctgatc agagacattc cagatgctaa agaaagtggg 1320
ctgcttcact tgtgtgaatt tattgaggac tgtgaattta catacctttc tactcagata 1380
ctacattttc ttggaaatga aggacctaag acatcagacc ccagtaagta catacgatat 1440
atatacaata gagttatact tgagaatgca acagttcggg ccagtgcagt gagcacctta 1500
gctaagtttg gtgccttggt tgattcattg aagccccgta tatttgtgct attgaaacgt 1560
tgcctattcg acggtgatga tgaggttcgc gatagggcaa cactgtattt gaataccctt 1620
ggaggtgatg gtgcagttgt tgaaactgat gatgaggtga aagagttcct attcgggtca 1680
ctcggtgtcc ctctaaccaa tctggagaca agtttaaaga actatgagcc atcagaggag 1740
gcgtttgata ttttttctgt tcccaaggaa gttaaatctc agcctttggc agagaagaaa 1800
gcaccgggta aaaagccaac tggtttgggt gctccacctg tcggccccac ctctactgtt 1860
gattcatatg aaagattact gtcctctatc ccagaattcg ctagctatgg gaagcttttc 1920
aagtcatcgg cgccagtgga gctcacagaa gctgaaacag agtatgcagt taatgtcgtg 1980
aagcacattt ttgatagtca tgtagtgttc cagtacaact gcaccaatac cattcctgag 2040
caattgttgg aaaatggcag acatttgtgg cttttgagaa aacctgaagg agtccctgct 2100
gttgggaaat tctcgaacac actaagattc attgttaaag aggttgatcc aaccactggt 2160
gaggctgaag atgatggtgt tgaagatgaa taccaactag aagaccttga ggttgtcact 2220
gcagattaca tgctgaaatt gggagtctcc aattttagga atgcatggga gagcttggga 2280
ccagattgtg aacgcggcac tgaggtagtc ccaagcaact caagatcgca cacatgttta 2340
ttatctggtg tatacattgg cagcgtaaag gtacttgttc ggttatcatt tggattggat 2400
ggggcaaagg aggttgcaat gaagctggct gttaggtcag aagatatatc tgtaagtgat 2460
gcaattcatg aagttgttgc aagcggctag 2490

<210> SEQ ID NO 47
<211> LENGTH: 1701
<212> TYPE: DNA
<213> ORGANISM: Nicotiana tabacum

<400> SEQUENCE: 47
atgaaaatga ggggctattc attctttact gctactctca ttcttgttgc tgtttctatt 60
tttcttagct caatccatac tgatgcttta ccaagagata ctttcaagtc tattttaggg 120
gagggaaatc tggaatcatg gaagaatgga gtattggact cagcaggtat ggcacaagcg 180
ccaggtcctg ccgatgggca tgttggcacg cttgtgctag cgggaaacag gacgaggaga 240
ccggactttc tttctggttt ccacaaatac agaggtggat gggatattgc caataaacac 300
tactgggctt ctgttggttt tacaggcctt gctggtatca tacttgctct gctttggttt 360
atttcatttg gcttggctct cgtcgtgcat tattgctgcg gatggaaatt caatatcaga 420
ggcagagaat ggcatttttc acagaatatt tgcctgggcg tgcttattgt cttgacatgc 480
gctgcagcga ttggatgcgt cctactttct gttggacaag atgactttca tgctgaagca 540
ttggacactt taaaatatgt tgtaaatcag tcagattata ctgtgcagac attgagaaat 600
gtaacgcaat acttgttact cgcaaaaact gtaaatgtgg cccagatttt cctcccttca 660
gatgtaaaag atgatatcga tcacctaaat ggcgatctag attctgcagc ggataaactt 720
gaggataaaa caaatgaaaa ctcaggaaag atacgaaggg tcttcaatgc tgtgcgttca 780
gctttgatca ctattgccat cgtcatgctc ctcatctcta ttcttggtct ttgcctctct 840
atccttggcc atcaacacgc aattcacata tttatcatta gtggatggtt actggtggca 900
gttacattcg ttctctatgg agtttttgtc atcataaaca gtgcaatttc agatacttgt 960
atggcgatgg gagagtgggt ggacaatccg catgctgaaa gtgctcttag caacatcctt 1020
ccatgtgttg acccgagaac tacaaaccgg acgctgttca agagcaaaca agtcactgtt 1080
gatcttgtaa atattgtcaa cggatttatc gacacatatg caaattccaa tccatctaat 1140
catgccaatt caaattacta taatcagtca ggacccgtta tgccacatct ctgctatcca 1200
tatgactccc aattgcaaga tcttccgtgc cctgctgatc aagtttctat ggcaaattct 1260
tcaatggttt ggcagaactt tacttgcaac gtatctgcag ctgcaatatg cactagtgtc 1320
gggaggctga ctcctgacat gtacggacag ttggtggcga cggtcaacat tagctatgca 1380
cttgaacatt atgcaccacc gttgcttaat ctccagaact gtgatttcgt tcgtgataca 1440
tttaggaaca tcacggtcaa ccactgccct ccgttggaac accatcttcg ggttgttaat 1500
gcaggattag ctgtcatatc agtcggagtc atgctaagtc tcgcattgtg gatagtatat 1560
gcaaaccgcc cccaaaggga ggaagtgttt gcgaagctct cttcgcgaat aaagagcagc 1620
tgtaacggca agaatattag ctgcagtaat agtaatattg atttgtcatc aagaggtaca 1680
actccaaaga ctggagtgta g 1701

<210> SEQ ID NO 48
<211> LENGTH: 843
<212> TYPE: DNA
<213> ORGANISM: Nicotiana tabacum

<400> SEQUENCE: 48
atgttggacg cgtcagcagt agcatatatt cagattgcta gcattgccat agcagaccag 60
gttgcacgtg gtcagatcga actagcaaaa aatgtaagac agaggctgac atctcccagt 120
gttgctgctc caccattgag tactggaaag caaaagggcg gcagcagctc ttgctgcaaa 180
cttgctgctt caacatcttc tgctcaaatg ttgacctctg ttctttcgtc tcttgttgct 240
gaagaagctg cgtcactgag cagtggattg aaatcagctg gtttttcttc tagcttacct 300
tttgcatctc cagagaaacg gctcaagtta gacaagccaa tgactttttc tgatatgaac 360
agttccgaag gggggtaattc cacttacttc acttcatcac agcaaccgat tactagcatt 420
cctcttgccc cttcctcagg cttacaatcg tcaaaccaga tacaagctcc gtttccacca 480
cctccacctc caccaccacc tttacctcca gcaaattccc ctggaagtca gttaggtcag 540
tctgcagcta tgatgatggg gatgatgccc tatggatata gtgccggcag ccttcagcca 600
cctcaaattg caatgggact gaggccacct ccaccactac cccagcaagc acaacagctg 660
catctccaga ctcagcagcc acaatctcaa cagcagcctg ccaatggtgg attttatcgt 720
cctctggtat tggattctat ggacagaccc atcagcagac aacaccagca gcacccaggc 780
agtaaatccc tttggaatag ggagcacatg ttacattgta cattaatagt aaaagtagac 840
tag 843

<210> SEQ ID NO 49
<211> LENGTH: 678
<212> TYPE: DNA
<213> ORGANISM: Nicotiana tabacum

<400> SEQUENCE: 49
atggaatccg atgctcattt tctagcaaag gaagacggga tcatagcagg aattgcactt 60
gctgagatga tattcgcgga agttgatcct tcattaaagg aaatggcaga tgctgcacac 120
cctgcttaca tcttggagac taggaaaact gctcctggat tacgtttggt ggataaatgg 180
gcggtattga tcggtggggg gaagaatcac agaatgggct tatttgatat ggtaatgata 240
aaagacaatc acatatctgc tgctggaggt gtcggcaaag ctctaaaatc tgtggatcag 300
tatttggagc aaaataaact tcaaataggg gttgaggttg aaaccaggac aattgaagaa 360
gtacgtgagg ttctagacta tgcatctcaa acaaagactt cgttgactag gataatgctg 420
gacaatatgg ttgttccatt atctaacgga gatattgatg tatccatgct taaggaggct 480
gtagaattga tcaatgggag gtttgatacg gaggcttcag gaaatgttac ccttgaaaca 540
gtacacaaga ttggacaaac tggtgttacc tacatttcta gtggtgccct gacgcattcc 600
gtgaaagcac ttgacatttc cctgaagatc gatacagagc tcgcccttga agttggaagg 660
cgtacaaaac gagcatga 678

<210> SEQ ID NO 50
<211> LENGTH: 2154
<212> TYPE: DNA
<213> ORGANISM: Nicotiana tabacum

<400> SEQUENCE: 50
atgacggaag tggcgacgag caacgttgtg cacgacgtct tagggcgacg agctgaagat 60
gtagatcagc cgattattga ctatataatc aatgttctag ccgatgaaga tttcgatttt 120
ggacttgacg gtgaaggtgc ttttgaagcc ctcggcgaat tactcgtaga ttctggttgc 180
gttgctgact tccccgaatg tcgtgcggtt tgtagcaagt tgtctgagaa gttagagaag 240
catggattgg ttaaacctca accaactgtg agaagcttaa aaatgccgct gagaatgtat 300
gatggaatgg atgaagagga agctccaaag aataaaaagc cagaaccagt tgatggtcct 360
ttgctcacag aacgtgacaa gattaagatc gaaaggagga agaggaaaga tgaacgcctg 420
agagaggcag aataccaagc acacttgaaa gaagtggaag aagtgaaagc tggtatgccg 480
ttagtgtgtg tgaatcatga tggtcagggt gatggaccaa ctgttaagga tatccgtatg 540
gaaaatttca atatatctgt tgctggtcgt gaccttattg tcgatggttc tgttacgctt 600
tcttttggaa gacactatgg ccttattgga agaaacggta cggggaaaac aactctccta 660
agacacatgg ctatgcacgc tattgatggt attcccaaga actgccagat attgcatgtt 720
gagcaagaag tggttggtga tgatacctca gttttgcaat gtattcttaa cactgatatg 780
gagagaaccc aacttctgga agaagagggt cgtctgcttg aattacagag agaaattgac 840
ctagaaggcg aagctggaaa gagtgataag ttgaatgggg agatcgacaa aaatgccctc 900
gcgaaaaggc ttgaagagat atacaaaaga cttgatttca ttgatgctta ctcggctgag 960
tcacgtgcag caactatact ttcgggtttg agcttcacta cagaaatgca aaagagagca 1020
actaaaacat tttctggagg atggagaatg agaatagctc ttgctcgggc gttgttcatt 1080
gaacctgatc tattgttgct tgatgaaccc acgaatcatc ttgatctaca tgctgtctta 1140
tggctggaaa cttacctggt gaagtggccg aagacattta tagttgtctc tcatgctaga 1200
gagttcttga atactgtagt cacagacatt atccatctac aaaatcagaa attgagtacc 1260
tacaaaggag actatgatac attcgaaagg acacgagatg aacaagttaa gaatcaacag 1320
aaggcgttcg aggcgaatga acgtacaagg gcccacatgc agacctttat tgataagttc 1380
cggtacaatg caaagcgtgc atctcttgtt caatctagaa ttaaggcact ggaacgaatt 1440
ggtcgtgtgg atgaagtcat caatgatcct gactacaagt ttgagttccc ttctcctgat 1500
gatagacctg gtgctcctat tataagcttc agtgatgcat cctttggata tcctgggggc 1560
ccattattgt tcaaaaattt gaattttgga atagatctgg atagccgagt agcaatggtt 1620
ggtcctaatg gtattggaaa gtcaacaata cttaagctta tttctgggga gcttcaacca 1680

```
acttcaggaa ctgttttccg ctctgctaag gtccgaattg ctgtatttag tcagcatcat   1740

gttgatgggc tggatctgtc ctcaaatccc ctcttataca tgatgcgttg ctttccagga   1800

gtgcctgaac aaaaattacg tggtcatcta ggttcatttg gtatcactgg aaatcttgct   1860

cttcagccca tgtacacttt gtctggtggc caaaaaagca gagttgcatt tgcaaagata   1920

accttcaaga agcctcacat attgcttctt gatgagccat caaatcactt ggatcttgac   1980

gctgtggagg ctctgataca aggtcttgtc ttgttccaag gaggcgtact gatggtcagt   2040

cacgatgaac atttaatatc tggtagtgtt gatcaactct gggccgtctc tgagggcagg   2100

gtgacgcctt tcgacgggac attccaggat tacaagaaaa ttctgcaatc ataa         2154
```

```
<210> SEQ ID NO 51
<211> LENGTH: 1155
<212> TYPE: DNA
<213> ORGANISM: Nicotiana tabacum

<400> SEQUENCE: 51

atgggtgctc agatatccgt atctaagctt gccaatttgt cctttgtccc cagaatacgc     60

gttcctgtgc ctaacataag tgttccaagt cccagcatca gttctggttt tgtttcaaat    120

ctttcgtgtt ctgccatagg catttcttcc gtgttggtca atttttatca atcagcatca    180

ttggctaagt cggcaaatcc atcaacatat acttatacag ttccttcttc gccttcagag    240

gtgttgtata gatggcattt accagagcca aatgtcgttg atatatcagg gaattatgat    300

tgttcatcag taaagtctag gactgtggta gtactgttgg gatggttagg tgcaaaaacag   360

aagcatctaa agagatatgc agagtggtat gcctcagcag gatatcatgt cattacattt    420

actttcccaa tgtctgagat tcttagctat caagtcgggg gaaaggcaga gcaggatata    480

gaactgcttg tgaaccatct tgttgattgg ttggaagaag agcatggaaa gaacttggtc    540

ttccacactt tcagtaacac gggatggtta acttatggtg tcattttgga gaagtttcag    600

aaacaagatc ctgttttaat gacaaggatc aaaggttgta ttgttgattc tgctcctgta    660

gctgctcccg atccacaggt atgggcttct ggattctctg ctgccttttt gaagaagaat    720

agtgttgcaa ccaaacacat catgactata aacaacaaag atgcagatgt gacaatagaa    780

accaaaactt cttcggatgc tacacctgca gtaactgaag cagctttgct agtagtactg    840

gagaagttct ttgaggtggt tttgagcctt cccgccgtaa ataggagact ttctgatgtt    900

ctagatctat tgacatccca gcaaccaagt tgcccacaat tgtacatata cagcagtgca    960

gacagagtga ttcctgcgat ttctgttgag tcctttgtag aggagcaacg aagaattggt   1020

cgcaacgtta gagcttgcaa cttcatttct acacctcatg ttgatcattt cagaaatgac   1080

ccagaattat atactttaca gcttacccaa tttcttgagg actccgttct aagctcttgc   1140

aaacagtctt cctga                                                    1155
```

```
<210> SEQ ID NO 52
<211> LENGTH: 1644
<212> TYPE: DNA
<213> ORGANISM: Nicotiana tabacum

<400> SEQUENCE: 52

atgggaggtg cagaggatgc tgaaccacca tccaaacgtg tgaaagtatc ctctgggaaa     60

ccaggagatc tttcaaacgg cacatttcct agagatcctg caagttgctc attgaatgac    120

ttgatggctc gcccccctggt ttgtcaaggg gacgatgagg ttgttggtac aaaaggggtc   180

atcaagaaag ttgaatttgt gcgaatttta gctgaggcat tatattctct tggttataac    240
```

aaaactgggg cacatctaga agaagagtct gggatacctt tgcaatctgc tgtggtaaag 300
ttatttatgc agcaagtcct tgatggtaaa tgggatgaaa gtgtagccac attacgtaaa 360
atcggtctag tggatgaaaa ggttgttcaa ttggcatcat ttctgatatt ggaacagaag 420
ttttttgaac tgttggatga aaaaaaagtc atggatgctt tgaagacatt gagcactgag 480
attggacctc tttgcataaa cactgataga gtccgtgagc tttctttgtg cattttatca 540
cctttgcagc aggttcgtgc tgtggtgtca ggtcaagttg ttgtgagagc aaagccacga 600
agaaagctac tagaggaatt gcaaaaattg cttcccccaa cagttataat tcctgaacaa 660
agattgatac gtcttgttga acaggctctt gacttgcaac tagatgcttg taggtttcac 720
aactctttgg taggtgagat gtctttgctc actgatcatc agtgcggaag ggatcaaatt 780
ccttctcaaa ctttgcaggt gaaattggat ggtttgttct gcatgaagca ccagtttttct 840 ggtcaccaga aacctgtctc ctatatgtca tggagtcctg atgaccatca gcttctcact 900
tgtggagtag aggaagttgt cagacggtgg gatattgaat caggtgaatg tacacatatt 960
tatgagaaaa atggtcttgg tctgatctca tgtggatggg ctcctgatgg caaaaggata 1020
ttatgcggtg ttacggacaa gagcattagc atgtgggatc tggaagggaa agagttggag 1080
tgttggaaag gccatcgaac tattagaata tctgacttgg ggataactag tgatgggcag 1140
catatagtct ctgtttgcaa agataatatg atattactat ttggatggga atcaaaagca 1200
gagaaagtaa ttcaggagga tcaaacaata acttcatttg tattgtccat ggacagtaag 1260
tatttattgg ttagtctttg gaatcaagaa atccatctgt ggaatataga gggaactgta 1320
aagctcatat ccaaatataa agggcataaa cgttcacgct ttgttgtaag gtcttgcttt 1380
ggcggactgg gtcaagcatt tgttgccagt ggaagtgagg actcacaggt ttatatatgg 1440
catagaagct caggagaact cattgagaca ttggctggac attctggtac agtaaactgt 1500
gttagctgga acccagcaaa tcctcatatg ttggcatctg caagtgatga tcatactatt 1560
cgcatatggg gcatgaatca agtaaacatg aaacactatg acacagttag taatggcgtg 1620
cattactgca atggcggaac ttag 1644

<210> SEQ ID NO 53
<211> LENGTH: 1764
<212> TYPE: DNA
<213> ORGANISM: Nicotiana tabacum

<400> SEQUENCE: 53
atggcaatgg tagatgagcc attgtacccc atagccgtgt taatagatga acttaagaac 60
gatgatatac aattacggtt gaattcaatt aggaggttat cgactattgc acgtgccctt 120
ggtgaggaaa gaactcgaaa ggaattgatc cctttttga gtgaaaacaa tgatgatgat 180
gatgaggtgt tattggcaat ggctgaagag cttggtgtgt ttatccctta tgttggaggt 240
gtagagcatg ctcatgtttt gctcccgccg ttggagacgc tttgtactgt tgaggagacc 300
tgtgtgaggg ataaagctgt tgaatcgttg tgtaggattg gatctcagat gagggagagt 360
gatttggttg attggttcgt ccctcttgtg aagaggctgg cagctggtga atggttcaca 420
gctagagttt ctgcctgtgg actctttcat attgcttact caagtgcccc agagatgttg 480
aaggcagaac ttcggtctat ttacagtcaa ttgtgtcaag acgacatgcc tatggtgcga 540
agatcagctg ccacaaactt ggggaagttt gctgctactg ttgaatctac ttacctcaag 600
agtgacatca tgtcaatatt tgatgatctt acacaggatg atcaggattc tgtacgctta 660

```
ttagctgttg agggctgtgc tgcacttggc aagctgttgg agccccagga ttgtgttgca    720

cacatcctgc ctgtcattgt caacttctct caggacaagt cttggcgcgt ccgctacatg    780

gttgctaacc agttgtacga actatgtgaa gctgtagggc ctgagcccac taggacggat    840

ttggtgcctg cctatgtccg tttgcttcga gataatgaag ctgaagttcg catagctgct    900

gcagggaaag tcaccaaatt ctgtcggatt cttagtcccg agcttgctat tcagcatatt    960

cttccctgtg tgaaggaatt atcatcagac tcttcacagc atgtcagatc tgctttggct   1020

tctgttataa tggggatggc tcctgttttg ggaaaggatg caaccattga gcatcttctt   1080

ccaatatttc tttcccttct gaaggacgag tttcctgatg tgcgcctgaa catcattagc   1140

aagcttgatc aagtcaatca ggtgattgga attgatttat tatcccaatc tttgttgcca   1200

gctattgttg agctagcaga ggacaggcat tggcgagtcc gtcttgcaat aatagaatac   1260

atacctctat tggcaagtca attgggcata ggatttttg atgataagct tggtgccctt   1320

tgtatgcaat ggttacagga caaggtttat tcaatcagag atgctgctgc taataaccta   1380

aagcgtcttg cagaagaatt tggtccagag tgggcaatgc agcatataat tcctcaggtc   1440

ttggatatga ctaccagtcc acattatttg tatagaatga caattcttag agcaatttca   1500

ttgcttgcac ctgtaatggg ctctgaaata acttgttcta aattgctgcc tgtggttatt   1560

actgcaacaa aggatagagt gcccaacatt aaatttaatg tggcaaaggt gttgcaatcc   1620

cttataccta ttgttgacca ctcggtggtg gagaaaacca ttcgccctag tttagtagag   1680

ctagctgaag accctgatgt tgatgttcgc ttttatgcca atcaagcact tcagtcaatt   1740

gataacgtca tgatgtcagg ctag                                          1764
```

<210> SEQ ID NO 54
<211> LENGTH: 1866
<212> TYPE: DNA
<213> ORGANISM: Nicotiana tabacum

<400> SEQUENCE: 54

```
atgggattca tcgaatcatg ttcccagact gcagaaatgg aaatcaggaa gtgctcgcct     60

tttctggaaa gtgaattgtt gtccggtaat ggtgggttgc ccttgacaga gtggagaact    120

gttcccgaca tttggcggac ttcggcagag aagtttggtg accgtgtagc agttgtggac    180

ccatatcatg atcctcctac aaccatgact tataaacagc tttatcagga gattgtggat    240

ttctctgaag gtttgagagt tgttgggcta aacccaaatg agaagattgc gctttttgct    300

gataattcat gtcgatggct tgttgcagat caaggtacga tggcgagtgg ggctatcaac    360

gttgtgaggg gttcaaggtc atcaaatcaa gagctattgc aattatacag ccactctgaa    420

agtgtcgctc ttgctattga caatcctgag atgtacaacc ggatttcaga cacctttggt    480

tcccacacag ctgtacgatt tgctatttta ctttggggcg agaaatcaag ccttggaaga    540

gaagccgtgc agggatatcc tgtatatact tataaggaga ttatagaatt gggtcacaag    600

agtcgtgtgg atctgcttga ttctgaagat gccaggaaac aatattcatt tgaggcaatc    660

aactctgatg atgtggctac aattgtctat accagtggaa ccaccggtaa tccaaaaggt    720

gtcatgctta cgcataaaaa tctgcttcac cagattttga atctggggga gattgtacct    780

gctgtacctg gggacagatt tctaagcatg cttccgcctt ggcatgcata tgagcgtgct    840

tgtgaatatt tcatattcac acatggaaca gagcaagtgt acacaactgt gaaaaatttg    900

aagccacatt acttgataag tgttccttta gtttatgaga cattatacag tggaattcta    960

aagcagatca attcaaactc tgctgctagt aaactcattg ccctattatt tttaaggatc   1020
```

agtatgactt acatggaggc aaaaaggatt tacgaggctg gcgtaagtgg aggtggtagt 1080
ctttcttcac atgttgacaa gttctttgag gcaattggca taaagattca gaatggatat 1140
ggtctgactg agtcatctcc cgtgatttct gcccgtcatc ttgcgtgtaa tgtacttggc 1200
tcagttgggc atcccattcg gcatgtagaa gtaaaaattg taaatgctga aacagatgag 1260
gtccttcctc ctggctcaag gggcattgtc aaagccagag ggccactagt aatgaagggc 1320
tactataaga atccgttggc aacaaaacac gctattgatg agaatggatg gctgaacact 1380
ggtgatcttg gttggattgc gcctgatcat tctgtagggc gaagtcgtaa aagtgggggt 1440
gtaatagtcc ttgaaggccg tgcaaaggat accatagtcc tttcaactgg cgagaatgtt 1500
gaaccatcag agattgaaga agctgcaatg ggaagtagtc tgatccagca gattgttgtc 1560
attggccagg atcaacgacg tcttggagct ataattgtac caaataagga ggaggttctg 1620
ttagcagcta aaaaatcagc tattgtggat tctgaaacca ctgaagttag caaggaaaaa 1680
gcagttggca tattatatga ggagttaaga aaatggactt caggttgctc atttcaagtt 1740
ggacctatcc ttattgtcga tgaacctttc acgattgata gtggcttact aacaccaacc 1800
atgaaaatca agagagacaa aattgcagct ctatacaaag agcaaattga gaacttgtac 1860
aaatga 1866

<210> SEQ ID NO 55
<211> LENGTH: 2610
<212> TYPE: DNA
<213> ORGANISM: Nicotiana tabacum

<400> SEQUENCE: 55
atgggtggtg acgaaactaa aaagaccact ataatggtgc tcaaggttga tcttcagtgc 60
tccagctgct ataagaaggt caaaaaagtt ctctgtaaat tccctcgatg tggagtaatt 120
aagagcattg aaatcaaaga acctccaaag cccaaagctc ctgaaaagcc caaggagcct 180
gtgaaaccaa aagaacccga gaagcccaaa caaccggaga agcccaaaga gcccgaaaag 240
cctaaacaac ctgagaagac tacggttgtc gtcattgaaa agcccaagga gcccgagaag 300
cctaaggcac cggaaaagtc aaaagagccc gagaagccca aagaaccaga aaagccgaaa 360
gaagttgaaa agcccaagcc caaagagccc gaaaagccca aagaagctcc taaacctaat 420
ccagtggctc caccatcaca accaccacca ccgccagcac cagagccaat aatggttcaa 480
caataccctc agccaccact aggatattgt tgtggacaat gctacgaggg tcatatcggg 540
ggcccatgtt atcaatggta cggaagacct gtccttccgg ccccatgtta cgataactat 600
gggtataact atgggcctgg gcctgggcct gggccgtatg gctacggaag gggttgttat 660
gtgagtagat gtgaccaata ctttagtgaa gaaaatgcca caggatgctc aattataaag 720
tgggagccaa atattgtggc tagcaaagct aaagaagtct actccgccgt ttgggttcgc 780
ctcctccaat tacccacaga attctatgat agaattgtcc ttagtagaat tggaaactca 840
attggccgac tactacgcat agatgcttgt acaagttcaa cgcttagaag gaggtacgcg 900
cgactgtgtg tgcaagtgca aatggaccaa ctagtccaaa caacaatcca gattggctcc 960
catatacaac aactggtata tgaaggagaa aaatttcttt gtaaggcctg tgggcgactg 1020
ggaaacacga catcaacatg ctcccacact ctacttgact tccaaaagca acaacaagaa 1080
gagccatgtc ctaactcgac tggcttcata ggcaaggaaa ggcaattgaa gagcaatgac 1140
aaaccgtctc cttccccaaa ggtaacaagc caaaaagagg cacaaccaat ggatctcaaa 1200

```
ataaaactca agcgacacct ccaggtatca atgtcaatat ttttgatgcg gcatcagccc   1260
atccttacat ctaataaatt cgaatcactt cttaatgata gcagtattac attcccggaa   1320
ataattgaat cccaaatgga attggatggg caaaactcta acctctcccc agactctaaa   1380
ctgtcgttct ctccaagaaa ccattcctct tccctgctcc ctcctctctc tccacgtggc   1440
caaaaggcta catgcaactc caataaacca cacaaaacag cgggcccatc cactaatcct   1500
ctaccatgca cgccacttcc cacactaatg acacctatta ccactgaaaa ccctataact   1560
gacttgtcac ttaccacctg ccaattggcc atgcaactca actctccaat actggctagt   1620
ctaaggttgc acgttaaaaa tcgaaccatg cacacaaaat ttctactaac agattttcaa   1680
tcattacctc acgaaaacca atccccctca tccccttcat cttctcctac acactatgaa   1740
tctactccac tcctcccatc aaacgaaaat ccctctaaaa taactctcac accaccatcg   1800
ttcctcaata ctgtccagaa tgaaccaccc actcctggat acaaaccttc cgatctacat   1860
caccaatgcc ctctcactgg accaccaacc aacgccatgg ttggaacaag gacttcaggt   1920
ccaagtggct ttcttcactc tcaatatcca aaatcacgaa gtcctgtttg ttctacagaa   1980
cccacaggtc ctagctcaat taatctcgga gggtatgagg ctagcaatgt cgaactacat   2040
caaccacctt tagttgacaa atgttctaga gcccatagcc ccaccctagc accagccctt   2100
cttcacaaca tgcaagccca ctggaatcca ccacatcact tcaatcccct acaaaacatg   2160
caactttttt accaacttcc cttttttgct ccacaggatc aaaacacccc acccttgatc   2220
catgcatggc aacccatccc tcaacactac ccagctccga tggattttca ccacacacat   2280
tcccatcccc atcacagtgc acctgtacca ggagagcaag aaatggaaac ccaaaatcaa   2340
accatcccac cactaaatat aacatcgtac acagaaaatt caaacctaca cgaggtcaaa   2400
atcttgttat tccaagcgat ggaagaaaag aagtatgtcc gcaaatgtcc cacagagcta   2460
tacaaatgct ccctcgacat aaggccccca ctcaatgcag cagtaggcaa tttcgccgta   2520
atactcagtc catcattgaa tggtcttcct gttccaccaa tggggagcca gttcaatgtc   2580
accccccagc caacacccat caatgactag                                    2610
```

<210> SEQ ID NO 56
<211> LENGTH: 1110
<212> TYPE: DNA
<213> ORGANISM: Nicotiana tabacum

<400> SEQUENCE: 56

```
atgcatatat tgtatacttg tccgctgatt ctgtttatgg ctttactctt tgcttatgct     60
gctgctactg ctgctgattt agagaccaat ggagctgaaa aggcgggtgc ggatgcagga    120
attttgagta gtaatagcag tgtgaatgag aatttagacc tgataaatat gaatagaaaa    180
aaggatggtc atttggataa cgatagttcg aatgttgggg atcaaaacaa gtccaatgat    240
agtagtgcga aaaagggtga cgacagagaa gggttgaaag aagctgaggt ggaaaagaaa    300
agaattgata gtggttctaa gagagatgac aggaaggagg agacgaaaga agctgaacag    360
caagacaaag caaaagatat tagttccgag aagcagggtg agatggaaaa gattctgccg    420
gatggaattc agtcgagaga ggagattttg cctacaagaa aggagagttt ccatggtgaa    480
gaatgcgatt catcttatag ttgcacgata gaggaaaaag cagtggttgc atgtcttaga    540
gttccgggca atgaatctcc agacctttca cttttggttc aaaacaatgg aaaaggaact    600
gtcaatattt tgattaaggc tcctgagttt gtacaactgg agaaagagaa gattgaactg    660
caaggaaagg aaaatcagag gatgaaggtt tctataagga atgcaggaaa tgacaacaat    720
```

atcattctaa aggccgggga tggccaatgc actcttgatt tcaggggtct gattgacaat 780
gctgataaaa catctcaatt caagtatggt ttcctatctt ttgcaataat gtgtttggct 840
gctattgcat tagtggccac agtcttgatg tactttaaac ggaggcttct agtaagtagc 900
ggccacaagt atcaaaagtt ggacatggat ttaccagttt ccagtggcag aaagacggag 960
acactctcaa ctgatggatg ggacaatagc tgggatgacg attgggatga tgaggaggcg 1020
cccaaagcac catccgtgcc agtcactcct tccttctcgt ctaaaagcat tacctcacga 1080
cggtctagta aggaaagctg gaaagactag 1110

<210> SEQ ID NO 57
<211> LENGTH: 314
<212> TYPE: DNA
<213> ORGANISM: Nicotiana tabacum

<400> SEQUENCE: 57
cttttctcaa gaaacatatt tattaaataa tttctttttc gttacattca tttttataat 60
ctattccttt atgttctctt agagaaaagt atactattct aaaatacatt tatcccaaaa 120
aatagaaaaa tgaatgtagt attcatktac tcaagcgtgt tatattttgt caataaaatg 180
tctcccaaaa tattcaaatc ttgttcaata ccacatttcg tgataatcct tcctgtatat 240
taattaaaat ctattttacc ccagaattgt actaaaaaag tcagctaggt gtactaccta 300
tttcgcattc atgc 314

<210> SEQ ID NO 58
<211> LENGTH: 160
<212> TYPE: DNA
<213> ORGANISM: Nicotiana tabacum

<400> SEQUENCE: 58
agcccgattt gtcgtgagga tttgatatgt ctccctccaa aggtagcagc tagtttrgga 60
aatatcggtc ctcttgtgat ctgcaccaaa gtgagcaaca atattgcttt attagayccg 120
tttactctga ggcattgttt cttggatgct gatcagtact 160

<210> SEQ ID NO 59
<211> LENGTH: 322
<212> TYPE: DNA
<213> ORGANISM: Nicotiana tabacum

<400> SEQUENCE: 59
aaaagtgcga tctaaaacga tgcagtaacc aaaccgaagg ggcctgttgc ccatatccac 60
caagtttcag gacgtgttta acatttagct aacaaattct ctcatgagat ttaactcgag 120
ttagagcttc aacctgcatg ggcataagtg tacaatacat crggtatgtt actggtgacc 180
aagagtttaa gactgaaaaa ttggagggcg acaataagag tactatacct tttgcaggca 240
ccacaaccac aaatttcaga catgtcatga aagatgcgta gcctcctact gtggcagagg 300
aaagcatgca tggttaattt gg 322

<210> SEQ ID NO 60
<211> LENGTH: 71
<212> TYPE: DNA
<213> ORGANISM: Nicotiana tabacum

<400> SEQUENCE: 60
cataaatttt gtccaacatg gaagtatata ggtcamgttg tagttgattt caaacacttg 60
ttagaaaagt a 71

<210> SEQ ID NO 61
<211> LENGTH: 71
<212> TYPE: DNA
<213> ORGANISM: Nicotiana tabacum

<400> SEQUENCE: 61
tttcccgctg gggatttcag ttgtattcct ctctgytgtt tctttacttc gggctcgact 60
tgtggtcttc c 71

<210> SEQ ID NO 62
<211> LENGTH: 71
<212> TYPE: DNA
<213> ORGANISM: Nicotiana tabacum

<400> SEQUENCE: 62
acagtaaatt ttctcactct tgattctgca tcaaayacac ttcttgtgct gttaagattc 60
ttcatagttg t 71

<210> SEQ ID NO 63
<211> LENGTH: 71
<212> TYPE: DNA
<213> ORGANISM: Nicotiana tabacum

<400> SEQUENCE: 63
cgcctgtgca taatgaggcg catatggtgg gtatgsttta ttttagaaag gaatatgaga 60
gttcatctgg a 71

<210> SEQ ID NO 64
<211> LENGTH: 71
<212> TYPE: DNA
<213> ORGANISM: Nicotiana tabacum

<400> SEQUENCE: 64
ttgtaattat tatgatagaa ttagtattgc tttatwtatt gtatttttat ccctttaaaa 60
gtcaactgct g 71

<210> SEQ ID NO 65
<211> LENGTH: 11801
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 65
tgagcgtcgc aaaggcgctc ggtcttgcct tgctcgtcgg tgatgtactt caccagctcc 60
gcgaagtcgc tcttcttgat ggagcgcatg gggacgtgct tggcaatcac gcgcaccccc 120
cggccgtttt agcggctaaa aaagtcatgg ctctgccctc gggcggacca cgcccatcat 180
gaccttgcca agctcgtcct gcttctcttc gatcttcgcc agcagggcga ggatcgtggc 240
atcaccgaac cgcgccgtgc gcgggtcgtc ggtgagccag agtttcagca ggccgcccag 300
gcggcccagg tcgccattga tgcgggccag ctcgcggacg tgctcatagt ccacgacgcc 360
cgtgattttg tagccctggc cgacggccag caggtaggcc gacaggctca tgccggccgc 420
cgccgccttt tcctcaatcg ctcttcgttc gtctggaagg cagtacacct tgataggtgg 480
gctgcccttc ctggttggct tggtttcatc agccatccgc ttgccctcat ctgttacgcc 540

-continued

```
ggcggtagcc ggccagcctc gcagagcagg attcccgttg agcaccgcca ggtgcgaata    600
agggacagtg aagaaggaac acccgctcgc gggtgggcct acttcaccta tcctgcccgg    660
ctgacgccgt tggatacacc aaggaaagtc tacacgaacc ctttggcaaa atcctgtata    720
tcgtgcgaaa aaggatggat ataccgaaaa aatcgctata atgaccccga agcagggtta    780
tgcagcggaa aagcgccacg cttcccgaag ggagaaaggc ggacaggtat ccggtaagcg    840
gcagggtcgg aacaggagag cgcacgaggg agcttccagg gggaaacgcc tggtatcttt    900
atagtcctgt cgggtttcgc cacctctgac ttgagcgtcg atttttgtga tgctcgtcag    960
gggggcggag cctatggaaa aacgccagca acgcggcctt tttacggttc ctggcctttt   1020
gctggccttt tgctcacatg ttctttcctg cgttatcccc tgattctgtg gataaccgta   1080
ttaccgcctt tgagtgagct gataccgctc gccgcagccg aacgaccgag cgcagcgagt   1140
cagtgagcga ggaagcggaa gagcgccaga aggccgccag agaggccgag cgcggccgtg   1200
aggcttggac gctagggcag ggcatgaaaa agcccgtagc gggctgctac gggcgtctga   1260
cgcggtggaa agggggaggg gatgttgtct acatggctct gctgtagtga gtgggttgcg   1320
ctccggcagc ggtcctgatc aatcgtcacc ctttctcggt ccttcaacgt tcctgacaac   1380
gagcctcctt ttcgccaatc catcgacaat caccgcgagt ccctgctcga acgctgcgtc   1440
cggaccggct tcgtcgaagg cgtctatcgc ggcccgcaac agcggcgaga gcggagcctg   1500
ttcaacggtg ccgccgcgct cgccggcatc gctgtcgccg gcctgctcct caagcacggc   1560
cccaacagtg aagtagctga ttgtcatcag cgcattgacg gcgtccccgg ccgaaaaacc   1620
cgcctcgcag aggaagcgaa gctgcgcgtc ggccgtttcc atctgcggtg cgcccggtcg   1680
cgtgccggca tggatgcgcg cgccatcgcg gtaggcgagc agcgcctgcc tgaagctgcg   1740
ggcattcccg atcagaaatg agcgccagtc gtcgtcggct ctcggcaccg aatgcgtatg   1800
attctccgcc agcatggctt cggccagtgc gtcgagcagc gcccgcttgt tcctgaagtg   1860
ccagtaaagc gccggctgct gaacccccaa ccgttccgcc agtttgcgtg tcgtcagacc   1920
gtctacgccg acctcgttca acaggtccag ggcggcacgg atcactgtat tcggctgcaa   1980
ctttgtcatg cttgacactt tatcactgat aaacataata tgtccaccaa cttatcagtg   2040
ataaagaatc cgcgcgttca atcggaccag cggaggctgg tccggaggcc agacgtgaaa   2100
cccaacatac ccctgatcgt aattctgagc actgtcgcgc tcgacgctgt cggcatcggc   2160
ctgattatgc cggtgctgcc gggcctcctg cgcgatctgg ttcactcgaa cgacgtcacc   2220
gcccactatg gcattctgct ggcgctgtat gcgttggtgc aatttgcctg cgcacctgtg   2280
ctgggcgcgc tgtcggatcg tttcgggcgg cggccaatct tgctcgtctc gctggccggc   2340
gccagatctg ggaaccctg tggttggcat gcacatacaa atggacgaac ggataaacct    2400
tttcacgccc ttttaaatat ccgattattc taataaacgc tcttttctct taggtttacc   2460
cgccaatata tcctgtcaaa cactgatagt ttaaactgaa ggcgggaaac gaagcttcca   2520
gaaggtaatt atccaagatg tagcatcaag aatccaatgt ttacgggaaa aactatggaa   2580
gtattatgtg agctcagcaa gaagcagatc aatatgcggc acatatgcaa cctatgttca   2640
aaaatgaaga atgtacagat acaagatcct atactgccag aatacgaaga agaatacgta   2700
gaaattgaaa aagaagaacc aggcgaagaa aagaatcttg aagacgtaag cactgacgac   2760
aacaatgaaa agaagaagat aaggtcggtg attgtgaaag agacatagag gacacatgta   2820
aggtggaaaa tgtaagggcg gaaagtaacc ttatcacaaa ggaatcttat cccccactac   2880
ttatcctttt atatttttcc gtgtcatttt tgcccttgag ttttcctata taaggaacca   2940
```

agttcggcat ttgtgaaaac aagaaaaaat ttggtgtaag ctattttctt tgaagtactg 3000
aggatacaac ttcagagaaa tttgtaagtt tgtggatcct gcaggctagc gtgcactcta 3060
gactcgacga actgacgagc tcgaatttcc ccgatcgttc aaacatttgg caataaagtt 3120
tcttaagatt gaatcctgtt gccggtcttg cgatgattat catataattt ctgttgaatt 3180
acgttaagca tgtaataatt aacatgtaat gcatgacgtt atttatgaga tgggttttta 3240
tgattagagt cccgcaatta tacatttaat acgcgataga aaacaaaata tagcgcgcaa 3300
actatgataa attatcgcgc gcggtgtcat ctatgttact agatcgggaa ttcctcgagc 3360
aactattttt atgtatgcaa gagtcagcat atgtataatt gattcagaat cgttttgacg 3420
agttcggatg tagtagtagc cattatttaa tgtacatact aatcgtgaat agtgaatatg 3480
atgaaacatt gtatcttatt gtataaatat ccataaacac atcatgaaag acactttctt 3540
tcacggtctg aattaattat gatacaattc taatagaaaa cgaattaaat tacgttgaat 3600
tgtatgaaat ctaattgaac aagccaacca cgacgacgac taacgttgcc tggattgact 3660
cggtttaagt taaccactaa aaaaacggag ctgtcatgta acacgcggat cgagcaggtc 3720
acagtcatga agccatcaaa gcaaaagaac taatccaagg gctgagatga ttaattagtt 3780
taaaaattag ttaacacgag ggaaaaggct gtctgacagc caggtcacgt tatctttacc 3840
tgtggtcgaa atgattcgtg tctgtcgatt ttaattattt ttttgaaagg ccgaaaataa 3900
agttgtaaga gataaacccg cctatataaa ttcatatatt ttcctctccg ctttgaattg 3960
tctcgttgtc ctcctcactt tcatcagccg ttttgaatct ccggcgactt gacagagaag 4020
aacaaggaag aagactaaga gagaaagtaa gagataatcc aggagattca ttctccgttt 4080
tgaatcttcc tcaatctcat cttcttccgc tctttctttc caaggtaata ggaactttct 4140
ggatctactt tatttgctgg atctcgatct tgttttctca atttccttga gatctggaat 4200
tcgtttaatt tggatctgtg aacctccact aaatcttttg gttttactag aatcgatcta 4260
agttgaccga tcagttagct cgattatagc taccagaatt tggcttgacc ttgatggaga 4320
gatccatgtt catgttacct gggaaatgat ttgtatatgt gaattgaaat ctgaactgtt 4380
gaagttagat tgaatctgaa cactgtcaat gttagattga atctgaacac tgtttaaggt 4440
tagatgaagt ttgtgtatag attcttcgaa actttaggat ttgtagtgtc gtacgttgaa 4500
cagaaagcta tttctgattc aatcagggtt tatttgactg tattgaactc tttttgtgtg 4560
tttgcagctc ataaaaggta ccaaacaatg attgaacaag atggattgca cgcaggttct 4620
ccggccgctt gggtggagag gctattcggc tatgactggg cacaacagac aatcggctgc 4680
tctgatgccg ccgtgttccg gctgtcagcg caggggcgcc cggttctttt tgtcaagacc 4740
gacctgtccg gtgccctgaa tgaactgcag gacgaggcag cgcggctatc gtggctggcc 4800
acgacgggcg ttccttgcgc agctgtgctc gacgttgtca ctgaagcggg aagggactgg 4860
ctgctattgg gcgaagtgcc ggggcaggat ctcctgtcat ctcaccttgc tcctgccgag 4920
aaagtatcca tcatggctga tgcaatgcgg cggctgcata cgcttgatcc ggctacctgc 4980
ccattcgacc accaagcgaa acatcgcatc gagcgagcac gtactcggat ggaagccggt 5040
cttgtcgatc aggatgatct ggacgaagag catcaggggc tcgcgccagc cgaactgttc 5100
gccaggctca aggcgcgcat gcccgacggc gaggatctcg tcgtgaccca tggcgatgcc 5160
tgcttgccga atatcatggt ggaaaatggc cgcttttctg gattcatcga ctgtggccgg 5220
ctgggtgtgg cggaccgcta tcaggacata gcgttggcta cccgtgatat tgctgaagag 5280

```
cttggcggcg aatgggctga ccgcttcctc gtgctttacg gtatcgccgc tcccgattcg   5340
cagcgcatcg ccttctatcg ccttcttgac gagttctttt gagcgggact ctggcgatcg   5400
ccccgatcgt tcaaacattt ggcaataaag tttcttaaga ttgaatcctg ttgccggtct   5460
tgcgatgatt atcatataat ttctgttgaa ttacgttaag catgtaataa ttaacatgta   5520
atgcatgacg ttatttatga gatgggtttt tatgattaga gtcccgcaat tatacattta   5580
atacgcgata gaaaacaaaa tatagcgcgc aaactaggat aaattatcgc gcgcggtgtc   5640
atctatgtta ctagatcggg actagtttac accacaatat atcctgccac cagccagcca   5700
acagctcccc gaccggcagc tcggcacaaa atcaccactc gatacaggca gcccatcagt   5760
ccgggacggc gtcagcggga gagccgttgt aaggcggcag actttgctca tgttaccgat   5820
gctattcgga agaacggcaa ctaagctgcc gggtttgaaa cacggatgat ctcgcggagg   5880
gtagcatgtt gattgtaacg atgacagagc gttgctgcct gtgatcaaat atcatctccc   5940
tcgcagagat ccgaattatc agccttctta ttcatttctc gcttaaccgt gacaggctgt   6000
cgatcttgag aactatgccg acataatagg aaatcgctgg ataaagccgc tgaggaagct   6060
gagtggcgct atttctttag aagtgaacgt tgacgatatc aactccccta tccattgctc   6120
accgaatggt acaggtcggg gacccgaagt tccgactgtc ggcctgatgc atccccggct   6180
gatcgacccc agatctgggg ctgagaaagc ccagtaagga aacaactgta ggttcgagtc   6240
gcgagatccc ccggaaccaa aggaagtagg ttaaacccgc tccgatcagg ccgagccacg   6300
ccaggccgag aacattggtt cctgtaggca tcgggattgg cggatcaaac actaaagcta   6360
ctggaacgag cagaagtcct ccggccgcca gttgccaggc ggtaaaggtg agcagaggca   6420
cgggaggttg ccacttgcgg gtcagcacgg ttccgaacgc catggaaacc gccccccgcca   6480
ggcccgctgc gacgccgaca ggatctagcg ctgcgtttgg tgtcaacacc aacagcgcca   6540
cgcccgcagt tccgcaaata gcccccagga ccgccatcaa tcgtatcggg ctacctagca   6600
gagcggcaga gatgaacacg accatcagcg gctgcacagc gcctaccgtc gccgcgaccc   6660
cgcccggcag gcggtagacc gaaataaaca acaagctcca gaatagcgaa atattaagtg   6720
cgccgaggat gaagatgcgc atccaccaga ttcccgttgg aatctgtcgg acgatcatca   6780
cgagcaataa acccgccggc aacgcccgca gcagcatacc ggcgacccct cggcctcgct   6840
gttcgggctc cacgaaaacg ccggacagat gcgccttgtg agcgtccttg gggccgtcct   6900
cctgtttgaa gaccgacagc ccaatgatct cgccgtcgat gtaggcgccg aatgccacgg   6960
catctcgcaa ccgttcagcg aacgcctcca tgggcttttt ctcctcgtgc tcgtaaacgg   7020
acccgaacat ctctggagct ttcttcaggg ccgacaatcg gatctcgcgg aaatcctgca   7080
cgtcggccgc tccaagccgt cgaatctgag ccttaatcac aattgtcaat tttaatcctc   7140
tgtttatcgg cagttcgtag agcgcgccgt gcgtcccgag cgatactgag cgaagcaagt   7200
gcgtcgagca gtgcccgctt gttcctgaaa tgccagtaaa gcgctggctg ctgaaccccc   7260
agccggaact gaccccacaa ggccctagcg tttgcaatgc accaggtcat cattgaccca   7320
ggcgtgttcc accaggccgc tgcctcgcaa ctcttcgcag gcttcgccga cctgctcgcg   7380
ccacttcttc acgcgggtgg aatccgatcc gcacatgagg cggaaggttt ccagcttgag   7440
cgggtacggc tcccggtgcg agctgaaata gtcgaacatc cgtcgggccg tcggcgacag   7500
cttgcggtac ttctcccata tgaatttcgt gtagtggtcg ccagcaaaca gcacgacgat   7560
ttcctcgtcg atcaggacct ggcaacggga cgttttcttg ccacggtcca ggacgcggaa   7620
gcggtgcagc agcgacaccg attccaggtg cccaacgcgg tcggacgtga agcccatcgc   7680
```

cgtcgcctgt aggcgcgaca ggcattcctc ggccttcgtg taataccggc cattgatcga 7740
ccagcccagg tcctggcaaa gctcgtagaa cgtgaaggtg atcggctcgc cgataggggt 7800
gcgcttcgcg tactccaaca cctgctgcca caccagttcg tcatcgtcgg cccgcagctc 7860
gacgccggtg taggtgatct tcacgtcctt gttgacgtgg aaaatgacct tgttttgcag 7920
cgcctcgcgc gggatttct tgttgcgcgt ggtgaacagg gcagagcggg ccgtgtcgtt 7980
tggcatcgct cgcatcgtgt ccggccacgg cgcaatatcg aacaaggaaa gctgcatttc 8040
cttgatctgc tgcttcgtgt gtttcagcaa cgcggcctgc ttggcctcgc tgacctgttt 8100
tgccaggtcc tcgccggcgg tttttcgctt cttggtcgtc atagttcctc gcgtgtcgat 8160
ggtcatcgac ttcgccaaac ctgccgcctc ctgttcgaga cgacgcgaac gctccacggc 8220
ggccgatggc gcgggcaggg cagggggagc cagttgcacg ctgtcgcgct cgatcttggc 8280
cgtagcttgc tggaccatcg agccgacgga ctggaaggtt tcgcggggcg cacgcatgac 8340
ggtgcggctt gcgatggttt cggcatcctc ggcggaaaac cccgcgtcga tcagttcttg 8400
cctgtatgcc ttccggtcaa acgtccgatt cattcaccct ccttgcggga ttgccccgac 8460
tcacgccggg gcaatgtgcc cttattcctg atttgacccg cctggtgcct tggtgtccag 8520
ataatccacc ttatcggcaa tgaagtcggt cccgtagacc gtctggccgt ccttctcgta 8580
cttggtattc cgaatcttgc cctgcacgaa taccagcgac cccttgccca aatacttgcc 8640
gtgggcctcg gcctgagagc caaaacactt gatgcggaag aagtcggtgc gctcctgctt 8700
gtcgccggca tcgttgcgcc acatctaggt actaaaacaa ttcatccagt aaaatataat 8760
attttatttt ctcccaatca ggcttgatcc ccagtaagtc aaaaaatagc tcgacatact 8820
gttcttcccc gatatcctcc ctgatcgacc ggacgcagaa ggcaatgtca taccacttgt 8880
ccgccctgcc gcttctccca agatcaataa agccacttac tttgccatct ttcacaaaga 8940
tgttgctgtc tcccaggtcg ccgtgggaaa agacaagttc ctcttcgggc ttttccgtct 9000
ttaaaaaatc atacagctcg cgcggatctt taaatggagt gtcttcttcc cagttttcgc 9060
aatccacatc ggccagatcg ttattcagta agtaatccaa ttcggctaag cggctgtcta 9120
agctattcgt atagggacaa tccgatatgt cgatggagtg aaagagcctg atgcactccg 9180
catacagctc gataatcttt tcagggcttt gttcatcttc atactcttcc gagcaaagga 9240
cgccatcggc ctcactcatg agcagattgc tccagccatc atgccgttca aagtgcagga 9300
cctttggaac aggcagcttt ccttccagcc atagcatcat gtccttttcc cgttccacat 9360
cataggtggt ccctttatac cggctgtccg tcatttttaa atataggttt tcattttctc 9420
ccaccagctt atatacctta gcaggagaca ttccttccgt atcttttacg cagcggtatt 9480
tttcgatcag ttttttcaat tccggtgata ttctcatttt agccatttat tatttccttc 9540
ctcttttcta cagtatttaa agatacccca agaagctaat tataacaaga cgaactccaa 9600
ttcactgttc cttgcattct aaaaccttaa ataccagaaa acagcttttt caaagttgtt 9660
ttcaaagttg gcgtataaca tagtatcgac ggagccgatt ttgaaaccac aattatgggt 9720
gatgctgcca acttactgat ttagtgtatg atggtgtttt tgaggtgctc cagtggcttc 9780
tgtgtctatc agctgtccct cctgttcagc tactgacggg gtggtgcgta acggcaaaag 9840
caccgccgga catcagcgct atctctgctc tcactgccgt aaaacatggc aactgcagtt 9900
cacttacacc gcttctcaac ccggtacgca ccagaaaatc attgatatgg ccatgaatgg 9960
cgttggatgc cgggcaacag cccgcattat gggcgttggc ctcaacacga ttttacgtca 10020

-continued

```
cttaaaaaac tcaggccgca gtcggtaacc tcgcgcatac agccgggcag tgacgtcatc  10080
gtctgcgcgg aaatggacga acagtggggc tatgtcgggg ctaaatcgcg ccagcgctgg  10140
ctgttttacg cgtatgacag tctccggaag acggttgttg cgcacgtatt cggtgaacgc  10200
actatggcga cgctggggcg tcttatgagc ctgctgtcac cctttgacgt ggtgatatgg  10260
atgacggatg gctggccgct gtatgaatcc cgcctgaagg gaaagctgca cgtaatcagc  10320
aagcgatata cgcagcgaat tgagcggcat aacctgaatc tgaggcagca cctggcacgg  10380
ctgggacgga agtcgctgtc gttctcaaaa tcggtggagc tgcatgacaa agtcatcggg  10440
cattatctga acataaaaca ctatcaataa gttggagtca ttacccaatt atgatagaat  10500
ttacaagcta taaggttatt gtcctgggtt tcaagcatta gtccatgcaa gtttttatgc  10560
tttgcccatt ctatagatat attgataagc gcgctgccta tgccttgccc cctgaaatcc  10620
ttacatacgg cgatatcttc tatataaaag atatattatc ttatcagtat tgtcaatata  10680
ttcaaggcaa tctgcctcct catcctcttc atcctcttcg tcttggtagc tttttaaata  10740
tggcgcttca tagagtaatt ctgtaaaggt ccaattctcg ttttcatacc tcggtataat  10800
cttacctatc acctcaaatg gttcgctggg tttatcgcac ccccgaacac gagcacggca  10860
cccgcgacca ctatgccaag aatgcccaag gtaaaaattg ccggccccgc catgaagtcc  10920
gtgaatgccc cgacggccga agtgaagggc aggccgccac ccaggccgcc gccctcactg  10980
cccggcacct ggtcgctgaa tgtcgatgcc agcacctgcg gcacgtcaat gcttccgggc  11040
gtcgcgctcg ggctgatcgc ccatcccgtt actgccccga tcccggcaat ggcaaggact  11100
gccagcgctg ccatttttgg ggtgaggccg ttcgcggccg aggggcgcag cccctggggg  11160
gatgggaggc ccgcgttagc gggccgggag ggttcgagaa ggggggggcac ccccccttcgg  11220
cgtgcgcggt cacgcgcaca gggcgcagcc ctggttaaaa acaaggttta taaatattgg  11280
tttaaaagca ggttaaaaga caggttagcg gtggccgaaa aacgggcgga aacccttgca  11340
aatgctggat tttctgcctg tggacagccc ctcaaatgtc aataggtgcg cccctcatct  11400
gtcagcactc tgcccctcaa gtgtcaagga tcgcgcccct catctgtcag tagtcgcgcc  11460
cctcaagtgt caataccgca gggcacttat ccccaggctt gtccacatca tctgtgggaa  11520
actcgcgtaa aatcaggcgt tttcgccgat ttgcgaggct ggccagctcc acgtcgccgg  11580
ccgaaatcga gcctgcccct catctgtcaa cgccgcgccg ggtgagtcgg cccctcaagt  11640
gtcaacgtcc gcccctcatc tgtcagtgag ggccaagttt tccgcgaggt atccacaacg  11700
ccggcggccg cggtgtctcg cacacggctt cgacggcgtt tctggcgcgt ttgcagggcc  11760
atagacggcc gccagcccag cggcgagggc aaccagcccg g                      11801
```

TOBACCO PLANTS COMPRISING IMPROVED NITROGEN USE EFFICIENCY AND BURLEY CHARACTERISTICS AND PRODUCTS THEREOF

CROSS-REFERENCE TO RELATED APPLICATION AND INCORPORATION OF SEQUENCE LISTING

This application claims the benefit of U.S. Provisional Application No. 62/962,380, filed Jan. 17, 2020, which is incorporated by reference in its entirety herein. A sequence listing contained in the file named "P34788WO00_SL.TXT" which is 188,388 bytes (measured in MS-Windows®) and created on Jan. 15, 2021, is filed electronically herewith and incorporated by reference in its entirety.

FIELD

The present disclosure provides compositions and methods useful for making and identifying tobacco plants comprising improved nitrogen use efficiency via e.g. breeding, gene editing, transgenic approaches, and cisgenic approaches.

BACKGROUND

Different tobacco varieties require different levels of nitrogen fertilizer to achieve the maximum yield for each variety. Burley tobacco requires high amounts of added nitrogen fertilizer in order to provide the best yields. Maryland tobacco, on the other hand, requires approximately 25% of the level of nitrogen fertilizer typically used in cultivating burley tobacco. Fertilizer is a major input cost in the cultivation of tobacco and high levels of nitrogen can lead to increases in nitrogen containing constituents such as alkaloids and tobacco-specific nitrosamines (TSNAs) in plant tissues.

Improving Nitrogen Use Efficiency (NUE) in different tobacco varieties would increase tobacco harvestable yield per unit of input nitrogen fertilizer. Nitrogen use efficiency improvement also allows decreases in on-farm input costs, decreases in use and dependence on non-renewable energy sources required for nitrogen fertilizer production, and reduces the overall environmental impact of nitrogen fertilizer manufacturing and applications in agricultural use.

SUMMARY

In one aspect, the present specification provides for, and includes, a tobacco plant, or part thereof, comprising enhanced NUE, wherein the tobacco plant comprises at least one functional allele of a YB1 locus and further comprises at least one allele associated with enhanced NUE at one or more molecular markers selected from the group consisting of SEQ ID NOs: 57 to 64, where enhanced NUE is relative to a control tobacco plant without at least one functional allele of a YB1 locus.

In one aspect, the present specification provides for, and includes, a tobacco plant, or part thereof, comprising enhanced NUE, where a tobacco plant comprises at least one functional allele of a YB1 locus, and further comprises at least one allele associated with enhanced NUE at one or more molecular markers located within 20 cM of a sequence selected from the group consisting of SEQ ID NOs: 57 to 64.

In one aspect, the present specification provides for, and includes, a tobacco plant, or part thereof, comprising enhanced NUE, where a tobacco plant comprises at least one functional allele of a YB1 locus, and further comprises at least one allele associated with enhanced NUE at one or more molecular markers located within 5,000,000 nucleotides of a sequence selected from the group consisting of SEQ ID NOs: 57 to 64.

In one aspect, the present specification provides for, and includes, a tobacco plant, or part thereof, that comprises relative to a control plant, one or more traits selected from the group consisting of exhibiting more consistent leaf grade from top to bottom of the plant when grown at recommended Burley fertilization rates of 180 pounds (lbs) nitrogen per acre, increased leaf grade index in leaves from the lower half of the plant, increased nitrogen use efficiency, increased nitrogen use efficiency, decreased leaf nitrate nitrogen (NO3-N), reduced TSNA levels, and a lack of chlorophyll-deficient phenotype.

In one aspect, the present specification provides for, and includes, cured tobacco material, or a tobacco product comprising cured tobacco material made from a tobacco plant comprising at least one functional allele of a YB1 locus and at least one allele associated with enhanced NUE at one or more molecular markers selected from the group consisting of SEQ ID NOs: 57 to 64.

In one aspect, the present specification provides for, and includes, a method of creating a tobacco plant or a population of tobacco plants comprising enhanced NUE comprising genotyping and selecting a first population of tobacco plants with at least one enhanced NUE trait for the presence of one or more molecular markers within 20 cM of an allele associated with enhanced NUE comprising a sequence selected from the group consisting of SEQ ID NOs: 57 to 64, genotyping and selecting a second population of tobacco plants comprising at least one functional allele of a YB1 locus, and crossing at least one plant of the first population with at least one plant of the second population to produce progeny tobacco plants or tobacco seeds that comprise an enhanced NUE trait, one or more molecular markers associated with enhanced NUE, and at least one functional allele of a YB1 locus.

In one aspect, the present specification provides for, and includes, a method of creating a tobacco plant or a population of tobacco plants comprising enhanced NUE comprising genotyping and selecting a first population of tobacco plants with at least one enhanced NUE trait for the presence of one or more molecular markers within 5,000,000 nucleotides of an allele associated with enhanced NUE comprising a sequence selected from the group consisting of SEQ ID NOs: 57 to 64, genotyping and selecting a second population of tobacco plants comprising at least one functional allele of a YB1 locus, and crossing at least one plant of the first population with at least one plant of the second population to produce progeny tobacco plants or tobacco seeds that comprise an enhanced NUE trait, one or more molecular markers associated with enhanced NUE, and at least one functional allele of a YB1 locus.

In one aspect, the present specification provides for, and includes, a method of creating a tobacco plant or a population of tobacco plants comprising enhanced NUE comprising genotyping and selecting a first population of tobacco plants with at least one enhanced NUE trait for the presence of one or more molecular markers within 20 cM of an allele associated with enhanced NUE comprising a sequence selected from the group consisting of SEQ ID NOs: 57 to 64, and crossing at least one plant of the first population with at least one plant of a second population of tobacco plants that does not comprise at least one enhanced NUE trait to produce progeny tobacco plants or tobacco seeds that comprise an enhanced NUE trait, one or more molecular markers associated with enhanced NUE, and at least one functional allele of a YB1 locus.

In one aspect, the present specification provides for, and includes, a method of creating a tobacco plant or a population of tobacco plants comprising enhanced NUE comprising genotyping and selecting a first population of tobacco plants with at least one enhanced NUE trait for the presence of one or more molecular markers within 5,000,000 nucleotides of an allele associated with enhanced NUE comprising a sequence selected from the group consisting of SEQ ID NOs: 57 to 64, and crossing at least one plant of the first population with at least one plant of a second population of tobacco plants that does not comprise at least one enhanced NUE trait to produce progeny tobacco plants or tobacco seeds that comprise an enhanced NUE trait, one or more molecular markers associated with enhanced NUE, and at least one functional allele of a YB1 locus.

In one aspect, the present specification provides for, and includes, a method of selecting a tobacco plant comprising an enhanced NUE trait comprising isolating nucleic acids from at least one tobacco plant and assaying for one or more molecular markers located within 20 cM of one or more alleles associated with enhanced NUE selected from the group consisting of SEQ ID NOs: 57 to 64, and for at least one functional allele of a YB1 locus, and selecting a tobacco plant comprising an enhanced NUE trait, one or more alleles associated with enhanced NUE, and at least one functional allele of a YB1 locus.

In one aspect, the present specification provides for, and includes, a method of selecting a tobacco plant comprising an enhanced NUE trait comprising isolating nucleic acids from at least one tobacco plant and assaying for one or more molecular markers located within 5,000,000 nucleotides of one or more alleles associated with enhanced NUE selected from the group consisting of SEQ ID NOs: 57 to 64, and for at least one functional allele of a YB1 locus, and selecting a tobacco plant comprising an enhanced NUE trait, one or more alleles associated with enhanced NUE, and at least one functional allele of a YB1 locus.

BRIEF DESCRIPTION OF THE SEQUENCES

SEQ ID NOs: 1 to 8 are amino acid sequences of genes positively correlated with enhanced NUE in root tissue, leaf tissue, or both.

SEQ ID NOs: 9 to 16 are nucleotide sequences of genes positively correlated with enhanced NUE in root tissue, leaf tissue, or both.

SEQ ID NOs: 17 to 19 are nucleotide sequences of promoter regions for genes with leaf-preferred expression.

SEQ ID NOs: 20 to 24 are nucleotide sequences of promoter regions for genes with root-preferred expression.

SEQ ID NOs: 25 to 40 are amino acid sequences of genes negatively correlated with enhanced NUE in root tissue, leaf tissue, or both.

SEQ ID NOs: 41 to 56 are nucleotide sequences of genes negatively correlated with enhanced NUE in root tissue, leaf tissue, or both.

SEQ ID NOs: 57 to 64 are nucleotide sequences of SNP markers comprising polymorphisms associated with enhanced NUE.

SEQ ID NO: 65 is the backbone sequence for expression vector p45-2-7.

Various sequences may include "N" in nucleotide sequences or "X" in amino acid sequences. "N" can be any nucleotide, e.g., A, T, G, C, or a deletion or insertion of one or more nucleotides. In some instances, a string of "N" are shown. The number of "N" does not necessarily correlate with the actual number of undetermined nucleotides at that position. The actual nucleotide sequences can be longer or shorter than the shown segment of "N". Similarly, "X" can be any amino acid residue or a deletion or insertion of one or more amino acids. Again, the number of "X" does not necessarily correlate with the actual number of undetermined amino acids at that position. The actual amino acid sequences can be longer or shorter than the shown segment of "X". Notwithstanding the use of A, T, G, C (compared to A, U, G, C) in describing any SEQ ID in the sequence listing, that SEQ ID can also refer to a RNA sequence, depending on the context in which the SEQ ID is mentioned.

DETAILED DESCRIPTION

Figure 1:
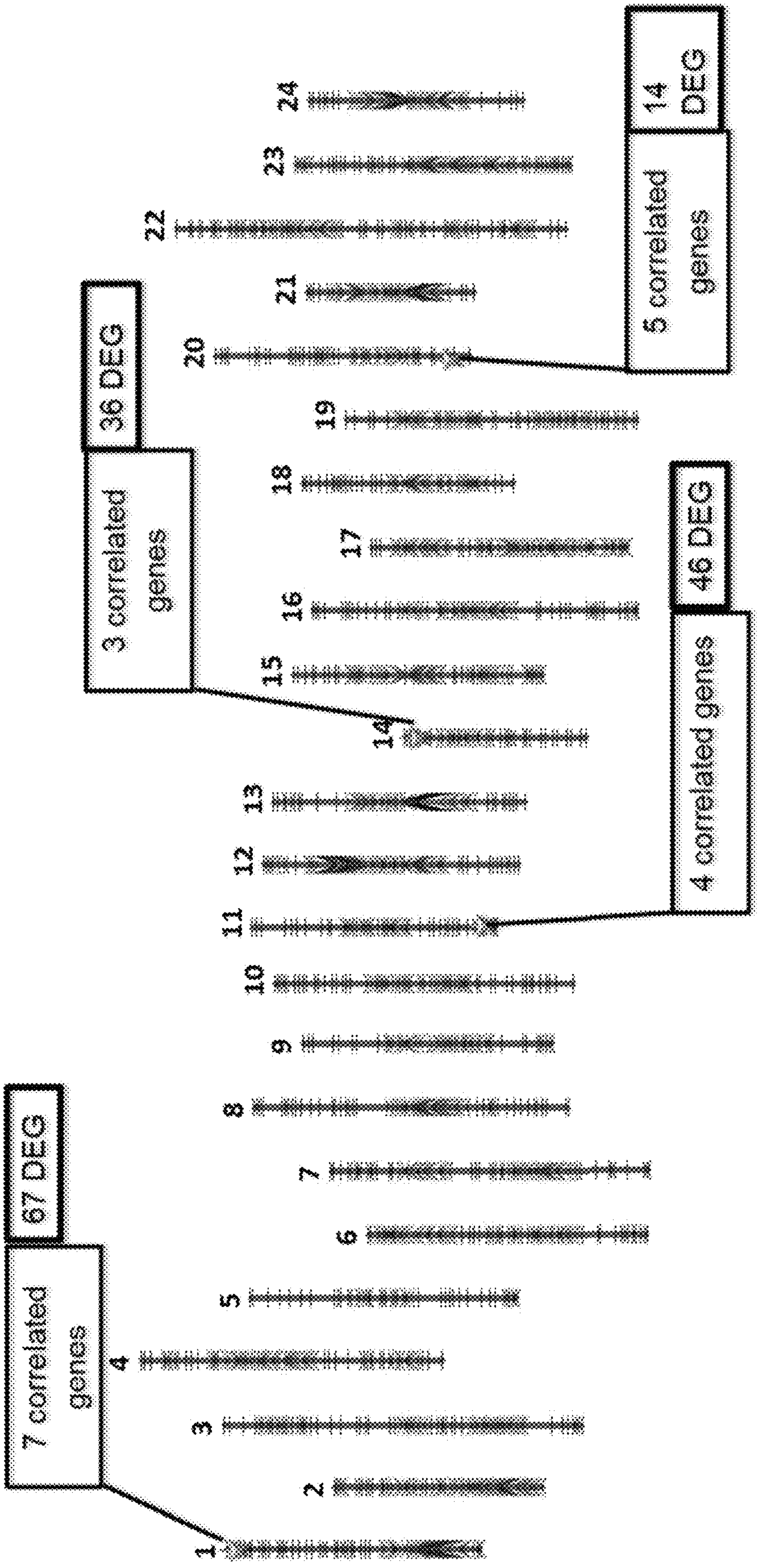
FIG. 1 depicts four gene clusters associated with NUE in the tobacco genome. Genes differentially expressed between low and normal nitrogen conditions in plants with an NUE metabolite fingerprint are indicated (correlated genes). The total number of differentially expressed genes (DEG), regardless of NUE metabolic fingerprinting, is also indicated.

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York).

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc. The term "and/or" when used in a list of two or more items means any one of the listed items by itself or in combination with any one or more of the other listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

When a range of numbers is provided herein, the range is understood to inclusive of the edges of the range as well as any number between the defined edges of the range. For example, "between 1 and 10" includes any number between 1 and 10, as well as the number 1 and the number 10.

When the term "about" is used, it is understood to mean plus or minus 10%. For example, "about 100" would include from 90 to 110.

As used herein, the singular form "a," "an," and "the" include plural references unless the context clearly dictates otherwise. For example, the term "a compound" or "at least one compound" may include a plurality of compounds, including mixtures thereof.

To avoid any doubt, used herein, terms or phrases such as "about", "at least", "at least about", "at most", "less than", "greater than", "within" or alike, when followed by a series of list of numbers of percentages, such terms or phrases are deemed to modify each and every number of percentage in the series or list, regardless whether the adverb, preposition, or other modifier phrase is reproduced prior to each and every member.

As used herein, the term "Yellow Burley 1" or "YB1" refers to a gene on chromosome 24 of the tobacco genome. The YB1 gene is a predicted homolog of the *Arabidopsis* ethylene-dependent gravitropism-deficient and yellow-green-like (EGY). See, Edwards et al. (2017) BMC Genomics, 18: 448 The Yellow Burley 1 loci is in non-functional in commercial Burley tobacco varieties due to a mutation in the YB1 locus. See, Lewis et al. (2012) J. Agric. Food Chem., 60, 6454-6461 and Yafei Li, et al. (2018) Sci. Rep., 8:13300. It is predicted that mutation in YB1 contributes to the documented low nitrogen use efficiency, high nitrate levels, and lower carbohydrate content present in Burley tobacco varieties. It is predicted that mutation in YB2 contributes to the documented low nitrogen use efficiency, high nitrate levels, and lower carbohydrate content present in Burley tobacco varieties. For the first time, this disclosure demonstrates that at least one functional allele of YB1 in combination with enhanced NUE alleles on chromosome 11 provides a synergistic and enhanced nitrogen use efficiency compared to commercial Burley varieties currently in the art.

As used herein, the term "Yellow Burley 2" or "YB2" refers to a gene on chromosome 5 of the tobacco genome. The YB2 gene is a predicted homolog of the *Arabidopsis* ethylene-dependent gravitropism-deficient and yellow-green-like (EGY). See, Edwards et al. (2017) BMC Genomics, 18:448. The Yellow Burley 2 loci is in non-functional in commercial Burley tobacco varieties due to a mutation in the YB2 locus. It is predicted that mutation in YB2 contributes to the documented low nitrogen use efficiency, high nitrate levels, and lower carbohydrate content present in Burley tobacco varieties. See, Lewis et al. (2012) J. Agric. Food Chem., 60, 6454-6461 and Yafei Li, et al. (2018) Sci. Rep., 8:13300.

As used herein, the term "non-functional allele" refers to a gene or open reading frame that is not capable of producing a functional gene product, e.g. a functional protein. A non-functional allele can be present in a wild-type genome, such as the yb1 or yb2 allele of Burley varieties or it can be created through any form of mutagenesis or gene editing. Mutation types and gene editing methods are known in the art and are described below. Natural variation across different varieties can spontaneously give rise to non-functional alleles provided the associated gene or open reading frame is incapable of producing a functional gene product. Non-functional proteins will typically result in phenotypes like the corresponding non-functional allele but can arise through post-transcriptional or post-translational modifications such as silencing or methylation.

As used herein, the term "functional allele" in reference to the YB1 or YB2 loci means that a functional gene product is produced from the YB1 or YB2 loci. This term is used in opposition to the non-functional alleles of YB1 or YB2 known to be present in commercial Burley varieties. Natural variation across different varieties can result in many different nucleotide sequences that all can produce a functional gene product or protein.

As used herein, "locus" is a chromosome region where a polymorphic nucleic acid, trait determinant, gene, or marker is located. The loci of this disclosure comprise one or more polymorphisms in a population; e.g., alternative alleles are present in some individuals. As used herein, "allele" refers to an alternative nucleic acid sequence at a particular locus. The length of an allele can be as small as 1 nucleotide base but is typically larger. For example, a first allele can occur on one chromosome, while a second allele occurs on a second homologous chromosome, e.g., as occurs for different chromosomes of a heterozygous individual, or between different homozygous or heterozygous individuals in a population. As used herein, a chromosome in a diploid plant is "hemizygous" when only one copy of a locus is present. For example, an inserted transgene is hemizygous when it only inserts into one sister chromosome (e.g., the second sister chromosome does not contain the inserted transgene).

As used herein, an "enhanced NUE locus" describes any locus or loci linked to any one of the genomic locations for any of the four clusters of genes associated with enhanced NUE in the tobacco genome that are presently disclosed. The four clusters of genes associated with enhanced NUE may be referred to as quantitative trait loci. Markers are disclosed herein for mapping and tracking the introgression of enhanced NUE loci. Generation of additional markers useful for tracking any loci in the genomic locations identified herein can be performed using techniques known in the art.

In one aspect, tobacco plants provided herein are double haploid plants. Typically, a haploid cell of a plant, such as an anther or a pollen grain in a plant, is induced to double its genetic content, or chromosome number. This results in a diploid cell in which each homologous chromosome pair is identical. Accordingly, as used herein, a "double haploid plant" is a plant which comprises homologous chromosomes that are genetically identical. Methods for the production of double haploid plants are known in the art (see, for example, Salej, (2013) "Plant Breeding", Blackwell publishing, Vol 132.6, 764-771, and Touraev (1999) "Methods in Molecular Biology", Humana Press, Vol. 111, 281-291).

In one aspect, a modified plant, seed, plant component, plant cell, or plant genome is homozygous for a transgene provided herein. In another aspect, a modified plant, seed, plant component, plant cell, or plant genome is heterozygous for a transgene provided herein. In one aspect, a modified plant, seed, plant component, plant cell, or plant genome is hemizygous for a transgene provided herein. In one aspect, a modified plant, seed, plant component, plant cell, or plant genome is homozygous for a mutation provided herein. In another aspect, a modified plant, seed, plant component, plant cell, or plant genome is heterozygous for a mutation provided herein. In one aspect, a modified plant, seed, plant component, plant cell, or plant genome is hemizygous for a mutation provided herein. Any plant of the present invention can be induced to become a double haploid plant using methods known in the art.

As used herein, "introgression" or "introgress" refers to the transmission of a desired allele of a genetic locus from one genetic background to another.

As used herein, "crossed" or "cross" means to produce progeny via fertilization (e.g. cells, seeds or plants) and includes crosses between different plants (sexual) and self-fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the Fi generation. The term "BC1" refers to the second use of the recurrent parent, "BC2" refers to the third use of the recurrent parent, and so on. In one aspect, a backcross is performed repeatedly, with a progeny individual of each successive backcross generation being itself backcrossed to the same parental genotype.

As used herein, "elite variety" means any variety that has resulted from breeding and selection for superior agronomic performance.

As used herein, "selecting" or "selection" in the context of breeding refer to the act of picking or choosing desired individuals, normally from a population, based on certain pre-determined criteria.

As used herein, the term "sequence identity" or "identity" in the context of two polynucleotide or polypeptide sequences refers to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." An alignment of two or more sequences may be performed using any suitable computer program. For example, a widely used and accepted computer program for performing sequence alignments is CLUSTALW v1.6 (Thompson, et al. (1994) Nucl. Acids Res., 22:4673-4680).

As used herein, the term "complementary" in reference to a nucleic acid molecule refers to pairing of nucleotide bases such that adenine is complementary to thymine or uracil, and guanine is complementary to cytosine. Two complementary nucleic acid molecules are capable of hybridizing with each other. As an example, the two strands of double stranded DNA are complementary to each other.

A specific polynucleotide of at least three nucleotides in length may be referred to as an "oligonucleotide". Nucleic acid molecules provided herein include deoxyribonucleic acids (DNA) and ribonucleic acids (RNA) and functional analogues thereof, such as complementary DNA (cDNA). Nucleic acid molecules provided herein can be single stranded or double stranded. Nucleic acid molecules comprise the nucleotide bases adenine (A), guanine (G), thymine (T), cytosine (C). Uracil (U) replaces thymine in RNA molecules. The symbol "R" can be used to represent a purine (e.g., A or G) nucleotide base. The symbol "Y" can be used to represent a pyrimidine (e.g., a C or T) nucleotide base. The symbol "W" can be used to represent an A or a T nucleotide base. The symbol S can be used to represent a G or a C nucleotide base. The symbol "M" can be used to represent an A or a C nucleotide base. The symbol "K" can be used to represent a G or a T nucleotide base. The symbol "B" can be used to represent a G, C, or T nucleotide base.

The symbol "H" can be used to represent an A, C, or T nucleotide base. The symbol "D" can be used to represent an A, G, or T nucleotide base. The symbol "V" can be used to represent an A, G, or C nucleotide base. The symbol "N" can be used to represent any nucleotide base (e.g., A, G, C, T, or U).

The use of the term "polynucleotide" is not intended to limit the present disclosure to polynucleotides comprising DNA. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like.

As used herein, the term "polypeptide" refers to a chain of at least two covalently linked amino acids. Polypeptides can be encoded by polynucleotides provided herein.

Nucleic acid molecules, polypeptides, or proteins provided herein can be isolated or substantially purified. An "isolated" or "purified" nucleic acid molecule, polypeptide, protein, or biologically active portion thereof, is substantially or essentially free from components that normally accompany or interact with the polynucleotide or protein as found in its naturally occurring environment. For example, an isolated or purified polynucleotide or protein is substantially free of other cellular material, or culture medium when produced by recombinant techniques, or substantially free of chemical precursors or other chemicals when chemically synthesized. In one aspect, an isolated polynucleotide provided herein can contain less than 10000 nucleotides, less than 5000 nucleotides, less than 4000 nucleotides, less than 3000 nucleotides, less than 2000 nucleotides, less than 1000 nucleotides, less than 500 nucleotides, or less than 100 nucleotides of nucleic acid sequence that naturally flank the polynucleotide in genomic DNA of the cell from which the polynucleotide is derived. In one aspect, an isolated polynucleotide provided herein can contain 100 to 10000 nucleotides, 500 to 10000 nucleotides, 1000 to 10000 nucleotides, 2000 to 10000 nucleotides, 3000 to 10000 nucleotides, 4000 to 10000 nucleotides, 1 to 500 nucleotides, 1 to 1000 nucleotides, 1 to 2000 nucleotides, 1 to 3000 nucleotides, 1 to 4000 nucleotides, 1 to 5000 nucleotides, 1 to 10000 nucleotides, 100 to 500 nucleotides, 100 to 1000 nucleotides, 100 to 2000 nucleotides, 100 to 3000 nucleotides, or 100 to 4000 nucleotides of nucleic acid sequence that naturally flank the polynucleotide in genomic DNA of the cell from which the polynucleotide is derived. In another aspect, an isolated polypeptide provided herein is substantially free of cellular material in preparations having less than 30%, less than 20%, less than 10%, less than 5%, or less than 1% (by dry weight) of chemical precursors or non-protein-of-interest chemicals. Fragments of the disclosed polynucleotides and polypeptides encoded thereby are also encompassed by the present invention. Fragments of a polynucleotide may encode polypeptide fragments that retain the biological activity of the native polypeptide. Alternatively, fragments of a polynucleotide that are useful as hybridization probes or PCR primers using methods known in the art generally do not encode fragment polypeptides retaining biological activity. Fragments of a polynucleotide provided herein can range from at least 20 nucleotides, at least 50 nucleotides, at least 70 nucleotides, at least 100 nucleotides, at least 150 nucleotides, at least 200 nucleotides, at least 250 nucleotides, at least 300 nucleotides, and up to the full-length polynucleotide encoding the polypeptides of the invention, depending on the desired outcome.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting recombinant nucleic acids and polypeptides in plant cells. Without being limiting, nucleic acids also can be detected using hybridization. Hybridization between nucleic acids is discussed in detail in Sambrook et al. (1989), Molecular Cloning: A Laboratory Manual, 2nd ed., Cold Spring Harbor Laboratory Press, Cold Spring Harbor, NY).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

As used herein, the phrase "associated with" or "linked to" refers to a recognizable and/or assayable relationship between two entities. For example, the phrase "associated with enhanced NUE" refers to a trait, locus, gene, allele, marker, phenotype, etc., or the expression thereof, the presence or absence of which can influence an extent, degree, and/or rate at which a plant or a part of interest thereof that has an enhanced NUE trait. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with enhanced NUE allele" refers to a marker whose presence or absence can be used to predict whether and to what extent a plant will display enhanced NUE phenotype.

As used herein, "heterologous" refers to a sequence that originates from a foreign species, or, if from the same species, is substantially modified from its native form in composition and/or genomic locus by deliberate human intervention. The term also is applicable to nucleic acid constructs, also referred to herein as "polynucleotide constructs" or "nucleotide constructs." In this manner, a "heterologous" nucleic acid construct is intended to mean a construct that originates from a foreign species, or, if from the same species, is substantially modified from its native form in composition and/or genomic locus by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest.

As used herein, a "centimorgan" (cM) is a unit of measure of recombination frequency and genetic distance between two loci. One cM is equal to a 1% chance that a marker at one genetic locus will be separated from a marker at a second locus due to crossing over in a single generation.

As used herein, "closely linked" means that the marker or locus is within about 20 cM, 15 cM, 10 cM, 5 CM, 4 cM, 3 CM, 2 cM, 1 cM, 0.5 CM, or less than 0.5 CM of another marker or locus. For example, 20 cM means that recombination occurs between the marker and the locus with a frequency of equal to or less than about 20%.

As used herein, "plant" refers to a whole plant. A cell or tissue culture derived from a plant can comprise any plant components or plant organs (e.g., leaves, stems, roots, etc.), plant tissues, seeds, plant cells, and/or progeny of the same. A progeny plant can be from any filial generation, e.g., $F_1$, $F_2$, $F_3$, $F_4$, $F_5$, $F_6$, $F_7$, etc. A plant cell is a biological cell of a plant, taken from a plant or derived through culture from a cell taken from a plant.

As used herein, a tobacco plant can be from any plant from the *Nicotiana tabacum* genus including, but not limited to *Nicotiana tabacum tabacum; Nicotiana tabacum amplexicaulis* PI 271989; *Nicotiana tabacum benthamiana* PI 555478; *Nicotiana tabacum bigelovii* PI 555485; *Nicotiana tabacum debneyi; Nicotiana tabacum excelsior* PI 224063; *Nicotiana tabacum glutinosa* PI 555507; *Nicotiana tabacum goodspeedii* PI 241012; *Nicotiana tabacum gossei* PI 230953; *Nicotiana tabacum hesperis* PI 271991; *Nicotiana tabacum knightiana* PI 555527; *Nicotiana tabacum maritima* PI 555535; *Nicotiana tabacum megalosiphon* PI 555536; *Nicotiana tabacum nudicaulis* PI 555540; *Nicotiana tabacum paniculata* PI 555545; *Nicotiana tabacum plumbaginifolia* PI 555548; *Nicotiana tabacum repanda* PI 555552; *Nicotiana tabacum rustica; Nicotiana tabacum suaveolens* PI 230960; *Nicotiana tabacum sylvestris* PI 555569; *Nicotiana tabacum tomentosa* PI 266379; *Nicotiana tabacum tomentosiformis*; and *Nicotiana tabacum trigonophylla* PI 555572.

In one aspect, a plant component provided herein includes, but is not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In further aspects, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic tobacco plant cells. Somatic cells, contrary to germline cells, do not mediate plant reproduction.

Provided cells, tissues and organs can be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, and vascular tissue. In another aspect, this disclosure provides a tobacco plant chloroplast. In a further aspect, this disclosure provides an epidermal cell, a stomata cell, a leaf hair (trichome), a root hair, or a storage root. In another aspect, this disclosure provides a tobacco protoplast.

Skilled artisans understand that tobacco plants naturally reproduce via seeds, not via asexual reproduction or vegetative propagation. In one aspect, this disclosure provides tobacco endosperm. In another aspect, this disclosure provides a tobacco endosperm cell. In a further aspect, this disclosure provides a male or female sterile tobacco plant, which cannot reproduce without human intervention.

In tobacco, new leaves are formed as the stalk grows. Therefore, the youngest leaf is the uppermost leaf on the stalk, and the oldest leaf is in the lowermost leaf on the stalk. Unlike dark tobacco varieties, conventional burley tobacco varieties yellow during the ripening process.

When burley tobacco is topped, some of the lower (older) leaves may have begun to yellow already. Conventional burley tobacco will continue to yellow, from bottom to top, after topping.

In one aspect, this disclosure provides methods and compositions related to modified tobacco plants, seeds, plant components, plant cells, and products made from modified tobacco plants, seeds, plant parts, and plant cells. In one aspect, a modified seed provided herein gives rise to a modified plant provided herein. In one aspect, a modified plant, seed, plant component, plant cell, or plant genome provided herein comprises a recombinant DNA construct provided herein. In another aspect, cured tobacco material or tobacco products provided herein comprise modified tobacco plants, plant components, plant cells, or plant genomes provided herein.

In a further aspect, a modified tobacco seed or tobacco plant of the present specification comprises a coding region encoding a polypeptide that is at least 70% identical or similar to a sequence selected from the group consisting of SEQ ID NOs: 1 to 8. In a further aspect, a modified tobacco seed or tobacco plant comprises a coding region encoding a polypeptide that is at least 75% identical or similar to a sequence selected from the group consisting of SEQ ID NOs: 1 to 8. In a further aspect, a modified tobacco seed or tobacco plant comprises a coding region encoding a polypeptide that is at least 80% identical or similar to a sequence selected from the group consisting of SEQ ID NOs: 1 to 8. In a further aspect, a modified tobacco seed or tobacco plant comprises a coding region encoding a polypeptide that is at least 85% identical or similar to a sequence selected from the group consisting of SEQ ID NOs: 1 to 8. In a further aspect, a modified tobacco seed or tobacco plant comprises a coding region encoding a polypeptide that is at least 90% identical or similar to a sequence selected from the group consisting of SEQ ID NOs: 1 to 8. In a further aspect, a modified tobacco seed or tobacco plant comprises a coding region encoding a polypeptide that is at least 95% identical or similar to a sequence selected from the group consisting of SEQ ID NOs: 1 to 8. In a further aspect, a modified tobacco seed or tobacco plant comprises a coding region encoding a polypeptide that is at least 96% identical or similar to a sequence selected from the group consisting of SEQ ID NOs: 1 to 8. In a further aspect, a modified tobacco seed or tobacco plant comprises a coding region encoding a polypeptide that is at least 97% identical or similar to a sequence selected from the group consisting of SEQ ID NOs: 1 to 8. In a further aspect, a modified tobacco seed or tobacco plant comprises a coding region encoding a polypeptide that is at least 98% identical or similar to a sequence selected from the group consisting of SEQ ID NOs: 1 to 8. In a further aspect, a modified tobacco seed or tobacco plant comprises a coding region encoding a polypeptide that is at least 99% identical or similar to a sequence selected from the group consisting of SEQ ID NOs: 1 to 8. In a further aspect, a modified tobacco seed or tobacco plant comprises a coding region encoding a polypeptide that is 100% identical to a sequence selected from the group consisting of SEQ ID NOs: 1 to 8.

In a further aspect, a modified tobacco seed or tobacco plant of the present specification comprises a coding region encoding a polynucleotide that is at least 70% identical or similar to a sequence selected from the group consisting of SEQ ID NOs: 9 to 16. In a further aspect, a modified tobacco seed or tobacco plant comprises a coding region encoding a polynucleotide that is at least 75% identical or similar to a sequence selected from the group consisting of SEQ ID NOs: 9 to 16. In a further aspect, a modified tobacco seed or tobacco plant comprises a coding region encoding a polynucleotide that is at least 80% identical or similar to a sequence selected from the group consisting of SEQ ID NOs: 9 to 16. In a further aspect, a modified tobacco seed or tobacco plant comprises a coding region encoding a polynucleotide that is at least 85% identical or similar to a sequence selected from the group consisting of SEQ ID NOs: 9 to 16. In a further aspect, a modified tobacco seed or tobacco plant comprises a coding region encoding a polynucleotide that is at least 90% identical or similar to a sequence selected from the group consisting of SEQ ID NOs: 9 to 16. In a further aspect, a modified tobacco seed or tobacco plant comprises a coding region encoding a polynucleotide that is at least 95% identical or similar to a sequence selected from the group consisting of SEQ ID NOs: 9 to 16. In a further aspect, a modified tobacco seed or tobacco plant comprises a coding region encoding a polynucleotide that is at least 96% identical or similar to a sequence selected from the group consisting of SEQ ID NOs: 9 to 16. In a further aspect, a modified tobacco seed or tobacco plant comprises a coding region encoding a polynucleotide that is at least 97% identical or similar to a sequence selected from the group consisting of SEQ ID NOs: 9 to 16. In a further aspect, a modified tobacco seed or tobacco plant comprises a coding region encoding a polynucleotide that is at least 98% identical or similar to a sequence selected from the group consisting of SEQ ID NOs: 9 to 16. In a further aspect, a modified tobacco seed or tobacco plant comprises a coding region encoding a polynucleotide that is at least 99% identical or similar to a sequence selected from the group consisting of SEQ ID NOs: 9 to 16. In a further aspect, a modified tobacco seed or tobacco plant comprises a coding region encoding a polynucleotide that is identical to a sequence selected from the group consisting of SEQ ID NOs: 9 to 16.

In a further aspect, a modified tobacco seed or tobacco plant comprises a leaf-preferred promoter that is encoded by a sequence at least 70% identical to a sequence selected from the group consisting of SEQ ID NOs: 17 to 19, or a functional fragment thereof. In a further aspect, a leaf-preferred promoter is encoded by a sequence at least 75% identical to a sequence selected from the group consisting of SEQ ID NOs: 17 to 19, or a functional fragment thereof. In a further aspect, a leaf-preferred promoter is encoded by a sequence at least 80% identical to a sequence selected from the group consisting of SEQ ID NOs: 17 to 19, or a functional fragment thereof. In a further aspect, a leaf-preferred promoter is encoded by a sequence at least 85% identical to a sequence selected from the group consisting of SEQ ID NOs: 17 to 19, or a functional fragment thereof. In a further aspect, a leaf-preferred promoter is encoded by a sequence at least 90% identical to a sequence selected from the group consisting of SEQ ID NOs: 17 to 19, or a functional fragment thereof. In a further aspect, a leaf-preferred promoter is encoded by a sequence at least 95% identical to a sequence selected from the group consisting of SEQ ID NOs: 17 to 19, or a functional fragment thereof. In a further aspect, a leaf-preferred promoter is encoded by a sequence at least 96% identical to a sequence selected from the group consisting of SEQ ID NOs: 17 to 19, or a functional fragment thereof. In a further aspect, a leaf-preferred promoter is encoded by a sequence at least 97% identical to a sequence selected from the group consisting of SEQ ID NOs: 17 to 19, or a functional fragment thereof. In a further aspect, a leaf-preferred promoter is encoded by a sequence at least 98% identical to a sequence selected from the group consisting of SEQ ID NOs: 17 to 19, or a functional fragment thereof. In a further aspect, a leaf-preferred promoter is encoded by a sequence at least 99% identical to a sequence selected from the group consisting of SEQ ID NOs: 17 to 19, or a functional fragment thereof. In a further aspect, a leaf-preferred promoter is encoded by to a sequence selected from the group consisting of SEQ ID NOs: 17 to 19, or a functional fragment thereof.

In a further aspect, a modified tobacco seed or tobacco plant comprises a root-preferred promoter that is encoded by a sequence at least 70% identical to a sequence selected from the group consisting of SEQ ID NOs: 20 to 24, or a functional fragment thereof. In a further aspect, a leaf-preferred promoter is encoded by a sequence at least 75% identical to a sequence selected from the group consisting of SEQ ID NOs: 20 to 24, or a functional fragment thereof. In a further aspect, a leaf-preferred promoter is encoded by a sequence at least 80% identical to a sequence selected from the group consisting of SEQ ID NOs: 20 to 24, or a functional fragment thereof. In a further aspect, a leaf-preferred promoter is encoded by a sequence at least 85% identical to a sequence selected from the group consisting of SEQ ID NOs: 20 to 24, or a functional fragment thereof. In a further aspect, a leaf-preferred promoter is encoded by a sequence at least 90% identical to a sequence selected from the group consisting of SEQ ID NOs: 20 to 24, or a functional fragment thereof. In a further aspect, a leaf-preferred promoter is encoded by a sequence at least 95% identical to a sequence selected from the group consisting of SEQ ID NOs: 20 to 24, or a functional fragment thereof. In a further aspect, a leaf-preferred promoter is encoded by a sequence at least 96% identical to a sequence selected from the group consisting of SEQ ID NOs: 20 to 24, or a functional fragment thereof. In a further aspect, a leaf-preferred promoter is encoded by a sequence at least 97% identical to a sequence selected from the group consisting of SEQ ID NOs: 20 to 24, or a functional fragment thereof. In a further aspect, a leaf-preferred promoter is encoded by a sequence at least 98% identical to a sequence selected from the group consisting of SEQ ID NOs: 20 to 24, or a functional fragment thereof. In a further aspect, a leaf-preferred promoter is encoded by a sequence at least 99% identical to a sequence selected from the group consisting of SEQ ID NOs: 20 to 24, or a functional fragment thereof. In a further aspect, a leaf-preferred promoter is encoded by to a sequence selected from the group consisting of SEQ ID NOs: 20 to 24, or a functional fragment thereof.

In a further aspect, a method provided herein comprises progeny seed comprising molecular markers. In a further aspect, a method provided herein comprises progeny seed comprising enhanced NUE. In a further aspect, a method provided herein comprises progeny seed comprising a molecular marker within 20 cM of an enhanced NUE efficiency locus provided herein. In a further aspect, a method provided herein comprises progeny seed comprising a molecular marker within 15 CM of an enhanced NUE efficiency locus provided herein. In a further aspect, a method provided herein comprises progeny seed comprising a molecular marker within 10 cM of an enhanced NUE efficiency locus provided herein. In a further aspect, a method provided herein comprises progeny seed comprising a molecular marker within 9 cM of an enhanced NUE efficiency locus provided herein. In a further aspect, a method provided herein comprises progeny seed comprising a molecular marker within 8 cM of an enhanced NUE efficiency locus provided herein. In a further aspect, a method provided herein comprises progeny seed comprising a molecular marker within 7 cM of an enhanced NUE efficiency locus provided herein. In a further aspect, a method provided herein comprises progeny seed comprising a molecular marker within 6 cM of an enhanced NUE efficiency locus provided herein. In a further aspect, a method provided herein comprises progeny seed comprising a molecular marker within 5 cM of an enhanced NUE efficiency locus provided herein. In a further aspect, a method provided herein comprises progeny seed comprising a molecular marker within 4 cM of an enhanced NUE efficiency locus provided herein. In a further aspect, a method provided herein comprises progeny seed comprising a molecular marker within 3 cM of an enhanced NUE efficiency locus provided herein. In a further aspect, a method provided herein comprises progeny seed comprising a molecular marker within 2 cM of an enhanced NUE efficiency locus provided herein. In a further aspect, a method provided herein comprises progeny seed comprising a molecular marker within 1 cM of an enhanced NUE efficiency locus provided herein. In a further aspect, a method provided herein comprises progeny seed comprising a molecular marker within 0.5 CM of an enhanced NUE efficiency locus provided herein.

In one aspect, the present specification provides for, and includes, a method comprising providing a first population of tobacco plants, genotyping the first population of tobacco plants for the presence of an enhanced NUE allele of a locus encoded by a sequence selected from the group consisting of SEQ ID NOs: 9 to 16; and selecting one or more genotyped tobacco plants that comprise an enhanced NUE allele. In a further aspect, the method further comprises crossing the one or more selected tobacco plants to a second tobacco plant; and obtaining progeny seed from the cross.

In one aspect, the present specification provides for, and includes, a method of introgressing an enhanced NUE trait into a tobacco variety comprising crossing a first tobacco variety comprising an enhanced nitrogen use efficiency trait with a second tobacco variety lacking the enhanced nitrogen use trait, obtaining progeny seed from the cross, genotyping at least one progeny seed for a molecular marker linked to an enhanced nitrogen use efficiency trait, where the molecular marker is within 20 cM of a locus having a sequence selected from the group consisting of SEQ ID NOs: 9 to 16; and selecting a progeny seed comprising an enhanced nitrogen use efficiency trait.

In one aspect, the present specification provides for, and includes, a method of selecting a tobacco plant with an enhanced NUE trait comprising isolating nucleic acids from a collection of tobacco germplasm, assaying the isolated nucleic acids for one or more markers located within 20 cM of a locus having a sequence selected from the group consisting of SEQ ID NOs: 9 to 16, and selecting a tobacco plant comprising an enhanced NUE trait. In a further aspect, the method further comprises crossing the one or more selected tobacco plants to a second tobacco plant; and obtaining progeny seed from the cross.

In one aspect, the present specification provides for, and includes, a method of selecting a tobacco plant with an enhanced NUE trait comprising isolating nucleic acids from a collection of tobacco germplasm, assaying the isolated nucleic acids for one or more markers located within 20 cM of a marker selected from the group consisting of SEQ ID NOs: 57 to 64, and selecting a tobacco plant comprising an enhanced NUE trait. In a further aspect, a method disclosed herein comprises assaying isolated nucleic acids for one or more markers located within 15 cM of a marker selected from the group consisting of SEQ ID NOs: 58. In a further aspect, a method disclosed herein comprises assaying isolated nucleic acids for one or more markers located within 10 cM of a marker selected from the group consisting of SEQ ID NOs: 57 to 64. In a further aspect, a method disclosed herein comprises assaying isolated nucleic acids for one or more markers located within 9 cM of a marker selected from the group consisting of SEQ ID NOs: 57 to 64. In a further aspect, a method disclosed herein comprises assaying isolated nucleic acids for one or more markers located within 8 cM of a marker selected from the group consisting of SEQ ID NOs: 57 to 64. In a further aspect, a method disclosed herein comprises assaying isolated nucleic acids for one or more markers located within 7 cM of a marker selected from the group consisting of SEQ ID NOs: 57 to 64. In a further aspect, a method disclosed herein comprises assaying isolated nucleic acids for one or more markers located within 6 cM of a marker selected from the group consisting of SEQ ID NOs: 57 to 64. In a further aspect, a method disclosed herein comprises assaying isolated nucleic acids for one or more markers located within 5 CM of a marker selected from the group consisting of SEQ ID NOs: 57 to 64. In a further aspect, a method disclosed herein comprises assaying isolated nucleic acids for one or more markers located within 4 cM of a marker selected from the group consisting of SEQ ID NOs: 57 to 64. In a further aspect, a method disclosed herein comprises assaying isolated nucleic acids for one or more markers located within 3 cM of a marker selected from the group consisting of SEQ ID NOs: 57 to 64. In a further aspect, a method disclosed herein comprises assaying isolated nucleic acids for one or more markers located within 2 cM of a marker selected from the group consisting of SEQ ID NOs: 57 to 64. In a further aspect, a method disclosed herein comprises assaying isolated nucleic acids for one or more markers located within 1 cM of a marker selected from the group consisting of SEQ ID NOs: 57 to 64. In a further aspect, a method disclosed herein comprises assaying isolated nucleic acids for one or more markers located within 0.5 CM of a marker selected from the group consisting of SEQ ID NOs: 57 to 64. In a further aspect, a method disclosed herein comprises assaying isolated nucleic acids for a marker selected from the group consisting of SEQ ID NOs: 57 to 64. In another aspect, an allele associated with enhanced NUE comprises a G nucleotide at position 57 of SEQ ID NO: 58. In another aspect an allele associated with enhanced NUE comprises a C nucleotide at position 117 of SEQ ID NO:58. In another aspect, an allele associated with enhanced NUE comprises a G nucleotide at position 57 and a C nucleotide at position 117 of SEQ ID NO:58. In another aspect, an allele associated with enhanced NUE comprises a T nucleotide at position 147 of SEQ ID NO:57. In another aspect, an allele associated with enhanced NUE comprises a G nucleotide at position 162 of SEQ ID NO:59. In another aspect, an allele associated with enhanced NUE comprises a C nucleotide at position 36 of SEQ ID NO:60. In another aspect, an allele associated with enhanced NUE comprises a T nucleotide at position 36 of SEQ ID NO:61. In another aspect, an allele associated with enhanced NUE comprises a T nucleotide at position 36 of SEQ ID NO:62. In another aspect, an allele associated with enhanced NUE comprises a G nucleotide at position 36 of SEQ ID NO:63. In another aspect, an allele associated with enhanced NUE comprises a T nucleotide at position 36 of SEQ ID NO:64. In a further aspect, a tobacco plant can be selected comprising any combination of alleles associated with enhanced NUE disclosed herein.

In one aspect, the present specification provides for, and includes, a method of selecting a tobacco plant with an enhanced NUE trait comprising isolating nucleic acids from at least one tobacco plant, assaying the isolated nucleic acids for one or more molecular markers located within 20 cM of one or more alleles associated with enhanced NUE selected from the group consisting of SEQ ID NOs: 57 to 64, assaying the isolated nucleic acids for at least one functional allele of a Yellow Burley 1 (YB1) locus, and selecting a tobacco plant comprising an enhanced NUE trait, one or more alleles associated with enhanced NUE, and at least one functional allele of a YB1 locus. In a further aspect, the tobacco plant is also assayed for at least one functional allele of a Yellow Burley 2 (YB2) locus. In another aspect, the tobacco plant is also selected for at least one functional allele of a YB2 locus.

In a further aspect, a modified tobacco plant of the present specification comprising a cisgenic polynucleotide comprises higher levels of a metabolite selected from the group consisting of 4-guanidinobutanoate, syringaldehyde, thiamin, and p-hydroxybenzaldehyde in root tissue as compared to an unmodified tobacco plant lacking the cisgenic polynucleotide when grown under the same conditions.

In a further aspect, a modified tobacco plant of the present specification comprising a cisgenic polynucleotide comprises higher levels of a metabolite selected from the group consisting of 4-guanidinobutanoate, X-23454, X-23580, and X-23852 in leaf tissue as compared to an unmodified tobacco plant lacking the cisgenic polynucleotide when grown under the same conditions.

In a further aspect, a modified tobacco plant of the present specification comprising a cisgenic polynucleotide comprises lower levels of a metabolite selected from the group consisting of X-2357, N-acetylmuramate, X-23319, X-23852, X-23330, alpha-ketoglutarate, X-21756, 4-hydroxy-2-oxoglutaric acid, X-23937, X-23916, and 1-methyladenine in root tissue as compared to an unmodified tobacco plant lacking the cisgenic polynucleotide when grown under the same conditions.

In a further aspect, a modified tobacco plant of the present specification comprising a cisgenic polynucleotide comprises lower levels of a metabolite selected from the group consisting of X-23453, X-21756, X-11429, X-21796, N'-methylnicotinamide, cotinine, X-23389, N-acetylarginine, N-23366, N-acetylphenylalanine, and naringenin in leaf tissue as compared to an unmodified tobacco plant lacking the cisgenic polynucleotide when grown under the same conditions.

In one aspect, the present specification provides for, and includes, a recombinant DNA construct comprising a heterologous promoter operably linked to a polynucleotide encoding a polypeptide at least 70% identical or similar to a polypeptide selected from the group consisting of SEQ ID NOs: 1 to 8. In a further aspect, a recombinant DNA construct comprises a polynucleotide encoding a polypeptide at least 75% identical or similar to a polypeptide selected from the group consisting of SEQ ID NOs: 1 to 8. In a further aspect, a recombinant DNA construct comprises a polynucleotide encoding a polypeptide at least 80% identical or similar to a polypeptide selected from the group consisting of SEQ ID NOs: 1 to 8. In a further aspect, a recombinant DNA construct comprises a polynucleotide encoding a polypeptide at least 85% identical or similar to a polypeptide selected from the group consisting of SEQ ID NOs: 1 to 8. In a further aspect, a recombinant DNA construct comprises a polynucleotide encoding a polypeptide at least 90% identical or similar to a polypeptide selected from the group consisting of SEQ ID NOs: 1 to 8. In a further aspect, a recombinant DNA construct comprises a polynucleotide encoding a polypeptide at least 95% identical or similar to a polypeptide selected from the group consisting of SEQ ID NOs: 1 to 8. In a further aspect, a recombinant DNA construct comprises a polynucleotide encoding a polypeptide at least 96% identical or similar to a polypeptide selected from the group consisting of SEQ ID NOs: 1 to 8. In a further aspect, a recombinant DNA construct comprises a polynucleotide encoding a polypeptide at least 97% identical or similar to a polypeptide selected from the group consisting of SEQ ID NOs: 1 to 8. In a further aspect, a recombinant DNA construct comprises a polynucleotide encoding a polypeptide at least 98% identical or similar to a polypeptide selected from the group consisting of SEQ ID NOs: 1 to 8. In a further aspect, a recombinant DNA construct comprises a polynucleotide encoding a polypeptide at least 99% identical or similar to a polypeptide selected from the group consisting of SEQ ID NOs: 1 to 8. In a further aspect, a recombinant DNA construct comprises a polynucleotide encoding a polypeptide 100-% identical to a polypeptide selected from the group consisting of SEQ ID NOs: 1 to 8.

In one aspect, the present specification provides for, and includes, cured tobacco material, or a tobacco product comprising the cured tobacco material, where the cured tobacco material is made from a tobacco plant comprising a cisgenic polynucleotide comprising a heterologous promoter operably linked to a coding region, where the modified tobacco plant comprises enhanced nitrogen use efficiency as compared to an unmodified control tobacco plant lacking the cisgenic polynucleotide when grown under the same conditions.

In one aspect, the present specification provides for, and includes, a greenhouse, growth chamber, or field comprising the modified tobacco seed or plant disclosed herein. In one aspect, the present specification provides for, and includes, a method to grow tobacco plants of the present specification in a greenhouse, growth chamber, or field.

In one aspect, the present specification provides for, and includes, a modified tobacco seed, or tobacco plant grown therefrom, comprising at least one mutation in an endogenous locus encoding a polypeptide selected from the group consisting of SEQ ID NOs: 25 to 40, and where a modified tobacco seed or tobacco plant comprises enhanced nitrogen use efficiency as compared to an unmodified control tobacco plant lacking at least one mutation when grown under the same conditions. In a further aspect, a mutation in an endogenous locus is selected from the group consisting of an insertion, a deletion, a substitution, and an inversion. In another aspect, a mutation in an endogenous locus is a silent mutation, a non-silent mutation, or a null mutation. In a further aspect, a modified tobacco seed or modified tobacco plant is of a Burley variety.

In a further aspect, a modified tobacco plant comprises higher levels of a metabolite selected from the group consisting of 4-guanidinobutanoate, syringaldehyde, thiamin, and p-hydroxybenzaldehyde in root tissue as compared to an unmodified tobacco plant when grown under the same conditions. In a further aspect, a modified tobacco plant comprises higher levels of a metabolite selected from the group consisting of 4-guanidinobutanoate, X-23454, X-23580, and X-23852 in leaf tissue as compared to an unmodified tobacco plant when grown under the same conditions. In a further aspect, a modified tobacco plant comprises lower levels of a metabolite selected from the group consisting of X-2357, N-acetylmuramate, X-23319, X-23852, X-23330, alpha-ketoglutarate, X-21756, 4-hydroxy-2-oxoglutaric acid, X-23937, X-23916, and 1-methyladenine in root tissue as compared to an unmodified tobacco plant lacking when grown under the same conditions. In a further aspect, a modified tobacco plant comprises lower levels of a metabolite selected from the group consisting of X-23453, X-21756, X-11429, X-21796, N'-methylnicotinamide, cotinine, X-23389, N-acetylarginine, N-23366, N-acetylphenylalanine, and naringenin in leaf tissue as compared to an unmodified tobacco plant when grown under the same conditions.

In one aspect, the present specification provides for, and includes, a recombinant DNA construct comprising a heterologous promoter operably linked to a guide RNA comprising at least 18 contiguous nucleotides identical or complementary to a polynucleotide encoding a polypeptide selected from the group consisting of SEQ ID NOs: 25 to 40. In a further aspect, a guide RNA comprises at least 19 contiguous nucleotides identical or complementary to a polynucleotide encoding a polypeptide selected from the group consisting of SEQ ID NOs: 25 to 40. In a further aspect, a guide RNA comprises at least 20 contiguous nucleotides identical or complementary to a polynucleotide encoding a polypeptide selected from the group consisting of SEQ ID NOs: 25 to 40. In a further aspect, a guide RNA comprises at least 21 contiguous nucleotides identical or complementary to a polynucleotide encoding a polypeptide selected from the group consisting of SEQ ID NOs: 25 to 40. In a further aspect, a guide RNA comprises at least 22 contiguous nucleotides identical or complementary to a polynucleotide encoding a polypeptide selected from the group consisting of SEQ ID NOs: 25 to 40. In a further aspect, a guide RNA comprises at least 23 contiguous nucleotides identical or complementary to a polynucleotide encoding a polypeptide selected from the group consisting of SEQ ID NOs: 25 to 40. In a further aspect, a guide RNA comprises at least 24 contiguous nucleotides identical or complementary to a polynucleotide encoding a polypeptide selected from the group consisting of SEQ ID NOs: 25 to 40. In a further aspect, a guide RNA comprises at least 25 contiguous nucleotides identical or complementary to a polynucleotide encoding a polypeptide selected from the group consisting of SEQ ID NOs: 25 to 40. In a further aspect, a guide RNA comprises at least 26 contiguous nucleotides identical or complementary to a polynucleotide encoding a polypeptide selected from the group consisting of SEQ ID NOs: 25 to 40. In a further aspect, a guide RNA comprises at least 27 contiguous nucleotides identical or complementary to a polynucleotide encoding a polypeptide selected from the group consisting of SEQ ID NOs: 25 to 40. In a further aspect, a guide RNA comprises at least 28 contiguous nucleotides 100% identical or complementary to a polynucleotide encoding a polypeptide selected from the group consisting of SEQ ID NOs: 25 to 40.

In one aspect, the present specification provides for, and includes, cured tobacco material, or a tobacco product comprising the cured tobacco material, where the cured tobacco material is made from a tobacco plant comprising at least one mutation in an endogenous locus encoding a polypeptide selected from the group consisting of SEQ ID NOs: 25 to 40, and where the modified tobacco seed or tobacco plant comprises enhanced NUE as compared to an unmodified control tobacco plant lacking at least one mutation when grown under the same conditions. In a further aspect, a tobacco plant comprises at least two mutations in an endogenous locus encoding a polypeptide selected from the group consisting of SEQ ID NOs: 25 to 40. In a further aspect, a tobacco plant comprises at least three mutations in an endogenous locus encoding a polypeptide selected from the group consisting of SEQ ID NOs: 25 to 40. In a further aspect, a tobacco plant comprises at least four mutations in an endogenous locus encoding a polypeptide selected from the group consisting of SEQ ID NOs: 25 to 40. In a further aspect, a tobacco plant comprises at least five mutations in an endogenous locus encoding a polypeptide selected from the group consisting of SEQ ID NOs: 25 to 40. In a further aspect, a tobacco plant comprises at least six mutations in an endogenous locus encoding a polypeptide selected from the group consisting of SEQ ID NOs: 25 to 40. In a further aspect, a tobacco plant comprises at least seven mutations in an endogenous locus encoding a polypeptide selected from the group consisting of SEQ ID NOs: 25 to 40. In a further aspect, a tobacco plant comprises at least eight mutations in an endogenous locus encoding a polypeptide selected from the group consisting of SEQ ID NOs: 25 to 40. In a further aspect, a tobacco plant comprises at least nine mutations in an endogenous locus encoding a polypeptide selected from the group consisting of SEQ ID NOs: 25 to 40. In a further aspect, a tobacco plant comprises at least ten mutations in an endogenous locus encoding a polypeptide selected from the group consisting of SEQ ID NOs: 25 to 40.

In one aspect, the present specification provides for, and includes, a modified tobacco seed, or tobacco plant grown therefrom, comprising a cisgenic polynucleotide comprising a heterologous promoter operably linked to a polynucleotide encoding a small RNA (sRNA) at least 85% identical or complementary to a polynucleotide selected from the group consisting of SEQ ID NOs: 41 to 56, and where the modified tobacco seed or tobacco plant comprises enhanced NUE as compared to an unmodified control tobacco plant lacking the cisgenic polynucleotide when grown under the same conditions. In a further aspect, a cisgenic polynucleotide comprises a polynucleotide encoding a sRNA at least 90% identical or complementary to a polynucleotide selected from the group consisting of SEQ ID NOs: 41 to 56. In a further aspect, a cisgenic polynucleotide comprises a polynucleotide encoding a sRNA at least 91% identical or complementary to a polynucleotide selected from the group consisting of SEQ ID NOs: 41 to 56. In a further aspect, a cisgenic polynucleotide comprises a polynucleotide encoding a sRNA at least 92% identical or complementary to a polynucleotide selected from the group consisting of SEQ ID NOs: 41 to 56. In a further aspect, a cisgenic polynucleotide comprises a polynucleotide encoding a sRNA at least 93% identical or complementary to a polynucleotide selected from the group consisting of SEQ ID NOs: 41 to 56. In a further aspect, a cisgenic polynucleotide comprises a polynucleotide encoding a sRNA at least 94% identical or complementary to a polynucleotide selected from the group consisting of SEQ ID NOs: 41 to 56. In a further aspect, a cisgenic polynucleotide comprises a polynucleotide encoding a sRNA at least 95% identical or complementary to a polynucleotide selected from the group consisting of SEQ ID NOs: 41 to 56. In a further aspect, a cisgenic polynucleotide comprises a polynucleotide encoding a sRNA at least 96% identical or complementary to a polynucleotide selected from the group consisting of SEQ ID NOs: 41 to 56. In a further aspect, a cisgenic polynucleotide comprises a polynucleotide encoding a sRNA at least 97% identical or complementary to a polynucleotide selected from the group consisting of SEQ ID NOs: 41 to 56. In a further aspect, a cisgenic polynucleotide comprises a polynucleotide encoding a sRNA at least 98% identical or complementary to a polynucleotide selected from the group consisting of SEQ ID NOs: 41 to 56. In a further aspect, a cisgenic polynucleotide comprises a polynucleotide encoding a sRNA at least 99% identical or complementary to a polynucleotide selected from the group consisting of SEQ ID NOs: 41 to 56. In a further aspect, a cisgenic polynucleotide comprises a polynucleotide encoding a sRNA 100-% identical or complementary to a polynucleotide selected from the group consisting of SEQ ID NOs: 41 to 56. In a further aspect, a heterologous promoter is selected from the group consisting of a constitutive promoter, an inducible promoter, a tissue-preferred promoter, and a tissue-specific promoter. In a further aspect, a tissue-preferred promoter is a leaf-preferred promoter. In a further aspect, a tissue-preferred promoter is a root-preferred promoter.

In a further aspect, a sRNA having at least 18 nucleotides. In a further aspect, a sRNA comprises at least 19 nucleotides. In a further aspect, a sRNA comprises at least 20 nucleotides. In a further aspect, a sRNA comprises at least 21 nucleotides. In a further aspect, a sRNA comprises at least 22 nucleotides. In a further aspect, a sRNA comprises at least 23 nucleotides. In a further aspect, a sRNA comprises at least 24 nucleotides. In a further aspect, a sRNA comprises at least 25 nucleotides. In a further aspect, a sRNA comprises at least 26 nucleotides. In a further aspect, a sRNA comprises at least 27 nucleotides. In a further aspect, a sRNA comprises at least 28 nucleotides. In a further aspect, a sRNA is selected from the group consisting of a microRNA, a small-interfering RNA (siRNA), a trans-acting siRNA, and precursors thereof. In a further aspect, a sRNA down-regulates the expression or translation of a polynucleotide selected from the group consisting of SEQ ID NOs: 41 to 56.

In one aspect, the present specification provides for, and includes, a recombinant DNA construct comprising a heterologous promoter operably linked to a polynucleotide encoding a small RNA (sRNA) at least 85% identical or complementary to a polynucleotide selected from the group consisting of SEQ ID NOs: 41 to 56. In a further aspect, a recombinant DNA construct comprises a polynucleotide encoding a sRNA at least 90% identical or complementary to a polynucleotide selected from the group consisting of SEQ ID NOs: 41 to 56. In a further aspect, a recombinant DNA construct comprises a polynucleotide encoding a sRNA at least 91% identical or complementary to a polynucleotide selected from the group consisting of SEQ ID NOs: 41 to 56. In a further aspect, a recombinant DNA construct comprises a polynucleotide encoding a sRNA at least 92% identical or complementary to a polynucleotide selected from the group consisting of SEQ ID NOs: 41 to 56. In a further aspect, a recombinant DNA construct comprises a polynucleotide encoding a sRNA at least 93% identical or complementary to a polynucleotide selected from the group consisting of SEQ ID NOs: 41 to 56. In a further aspect, a recombinant DNA construct comprises a polynucleotide encoding a sRNA at least 94% identical or complementary to a polynucleotide selected from the group consisting of SEQ ID NOs: 41 to 56. In a further aspect, a recombinant DNA construct comprises a polynucleotide encoding a sRNA at least 95% identical or complementary to a polynucleotide selected from the group consisting of SEQ ID NOs: 41 to 56. In a further aspect, a recombinant DNA construct comprises a polynucleotide encoding a sRNA at least 96% identical or complementary to a polynucleotide selected from the group consisting of SEQ ID NOs: 41 to 56. In a further aspect, a recombinant DNA construct comprises a polynucleotide encoding a sRNA at least 97% identical or complementary to a polynucleotide selected from the group consisting of SEQ ID NOs: 41 to 56. In a further aspect, a recombinant DNA construct comprises a polynucleotide encoding a sRNA at least 98% identical or complementary to a polynucleotide selected from the group consisting of SEQ ID NOs: 41 to 56. In a further aspect, a recombinant DNA construct comprises a polynucleotide encoding a sRNA at least 99% identical or complementary to a polynucleotide selected from the group consisting of SEQ ID NOs: 41 to 56. In a further aspect, a recombinant DNA construct comprises a polynucleotide encoding a sRNA 100-% identical or complementary to a polynucleotide selected from the group consisting of SEQ ID NOs: 41 to 56.

In one aspect, the present specification provides for, and includes, cured tobacco material, or a tobacco product comprising the cured tobacco material, where the cured tobacco material is made from a tobacco plant comprising a cisgenic polynucleotide comprising a heterologous promoter operably linked to a polynucleotide encoding a sRNA at least 85% identical or complementary to a polynucleotide selected from the group consisting of SEQ ID NOs: 41 to 56, and where the modified tobacco seed or tobacco plant comprises enhanced NUE as compared to an unmodified control tobacco plant lacking the cisgenic polynucleotide when grown under the same conditions. In a further aspect, a cisgenic polynucleotide encodes a sRNA at least 90% identical or complementary to a polynucleotide selected from the group consisting of SEQ ID NOs: 41 to 56. In a further aspect, a cisgenic polynucleotide encodes a sRNA at least 91% identical or complementary to a polynucleotide selected from the group consisting of SEQ ID NOs: 41 to 56. In a further aspect, a cisgenic polynucleotide encodes a sRNA at least 92% identical or complementary to a polynucleotide selected from the group consisting of SEQ ID NOs: 41 to 56. In a further aspect, a cisgenic polynucleotide encodes a sRNA at least 93% identical or complementary to a polynucleotide selected from the group consisting of SEQ ID NOs: 41 to 56. In a further aspect, a cisgenic polynucleotide encodes a sRNA at least 94% identical or complementary to a polynucleotide selected from the group consisting of SEQ ID NOs: 41 to 56. In a further aspect, a cisgenic polynucleotide encodes a sRNA at least 95% identical or complementary to a polynucleotide selected from the group consisting of SEQ ID NOs: 41 to 56. In a further aspect, a cisgenic polynucleotide encodes a sRNA at least 96% identical or complementary to a polynucleotide selected from the group consisting of SEQ ID NOs: 41 to 56. In a further aspect, a cisgenic polynucleotide encodes a sRNA at least 97% identical or complementary to a polynucleotide selected from the group consisting of SEQ ID NOs: 41 to 56. In a further aspect, a cisgenic polynucleotide encodes a sRNA at least 98% identical or complementary to a polynucleotide selected from the group consisting of SEQ ID NOs: 41 to 56. In a further aspect, a cisgenic polynucleotide encodes a sRNA at least 99% identical or complementary to a polynucleotide selected from the group consisting of SEQ ID NOs: 41 to 56. In a further aspect, a cisgenic polynucleotide encodes a sRNA 100-% identical or complementary to a polynucleotide selected from the group consisting of SEQ ID NOs: 41 to 56.

In one aspect, the present specification provides for, and includes, a method of enhancing the NUE of a tobacco plant comprising introducing a cisgenic nucleic acid molecule into a tobacco cell, and regenerating a modified tobacco plant from that tobacco cell where the modified tobacco plant comprises enhanced NUE as compared to a tobacco plant lacking the cisgenic nucleic acid molecule. In another aspect, the method further comprises crossing the modified tobacco plant with a second tobacco plant or self-pollinating the modified tobacco plant.

In one aspect, the present specification provides for, and includes, a method of enhancing the NUE of a tobacco plant comprising introducing a modification to a nucleic acid molecule encoding a gene having a sequence selected from the group consisting of SEQ ID NOs: 41 to 56 in a tobacco cell and regenerating a modified tobacco plant from the tobacco cell, where the modified tobacco plant comprises enhanced NUE as compared to a tobacco plant lacking the modification. In another aspect, the method further comprises crossing the modified tobacco plant with a second tobacco plant or self-pollinating the modified tobacco plant. In a further aspect, a modification is introducing via a method comprising the use of an RNA-guided nuclease. In a further aspect, an RNA-guided nuclease is selected from the group consisting of a Cas9 nuclease, a Cpf1 nuclease, a CasX nuclease, a CasY nuclease, and functional homologues thereof. In a further aspect, the modification is selected from the group consisting of an insertion, a substitution, an inversion, and a deletion In one aspect, the present specification provides for, and includes, a method of enhancing the NUE of a tobacco plant comprising introducing a nucleic acid encoding a small RNA (sRNA) homologous to at least 18 contiguous nucleic acids of a nucleic acid molecule encoding a gene having a sequence selected from the group consisting of SEQ ID NOs: 41 to 56 in a tobacco cell, and regenerating a modified tobacco plant from the tobacco cell, where the modified tobacco plant comprises enhanced NUE as compared to a tobacco plant lacking the sRNA. In another aspect, the method further comprises crossing the modified tobacco plant with a second tobacco plant or self-pollinating the modified tobacco plant. In a further aspect, the method comprises introducing a sRNA selected from the group consisting of a microRNA, a small-interfering RNA (siRNA), a trans-acting siRNA, and precursors thereof.

In one aspect, the present specification provides for, and includes, a method comprising providing a first population of tobacco plants comprising enhanced NUE, genotyping a first population of tobacco plants for the presence of a molecular marker within 20 cM of an enhanced NUE locus; and selecting one or more tobacco plants genotyped and found to comprise the molecular marker. In a further aspect, a method disclosed herein comprises genotyping a first population of tobacco plants for the presence of a molecular marker within 15 CM of an enhanced NUE locus. In a further aspect, a method disclosed herein comprises genotyping a first population of tobacco plants for the presence of a molecular marker within 10 cM of an enhanced NUE locus. In a further aspect, a method disclosed herein comprises genotyping a first population of tobacco plants for the presence of a molecular marker within 9 cM of an enhanced NUE locus. In a further aspect, a method disclosed herein comprises genotyping a first population of tobacco plants for the presence of a molecular marker within 8 cM of an enhanced NUE locus. In a further aspect, a method disclosed herein comprises genotyping a first population of tobacco plants for the presence of a molecular marker within 7 cM of an enhanced NUE locus. In a further aspect, a method disclosed herein comprises genotyping a first population of tobacco plants for the presence of a molecular marker within 6 cM of an enhanced NUE locus. In a further aspect, a method disclosed herein comprises genotyping a first population of tobacco plants for the presence of a molecular marker within 5 CM of an enhanced NUE locus. In a further aspect, a method disclosed herein comprises genotyping a first population of tobacco plants for the presence of a molecular marker within 4 cM of an enhanced NUE locus. In a further aspect, a method disclosed herein comprises genotyping a first population of tobacco plants for the presence of a molecular marker within 3 cM of an enhanced NUE locus. In a further aspect, a method disclosed herein comprises genotyping a first population of tobacco plants for the presence of a molecular marker within 2 cM of an enhanced NUE locus. In a further aspect, a method disclosed herein comprises genotyping a first population of tobacco plants for the presence of a molecular marker within 1 cM of an enhanced NUE locus. In a further aspect, a method disclosed herein comprises genotyping a first population of tobacco plants for the presence of a molecular marker within 0.5 cM of an enhanced NUE locus. In a further aspect, the method comprises crossing one or more selected tobacco plants to a second tobacco plant; and obtaining progeny seed from that cross. In a further aspect, a molecular marker is selected from the group consisting of a SNP marker, an INDEL marker, an RFLP marker, an SSR marker, an AFLP marker, and a RAPD marker.

In a further aspect, a method provided herein comprises a tobacco plant comprising an enhanced NUE locus comprising a polynucleotide encoding a polypeptide at least 70% identical or similar to a polypeptide selected from the group consisting of SEQ ID NOs: 1 to 8. In a further aspect, a polynucleotide encodes a polypeptide at least 75% identical or similar to a polypeptide selected from the group consisting of SEQ ID NOs: 1 to 8. In a further aspect, a polynucleotide encodes a polypeptide at least 80% identical or similar to a polypeptide selected from the group consisting of SEQ ID NOs: 1 to 8. In a further aspect, a polynucleotide encodes a polypeptide at least 85% identical or similar to a polypeptide selected from the group consisting of SEQ ID NOs: 1 to 8. In a further aspect, a polynucleotide encodes a polypeptide at least 90% identical or similar to a polypeptide selected from the group consisting of SEQ ID NOs: 1 to 8. In a further aspect, a polynucleotide encodes a polypeptide at least 95% identical or similar to a polypeptide selected from the group consisting of SEQ ID NOs: 1 to 8. In a further aspect, a polynucleotide encodes a polypeptide at least 96% identical or similar to a polypeptide selected from the group consisting of SEQ ID NOs: 1 to 8. In a further aspect, a polynucleotide encodes a polypeptide at least 97% identical or similar to a polypeptide selected from the group consisting of SEQ ID NOs: 1 to 8. In a further aspect, a polynucleotide encodes a polypeptide at least 98% identical or similar to a polypeptide selected from the group consisting of SEQ ID NOs: 1 to 8. In a further aspect, a polynucleotide encodes a polypeptide at least 99% identical or similar to a polypeptide selected from the group consisting of SEQ ID NOs: 1 to 8. In a further aspect, a polynucleotide encodes a polypeptide 100-% identical to a polypeptide selected from the group consisting of SEQ ID NOs: 1 to 8. In a further aspect, an enhanced NUE locus is genetically linked to a polynucleotide sequence selected from the group consisting of SEQ ID NOs: 57 to 64. In another aspect, an enhanced NUE locus is genetically linked to a G nucleotide at position 57 of SEQ ID NOs: 58. In another aspect, an enhanced NUE locus is genetically linked to a C nucleotide at position 117 of SEQ ID NOs: 58. In another aspect, an enhanced NUE locus is genetically linked to a G nucleotide at position 57 and a C nucleotide at position 117 of SEQ ID NOs: 58. In another aspect, an enhanced NUE locus is genetically linked to a T nucleotide at position 147 of SEQ ID NO:57. In another aspect, an enhanced NUE locus is genetically linked to a G nucleotide at position 162 of SEQ ID NO:59. In another aspect, an enhanced NUE locus is genetically linked to a C nucleotide at position 36 of SEQ ID NO:60. In another aspect, an enhanced NUE locus is genetically linked to a T nucleotide at position 36 of SEQ ID NO:61. In another aspect, an enhanced NUE locus is genetically linked to a T nucleotide at position 36 of SEQ ID NO:62. In another aspect, an enhanced NUE locus is genetically linked to a G nucleotide at position 36 of SEQ ID NO:63. In another aspect, an enhanced NUE locus is genetically linked to a T nucleotide at position 36 of SEQ ID NO:64.

In one aspect, the present specification provides for, and includes, cured tobacco material, or a tobacco product comprising the cured tobacco material, where the cured tobacco material is made from a tobacco plant comprising at least one functional allele of a Yellow Burley 1 (YB1) locus and at least one allele associated with enhanced NUE at one or more molecular markers selected from the group consisting of SEQ ID NOs: 57-64, where enhanced NUE is relative to a control tobacco plant without at least one functional allele of a YB1 locus and without one or more molecular markers selected from the group consisting of SEQ ID NOs: 57-64 when grown under the same conditions. In a further aspect, a tobacco plant comprises at least two molecular markers associated with enhanced NUE selected from the group consisting of SEQ ID NOs: 57 to 64. In a further aspect, a tobacco plant comprises at least three molecular markers associated with enhanced NUE selected from the group consisting of SEQ ID NOs: 57 to 64. In a further aspect, a tobacco plant comprises at least four molecular markers associated with enhanced NUE selected from the group consisting of SEQ ID NOs: 57 to 64. In a further aspect, a tobacco plant comprises at least five molecular markers associated with enhanced NUE selected from the group consisting of SEQ ID NOs: 57 to 64. In a further aspect, a tobacco plant comprises at least six molecular markers associated with enhanced NUE selected from the group consisting of SEQ ID NOs: 57 to 64. In a further aspect, a tobacco plant comprises at least seven molecular markers associated with enhanced NUE selected from the group consisting of SEQ ID NOs: 57 to 64. In a further aspect, a tobacco plant comprises at least eight molecular markers associated with enhanced NUE selected from the group consisting of SEQ ID NOs: 57 to 64. In a further aspect, a tobacco plant comprises at least nine molecular markers associated with enhanced NUE selected from the group consisting of SEQ ID NOs: 57 to 64. In a further aspect, a tobacco plant comprises at least ten molecular markers associated with enhanced NUE selected from the group consisting of SEQ ID NOs: 57 to 64. In a further aspect, a molecular marker is selected from the group consisting of a SNP marker, an INDEL marker, an RFLP marker, an SSR marker, an AFLP marker, and a RAPD marker. In another aspect, the cured tobacco material or a product derived therefrom also comprises at least one functional allele of a YB2 locus.

In one aspect, the present specification provides for, and includes, cured tobacco material, or a tobacco product comprising the cured tobacco material, where the cured tobacco material is made from a tobacco plant comprising enhanced NUE, and where the tobacco plant comprises at least one functional allele of a YB1 locus, and further comprises at least one allele associated with enhanced NUE at one or more molecular markers located within 20 cM of a sequence selected from the group consisting of SEQ ID NOs: 57, 58, 59, 60, 61, 62, 63, and 64. In a further aspect, the tobacco plant comprises at least one allele associated with enhanced NUE at one or more molecular markers located within 15 cM of a sequence selected from the group consisting of SEQ ID NOs: 57-64. In a further aspect, the tobacco plant comprises at least one allele associated with enhanced NUE at one or more molecular markers located within 10 cM of a sequence selected from the group consisting of SEQ ID NOs: 57-64. In a further aspect, the tobacco plant comprises at least one allele associated with enhanced NUE at one or more molecular markers located within 9 cM of a sequence selected from the group consisting of SEQ ID NOs: 57-64. In a further aspect, the tobacco plant comprises at least one allele associated with enhanced NUE at one or more molecular markers located within 8 cM of a sequence selected from the group consisting of SEQ ID NOs: 57-64. In a further aspect, the tobacco plant comprises at least one allele associated with enhanced NUE at one or more molecular markers located within 7 cM of a sequence selected from the group consisting of SEQ ID NOs: 57-64. In a further aspect, the tobacco plant comprises at least one allele associated with enhanced NUE at one or more molecular markers located within 6 cM of a sequence selected from the group consisting of SEQ ID NOs: 57-64. In a further aspect, the tobacco plant comprises at least one allele associated with enhanced NUE at one or more molecular markers located within 5 cM of a sequence selected from the group consisting of SEQ ID NOs: 57-64. In a further aspect, the tobacco plant comprises at least one allele associated with enhanced NUE at one or more molecular markers located within 4 cM of a sequence selected from the group consisting of SEQ ID NOs: 57-64. In a further aspect, the tobacco plant comprises at least one allele associated with enhanced NUE at one or more molecular markers located within 3 cM of a sequence selected from the group consisting of SEQ ID NOs: 57-64. In a further aspect, the tobacco plant comprises at least one allele associated with enhanced NUE at one or more molecular markers located within 2 cM of a sequence selected from the group consisting of SEQ ID NOs: 57-64. In a further aspect, the tobacco plant comprises at least one allele associated with enhanced NUE at one or more molecular markers located within 1 cM of a sequence selected from the group consisting of SEQ ID NOs: 57-64. In a further aspect, the tobacco plant comprises at least one allele associated with enhanced NUE at one or more molecular markers located within 0.5 CM of a sequence selected from the group consisting of SEQ ID NOs: 57-64. In a further aspect, a molecular marker is selected from the group consisting of a SNP marker, an INDEL marker, an RFLP marker, an SSR marker, an AFLP marker, and a RAPD marker.

In a further aspect, the tobacco plant comprising at least one functional allele of a YB1 locus is homozygous for a functional allele of a YB1 locus. In another aspect, the tobacco plant further comprises at least one functional allele of a YB2 locus. In another aspect, the tobacco plant is homozygous for a functional allele of a YB2 locus.

In a further aspect, the present specification provides for, and includes, cured tobacco material, or a tobacco product comprising the cured tobacco material, where the cured tobacco material is made from a double haploid tobacco plant.

In one aspect, the present specification provides for, and includes, cured tobacco material, or a tobacco product comprising the cured tobacco material, where the cured tobacco material is made from a tobacco plant comprising enhanced NUE, and where the tobacco plant comprises at least one functional allele of a YB1 locus, and further comprises at least one allele associated with enhanced NUE at one or more molecular markers located within 5,000,000 nucleotides of a sequence selected from the group consisting of SEQ ID NOs: 57, 58, 59, 60, 61, 62, 63, and 64. In a further aspect, the tobacco plant comprises at least one allele associated with enhanced NUE at one or more molecular markers located within 2,500,000 nucleotides of a sequence selected from the group consisting of SEQ ID NOs: 57-64. In a further aspect, the tobacco plant comprises at least one allele associated with enhanced NUE at one or more molecular markers located within 1,250,000 nucleotides of a sequence selected from the group consisting of SEQ ID NOs: 57-64. In a further aspect, the tobacco plant comprises at least one allele associated with enhanced NUE at one or more molecular markers located within 1,000,000 nucleotides of a sequence selected from the group consisting of SEQ ID NOs: 57-64. In a further aspect, the tobacco plant comprises at least one allele associated with enhanced NUE at one or more molecular markers located within 500,000 nucleotides of a sequence selected from the group consisting of SEQ ID NOs: 57-64. In a further aspect, the tobacco plant comprises at least one allele associated with enhanced NUE at one or more molecular markers located within 400,000 nucleotides of a sequence selected from the group consisting of SEQ ID NOs: 57-64. In a further aspect, the tobacco plant comprises at least one allele associated with enhanced NUE at one or more molecular markers located within 300,000 nucleotides of a sequence selected from the group consisting of SEQ ID NOs: 57-64. In a further aspect, the tobacco plant comprises at least one allele associated with enhanced NUE at one or more molecular markers located within 200,000 nucleotides of a sequence selected from the group consisting of SEQ ID NOs: 57-64. In a further aspect, the tobacco plant comprises at least one allele associated with enhanced NUE at one or more molecular markers located within 100,000 nucleotides of a sequence selected from the group consisting of SEQ ID NOs: 57-64. In a further aspect, the tobacco plant comprises at least one allele associated with enhanced NUE at one or more molecular markers located within 80,000 nucleotides of a sequence selected from the group consisting of SEQ ID NOs: 57-64. In a further aspect, the tobacco plant comprises at least one allele associated with enhanced NUE at one or more molecular markers located within 60,000 nucleotides of a sequence selected from the group consisting of SEQ ID NOs: 57-64. In a further aspect, the tobacco plant comprises at least one allele associated with enhanced NUE at one or more molecular markers located within 40,000 nucleotides of a sequence selected from the group consisting of SEQ ID NOs: 57-64. In a further aspect, the tobacco plant comprises at least one allele associated with enhanced NUE at one or more molecular markers located within 20,000 nucleotides of a sequence selected from the group consisting of SEQ ID NOs: 57-64. In a further aspect, the tobacco plant comprises at least one allele associated with enhanced NUE at one or more molecular markers located within 10,000 nucleotides of a sequence selected from the group consisting of SEQ ID NOs: 57-64. In a further aspect, the tobacco plant comprises at least one allele associated with enhanced NUE at one or more molecular markers located within 5,000 nucleotides of a sequence selected from the group consisting of SEQ ID NOs: 57-64. In a further aspect, the tobacco plant comprises at least one allele associated with enhanced NUE at one or more molecular markers located within 2,500 nucleotides of a sequence selected from the group consisting of SEQ ID NOs: 57-64. In a further aspect, the tobacco plant comprises at least one allele associated with enhanced NUE at one or more molecular markers located within 1,000 nucleotides of a sequence selected from the group consisting of SEQ ID NOs: 57-64. In a further aspect, the tobacco plant comprises at least one allele associated with enhanced NUE at one or more molecular markers located within 800 nucleotides of a sequence selected from the group consisting of SEQ ID NOs: 57-64. In a further aspect, the tobacco plant comprises at least one allele associated with enhanced NUE at one or more molecular markers located within 600 nucleotides of a sequence selected from the group consisting of SEQ ID NOs: 57-64. In a further aspect, the tobacco plant comprises at least one allele associated with enhanced NUE at one or more molecular markers located within 400 nucleotides of a sequence selected from the group consisting of SEQ ID NOs: 57-64. In a further aspect, the tobacco plant comprises at least one allele associated with enhanced NUE at one or more molecular markers located within 200 nucleotides of a sequence selected from the group consisting of SEQ ID NOs: 57-64. In a further aspect, the tobacco plant comprises at least one allele associated with enhanced NUE at one or more molecular markers located within 100 nucleotides of a sequence selected from the group consisting of SEQ ID NOs: 57-64. In a further aspect, a molecular marker is selected from the group consisting of a SNP marker, an INDEL marker, an RFLP marker, an SSR marker, an AFLP marker, and a RAPD marker.

In one aspect, the present specification provides for, and includes, a method of creating a tobacco plant or a population of tobacco plants comprising enhanced nitrogen use efficiency (NUE). In an aspect, the method comprises providing a first population of tobacco plants comprising at least one enhanced NUE trait and a second population of tobacco plants lacking at least one enhanced NUE trait. In another aspect, the method further comprises genotyping a first population of tobacco plants for the presence of one or more molecular markers within 20 cM of an allele associated with enhanced NUE comprising a sequence selected from the group consisting of SEQ ID NOs: 57, 58, 59, 60, 61, 62, 63, and 64. In another aspect, the method further comprises selecting one or more tobacco plants of a genotyped first population of tobacco plants that comprise one or more molecular markers within 20 cM of an allele associated with enhanced NUE comprising a sequence selected from the group consisting of SEQ ID NOs: 57-64. In another aspect, the method further comprises genotyping a second population of tobacco plants comprising at least one functional allele of a Yellow Burley 1 (YB1) locus. In another aspect, the method further comprises selecting one or more tobacco plants of a genotyped second population of tobacco plants that comprise at least one functional allele of a Yellow Burley 1 (YB1) locus. In another aspect, the method further comprises crossing at least one plant selected from a genotyped, selected first population comprising one or more molecular markers within 20 cM of an allele associated with enhanced NUE comprising a sequence selected from the group consisting of SEQ ID NOs: 57-64 with at least one plant of a genotyped, selected second population of tobacco plants comprising at least one functional allele of a Yellow Burley 1 (YB1) locus. In an aspect, the method further comprises producing progeny tobacco plants or tobacco seeds. In an aspect, the method further comprises obtaining progeny plants or progeny seeds that comprise an enhanced NUE trait, one or more molecular markers associated with enhanced NUE, and at least one functional allele of a YB1 locus. In a further aspect, the first population of tobacco plants is homozygous for an allele associated with enhanced NUE. In a further aspect, the second population of tobacco plants is homozygous for a functional allele at a Yellow Burley 1 (YB1) locus. In a further aspect, the progeny tobacco plant is also assayed for at least one functional allele of a Yellow Burley 2 (YB2) locus. In another aspect, the progeny tobacco plant is also selected for at least one functional allele of a YB2 locus.

In one aspect, the present specification provides for, and includes, a method of creating a tobacco plant or a population of tobacco plants comprising enhanced nitrogen use efficiency (NUE). In an aspect, the method comprises providing a first population of tobacco plants comprising at least one enhanced NUE trait and a second population of tobacco plants lacing at least one enhanced NUE trait. In another aspect, the method further comprises genotyping a first population of tobacco plants for the presence of one or more molecular markers within 5,000,000 nucleotides of an allele associated with enhanced NUE comprising a sequence selected from the group consisting of SEQ ID NOs: 57, 58, 59, 60, 61, 62, 63, and 64. In another aspect, the method further comprises selecting one or more tobacco plants of a genotyped first population of tobacco plants that comprise one or more molecular markers within 5,000,000 nucleotides of an allele associated with enhanced NUE comprising a sequence selected from the group consisting of SEQ ID NOs: 57-64. In another aspect, the method further comprises genotyping a second population of tobacco plants comprising at least one functional allele of a Yellow Burley 1 (YB1) locus. In another aspect, the method further comprises selecting one or more tobacco plants of a genotyped second population of tobacco plants that comprise at least one functional allele of a Yellow Burley 1 (YB1) locus. In another aspect, the method further comprises crossing at least one plant selected from a genotyped, selected first population comprising one or more molecular markers within 5,000,000 nucleotides of an allele associated with enhanced NUE comprising a sequence selected from the group consisting of SEQ ID NOs: 57-64 with at least one plant of a genotyped, selected second population of tobacco plants comprising at least one functional allele of a Yellow Burley 1 (YB1) locus to produce progeny tobacco plants or tobacco seeds. In an aspect, the method further comprises obtaining progeny plants or progeny seeds that comprise an enhanced NUE trait, one or more molecular markers associated with enhanced NUE, and at least one functional allele of a YB1 locus. In a further aspect, the first population of tobacco plants is homozygous for an allele associated with enhanced NUE. In a further aspect, the second population of tobacco plants is homozygous at a Yellow Burley 1 (YB1) locus. In a further aspect, the tobacco plant is also assayed for at least one functional allele of a Yellow Burley 2 (YB2) locus. In another aspect, the second population of tobacco plants is also comprises at least one functional allele of a YB2 locus.

In a further aspect, the present specification provides for, and includes, a method of creating a double haploid tobacco plant or a population of double haploid tobacco plants comprising enhanced nitrogen use efficiency (NUE).

In one aspect, the present specification provides for, and includes, a method of creating a tobacco plant or a population of tobacco plants comprising enhanced nitrogen use efficiency (NUE). In an aspect, the method further comprises providing a first population of tobacco plants comprising at least one enhanced NUE trait and second population of tobacco plants lacking at least one enhanced NUE trait. In an aspect, the method further comprises genotyping a first population of tobacco plants for the presence of one or more molecular markers within 20 cM of an allele associated with enhanced NUE comprising a sequence selected from the group consisting of SEQ ID NOs: 57-64. In an aspect, the method further comprises selecting one or more tobacco plants of a genotyped first population of tobacco plants that comprise one or more molecular markers within 20 cM of an allele associated with enhanced NUE comprising a sequence selected from the group consisting of SEQ ID NOs: 57-64. In an aspect, the method further comprises crossing at least one plant of a first selected, genotyped population with at least one plant of a second population that does not comprise said at least one enhanced NUE trait. In an aspect, the method further comprises obtaining progeny plants or progeny seeds that comprise an enhanced NUE trait, one or more molecular markers associated with enhanced NUE, and at least one functional allele of a Yellow Burley 1 locus. In a further aspect, the obtained progeny plants or seeds further comprise at least one functional allele of a YB2 locus.

In one aspect, the present specification provides for, and includes, a method of creating a tobacco plant or a population of tobacco plants comprising enhanced nitrogen use efficiency (NUE). In an aspect, the method further comprises providing a first population of tobacco plants comprising at least one enhanced NUE trait and second population of tobacco plants lacking said at least one enhanced NUE trait. In an aspect, the method further comprises genotyping a first population of tobacco plants for the presence of one or more molecular markers within 5,000,000 nucleotides of an allele associated with enhanced NUE comprising a sequence selected from the group consisting of SEQ ID NOs: 57-64. In an aspect, the method further comprises selecting one or more tobacco plants of a genotyped first population of tobacco plants that comprise one or more molecular markers within 5,000,000 nucleotides of an allele associated with enhanced NUE comprising a sequence selected from the group consisting of SEQ ID NOs: 57-64. In an aspect, the method further comprises crossing at least one plant of a first selected, genotyped population with at least one plant of a second population that does not comprise said at least one enhanced NUE trait. In an aspect, the method further comprises obtaining progeny plants or progeny seeds that comprise an enhanced NUE trait, one or more molecular markers associated with enhanced NUE, and at least one functional allele of a Yellow Burley 1 locus. In a further aspect, the obtained progeny plants or seeds further comprise at least one functional allele of a YB2 locus.

In one aspect, the present specification provides for, and includes, a method comprising providing a first population of tobacco plants comprising enhanced NUE, genotyping a first population of tobacco plants for the presence of a molecular marker within 5,000,000 nucleotides of an enhanced NUE locus; and selecting one or more tobacco plants genotyped and found to comprise the molecular marker. In a further aspect, a method disclosed herein comprises genotyping a first population of tobacco plants for the presence of a molecular marker within 2,500,000 nucleotides of an enhanced NUE locus. In a further aspect, a method disclosed herein comprises genotyping a first population of tobacco plants for the presence of a molecular marker within 2,000,000 nucleotides of an enhanced NUE locus. In a further aspect, a method disclosed herein comprises genotyping a first population of tobacco plants for the presence of a molecular marker within 1,250,000 nucleotides of an enhanced NUE locus. In a further aspect, a method disclosed herein comprises genotyping a first population of tobacco plants for the presence of a molecular marker within 1,000,000 nucleotides of an enhanced NUE locus. In a further aspect, a method disclosed herein comprises genotyping a first population of tobacco plants for the presence of a molecular marker within 750,000 nucleotides of an enhanced NUE locus. In a further aspect, a method disclosed herein comprises genotyping a first population of tobacco plants for the presence of a molecular marker within 500,000 nucleotides of an enhanced NUE locus. In a further aspect, a method disclosed herein comprises genotyping a first population of tobacco plants for the presence of a molecular marker within 400,000 nucleotides of an enhanced NUE locus. In a further aspect, a method disclosed herein comprises genotyping a first population of tobacco plants for the presence of a molecular marker within 300,000 nucleotides of an enhanced NUE locus. In a further aspect, a method disclosed herein comprises genotyping a first population of tobacco plants for the presence of a molecular marker within 200,000 nucleotides of an enhanced NUE locus. In a further aspect, a method disclosed herein comprises genotyping a first population of tobacco plants for the presence of a molecular marker within 100,000 nucleotides of an enhanced NUE locus. In a further aspect, a method disclosed herein comprises genotyping a first population of tobacco plants for the presence of a molecular marker within 80,000 nucleotides of an enhanced NUE locus. In a further aspect, a method disclosed herein comprises genotyping a first population of tobacco plants for the presence of a molecular marker within 60,000 nucleotides of an enhanced NUE locus. In a further aspect, a method disclosed herein comprises genotyping a first population of tobacco plants for the presence of a molecular marker within 40,000 nucleotides of an enhanced NUE locus. In a further aspect, a method disclosed herein comprises genotyping a first population of tobacco plants for the presence of a molecular marker within 20,000 nucleotides of an enhanced NUE locus. In a further aspect, a method disclosed herein comprises genotyping a first population of tobacco plants for the presence of a molecular marker within 10,000 nucleotides of an enhanced NUE locus. In a further aspect, a method disclosed herein comprises genotyping a first population of tobacco plants for the presence of a molecular marker within 5,000 nucleotides of an enhanced NUE locus. In a further aspect, a method disclosed herein comprises genotyping a first population of tobacco plants for the presence of a molecular marker within 2,500 nucleotides of an enhanced NUE locus. In a further aspect, a method disclosed herein comprises genotyping a first population of tobacco plants for the presence of a molecular marker within 1,000 nucleotides of an enhanced NUE locus. In a further aspect, a method disclosed herein comprises genotyping a first population of tobacco plants for the presence of a molecular marker within 800 nucleotides of an enhanced NUE locus. In a further aspect, a method disclosed herein comprises genotyping a first population of tobacco plants for the presence of a molecular marker within 600 nucleotides of an enhanced NUE locus. In a further aspect, a method disclosed herein comprises genotyping a first population of tobacco plants for the presence of a molecular marker within 400 nucleotides of an enhanced NUE locus. In a further aspect, a method disclosed herein comprises genotyping a first population of tobacco plants for the presence of a molecular marker within 200 nucleotides of an enhanced NUE locus. In a further aspect, a method disclosed herein comprises genotyping a first population of tobacco plants for the presence of a molecular marker within 100 nucleotides of an enhanced NUE locus.

In a further aspect, the method comprises crossing one or more selected tobacco plants to a second tobacco plant; and obtaining progeny seed from that cross. In a further aspect, a molecular marker is selected from the group consisting of a SNP marker, an INDEL marker, an RFLP marker, an SSR marker, an AFLP marker, and a RAPD marker.

In a further aspect of a method provided herein, a first population of tobacco plants is of a Maryland variety. In a further aspect, a method provided herein comprises a first population of tobacco plants of a Maryland tobacco variety selected from the group consisting of Md 10, Md 14D2, Md 21, Md 40, Md 59, Md 64, Md 201, Md 341, Md 402, Md 601, Md 609, Md 872, Md Mammoth, Banket A1, K326, K346, K358, K394, K399, K730, NC196, NC37NF, NC471, NC55, NC92, NC2326, NC95, and NC925. In a further aspect, a method provided herein comprises a second population of tobacco plants of the Burley variety. In a further aspect, a method provided herein comprises a second population of tobacco plants of a variety selected from the group consisting of TN86, TN86LC, TN90, TN90LC, TN97, TN97LC. In a further aspect, a method provided herein comprises a wild-type Burley variety that comprises a TN90 plant.

In a further aspect, a method provided herein comprises progeny seed comprising molecular markers. In a further aspect, a method provided herein comprises progeny seed comprising enhanced NUE. In a further aspect, a method provided herein comprises progeny seed comprising a molecular marker within 5,000,000 nucleotides of an enhanced NUE efficiency locus provided herein. In a further aspect, a method provided herein comprises progeny seed comprising a molecular marker within 2,500,000 nucleotides of an enhanced NUE efficiency locus provided herein. In a further aspect, a method provided herein comprises progeny seed comprising a molecular marker within 1,250,000 nucleotides of an enhanced NUE efficiency locus provided herein. In a further aspect, a method provided herein comprises progeny seed comprising a molecular marker within 1,000,000 nucleotides of an enhanced NUE efficiency locus provided herein. In a further aspect, a method provided herein comprises progeny seed comprising a molecular marker within 750,000 nucleotides of an enhanced NUE efficiency locus provided herein. In a further aspect, a method provided herein comprises progeny seed comprising a molecular marker within 500,000 nucleotides of an enhanced NUE efficiency locus provided herein. In a further aspect, a method provided herein comprises progeny seed comprising a molecular marker within 400,000 nucleotides of an enhanced NUE efficiency locus provided herein. In a further aspect, a method provided herein comprises progeny seed comprising a molecular marker within 300,000 nucleotides of an enhanced NUE efficiency locus provided herein. In a further aspect, a method provided herein comprises progeny seed comprising a molecular marker within 200,000 nucleotides of an enhanced NUE efficiency locus provided herein. In a further aspect, a method provided herein comprises progeny seed comprising a molecular marker within 100,000 nucleotides of an enhanced NUE efficiency locus provided herein. In a further aspect, a method provided herein comprises progeny seed comprising a molecular marker within 80,000 nucleotides of an enhanced NUE efficiency locus provided herein. In a further aspect, a method provided herein comprises progeny seed comprising a molecular marker within 60,000 nucleotides of an enhanced NUE efficiency locus provided herein. In a further aspect, a method provided herein comprises progeny seed comprising a molecular marker within 40,000 nucleotides of an enhanced NUE efficiency locus provided herein. In a further aspect, a method provided herein comprises progeny seed comprising a molecular marker within 20,000 nucleotides of an enhanced NUE efficiency locus provided herein. In a further aspect, a method provided herein comprises progeny seed comprising a molecular marker within 10,000 nucleotides of an enhanced NUE efficiency locus provided herein. In a further aspect, a method provided herein comprises progeny seed comprising a molecular marker within 5,000 nucleotides of an enhanced NUE efficiency locus provided herein. In a further aspect, a method provided herein comprises progeny seed comprising a molecular marker within 2,500 nucleotides of an enhanced NUE efficiency locus provided herein. In a further aspect, a method provided herein comprises progeny seed comprising a molecular marker within 1,000 nucleotides of an enhanced NUE efficiency locus provided herein. In a further aspect, a method provided herein comprises progeny seed comprising a molecular marker within 800 nucleotides of an enhanced NUE efficiency locus provided herein. In a further aspect, a method provided herein comprises progeny seed comprising a molecular marker within 600 nucleotides of an enhanced NUE efficiency locus provided herein. In a further aspect, a method provided herein comprises progeny seed comprising a molecular marker within 400 nucleotides of an enhanced NUE efficiency locus provided herein. In a further aspect, a method provided herein comprises progeny seed comprising a molecular marker within 200 nucleotides of an enhanced NUE efficiency locus provided herein. In a further aspect, a method provided herein comprises progeny seed comprising a molecular marker within 100 nucleotides of an enhanced NUE efficiency locus provided herein.

In one aspect, the present specification provides for, and includes, a method of selecting a tobacco plant with an enhanced NUE trait comprising isolating nucleic acids from at least one tobacco plant, assaying the isolated nucleic acids for one or more molecular markers located within 5,000,000 nucleotides of one or more alleles associated with enhanced NUE selected from the group consisting of SEQ ID NOs: 57 to 64, assaying the isolated nucleic acids for at least one functional allele of a Yellow Burley 1 (YB1) locus, and selecting a tobacco plant comprising an enhanced NUE trait, one or more alleles associated with enhanced NUE, and at least one functional allele of a YB1 locus. In a further aspect, the selected tobacco plant further comprises at least one functional allele of a YB2 locus.

In one aspect, the present specification provides for, and includes, a method of selecting a tobacco plant with an enhanced NUE trait comprising isolating nucleic acids from at least one tobacco plant, assaying the isolated nucleic acids for one or more molecular markers located within 5,000,000 nucleotides of one or more alleles associated with enhanced NUE selected from the group consisting of SEQ ID NOs: 57 to 64, assaying the isolated nucleic acids for at least one functional allele of a Yellow Burley 2 (YB2) locus, and selecting a tobacco plant comprising an enhanced NUE trait, one or more alleles associated with enhanced NUE, and at least one functional allele of a YB2 locus.

In a further aspect, a method disclosed herein comprises crossing a selected tobacco plant comprising an enhanced NUE trait, one or more alleles associated with enhanced NUE, and at least one functional allele of a YB1 locus with a second tobacco plant that does not comprise an enhanced NUE trait, and obtaining progeny plants or progeny seeds.

In a further aspect, a method disclosed herein comprises crossing a selected tobacco plant comprising an enhanced NUE trait, one or more alleles associated with enhanced NUE, and at least one functional allele of a YB2 locus with a second tobacco plant that does not comprise an enhanced NUE trait, and obtaining progeny plants or progeny seeds.

In a further aspect, a method disclosed herein comprises assaying the isolated nucleic acids for one or more molecular markers located within 2,500,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 2,000,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 1,250,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 1,000,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 750,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 500,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 400,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 300,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 200,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 100,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 80,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 60,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 40,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 20,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 10,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 5,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 2,500 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 1,000 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 800 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 600 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 400 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 200 nucleotides of one or more alleles associated with enhanced NUE selected from the group consisting of SEQ ID NOs: 57 to 64. In a further aspect, a method disclosed herein comprises assaying the isolated nucleic acids for one or more molecular markers located within 100 nucleotides of one or more alleles associated with enhanced NUE selected from the group consisting of SEQ ID NOs: 57 to 64.

In one aspect, the present specification provides for, and includes, a method comprising creating or selecting a tobacco plant or population of tobacco plants that comprises, relative to a control plant or a control population of plants, one or more traits selected from the group consisting of (i) exhibiting more consistent leaf grade from top to bottom of the plant when grown at recommended Burley fertilization rates of 180 lbs nitrogen per acre, (ii) increased leaf grade index in leaves from the lower half of the plant; (iii) increased nitrogen use efficiency, (iv) decreased leaf nitrate nitrogen (NO3-N), (v) reduced TSNA levels, and (vi) a lack of chlorophyll-deficient phenotype. In a further aspect, the method comprises creating or selecting a tobacco plant or population of tobacco plants that comprises, relative to a control plant or a control population of plants, two or more traits selected from the group consisting of (i) exhibiting more consistent leaf grade from top to bottom of the plant when grown at recommended Burley fertilization rates of 180 lbs nitrogen per acre, (ii) increased leaf grade index in leaves from the lower half of the plant; (iii) increased nitrogen use efficiency, (iv) decreased leaf nitrate nitrogen (NO3-N), (v) reduced TSNA levels, and (vi) a lack of chlorophyll-deficient phenotype. In a further aspect, the method comprises creating or selecting a tobacco plant or population of tobacco plants that comprises, relative to a control plant or a control population of plants, three or more traits selected from the group consisting of (i) exhibiting more consistent leaf grade from top to bottom of the plant when grown at recommended Burley fertilization rates of 180 lbs nitrogen per acre, (ii) increased leaf grade index in leaves from the lower half of the plant, (iii) increased nitrogen use efficiency, (iv) decreased leaf nitrate nitrogen (NO3-N), (v) reduced TSNA levels, and (vi) a lack of chlorophyll-deficient phenotype. In a further aspect, the method comprises creating or selecting a tobacco plant or population of tobacco plants that comprises, relative to a control plant or a control population of plants, four or more traits selected from the group consisting of (i) exhibiting more consistent leaf grade from top to bottom of the plant when grown at recommended Burley fertilization rates of 180 lbs nitrogen per acre, (ii) increased leaf grade index in leaves from the lower half of the plant; (iii) increased nitrogen use efficiency, (iv) decreased leaf nitrate nitrogen (NO3-N), (v) reduced TSNA levels, and (vi) a lack of chlorophyll-deficient phenotype.

Nitrogen Use Efficiency

As used herein, the term "nitrogen use efficiency" (NUE) refers to the ability of a plant to absorb, assimilate and/or use nitrogen (e.g., from soil, water and/or nitrogen fertilizer). NUE genes affect yield and have utility for improving the use of nitrogen in crop plants. Enhanced nitrogen use efficiency can result from improved uptake and assimilation of nitrogen fertilizer and/or the subsequent remobilization and reutilization of accumulated nitrogen reserves, as well as increased tolerance of plants to stress situations such as low nitrogen environments. NUE genes can be used to alter the genetic composition of a plant, rendering it more productive with current fertilizer application standards or maintaining its productive rates with significantly reduced fertilizer or reduced nitrogen availability.

As used herein, the term "nitrogen utilization efficiency" refers to a component of nitrogen use efficiency. It has been proposed that, in tobacco, nitrogen utilization efficiency can be measured as equal to the cured leaf yield in kilograms per hectare divided by the total nitrogen accumulation in the plant in kilograms per hectare (See Lewis et al. (2012) J. Agric. Food Chem., 60, 6454-6461).

Figure 9:
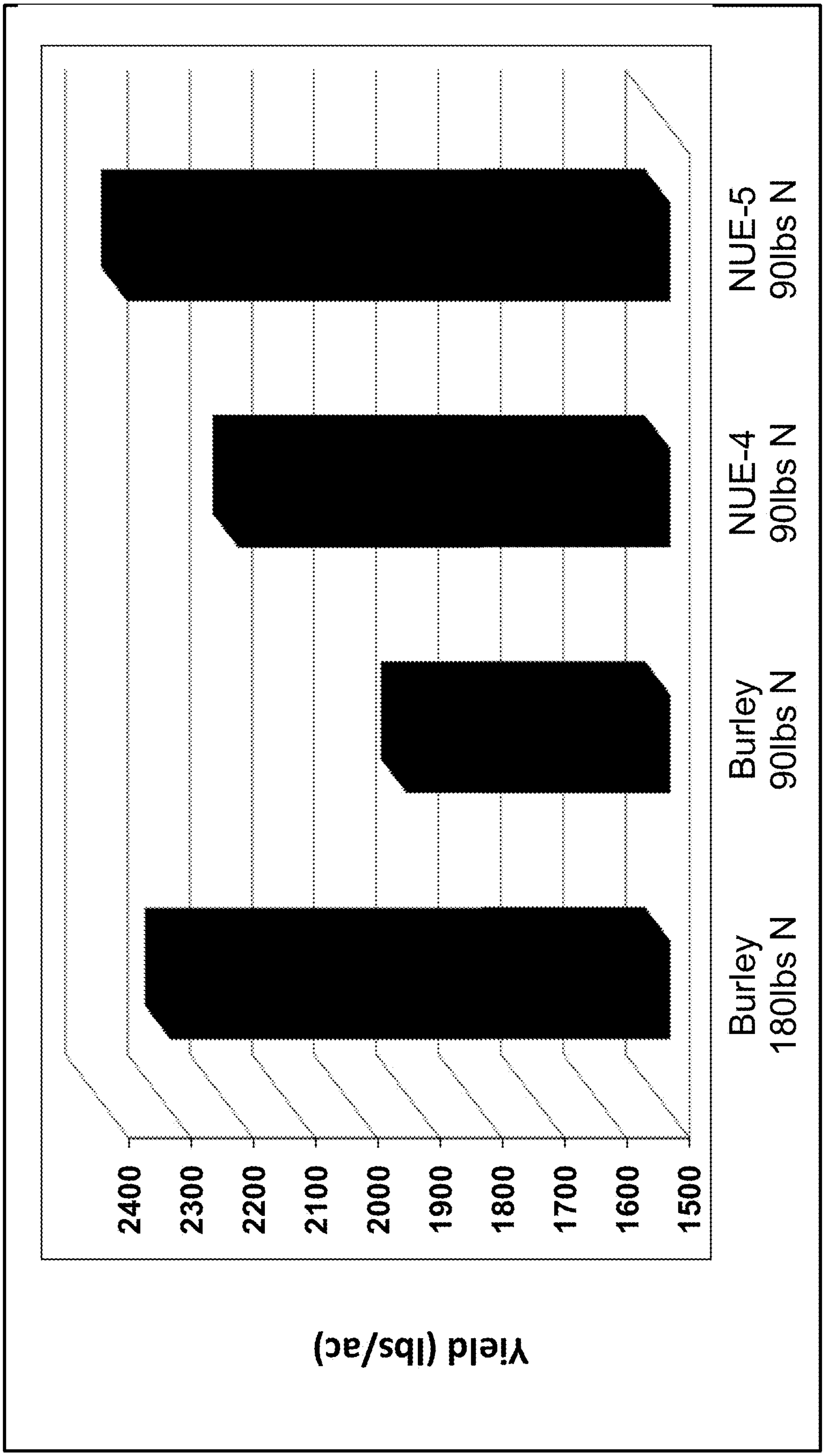
FIG. 9 depicts yield in pounds per acre after harvest for two independent field grown $F_4$ lines, NUE-4 and NUE-5 grown with application of 90 or 180 lbs/ac Nitrogen, in comparison to Burley TN90. The test lines are generated from crosses of MD609 to Burley TN90 as described.

Burley tobacco requires high amounts of added nitrogen fertilizer in order to provide the best yields (See, for example, FIG. 9, Burley at 180 lbs N compared to 90 lbs N). Maryland tobacco, on the other hand, requires approximately 25% of the level of nitrogen fertilizer typically used in cultivating burley tobacco. Fertilizer is a major cost involved in the cultivation of tobacco and high levels of nitrogen can lead to increases in nitrogen containing constituents such as alkaloids and TSNAs. Two loci known to give Burley tobacco its characteristic white stem and lower chlorophyll content have also been found to contribute to its lower nitrogen use efficiency, higher nitrate levels, lower carbohydrate content, and higher constituent levels (Lewis et al. (2012) J. Agric. Food Chem., 60, 6454-6461 and Yafei Li, et al. (2018) Sci. Rep., 8:13300). These loci are named yellow burley1 (YB1) and yellow burley 2 (YB2). The functional genes were mapped and found to be homologs of the *Arabidopsis* ethylene-dependent gravitropism-deficient and yellow-green-like (EGY) genes which are mutated in commercial burley tobacco lines (Edwards et al. (2017) BMC Genomics, 18:448). These genes are found on Chromosomes 5 and 24, locations that do not correlate with loci previously described as contributing to the Maryland NUE phenotype.

It was found that Maryland tobacco has the nonfunctional burley allele at the yb2 locus while retaining a functional allele at the yb1 locus. Surprisingly, it was discovered that plants homozygous or heterozygous for a wild-type allele at the YB1 locus demonstrate enhanced NUE phenotypes when combined with enhanced NUE markers previously discovered in Maryland tobacco. Exemplary embodiments include creation of a double haploid (DH) parent plant that has homozygous functional alleles at the YB1 locus (YB1/YB1), homozygous nonfunctional alleles at the YB2 locus (yb2/yb2), and homozygous Maryland alleles at the Chromosome 11 locus (MD11/MD11 as compared to Burley alleles at chromosome 11, Bu11). These plants retain the Maryland NUE traits while phenotypically resembling burley tobacco.

DH plants with the NUE genotype and phenotype are used as a pollen parent for the generation of commercial hybrids with available burley male sterile lines resulting in genotypes of YB1/yb1, yb2/yb2, and either MD11/Bull or MD11/MD11. These hybrids retain the Maryland NUE trait, phenotypically resemble burley tobacco, and have smoking quality characteristics that are closer to burley tobacco than Maryland tobacco. These new lines represent a novel advancement in the generation of nitrogen efficient Burley tobacco. Methods and compositions for burley tobacco with improved NUE are provided herein.

Though NUE has been defined in various ways, yield per unit of nitrogen available in the soil integrates all key parameters for evaluating fitness of crop cultivars and it is a common measure of NUE. See, for example, Ladha et al. 2005. *Advances in Agronomy,* 87:85-156, which is incorporated herein in its entirety. This indicator is sometimes referred to as "agricultural NUE." As another measure of NUE, the ratio of the plant product (e.g., tobacco leaf tissue) to above-ground nitrogen in the plant can be determined (sometimes referred to as "physiological NUE)." Enhanced NUE is related to three key components: 1) yield is not significantly different when grown on 25% normal nitrogen content compared to a plant grown at 100% normal nitrogen content); 2) the rate of chlorophyll loss is reduced compared to plants without enhanced NUE; and 3) cured leaf quality is not significantly different when grown on 25% normal nitrogen content compared to a plant grown at 100% normal nitrogen content. In a preferred aspect, a plant with enhanced NUE is capable of generating similar yields and leaf quality when grown under 25% of the Burley fertilization rate as compared to a Burley plant grown under 100% of the normal Burley fertilization rate.

At least five approaches and indices of NUE are used in the art and are discussed below.

(1) Partial factor productivity (PFP) from applied nitrogen (N) is a measure of how much yield is produced for each unit of nitrogen applied:

$PFP_N$=kilograms of yield/kilograms of N applied $PFP_N=Y_{+N}/FN$

Where $Y_{+N}$ is the yield (kilograms/hectare; kg/ha) and FN is the amount of fertilizer applied (kg/ha).

(2) Agronomic efficiency (AE) of applied nitrogen (N) is a measure of how much additional yield is produced for each unit of nitrogen applied:

$AE_N$=kilograms of yield increase/kilograms of N applied $AE_N=(Y_{+N}-Y_{0N})/FN$ Where $Y_{+N}$ is the yield in a treatment with N application (kg/ha); Yon is the yield in a control treatment without N application (kg/ha); and FN is the amount of N fertilizer applied (kg/ha).

(3) Recovery efficiency (RE) of applied nitrogen (N) is a measure of how much of the nitrogen that was applied was recovered and taken up by the crop.

$RE_N$=kilograms of N taken up/kilograms of N applied $RE_N=(UN_{+N}-UN_{0N})/FN$ Where $UN_{+N}$ is the total plant N uptake measured in aboveground biomass at physiological maturity (kg/ha) in plots that received applied N at the rate of FN (kg/ha); and $UN_{0N}$ is the total N uptake of a control plot without the addition of N.

(4) Physiological efficiency (PE) of applied nitrogen (N) is a measure of how much additional yield is produced for each additional unit of nitrogen uptake.

$PE_N$=kilograms of yield increase/kilograms of fertilizer N taken up $PE_N=(Y_{+N}-Y_{0N})/(UN_{+N}-UN_{0N})$ Where $Y_{+N}$ is the yield (kg/ha) in a treatment with N application; Yon is the yield (kg/ha) in a control treatment without N application; $UN_{+N}$ is the total N uptake (kg/ha) in the treatment that receives fertilizer N application; and $UN_{0N}$ is the total N uptake (kg/ha) in the treatment without fertilizer N application.

(5) Internal efficiency (IE) of nitrogen (N) addresses how much yield is produced per unit N taken up from both fertilizer and indigenous (e.g., soil) nutrient sources:

$IE_N$=kilograms of yield/kilograms of N taken up $IE_N=Y/UN$

Where Y is the yield (kg/ha); and UN is the total N uptake (kg/ha).

Nitrogen can be in any form, including organic and/or inorganic forms. Without being limiting, forms of nitrogen include nitrate (e.g., ammonium nitrate, calcium nitrate, potassium nitrate), nitrite, ammonia, aqua ammonia, anhydrous ammonia, ammonium sulfate, diammonium phosphate, a low-pressure nitrogen solution, a pressureless nitrogen solution, urea, and urea-ammonium nitrate (UAN). In an aspect, nitrogen is in a form that is immediately available to a plant (e.g., ammonia and/or nitrate) and/or can be readily converted to a form that is available to a plant (e.g., urea).

In an aspect, a modified tobacco plant comprising enhanced NUE provided herein comprises increased nitrogen uptake as compared to a control tobacco plant. In another aspect, a modified tobacco plant comprising enhanced NUE provided herein comprises increased nitrogen assimilation as compared to a control tobacco plant. In a further aspect, a modified tobacco plant comprising enhanced NUE provided herein comprises increased yield as compared to a control tobacco plant. In still another aspect, a modified tobacco plant comprising enhanced NUE provided herein comprises increased yield under low nitrogen conditions as compared to a control tobacco plant. In a preferred aspect, low nitrogen conditions as used in the field are approximately 25% nitrogen compared to levels typically used by those skilled in the art. In another aspect, low nitrogen conditions as used in the field can be between approximately 5% and 50% nitrogen compared to levels typically used by those skilled in the art. In a greenhouse setting, low nitrogen conditions are approximately 25 parts per million (ppm) and normal nitrogen conditions are approximately 100 ppm. In another aspect, low nitrogen conditions as used in a greenhouse can be between 5 ppm and 50 ppm.

In an aspect, a modified tobacco plant comprising enhanced NUE and at least one functional allele of YB1 provided herein comprises a yield increase of at least 5%, at least 10%, at least 20%, at least 30%, at least 40%, at least 50%, at least 60%, at least 70%, at least 80%, at least 90%, at least 100%, at least 110%, at least 120%, at least 130%, at least 140%, at least 150%, at least 200%, at least 300%, at least 400%, or at least 500% as compared to a control tobacco plant grown under similar growth conditions. In an aspect, a modified tobacco plant comprising enhanced NUE provided herein comprises a yield increase of between 5% and 100%, between 10% and 100%, between 20% and 100%, between 30% and 100%, between 40% and 100%, between 50% and 100%, between 60% and 100%, between 70% and 100%, between 80% and 100%, between 90% and 100%, between 10% and 200%, between 10% and 300%, between 10% and 400%, between 10% and 500%, or between 5% and 500% as compared to a control tobacco plant grown under similar growth conditions.

In an aspect, a population of modified tobacco plants comprising enhanced NUE and at least one functional allele of YB1 provided herein comprises a yield increase of at least 0.25 kg/ha, at least 0.5 kg/ha, at least 0.75 kg/ha, at least 1 kg/ha, at least 2 kg/ha, at least 3 kg/ha, at least 4 kg/ha, at least 5 kg/ha, at least 6 kg/ha, at least 7 kg/ha, at least 8 kg/ha, at least 9 kg/ha, at least 10 kg/ha, at least 15 kg/ha, at least 20 kg/ha, at least 25 kg/ha, at least 30 kg/ha, at least 35 kg/ha, at least 40 kg/ha, at least 45 kg/ha, at least 50 kg/ha, at least 75 kg/ha, at least 100 kg/ha, at least 200 kg/ha, at least 300 kg/ha, at least 400 kg/ha, or at least 500 kg/ha as compared to a population of control tobacco plants grown under similar growth conditions. In another aspect, a population of modified tobacco plant comprising enhanced NUE and at least one functional allele of YB1 provided herein comprises a yield increase of between 0.25 kg/ha and 100 kg/ha, between 0.5 kg/ha and 100 kg/ha, between 0.75 kg/ha and 100 kg/ha, between 1 kg/ha and 100 kg/ha, between 2 kg/ha and 100 kg/ha, between 3 kg/ha and 100 kg/ha, between 4 kg/ha and 100 kg/ha, between 5 kg/ha and 100 kg/ha, between 6 kg/ha and 100 kg/ha, between 7 kg/ha and 100 kg/ha, between 8 kg/ha and 100 kg/ha, between 9 kg/ha and 100 kg/ha, between 10 kg/ha and 100 kg/ha, between 15 kg/ha and 100 kg/ha, between 20 kg/ha and 100 kg/ha, between 30 kg/ha and 100 kg/ha, between 40 kg/ha and 100 kg/ha, between 50 kg/ha and 100 kg/ha, between 75 kg/ha and 100 kg/ha, between 100 kg/ha and 500 kg/ha, between 100 kg/ha and 400 kg/ha, between 100 and 300 kg/ha, or between 100 kg/ha and 200 kg/ha as compared to a population of control tobacco plants when grown under similar growth conditions. As used herein, a "population" of tobacco plants can be of any size for example, 5, 10, 15, 20, 25, 30, 35, 40, 50, 100, 500, 1000, 5000, 10000, 25000, 50000, 100000, 500000, or more. A population can be from a single variety, cultivar, or line. A population can be created using any breeding techniques known in the art.

In an aspect, a modified tobacco plant comprising enhanced NUE and at least one functional allele of YB1 provided herein comprises at least 1, at least 2, at least 3, at least 4, at least 5, at least 6, at least 7, at least 8, at least 9, at least 10, at least 11, at least 12, at least 13, at least 14, at least 15, at least 20, or at least 25 more leaves as compared to a control tobacco plant grown under similar growth conditions. In another aspect, a modified tobacco plant comprising enhanced NUE provided herein comprises between 1 and 25, between 2 and 25, between 3 and 25, between 4 and 25, between 5 and 25, between 6 and 25, between 7 and 25, between 8 and 25, between 9 and 25, between 10 and 25, between 11 and 25, between 12 and 25, between 13 and 25, between 14 and 25, between 15 and 25, or between 20 and 25 more leaves as compared to a control tobacco plant grown under similar growth conditions.

In an aspect, a tobacco plant comprising enhanced NUE and at least one functional allele of YB1 provided herein is grown at a fertilization rate of 75 to 95 pounds (lbs) nitrogen per acre. In a further aspect, a tobacco plant comprising enhanced NUE provided herein is grown at a fertilization rate of 76 to 95 lbs nitrogen per acre, 77 to 95 lbs nitrogen per acre, 78 to 95 lbs nitrogen per acre, 79 to 95 lbs nitrogen per acre, 80 to 95 lbs nitrogen per acre, 81 to 95 lbs nitrogen per acre, 82 to 95 lbs nitrogen per acre, 83 to 95 lbs nitrogen per acre, 84 to 95 lbs nitrogen per acre, 85 to 95 lbs nitrogen per acre, 86 to 95 lbs nitrogen per acre, 87 to 95 lbs nitrogen per acre, 88 to 95 lbs nitrogen per acre, 89 to 95 lbs nitrogen per acre, 90 to 95 lbs nitrogen per acre, 91 to 95 lbs nitrogen per acre, 92 to 95 lbs nitrogen per acre, 93 to 95 lbs nitrogen per acre, or 94 to 95 lbs nitrogen per acre.

In an aspect, a population of tobacco plants comprising enhanced NUE and at least one functional allele of YB1 provided herein comprises a yield ranging between 1500 to 3500 lbs/ac. In an aspect, a tobacco plant comprising enhanced NUE provided herein comprises a yield of between 1600 to 3500 lbs/ac, between 1700 to 3500 lbs/ac, between 1800 to 3500 lbs/ac, between 1900 to 3500 lbs/ac, between 2000 to 3500 lbs/ac, between 2100 to 3500 lbs/ac, between 2200 to 3500 lbs/ac, between 2300 to 3500 lbs/ac, between 2400 to 3500 lbs/ac, between 2500 to 3500 lbs/ac, between 2600 to 3500 lbs/ac, between 2700 to 3500 lbs/ac, between 2800 to 3500 lbs/ac, between 2900 to 3500 lbs/ac, between 3000 to 3500 lbs/ac, between 3100 to 3500 lbs/ac, between 3200 to 3500 lbs/ac, between 3300 to 3500 lbs/ac, or between 3400 to 3500 lbs/ac.

As used herein, "comparable conditions" "similar conditions" or "similar growth conditions" refers to similar environmental conditions, agronomic practices, and/or curing process for growing or curing tobacco and making meaningful comparisons between two or more plant genotypes so that neither environmental conditions nor agronomic practices (including curing process) would contribute to, or explain, any differences observed between the two or more plant genotypes. Environmental conditions include, for example, light, temperature, water, humidity, and nutrition (e.g., nitrogen and phosphorus). Agronomic practices include, for example, seeding, clipping, undercutting, transplanting, topping, suckering, and curing. See Chapters 4B and 4C of Tobacco, Production, Chemistry and Technology, Davis & Nielsen, eds., Blackwell Publishing, Oxford (1999), pp. 70-103. Referencing a control plant in a comparison requires that control plant to be grown under comparable or similar conditions.

In one aspect, a modified plant, seed, plant part, or plant cell provided herein comprises one or more non-naturally occurring mutations. In one aspect, a mutation provided herein improves nitrogen use efficiency in a plant. Types of mutations provided herein include, for example, substitutions (point mutations), deletions, insertions, duplications, and inversions. Such mutations are desirably present in the coding region of a gene; however, mutations in a promoter or other regulatory region, an intron, an intron-exon boundary, or an untranslated region of a gene may also be desirable.

In one aspect, methods and compositions provided herein comprise the introduction of one or more polynucleotides into one or more plant cells. In one aspect, a plant genome provided herein is modified to include an introduced polynucleotide or recombinant DNA construct. As used herein, "plant genome" refers to a nuclear genome, a mitochondrial genome, or a plastid (e.g., chloroplast) genome of a plant cell. In another aspect, a polynucleotide provided herein is integrated into an artificial chromosome. In one aspect, an artificial chromosome comprising a polynucleotide provided herein is integrated into a plant cell.

In one aspect, a modified plant, seed, plant component, plant cell, or plant genome provided herein comprises one or more transgenes. In one aspect, a transgene provided herein improves nitrogen use efficiency in a tobacco plant. As used herein, a "transgene" refers to a polynucleotide that has been transferred into a genome by any method known in the art. In one aspect, a transgene is an exogenous polynucleotide. In one aspect, a transgene is an endogenous polynucleotide that is integrated into a new genomic locus where it is not normally found. Therefore, a transgene can also be a cisgene under appropriate circumstances.

In one aspect, transgenes provided herein comprise a recombinant DNA construct. In one aspect, recombinant DNA constructs or expression cassettes provided herein can comprise a selectable marker gene for the selection of transgenic cells. Selectable marker genes include, but are not limited to, genes encoding antibiotic resistance, such as those encoding neomycin phosphotransferase II (NPTII) and hygromycin phosphotransferase (HPT), as well as genes conferring resistance to herbicidal compounds, such as glufosinate ammonium, bromoxynil, imidazolinones, triazolopyrimidines, sulfonylurea (e.g., chlorsulfuron and sulfometuron methyl), and 2,4-dichlorophenoxyacetate (2,4-D). Additional selectable markers include phenotypic markers such as β-galactosidase and fluorescent proteins such as green fluorescent protein (GFP).

In one aspect, methods and compositions provided herein comprise a vector. As used herein, the terms "vector" or "plasmid" are used interchangeably and refer to a circular, double-stranded DNA molecule that is physically separate from chromosomal DNA. In one aspect, a plasmid or vector used herein is capable of replication in vivo. A "transformation vector," as used herein, is a plasmid that is capable of transforming a plant cell. In an aspect, a plasmid provided herein is a bacterial plasmid. In another aspect, a plasmid provided herein is an *Agrobacterium* Ti plasmid or derived from an *Agrobacterium* Ti plasmid. In still another aspect, a vector provided herein is a viral vector.

In one aspect, a plasmid or vector provided herein is a recombinant vector. As used herein, the term "recombinant vector" refers to a vector formed by laboratory methods of genetic recombination, such as molecular cloning. In another aspect, a plasmid provided herein is a synthetic plasmid. As used herein, a "synthetic plasmid" is an artificially created plasmid that is capable of the same functions (e.g., replication) as a natural plasmid (e.g., Ti plasmid). Without being limited, one skilled in the art can create a synthetic plasmid de novo via synthesizing a plasmid by individual nucleotides, or by splicing together nucleic acid molecules from different pre-existing plasmids.

Vectors are commercially available or can be produced by recombinant DNA techniques routine in the art. In one aspect, a vector provided herein comprises all or part of SEQ ID NO: 65. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6×His tag, glutathione S-transferase (GST)).

In another aspect, recombinant constructs or expression cassettes provided herein may be introduced into plants by contacting plants with a virus or viral nucleic acids. Generally, such methods involve incorporating an expression cassette of the present disclosure within a viral DNA or RNA molecule. It is recognized that promoters for use in the expression cassettes provided herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221.

Promoters

As commonly understood in the art, the term "promoter" may generally refer to a DNA sequence that contains an RNA polymerase binding site, transcription start site, and/or TATA box and assists or promotes the transcription and expression of an associated transcribable polynucleotide sequence and/or gene (or transgene). A promoter may be synthetically produced, varied or derived from a known or naturally occurring promoter sequence or other promoter sequence (e.g., as provided herein). A promoter may also include a chimeric promoter comprising a combination of two or more heterologous sequences. A promoter of the present invention may thus include variants of promoter sequences that are similar in composition, but not identical to or complimentary to, other promoter sequence(s) known or provided herein. As used herein, a "heterologous promoter" in the context of a DNA construct refers to either: (i) a promoter that is derived from a source distinct from the operably linked structural gene or coding region or (ii) a promoter derived from the same source as the operably linked structural gene or coding region, where the promoter's sequence is modified from its original form. As used herein, the term "operably linked" refers to a functional linkage between a promoter or other regulatory element and an associated transcribable polynucleotide sequence or coding sequence of a gene (or transgene), such that the promoter, etc., operates to initiate, assist, affect, cause, and/or promote the transcription and expression of the associated coding or transcribable polynucleotide sequence, at least in particular tissue(s), developmental stage(s), and/or under certain condition(s). A "plant expressible promoter" refers to a promoter that may be used to express in a plant, plant cell and/or plant tissue an associated coding sequence, transgene or transcribable polynucleotide sequence that is operably linked to the promoter.

A promoter may be classified according to a variety of criteria relating to the pattern of expression of a coding sequence or gene (including a transgene) operably linked to the promoter, such as constitutive, developmental, tissue-specific, inducible, etc. Promoters that initiate transcription in all or most tissues of the plant are referred to as "constitutive" promoters. Promoters that initiate transcription during certain periods or stages of development are referred to as "developmental" promoters. Promoters whose expression is enhanced in certain tissues of the plant relative to other plant tissues are referred to as "tissue-enhanced" or "tissue-preferred" promoters. Thus, a "tissue-preferred" promoter causes relatively higher or preferential expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. A promoter that expresses in a certain cell type of the plant is referred to as a "cell type specific" promoter. An "inducible" promoter is a promoter that initiates transcription in response to an environmental stimulus such as cold, drought or light, or other stimuli, such as wounding or chemical application. A promoter may also be classified in terms of its origin, such as being heterologous, homologous, chimeric, synthetic, etc. A "heterologous" promoter is a promoter sequence having a different origin relative to its associated transcribable sequence, coding sequence, or gene (or transgene), and/or not naturally occurring in the plant species to be transformed. The term "heterologous" may refer more broadly to a combination of two or more DNA molecules or sequences when such a combination is not normally found in nature. For example, two or more DNA molecules or sequences would be heterologous with respect to each other if they are normally found in different genomes or at different loci in the same genome, or if they are not identically combined in nature.

Exemplary constitutive promoters include the core promoter of the Rsyn7 promoter and other constitutive promoters disclosed in U.S. Pat. No. 6,072,050; the core CaMV 35S promoter (Odell et al. (1985) Nature 313:810-812); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J 3:2723-2730); ALS promoter (U.S. Pat. No. 5,659,026), and the like.

Exemplary chemical-inducible promoters include the tobacco PR-la promoter, which is activated by salicylic acid. Other chemical-inducible promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14 (2): 247-257) and tetracycline-inducible promoters (see, for example, Gatz et al. (1991) Mol. Gen. Genet. 227:229-237, and U.S. Pat. Nos. 5,814,618 and 5,789,156). Additional exemplary promoters that can be used herein are those responsible for heat-regulated gene expression, light-regulated gene expression (for example, the pea rbcS-3A; the maize rbcS promoter; the chlorophyll alb-binding protein gene found in pea; or the Arabssu promoter), hormone-regulated gene expression (for example, the abscisic acid (ABA) responsive sequences from the Em gene of wheat; the ABA-inducible HVA1 and HVA22, and rd29A promoters of barley and *Arabidopsis*; and wound-induced gene expression (for example, of wunl), organ specific gene expression (for example, of the tuber-specific storage protein gene; the 23-kDa zein gene from maize described by; or the French bean (ß-phaseolin gene), or pathogen-inducible promoters (for example, the PR-1, prp-1, or (ß-1,3 glucanase promoters, the fungal-inducible wirla promoter of wheat, and the nematode-inducible promoters, TobRB7-5A and Hmg-1, of tobacco arid parsley, respectively).

As used herein, a "leaf" promoter includes any promoter that initiates, causes, drives, etc., transcription or expression of its associated gene, transgene or transcribable DNA sequence in leaf tissue derived from any part of a plant. Such a "leaf" promoter may be further defined as initiating, causing, driving, etc., transcription or expression of its associated gene/transgene or transcribable DNA sequence in one or more tissue(s) of a plant, such as one or more floral tissue(s). Such a "leaf" promoter may be further defined as a "leaf preferred" promoter that initiates, causes, drives, etc., transcription or expression of its associated gene, transgene or transcribable DNA sequence at least preferentially or mostly, if not exclusively, in leaf tissue derived from any part of a plant (as opposed to floral tissue). However, a "leaf" and a "leaf preferred" promoter may each also permit, allow, cause, drive, etc., transcription or expression of its associated gene, transgene or transcribable DNA sequence during reproductive phase(s) or stage(s) of development in one or more cells or tissues of the plant, such as in one or more vegetative or reproductive tissue(s). In fact, a "leaf" promoter may even initiate, cause, drive, etc., transcription or expression of its associated gene, transgene or transcribable DNA sequence in one or more reproductive or vegetative tissues at a greater level or extent than in leaf tissue(s).

As used herein, a "root" promoter includes any promoter that initiates, causes, drives, etc., transcription or expression of its associated gene, transgene or transcribable DNA sequence in root tissue derived from any part of a plant. Such a "root" promoter may be further defined as initiating, causing, driving, etc., transcription or expression of its associated gene/transgene or transcribable DNA sequence in one or more tissue(s) of a plant, such as one or more floral tissue(s). Such a "root" promoter may be further defined as a "root preferred" promoter that initiates, causes, drives, etc., transcription or expression of its associated gene, transgene or transcribable DNA sequence at least preferentially or mostly, if not exclusively, in root tissue derived from any part of a plant (as opposed to floral tissue). However, a "root" and a "root preferred" promoter may each also permit, allow, cause, drive, etc., transcription or expression of its associated gene, transgene or transcribable DNA sequence during reproductive phase(s) or stage(s) of development in one or more cells or tissues of the plant, such as in one or more vegetative or reproductive tissue(s). In fact, a "root" promoter may even initiate, cause, drive, etc., transcription or expression of its associated gene, transgene or transcribable DNA sequence in one or more reproductive or vegetative tissues at a greater level or extent than in root tissue(s).

Additional exemplary tissue-preferred promoters include those disclosed in Yamamoto et al. (1997) Plant J. 12 (2): 255-265; Kawamata et al. (1997) Plant Cell Physiol. 38 (7): 792-803; Hansen et al. (1997) Mol. Gen. Genet. 254 (3): 337-343; Russell et al. (1997) Transgenic Res. 6 (2): 157-168; Rinehart et al. (1996) Plant Physiol. 112 (3): 1331-1341; Van Camp et al. (1996) Plant Physiol. 112 (2): 525-535-; Canevascini et al. (1996) Plant Physiol. 112 (2): 513-524-; Yamamoto et al. (1994) Plant Cell Physiol. 35 (5): 773-778; Lam (1994) Results Probl. Cell Differ. 20:181-196;

Orozco et al. (1993) Plant Mol. Biol. 23 (6): 1129-1138; Matsuoka et al. (1993) Proc Natl. Acad. Sci. USA 90 (20): 9586-9590; and Guevara-Garcia et al. (1993) Plant J. 4 (3): 495-505.

Curing/Products

The present disclosure also provides methods for breeding tobacco lines, cultivars, or varieties comprising enhanced nitrogen use efficiency. Breeding can be carried out via any known procedures. DNA fingerprinting, SNP mapping, haplotype mapping or similar technologies may be used in a marker-assisted selection (MAS) breeding program to transfer or breed a desirable trait or allele into a tobacco plant. For example, a breeder can create segregating populations in an $F_2$ or backcross generation using $F_1$ hybrid plants provided herein or further crossing the $F_1$ hybrid plants with other donor plants with an agronomically desirable genotype. Plants in the $F_2$ or backcross generations can be screened for a desired agronomic trait or a desirable chemical profile using one of the techniques known in the art or listed herein. Depending on the expected inheritance pattern or the MAS technology used, self-pollination of selected plants before each cycle of backcrossing to aid identification of the desired individual plants can be performed. Backcrossing or other breeding procedure can be repeated until the desired phenotype of the recurrent parent is recovered. In one aspect, a recurrent parent in the present disclosure can be a flue-cured variety, a Burley variety, a dark air-cured variety, a dark fire-cured variety, or an Oriental variety. In another aspect, a recurrent parent can be a modified tobacco plant, line, or variety. In one aspect, a recurrent parent provided herein is TN90. In another aspect, a recurrent parent provided herein is MD609. Other breeding techniques can be found, for example, in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y., incorporated herein by reference in their entirety.

Results of a plant breeding program using modified tobacco plants described herein includes useful lines, cultivars, varieties, progeny, inbreds, and hybrids of the present disclosure. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972; on Oct. 23, 1978; and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A first tobacco variety and a second tobacco variety from which the first variety is essentially derived, are considered as having essentially identical genetic background. A "line" as distinguished from a variety most often denotes a group of plants used non-commercially, for example in plant research. A line typically displays little overall variation between individuals for one or more traits of interest, although there may be some variation between individuals for other traits.

In one aspect, the present disclosure provides a method of producing a tobacco plant comprising crossing at least one tobacco plant of a first tobacco variety with at least one tobacco plant of a second tobacco variety, where the at least one tobacco plant of the first tobacco variety exhibits enhanced nitrogen use efficiency compared to a control tobacco plant of the same variety grown under comparable conditions; and selecting for progeny tobacco plants that exhibit enhanced nitrogen use efficiency compared to a control tobacco plant of the same cross grown under comparable conditions. In one aspect, a first tobacco variety provided herein comprises modified tobacco plants. In another aspect, a second tobacco variety provided herein comprises modified tobacco plants. In one aspect, a first or second tobacco variety is male sterile. In another aspect, a first or second tobacco variety is cytoplasmically male sterile. In another aspect, a first or second tobacco variety is female sterile. In one aspect, a first or second tobacco variety is an elite variety. In another aspect, a first or second tobacco variety is a hybrid.

In one aspect, the present disclosure provides a method of introgressing one or more transgenes into a tobacco variety, the method comprising: (a) crossing a first tobacco variety comprising one or more transgenes with a second tobacco variety without the one or more transgenes to produce one or more progeny tobacco plants; (b) genotyping the one or more progeny tobacco plants for the one or more transgenes; and (c) selecting a progeny tobacco plant comprising the one or more transgenes. In another aspect, these methods further comprise backcrossing the selected progeny tobacco plant with the second tobacco variety. In further aspects, these methods further comprise: (d) crossing the selected progeny plant with itself or with the second tobacco variety to produce one or more further progeny tobacco plants; and (e) selecting a further progeny tobacco plant comprising the one or more transgenes. In one aspect, the second tobacco variety is an elite variety.

In one aspect, the present disclosure provides a method of introgressing one or more mutations into a tobacco variety, the method comprising: (a) crossing a first tobacco variety comprising one or more mutations with a second tobacco variety without the one or more mutations to produce one or more progeny tobacco plants; (b) genotyping the one or more progeny tobacco plants for the one or more mutations; and (c) selecting a progeny tobacco plant comprising the one or more mutations. In another aspect, these methods further comprise backcrossing the selected progeny tobacco plant with the second tobacco variety. In further aspects, these methods further comprise: (d) crossing the selected progeny plant with itself or with the second tobacco variety to produce one or more further progeny tobacco plants; and (e) selecting a further progeny tobacco plant comprising the one or more mutations. In one aspect, the second tobacco variety is an elite variety.

In one aspect, the present disclosure provides a method of growing a population of tobacco plants comprising enhanced nitrogen use efficiency, where the method comprises planting a population of tobacco seeds comprising one or more molecular markers associated with enhanced NUE and at least one functional allele of a Yellow Burley (YB1) locus, where the one or more tobacco plants exhibit enhanced nitrogen use efficiency compared to control tobacco plants of the same variety when grown under comparable conditions. In a further aspect, the population of tobacco seeds comprises at least one functional allele of a YB2 locus.

In one aspect, this disclosure provides a method for manufacturing a seed comprising an enhanced NUE trait, comprising crossing a first population of plants comprising one or more molecular markers associated with enhanced NUE with a second population of plants comprising at least one functional allele of a Yellow Burley 1 (YB1) locus, and obtaining progeny seeds that comprise an enhanced NUE trait, one or more molecular markers associated with enhanced NUE, and at least one functional allele of a Yellow Burley 1 (YB1) locus. In a further aspect, the progeny seeds comprises at least one functional allele of a YB2 locus In one aspect, tobacco plants provided herein are hybrid plants. Hybrids can be produced by preventing self-pollination of female parent plants (e.g., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by male sterility (MS), or transgenic male sterility where a transgene inhibits microsporogenesis and/or pollen formation, or self-incompatibility. Female parent plants containing MS are particularly useful. In aspects in which the female parent plants are MS, pollen may be harvested from male fertile plants and applied manually to the stigmas of MS female parent plants, and the resulting $F_1$ seed is harvested. Additionally, female sterile plants can also be used to prevent self-fertilization.

Plants can be used to form single-cross tobacco $F_1$ hybrids. Pollen from a male parent plant is manually transferred to an emasculated female parent plant or a female parent plant that is male sterile to form $F_1$ seed. Alternatively, three-way crosses can be carried out where a single-cross $F_1$ hybrid is used as a female parent and is crossed with a different male parent. As another alternative, double-cross hybrids can be created where the $F_1$ progeny of two different single crosses are themselves crossed. Self-incompatibility can be used to particular advantage to prevent self-pollination of female parents when forming a double-cross hybrid.

In one aspect, a tobacco variety provided herein is male sterile. In another aspect, a tobacco variety provided herein is cytoplasmic male sterile (CMS). Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp. In another aspect, a tobacco variety provided herein is female sterile. As a non-limiting example, female sterile plants can be made by mutating the STIG1 gene. See, for example, Goldman et al. 1994, *EMBO Journal* 13:2976-2984.

In one aspect, the present disclosure provides for, and includes, a method of determining the NUE of a tobacco line comprising obtaining at least one metabolite from a tobacco plant of a tobacco line, determining the amount of the at least one obtained metabolites, and determining the NUE of the tobacco line based on the amount of the at least one metabolite determined. In a further aspect, the at least one metabolite is obtained from a plant tissue selected from the group consisting of root tissue, leaf tissue, floral tissue, meristem tissue, and stem tissue. In a further aspect of this method, at least two metabolites are obtained. In a further aspect of this method, at least three metabolites are obtained. In a further aspect of this method, at least four metabolites are obtained. In a further aspect of this method, at least five metabolites are obtained. In a further aspect of this method, at least six metabolites are obtained. In a further aspect of this method, at least seven metabolites are obtained. In a further aspect of this method, at least eight metabolites are obtained. In a further aspect of this method, at least nine metabolites are obtained. In a further aspect of this method, at least ten metabolites are obtained. In a further aspect of this method, the amount of at least two metabolites is determined. In a further aspect of this method, the amount of at least three metabolites is determined. In a further aspect of this method, the amount of at least four metabolites is determined. In a further aspect of this method, the amount of at least five metabolites is determined. In a further aspect of this method, the amount of at least six metabolites is determined. In a further aspect of this method, the amount of at least seven metabolites is determined. In a further aspect of this method, the amount of at least eight metabolites is determined. In a further aspect of this method, the amount of at least nine metabolites is determined. In a further aspect of this method, the amount of at least ten metabolites is determined.

In another aspect of a method provided herein, the amount of a metabolite selected from the group consisting of X-2357, N-acetylmuramate, X-23319, X-23852, X-23330, alpha-ketoglutarate, X-21756, 4-hydroxy-2-oxoglutaric acid, D-23937, X-23937, X-23916, 1-methyladenine, 4-guanidinobutanoate, syringaldehyde, thiamin, p-hydroxybenzaldehyde, X-23453, X-11429, X-21796, N'-methylnicotinamide, cotinine, X-23389, N-acetylarginine, X-23366, N-acetylphenylalanine, naringenin, X-23454, X-23580, and X-23852 is determined.

In another aspect of a method provided herein, a tobacco plant with enhanced NUE comprises enhanced NUE as compared to a tobacco plant that comprises a lower amount of at least one metabolite in at least one tissue. In a further aspect, a tobacco plant with enhanced NUE comprises a lower amount of at least two metabolites in at least one tissue. In a further aspect, a tobacco plant with enhanced NUE comprises a lower amount of at least three metabolites in at least one tissue. In a further aspect, a tobacco plant with enhanced NUE comprises a lower amount of at least four metabolites in at least one tissue. In a further aspect, a tobacco plant with enhanced NUE comprises a lower amount of at least five metabolites in at least one tissue. In a further aspect, a tobacco plant with enhanced NUE comprises a lower amount of at least one metabolite in two tissues. In a further aspect, a tobacco plant with enhanced NUE comprises a lower amount of at least two metabolites in at least two tissues. In a further aspect, a tobacco plant with enhanced NUE comprises a lower amount of at least three metabolites in at least two tissues. In a further aspect, a tobacco plant with enhanced NUE comprises a lower amount of at least four metabolites in at least two tissues. In a further aspect, a tobacco plant with enhanced NUE comprises a lower amount of at least five metabolites in at least two tissues. In a further aspect, a tobacco plant with enhanced NUE comprises a lower amount of at least one metabolite in three tissues. In a further aspect, a tobacco plant with enhanced NUE comprises a lower amount of at least two metabolites in at least three tissues. In a further aspect, a tobacco plant with enhanced NUE comprises a lower amount of at least three metabolites in at least three tissues. In a further aspect, a tobacco plant with enhanced NUE comprises a lower amount of at least four metabolites in at least three tissues. In a further aspect, a tobacco plant with enhanced NUE comprises a lower amount of at least five metabolites in at least three tissues. In a further aspect, a tobacco plant with enhanced NUE comprises a lower amount of at least one metabolite in four tissues. In a further aspect, a tobacco plant with enhanced NUE comprises a lower amount of at least two metabolites in at least four tissues. In a further aspect, a tobacco plant with enhanced NUE comprises a lower amount of at least three metabolites in at least four tissues. In a further aspect, a tobacco plant with enhanced NUE comprises a lower amount of at least four metabolites in at least four tissues. In a further aspect, a tobacco plant with enhanced NUE comprises a lower amount of at least five metabolites in at least four tissues. In a further aspect, a tobacco plant with enhanced NUE comprises a lower amount of at least one metabolite in five tissues. In a further aspect, a tobacco plant with enhanced NUE comprises a lower amount of at least two metabolites in at least five tissues. In a further aspect, a tobacco plant with enhanced NUE comprises a lower amount of at least three metabolites in at least five tissues. In a further aspect, a tobacco plant with enhanced NUE comprises a lower amount of at least four metabolites in at least five tissues. In a further aspect, a tobacco plant with enhanced NUE comprises a lower amount of at least five metabolites in at least five tissues.

In another aspect of a method provided herein, a tobacco plant with enhanced NUE comprises enhanced NUE as compared to a tobacco line that comprises a higher amount of at least one metabolite in at least one tissue. In a further aspect, a tobacco plant with enhanced NUE comprises a higher amount of at least two metabolites in at least one tissue. In a further aspect, a tobacco plant with enhanced NUE comprises a higher amount of at least three metabolites in at least one tissue. In a further aspect, a tobacco plant with enhanced NUE comprises a higher amount of at least four metabolites in at least one tissue. In a further aspect, a tobacco plant with enhanced NUE comprises a higher amount of at least five metabolites in at least one tissue. In a further aspect, a tobacco plant with enhanced NUE comprises a higher amount of at least one metabolite in two tissues. In a further aspect, a tobacco plant with enhanced NUE comprises a higher amount of at least two metabolites in at least two tissues. In a further aspect, a tobacco plant with enhanced NUE comprises a higher amount of at least three metabolites in at least two tissues. In a further aspect, a tobacco plant with enhanced NUE comprises a higher amount of at least four metabolites in at least two tissues. In a further aspect, a tobacco plant with enhanced NUE comprises a higher amount of at least five metabolites in at least two tissues. In a further aspect, a tobacco plant with enhanced NUE comprises a higher amount of at least one metabolite in three tissues. In a further aspect, a tobacco plant with enhanced NUE comprises a higher amount of at least two metabolites in at least three tissues. In a further aspect, a tobacco plant with enhanced NUE comprises a higher amount of at least three metabolites in at least three tissues. In a further aspect, a tobacco plant with enhanced NUE comprises a higher amount of at least four metabolites in at least three tissues. In a further aspect, a tobacco plant with enhanced NUE comprises a higher amount of at least five metabolites in at least three tissues. In a further aspect, a tobacco plant with enhanced NUE comprises a higher amount of at least one metabolite in four tissues. In a further aspect, a tobacco plant with enhanced NUE comprises a higher amount of at least two metabolites in at least four tissues. In a further aspect, a tobacco plant with enhanced NUE comprises a higher amount of at least three metabolites in at least four tissues. In a further aspect, a tobacco plant with enhanced NUE comprises a higher amount of at least four metabolites in at least four tissues. In a further aspect, a tobacco plant with enhanced NUE comprises a higher amount of at least five metabolites in at least four tissues. In a further aspect, a tobacco plant with enhanced NUE comprises a higher amount of at least one metabolite in five tissues. In a further aspect, a tobacco plant with enhanced NUE comprises a higher amount of at least two metabolites in at least five tissues. In a further aspect, a tobacco plant with enhanced NUE comprises a higher amount of at least three metabolites in at least five tissues. In a further aspect, a tobacco plant with enhanced NUE comprises a higher amount of at least four metabolites in at least five tissues. In a further aspect, a tobacco plant with enhanced NUE comprises a higher amount of at least five metabolites in at least five tissues.

In another aspect of a method provided herein, a tobacco plant with enhanced NUE comprises enhanced NUE as compared to a tobacco line that comprises an equal amount of at least one metabolite in at least one tissue. In a further aspect, a tobacco plant with enhanced NUE comprises an equal amount of at least two metabolites in at least one tissue. In a further aspect, a tobacco plant with enhanced NUE comprises an equal amount of at least three metabolites in at least one tissue. In a further aspect, a tobacco plant with enhanced NUE comprises an equal amount of at least four metabolites in at least one tissue. In a further aspect, a tobacco plant with enhanced NUE comprises an equal amount of at least five metabolites in at least one tissue. In a further aspect, a tobacco plant with enhanced NUE comprises an equal amount of at least one metabolite in two tissues. In a further aspect, a tobacco plant with enhanced NUE comprises an equal amount of at least two metabolites in at least two tissues. In a further aspect, a tobacco plant with enhanced NUE comprises an equal amount of at least three metabolites in at least two tissues. In a further aspect, a tobacco plant with enhanced NUE comprises an equal amount of at least four metabolites in at least two tissues. In a further aspect, a tobacco plant with enhanced NUE comprises an equal amount of at least five metabolites in at least two tissues. In a further aspect, a tobacco plant with enhanced NUE comprises an equal amount of at least one metabolite in three tissues. In a further aspect, a tobacco plant with enhanced NUE comprises an equal amount of at least two metabolites in at least three tissues. In a further aspect, a tobacco plant with enhanced NUE comprises an equal amount of at least three metabolites in at least three tissues. In a further aspect, a tobacco plant with enhanced NUE comprises an equal amount of at least four metabolites in at least three tissues. In a further aspect, a tobacco plant with enhanced NUE comprises an equal amount of at least five metabolites in at least three tissues. In a further aspect, a tobacco plant with enhanced NUE comprises an equal amount of at least one metabolite in four tissues. In a further aspect, a tobacco plant with enhanced NUE comprises an equal amount of at least two metabolites in at least four tissues. In a further aspect, a tobacco plant with enhanced NUE comprises an equal amount of at least three metabolites in at least four tissues. In a further aspect, a tobacco plant with enhanced NUE comprises an equal amount of at least four metabolites in at least four tissues. In a further aspect, a tobacco plant with enhanced NUE comprises an equal amount of at least five metabolites in at least four tissues. In a further aspect, a tobacco plant with enhanced NUE comprises an equal amount of at least one metabolite in five tissues. In a further aspect, a tobacco plant with enhanced NUE comprises an equal amount of at least two metabolites in at least five tissues. In a further aspect, a tobacco plant with enhanced NUE comprises an equal amount of at least three metabolites in at least five tissues. In a further aspect, a tobacco plant with enhanced NUE comprises an equal amount of at least four metabolites in at least five tissues. In a further aspect, a tobacco plant with enhanced NUE comprises an equal amount of at least five metabolites in at least five tissues.

In another aspect of a method provided herein, a tobacco plant with enhanced NUE comprises decreased NUE as compared to a tobacco line that comprises a lower amount of at least one metabolite in at least one tissue. In a further aspect, a tobacco plant with enhanced NUE comprises a lower amount of at least two metabolites in at least one tissue. In a further aspect, a tobacco plant with enhanced NUE comprises a lower amount of at least three metabolites in at least one tissue. In a further aspect, a tobacco plant with enhanced NUE comprises a lower amount of at least four metabolites in at least one tissue. In a further aspect, a tobacco plant with enhanced NUE comprises a lower amount of at least five metabolites in at least one tissue. In a further aspect, a tobacco plant with enhanced NUE comprises a lower amount of at least one metabolite in two tissues. In a further aspect, a tobacco plant with enhanced NUE comprises a lower amount of at least two metabolites in at least two tissues. In a further aspect, a tobacco plant with enhanced NUE comprises a lower amount of at least three metabolites in at least two tissues. In a further aspect, a tobacco plant with enhanced NUE comprises a lower amount of at least four metabolites in at least two tissues. In a further aspect, a tobacco plant with enhanced NUE comprises a lower amount of at least five metabolites in at least two tissues. In a further aspect, a tobacco plant with enhanced NUE comprises a lower amount of at least one metabolite in three tissues. In a further aspect, a tobacco plant with enhanced NUE comprises a lower amount of at least two metabolites in at least three tissues. In a further aspect, a tobacco plant with enhanced NUE comprises a lower amount of at least three metabolites in at least three tissues. In a further aspect, a tobacco plant with enhanced NUE comprises a lower amount of at least four metabolites in at least three tissues. In a further aspect, a tobacco plant with enhanced NUE comprises a lower amount of at least five metabolites in at least three tissues. In a further aspect, a tobacco plant with enhanced NUE comprises a lower amount of at least one metabolite in four tissues. In a further aspect, a tobacco plant with enhanced NUE comprises a lower amount of at least two metabolites in at least four tissues. In a further aspect, a tobacco plant with enhanced NUE comprises a lower amount of at least three metabolites in at least four tissues. In a further aspect, a tobacco plant with enhanced NUE comprises a lower amount of at least four metabolites in at least four tissues. In a further aspect, a tobacco plant with enhanced NUE comprises a lower amount of at least five metabolites in at least four tissues. In a further aspect, a tobacco plant with enhanced NUE comprises a lower amount of at least one metabolite in five tissues. In a further aspect, a tobacco plant with enhanced NUE comprises a lower amount of at least two metabolites in at least five tissues. In a further aspect, a tobacco plant with enhanced NUE comprises a lower amount of at least three metabolites in at least five tissues. In a further aspect, a tobacco plant with enhanced NUE comprises a lower amount of at least four metabolites in at least five tissues. In a further aspect, a tobacco plant with enhanced NUE comprises a lower amount of at least five metabolites in at least five tissues.

In another aspect of a method provided herein, a tobacco plant with enhanced NUE comprises decreased NUE as compared to a tobacco line that comprises a higher amount of at least one metabolite in at least one tissue. In a further aspect, a tobacco plant with enhanced NUE comprises a higher amount of at least two metabolites in at least one tissue. In a further aspect, a tobacco plant with enhanced NUE comprises a higher amount of at least three metabolites in at least one tissue. In a further aspect, a tobacco plant with enhanced NUE comprises a higher amount of at least four metabolites in at least one tissue. In a further aspect, a tobacco plant with enhanced NUE comprises a higher amount of at least five metabolites in at least one tissue. In a further aspect, a tobacco plant with enhanced NUE comprises a higher amount of at least one metabolite in two tissues. In a further aspect, a tobacco plant with enhanced NUE comprises a higher amount of at least two metabolites in at least two tissues. In a further aspect, a tobacco plant with enhanced NUE comprises a higher amount of at least three metabolites in at least two tissues. In a further aspect, a tobacco plant with enhanced NUE comprises a higher amount of at least four metabolites in at least two tissues. In a further aspect, a tobacco plant with enhanced NUE comprises a higher amount of at least five metabolites in at least two tissues. In a further aspect, a tobacco plant with enhanced NUE comprises a higher amount of at least one metabolite in three tissues. In a further aspect, a tobacco plant with enhanced NUE comprises a higher amount of at least two metabolites in at least three tissues. In a further aspect, a tobacco plant with enhanced NUE comprises a higher amount of at least three metabolites in at least three tissues. In a further aspect, a tobacco plant with enhanced NUE comprises a higher amount of at least four metabolites in at least three tissues. In a further aspect, a tobacco plant with enhanced NUE comprises a higher amount of at least five metabolites in at least three tissues. In a further aspect, a tobacco plant with enhanced NUE comprises a higher amount of at least one metabolite in four tissues. In a further aspect, a tobacco plant with enhanced NUE comprises a higher amount of at least two metabolites in at least four tissues. In a further aspect, a tobacco plant with enhanced NUE comprises a higher amount of at least three metabolites in at least four tissues. In a further aspect, a tobacco plant with enhanced NUE comprises a higher amount of at least four metabolites in at least four tissues. In a further aspect, a tobacco plant with enhanced NUE comprises a higher amount of at least five metabolites in at least four tissues. In a further aspect, a tobacco plant with enhanced NUE comprises a higher amount of at least one metabolite in five tissues. In a further aspect, a tobacco plant with enhanced NUE comprises a higher amount of at least two metabolites in at least five tissues. In a further aspect, a tobacco plant with enhanced NUE comprises a higher amount of at least three metabolites in at least five tissues. In a further aspect, a tobacco plant with enhanced NUE comprises a higher amount of at least four metabolites in at least five tissues. In a further aspect, a tobacco plant with enhanced NUE comprises a higher amount of at least five metabolites in at least five tissues.

In another aspect of a method provided herein, a tobacco plant with enhanced NUE comprises decreased NUE as compared to a tobacco line that comprises an equal amount of at least one metabolite in at least one tissue. In a further aspect, a tobacco plant with enhanced NUE comprises an equal amount of at least two metabolites in at least one tissue. In a further aspect, a tobacco plant with enhanced NUE comprises an equal amount of at least three metabolites in at least one tissue. In a further aspect, a tobacco plant with enhanced NUE comprises an equal amount of at least four metabolites in at least one tissue. In a further aspect, a tobacco plant with enhanced NUE comprises an equal amount of at least five metabolites in at least one tissue. In a further aspect, a tobacco plant with enhanced NUE comprises an equal amount of at least one metabolite in two tissues. In a further aspect, a tobacco plant with enhanced NUE comprises an equal amount of at least two metabolites in at least two tissues. In a further aspect, a tobacco plant with enhanced NUE comprises an equal amount of at least three metabolites in at least two tissues. In a further aspect, a tobacco plant with enhanced NUE comprises an equal amount of at least four metabolites in at least two tissues. In a further aspect, a tobacco plant with enhanced NUE comprises an equal amount of at least five metabolites in at least two tissues. In a further aspect, a tobacco plant with enhanced NUE comprises an equal amount of at least one metabolite in three tissues. In a further aspect, a tobacco plant with enhanced NUE comprises an equal amount of at least two metabolites in at least three tissues. In a further aspect, a tobacco plant with enhanced NUE comprises an equal amount of at least three metabolites in at least three tissues. In a further aspect, a tobacco plant with enhanced NUE comprises an equal amount of at least four metabolites in at least three tissues. In a further aspect, a tobacco plant with enhanced NUE comprises an equal amount of at least five metabolites in at least three tissues. In a further aspect, a tobacco plant with enhanced NUE comprises an equal amount of at least one metabolite in four tissues. In a further aspect, a tobacco plant with enhanced NUE comprises an equal amount of at least two metabolites in at least four tissues. In a further aspect, a tobacco plant with enhanced NUE comprises an equal amount of at least three metabolites in at least four tissues. In a further aspect, a tobacco plant with enhanced NUE comprises an equal amount of at least four metabolites in at least four tissues. In a further aspect, a tobacco plant with enhanced NUE comprises an equal amount of at least five metabolites in at least four tissues. In a further aspect, a tobacco plant with enhanced NUE comprises an equal amount of at least one metabolite in five tissues. In a further aspect, a tobacco plant with enhanced NUE comprises an equal amount of at least two metabolites in at least five tissues. In a further aspect, a tobacco plant with enhanced NUE comprises an equal amount of at least three metabolites in at least five tissues. In a further aspect, a tobacco plant with enhanced NUE comprises an equal amount of at least four metabolites in at least five tissues. In a further aspect, a tobacco plant with enhanced NUE comprises an equal amount of at least five metabolites in at least five tissues.

In another aspect, a method provided herein comprises determining the amount of a metabolite using a method selected from the group consisting of liquid chromatography/mass spectrometry (LC/MS), high-performance liquid chromatography (HPLC), ultra HPLC (UHPLC), mass spectrometry (MS), tandem mass spectrometry (MS/MS), matrix assisted laser desorption/ionization mass spectrometry (MALDI-MS), X-ray fluorescence spectrometry (XRF), ion chromatography (IC), gas chromatography (GC), gas chromatography/mass spectrometry (GC/MS), capillary electrophoresis/mass spectrometry (CE-MS), ion mobility spectrometry/mass spectrometry (IMS/MS), X-ray diffraction, nuclear magnetic resonance (NMR), emission spectral analysis, polarography, ultraviolet-visual spectrometry, infrared spectrometry, and thin-layer chromatography.

In one aspect, the present specification provides for, and includes, a method of determining the NUE of a tobacco line using a metabolite signature comprising isolating a metabolite signature from a tobacco plant of a tobacco line, determining the amount of each metabolite comprising a metabolite signature, and determining the NUE of a tobacco line by comparing the metabolite signature to a control metabolite signature from a control tobacco line comprising a known NUE. In a further aspect of this method, NUE comprises enhanced NUE as compared to a control tobacco line. In another aspect of this method, a metabolite signature is isolated from a plant tissue selected from the group consisting of root tissue, leaf tissue, floral tissue, meristem tissue, and stem tissue.

In an aspect of a method provided herein, a metabolite signature comprises at least two metabolites. In a further aspect, a metabolite signature comprises at least three metabolites. In a further aspect, a metabolite signature comprises at least four metabolites. In a further aspect, a metabolite signature comprises at least five metabolites. In a further aspect, a metabolite signature comprises at least six metabolites. In a further aspect, a metabolite signature comprises at least seven metabolites. In a further aspect, a metabolite signature comprises at least eight metabolites. In a further aspect, a metabolite signature comprises at least nine metabolites. In a further aspect, a metabolite signature comprises at least ten metabolites. In a further aspect, a metabolite signature comprises at least eleven metabolites. In a further aspect, a metabolite signature comprises at least twelve metabolites. In a further aspect, a metabolite signature comprises at least thirteen metabolites. In a further aspect, a metabolite signature comprises at least fourteen metabolites. In a further aspect, a metabolite signature comprises at least fifteen metabolites. In a further aspect, a metabolite signature comprises at least twenty metabolites. In a further aspect, a metabolite signature comprises at least twenty-five metabolites. In a further aspect, a metabolite signature comprises at least thirty metabolites. In a further aspect, a metabolite signature comprises at least thirty-five metabolites. In a further aspect, a metabolite signature comprises at least forty metabolites. In a further aspect, a metabolite signature comprises at least forty-five metabolites. In a further aspect, a metabolite signature comprises at least fifty metabolites. In a further aspect, metabolite signature comprises between two and fifty metabolites. In a further aspect, metabolite signature comprises between three and forty-five metabolites. In a further aspect, metabolite signature comprises between three and forty metabolites. In a further aspect, metabolite signature comprises between four and thirty-five metabolites. In a further aspect, metabolite signature comprises between five and thirty metabolites. In a further aspect, metabolite signature comprises between six and twenty-five metabolites. In a further aspect, metabolite signature comprises between seven and twenty metabolites. In a further aspect, metabolite signature comprises between eight and fifteen metabolites. In a further aspect, metabolite signature comprises between nine and fourteen metabolites. In a further aspect, metabolite signature comprises between ten and thirteen metabolites. In a further aspect, metabolite signature comprises between ten and twelve metabolites.

In one aspect, the current specification provides for, and includes, a method of breeding a tobacco line comprising a metabolite signature associated with enhanced NUE comprising determining the metabolite signature of a first tobacco plant from a first tobacco line, where a first tobacco plant comprises enhanced NUE as compared to a control tobacco plant lacking the metabolite signature, crossing the first plant with a second plant of a second tobacco line, and obtaining at least one progeny seed from the crossing, where a progeny plant grown from at least one progeny seed comprises the metabolite signature, and where the progeny plant comprises enhanced NUE as compared to a control plant lacking the metabolite signature. In a further aspect of this method, a progeny plant is crossed to third plant that is from the first tobacco line. In another aspect, a first tobacco line is selected from the group consisting of MD609, MD601, Banket A1, K326, K346, K358, K394, K399, K730, NC196, NC37NF, NC471, NC55, NC92, NC2326, NC95, NC925. In another aspect, a second tobacco line is selected from the group consisting of TN86, TN86LC, TN90, TN90LC, TN97, TN97LC. In a further aspect, a metabolite signature comprises a leaf metabolite signature. In a further aspect, a metabolite signature comprises a root metabolite signature. In another aspect, a metabolite signature comprises higher amounts of 4-guanidinobutanoate, syringaldehyde, thiamin, p-hydroxybenzaldehyde, X-23454, X-23580, X-23852, or any combination thereof as compared to the metabolite signature of a control tobacco plant. In another aspect, a metabolite signature comprises lower amounts of X-2357, N-acetylmuramate, X-23319, X-23852, X-23330, alpha-ketoglutarate, X-21756, 4-hydroxy-2-oxoglutaric acid, X-23937, X-23916, 1-methyladenine, X-23453, X-11429, X-21796, N'-methylnicotinamide, cotinine, X-23389, N-acetylarginine, N-23366, N-acetylphenylalanine, naringenin, or any combination thereof as compared to the metabolite signature of a control tobacco plant.

In another aspect, a method provided herein comprises tobacco plants comprising enhanced NUE where enhanced NUE comprises an increased partial factor productivity (PFP) compared to a tobacco plant lacking enhanced NUE grown in the same conditions. In a further aspect, enhanced NUE comprises an increased agronomic efficiency (AE) compared to a tobacco plant lacking enhanced NUE grown in the same conditions. In a further aspect, enhanced NUE comprises an increased recovery efficiency (RE) compared to a tobacco plant lacking enhanced NUE grown in the same conditions. In a further aspect, enhanced NUE comprises an increased physiological efficiency (PE) compared to a tobacco plant lacking said enhanced NUE grown in the same conditions. In a further aspect, enhanced NUE comprises an increased internal efficiency (IE) compared to a tobacco plant lacking said enhanced NUE grown in the same conditions.

In one aspect, the present specification provides for, and includes, a method of selecting a tobacco plant comprising obtaining a population of tobacco plants, isolating at least one metabolite associated with enhanced NUE from at least one tobacco plant from the population of tobacco plants, and selecting at least one tobacco plant that comprises a higher amount of at least one metabolite as compared to a control tobacco plant. In a further aspect of this method, a selected tobacco plant comprises enhanced NUE as compared to a control tobacco plant. In a further aspect of this method, at least one metabolite is selected from the group consisting of 4-guanidinobutanoate, syringaldehyde, thiamin, p-hydroxybenzaldehyde, X-23454, X-23580, X-23852, or any combination thereof. In a further aspect of this method, a metabolite is isolated from a plant tissue selected from the group consisting of root tissue, leaf tissue, floral tissue, meristem tissue, and stem tissue.

In one aspect, the present specification provides for, and includes, a method of selecting a tobacco plant comprising obtaining a population of tobacco plants, isolating at least one metabolite associated with enhanced NUE from at least one tobacco plant from the population of tobacco plants, and selecting at least one tobacco plant that comprises a lower amount of at least one metabolite as compared to a control tobacco plant. In a further aspect of this method, a selected tobacco plant comprises an enhanced NUE as compared to a control tobacco plant. In a further aspect of this method, at least one metabolite is selected from the group consisting of X-2357, N-acetylmuramate, X-23319, X-23852, X-23330, alpha-ketoglutarate, X-21756, 4-hydroxy-2-oxoglutaric acid, X-23937, X-23916, 1-methyladenine, X-23453, X-11429, X-21796, N'-methylnicotinamide, cotinine, X-23389, N-acetylarginine, N-23366, N-acetylphenylalanine, naringenin, or any combination thereof. In a further aspect of this method, a metabolite is isolated from a plant tissue selected from the group consisting of root tissue, leaf tissue, floral tissue, meristem tissue, and stem tissue.

In one aspect, the present specification provides for, and includes, a method of screening a tobacco plant for a first metabolite signature associated with enhanced NUE comprising isolating a first metabolite signature from a tobacco plant, determining the amount of at least one metabolite that comprises that first metabolite signature, comparing the first metabolite signature to a second metabolite signature of a control tobacco plant comprising a known NUE, and determining if the first metabolite signature is associated with enhanced NUE.

In one aspect, the present specification provides for, and includes, a modified tobacco seed, or tobacco plant grown therefrom, comprising a cisgenic polynucleotide comprising a heterologous promoter operably linked to a coding region, where the modified tobacco plant comprises enhanced nitrogen use efficiency as compared to an unmodified control tobacco plant lacking the cisgenic polynucleotide when grown under the same conditions. In a further aspect, a modified tobacco seed or tobacco plant comprises a heterologous promoter that is selected from the group consisting of a constitutive promoter, an inducible promoter, a tissue-preferred promoter, and a tissue-specific promoter. In another aspect, a heterologous promoter comprises a polynucleotide sequence from a tobacco genome. In another aspect, a heterologous promoter comprises a polynucleotide sequence from a plant genome. In another aspect, a tissue-preferred promoter is a leaf-preferred promoter. In another aspect, a tissue-preferred promoter is a root-preferred promoter. In a further aspect, a modified tobacco seed or tobacco plant is of a Burley variety.

In a further aspect, a modified tobacco seed or tobacco plant of the present specification comprises lower amounts of TSNAs as compared to an unmodified tobacco plant lacking the cisgenic polynucleotide when grown under the same conditions. In a further aspect, a modified tobacco seed or tobacco plant comprises lower amount N'-nitrosonornicotine (NNN) as compared to an unmodified tobacco plant lacking the cisgenic polynucleotide when grown under the same conditions. In a further aspect, a modified tobacco seed or tobacco plant comprises lower amount 4-methylnitrosoamino-1-(3-pyridyl)-1-butanone (NNK) as compared to an unmodified tobacco plant lacking the cisgenic polynucleotide when grown under the same conditions. In a further aspect, a modified tobacco seed or tobacco plant comprises lower amount N'-nitrosoanatabine (NAT) as compared to an unmodified tobacco plant lacking the cisgenic polynucleotide when grown under the same conditions. In a further aspect, a modified tobacco seed or tobacco plant comprises lower amount N'-nitrosoanabasine (NAB) as compared to an unmodified tobacco plant lacking the cisgenic polynucleotide when grown under the same conditions. In a further aspect, a modified tobacco seed or tobacco plant comprises lower amounts of alkaloids as compared to an unmodified tobacco plant lacking the cisgenic polynucleotide when grown under the same conditions. In a further aspect, a modified tobacco seed or tobacco plant comprises lower amounts of nicotine as compared to an unmodified tobacco plant lacking the cisgenic polynucleotide when grown under the same conditions. In a further aspect, a modified tobacco seed or tobacco plant comprises lower amounts of nornicotine as compared to an unmodified tobacco plant lacking the cisgenic polynucleotide when grown under the same conditions. In a further aspect, a modified tobacco seed or tobacco plant comprises lower amounts of anabasine as compared to an unmodified tobacco plant lacking the cisgenic polynucleotide when grown under the same conditions. In a further aspect, a modified tobacco seed or tobacco plant comprises lower amounts of anatabine as compared to an unmodified tobacco plant lacking the cisgenic polynucleotide when grown under the same conditions.

Leaf Quality/Grading

In an aspect, the present disclosure provides breeding tobacco lines, cultivars, or varieties comprising enhanced nitrogen use efficiency, a tobacco plant, or part thereof, comprising a genetic modification in or targeting one or more enhanced NUE loci, YB1, YB2, or any combination thereof. The present disclosure also provides mutant or transgenic tobacco plants having enhanced NUE without negative impacts over other tobacco traits, e.g., leaf grade index value. In an aspect, an enhanced NUE tobacco plants of the present disclosure provide cured tobacco of commercially acceptable grade.

Tobacco grades are evaluated based on factors including, but not limited to, the leaf stalk position, leaf size, leaf color, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast. Leaf grade can be determined, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania Seedleaf Tobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida Shade-Grown Cigar-Wrapper Tobacco (U.S. Type 62), Effective April 1971. A USDA grade index value can be determined according to an industry accepted grade index. See, e.g., Bowman et al, Tobacco Science, 32:39-40 (1988); Legacy Tobacco Document Library (Bates Document #523267826-523267833, Jul. 1, 1988, Memorandum on the Proposed Burley Tobacco Grade Index); and Miller et al., 1990, Tobacco Intern., 192:55-57 (all foregoing references are incorporated by inference in their entirety). Unless specified otherwise, a USDA grade index is a 0-100 numerical representation of federal grade received and is a weighted average of all stalk positions. A higher-grade index indicates higher quality. Alternatively, leaf grade can be determined via hyper-spectral imaging. See e.g., WO 2011/027315 (published on Mar. 10, 2011, and incorporated by inference in its entirety).

In an aspect, tobacco plants comprising enhanced NUE described here are capable of producing leaves, when cured, having a USDA grade index value selected from the group consisting of 55 or more, 60 or more, 65 or more, 70 or more, 75 or more, 80 or more, 85 or more, 90 or more, and 95 or more. In another aspect, tobacco plants are capable of producing leaves, when cured, having a USDA grade index value comparable to that of a control plant when grown and cured in similar conditions, where the control plant shares an essentially identical genetic background with the tobacco plant except for the combination of enhanced NUE loci, YB1, or YB2 alleles disclosed herein. In a further aspect, tobacco plants are capable of producing leaves, when cured, having a USDA grade index value of at least about 65%, at least about 70%, at least about 75%, at least about 80%, at least about 85%, at least about 90%, at least about 95%, or at least about 98% of the USDA grade index value of a control plant when grown in similar conditions, where the control plant shares an essentially identical genetic background with the tobacco plant except a low-nicotine conferring mutation or transgene. In a further aspect, tobacco plants are capable of producing leaves, when cured, having a USDA grade index value of between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the USDA grade index value of the control plant. In a further aspect, tobacco plants are capable of producing leaves, when cured, having a USDA grade index value of between 70% and 125%, between 75% and 120%, between 80% and 115%, between 85% and 110%, or between 90% and 100% of the USDA grade index value of the control plant.

In another aspect, tobacco plants comprising enhanced NUE tobacco plants described here are capable of producing leaves, when cured, having a USDA grade index value selected from the group consisting of 55 or more, 60 or more, 65 or more, 70 or more, 75 or more, 80 or more, 85 or more, 90 or more, and 95 or more. In another aspect, tobacco plants are capable of producing leaves, when cured, having a USDA grade index value selected from the group consisting of between 50 and 95, between 55 and 95, between 60 and 95, between 65 and 95, between 70 and 95, between 75 and 95, between 80 and 95, between 85 and 95, between 90 and 95, between 55 and 90, between 60 and 85, between 65 and 80, between 70 and 75, between 50 and 55, between 55 and 60, between 60 and 65, between 65 and 70, between 70 and 75, between 75 and 80, between 80 and 85, between 85 and 90, and between 90 and 95. In a further aspect, tobacco plants are capable of producing leaves, when cured, having a USDA grade index value of at least about 65%, at least about 70%, at least about 75%, at least about 80%, at least about 85%, at least about 90%, at least about 95%, or at least about 98% of the USDA grade index value of a control plant. In a further aspect, tobacco plants are capable of producing leaves, when cured, having a USDA grade index value of between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the USDA grade index value of a control plant. In a further aspect, tobacco plants are capable of producing leaves, when cured, having a USDA grade index value of between 70% and 125%, between 75% and 120%, between 80% and 115%, between 85% and 110%, or between 90% and 100% of the USDA grade index value of a control plant.

In an aspect, the present disclosure further provides an tobacco plants comprising enhanced NUE, or parts thereof, comprising a nicotine or total alkaloid level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, and less than 0.05%, where the tobacco plants are capable of producing leaves, when cured, having a USDA grade index value of 50 or more 55 or more, 60 or more, 65 or more, 70 or more, 75 or more, 80 or more, 85 or more, 90 or more, and 95 or more. In another aspect, such enhanced NUE tobacco plants comprise a nicotine level of less than 2.0% and are capable of producing leaves, when cured, having a USDA grade index value of 70 or more. In a further aspect, such enhanced NUE tobacco plants comprise a nicotine level of less than 1.0% and are capable of producing leaves, when cured, having a USDA grade index value of 70 or more.

In an aspect, the present disclosure also provides an tobacco plants comprising enhanced NUE, or parts thereof, the nicotine or total alkaloid level of the tobacco plant to below 1%, below 2%, below 5%, below 8%, below 10%, below 12%, below 15%, below 20%, below 25%, below 30%, below 40%, below 50%, below 60%, below 70%, or below 80% of the nicotine level of a control plant when grown in similar growth conditions, where the tobacco plant is capable of producing leaves, when cured, having a USDA grade index value comparable to the USDA grade index value of the control plant.

Chemical Measurements

In one aspect, tobacco plants, seeds, plant components, plant cells, and plant genomes provided herein are from a tobacco type selected from the group consisting of flue-cured tobacco, sun-cured tobacco, air-cured tobacco, dark air-cured tobacco, and dark fire-cured tobacco. In another aspect, tobacco plants, seeds, plant components, plant cells, and plant genomes provided herein are from a tobacco type selected from the group consisting of Burley tobacco, Maryland tobacco, bright tobacco, Virginia tobacco, Oriental tobacco, Turkish tobacco, and Galpão tobacco. In one aspect, a tobacco plants or seed provided herein is a hybrid plants or seed. As used herein, a "hybrid" is created by crossing two plants from different varieties or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an Ex F hybrid. The first and second hybrids can be further crossed to create the higher order hybrid (C×D)×(E×F) comprising genetic information from all four parent varieties.

Also provided herein are populations of tobacco plants described herein. In one aspect, a population of tobacco plants provided herein has a planting density of between 5,000 and 8000, between 5,000 and 7,600, between 5,000 and 7,200, between 5,000 and 6,800, between 5,000 and 6,400, between 5,000 and 6,000, between 5,000 and 5,600, between 5,000 and 5,200, between 5,200 and 8,000, between 5,600 and 8,000, between 6,000 and 8,000, between 6,400 and 8,000, between 6,800 and 8,000, between 7,200 and 8,000, or between 7,600 and 8,000 plants per acre.

"Alkaloids" are complex, nitrogen-containing compounds that naturally occur in plants, and have pharmacological effects in humans and animals. "Nicotine" is the primary natural alkaloid in commercialized cigarette tobacco and accounts for about 90 percent of the alkaloid content in *Nicotiana tabacum*. Other major alkaloids in tobacco include cotinine, nornicotine, myosmine, nicotyrine, anabasine and anatabine. Minor tobacco alkaloids include nicotine-n-oxide, N-methyl anatabine, N-methyl anabasine, pseudooxynicotine, 2,3 dipyridyl and others.

In an aspect, an enhanced NUE tobacco plant provided herein further comprises a genetic modification providing a lower level of one or more alkaloids selected from the group consisting of cotinine, nornicotine, myosmine, nicotyrine, anabasine and anatabine, compared to a control tobacco plant without the genetic modification, when grown in similar growth conditions. In an aspect, a lower alkaloid or nicotine level refers to an alkaloid or nicotine level of below 1%, below 2%, below 5%, below 8%, below 10%, below 12%, below 15%, below 20%, below 25%, below 30%, below 40%, below 50%, below 60%, below 70%, or below 80% of the alkaloid or nicotine level of a control tobacco plant. In another aspect, a lower alkaloid or nicotine level refers to an alkaloid or nicotine level of about between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, between 19% and 20%, between 21% and 22%, between 22% and 23%, between 23% and 24%, between 24% and 25%, between 25% and 26%, between 26% and 27%, between 27% and 28%, between 28% and 29%, or between 29% and 30% of the alkaloid or nicotine level of a control tobacco plant. In a further aspect, a lower alkaloid or nicotine level refers to an alkaloid or nicotine level of about between 0.5% and 5%, between 5% and 10%, between 10% and 20%, between 20% and 30% of the alkaloid or nicotine level of a control tobacco plant.

In an aspect, an enhanced NUE tobacco plant provided herein further comprises an average nicotine or total alkaloid level selected from the group consisting of about 0.01%, 0.02%, 0.05%, 0.75%, 0.1%, 0.15%, 0.2%, 0.3%, 0.35%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 6%, 7%, 8%, and 9% on a dry weight basis. In another aspect, tobacco plants provided herein comprise an average nicotine or total alkaloid level selected from the group consisting of about between 0.01% and 0.02%, between 0.02% and 0.05%, between 0.05% and 0.75%, between 0.75% and 0.1%, between 0.1% and 0.15%, between 0.15% and 0.2%, between 0.2% and 0.3%, between 0.3% and 0.35%, between 0.35% and 0.4%, between 0.4% and 0.5%, between 0.5% and 0.6%, between 0.6% and 0.7%, between 0.7% and 0.8%, between 0.8% and 0.9%, between 0.9% and 1%, between 1% and 1.1%, between 1.1% and 1.2%, between 1.2% and 1.3%, between 1.3% and 1.4%, between 1.4% and 1.5%, between 1.5% and 1.6%, between 1.6% and 1.7%, between 1.7% and 1.8%, between 1.8% and 1.9%, between 1.9% and 2%, between 2% and 2.1%, between 2.1% and 2.2%, between 2.2% and 2.3%, between 2.3% and 2.4%, between 2.4% and 2.5%, between 2.5% and 2.6%, between 2.6% and 2.7%, between 2.7% and 2.8%, between 2.8% and 2.9%, between 2.9% and 3%, between 3% and 3.1%, between 3.1% and 3.2%, between 3.2% and 3.3%, between 3.3% and 3.4%, between 3.4% and 3.5%, and between 3.5% and 3.6% on a dry weight basis. In a further aspect, tobacco plants provided herein comprise an average nicotine or total alkaloid level selected from the group consisting of about between 0.01% and 0.1%, between 0.02% and 0.2%, between 0.03% and 0.3%, between 0.04% and 0.4%, between 0.05% and 0.5%, between 0.75% and 1%, between 0.1% and 1.5%, between 0.15% and 2%, between 0.2% and 3%, and between 0.3% and 3.5% on a dry weight basis.

Unless specified otherwise, measurements of alkaloid, polyamine, or nicotine levels (or another leaf chemistry or property characterization) or leaf grade index values mentioned herein for a tobacco plant, variety, cultivar, or line refer to average measurements, including, for example, an average of multiple leaves of a single plant or an average measurement from a population of tobacco plants from a single variety, cultivar, or line. Unless specified otherwise, the nicotine, alkaloid, or polyamine level (or another leaf chemistry or property characterization) of a tobacco plant described here is measured 2 weeks after topping in a pooled leaf sample collected from leaf number 3, 4, and 5 after topping. In another aspect, the nicotine, alkaloid, or polyamine level (or another leaf chemistry or property characterization) of a tobacco plant is measured after topping in a leaf having the highest level of nicotine, alkaloid, or polyamine (or another leaf chemistry or property characterization). In an aspect, the nicotine, alkaloid, or polyamine level of a tobacco plant is measured after topping in leaf number 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In another aspect, the nicotine, alkaloid, or polyamine level (or another leaf chemistry or property characterization) of a tobacco plant is measured after topping in a pool of two or more leaves with consecutive leaf numbers selected from the group consisting of leaf number 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30. In another aspect, the nicotine, alkaloid, or polyamine level (or another leaf chemistry or property characterization) of a tobacco plant is measured after topping in a leaf with a leaf number selected from the group consisting of between 1 and 5, between 6 and 10, between 11 and 15, between 16 and 20, between 21 and 25, and between 26 and 30. In another aspect, the nicotine, alkaloid, or polyamine level (or another leaf chemistry or property characterization) of a tobacco plant is measured after topping in a pool of two or more leaves with leaf numbers selected from the group consisting of between 1 and 5, between 6 and 10, between 11 and 15, between 16 and 20, between 21 and 25, and between 26 and 30. In another aspect, the nicotine, alkaloid, or polyamine level (or another leaf chemistry or property characterization) of a tobacco plant is measured after topping in a pool of three or more leaves with leaf numbers selected from the group consisting of between 1 and 5, between 6 and 10, between 11 and 15, between 16 and 20, between 21 and 25, and between 26 and 30.

Alkaloid levels can be assayed by methods known in the art, for example by quantification based on gas-liquid chromatography, high performance liquid chromatography, radio-immunoassays, and enzyme-linked immunosorbent assays. For example, nicotinic alkaloid levels can be measured by a GC-FID method based on CORESTA Recommended Method No. 7, 1987 and ISO Standards (ISO TC 126N 394 E). See also Hibi et al., *Plant Physiology* 100: 826-35 (1992) for a method using gas-liquid chromatography equipped with a capillary column and an FID detector. Unless specified otherwise, all alkaloid levels described here are measured using a method in accordance with CORESTA Method No 62, *Determination of Nicotine in Tobacco and Tobacco Products by Gas Chromatographic Analysis*, February 2005, and those defined in the Centers for Disease Control and Prevention's *Protocol for Analysis of Nicotine, Total Moisture and pH in Smokeless Tobacco Products*, as published in the Federal Register Vol. 64, No. 55 Mar. 23, 1999 (and as amended in Vol. 74, No. 4, Jan. 7, 2009).

Alternatively, tobacco total alkaloids can be measured using a segmented-flow colorimetric method developed for analysis of tobacco samples as adapted by Skalar Instrument Co (West Chester, PA) and described by Collins et al., *Tobacco Science* 13:79-81 (1969). In short, samples of tobacco are dried, ground, and extracted prior to analysis of total alkaloids and reducing sugars. The method then employs an acetic acid/methanol/water extraction and charcoal for decolorization. Determination of total alkaloids was based on the reaction of cyanogen chloride with nicotine alkaloids in the presence of an aromatic amine to form a colored complex which is measured at 460 nm. Unless specified otherwise, total alkaloid levels or nicotine levels shown herein are on a dry weight basis (e.g., percent total alkaloid or percent nicotine).

As used herein, leaf numbering is based on the leaf position on a tobacco stalk with leaf number 1 being the oldest leaf (at the base) after topping and the highest leaf number assigned to the youngest leaf (at the tip).

A population of tobacco plants or a collection of tobacco leaves for determining an average measurement (e.g., alkaloid or nicotine level or leaf grading) can be of any size, for example, 5, 10, 15, 20, 25, 30, 35, 40, or 50. Industry-accepted standard protocols are followed for determining average measurements or grade index values.

As used herein, "topping" refers to the removal of the stalk apex, including the SAM, flowers, and up to several adjacent leaves, when a tobacco plant is near vegetative maturity and around the start of reproductive growth. Typically, tobacco plants are topped in the button stage (soon after the flower begins to appear). For example, greenhouse or field-grown tobacco plants can be topped when 50% of the plants have at least one open flower. Topping a tobacco plant results in the loss of apical dominance and also induce increased alkaloid production.

Typically, the nicotine, alkaloid, or polyamine level (or another leaf chemistry or property characterization) of a tobacco plant is measured about 2 weeks after topping. Other time points can also be used. In an aspect, the nicotine, alkaloid, or polyamine level (or another leaf chemistry or property characterization) of a tobacco plant is measured about 1, 2, 3, 4, or 5 weeks after topping. In another aspect, the nicotine, alkaloid, or polyamine level (or another leaf chemistry or property characterization) of a tobacco plant is measured about 3, 5, 7, 10, 12, 14, 17, 19, or 21 days after topping.

As used herein, "similar growth conditions" refer to similar environmental conditions and/or agronomic practices for growing and making meaningful comparisons between two or more plant genotypes so that neither environmental conditions nor agronomic practices would contribute to or explain any difference observed between the two or more plant genotypes. Environmental conditions include, for example, light, temperature, water (humidity), and nutrition (e.g., nitrogen and phosphorus). Agronomic practices include, for example, seeding, clipping, undercutting, transplanting, topping, and suckering. See Chapters 4B and 4C of Tobacco, Production, Chemistry and Technology, Davis & Nielsen, eds., Blackwell Publishing, Oxford (1999), pp 70-103.

As used herein, "comparable leaves" refer to leaves having similar size, shape, age, and/or stalk position.

TSNA

In still another aspect, a tobacco plant provided further comprises one or more mutations in one or more loci encoding a nicotine demethylase (e.g., CYP82E4, CYP82E5, CYP82E10) that confer reduced amounts of nornicotine (See U.S. Pat. Nos. 8,319,011; 8,124,851; 9,187,759; 9,228,194; 9,228,195; 9,247,706) compared to control plant lacking one or more mutations in one or more loci encoding a nicotine demethylase. In an aspect, a modified tobacco plant described further comprises reduced nicotine demethylase activity compared to a control plant when grown and cured under comparable conditions. In a further aspect, a tobacco plant provided further comprises one or more mutations or transgenes providing an elevated level of one or more antioxidants (See U.S. Patent Application Publication No. 2018/0119163 and WO 2018/067985). In another aspect, a tobacco plant provided further comprises one or more mutations or transgenes providing a reduced level of one or more tobacco-specific nitrosamines (TSNAs) (such as N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof). In one aspect, the level of total TSNAs or an individual TSNA is measured based on a freeze-dried cured leaf sample using liquid chromatograph with tandem mass spectrometry (LC/MS/MS).

Aroma/Flavor

In an aspect, enhanced NUE tobacco plants provided herein further comprise a similar level of one or more tobacco aroma compounds selected from the group consisting of 3-methylvaleric acid, valeric acid, isovaleric acid, a labdenoid, a cembrenoid, a sugar ester, and a reducing sugar, compared to control tobacco plants when grown in similar growth conditions.

As used herein, tobacco aroma compounds are compounds associated with the flavor and aroma of tobacco smoke. These compounds include, but are not limited to, 3-methylvaleric acid, valeric acid, isovaleric acid, cembrenoid and labdenoid diterpenes, and sugar esters. Concentrations of tobacco aroma compounds can be measured by any known metabolite profiling methods in the art including, without limitation, gas chromatography mass spectrometry (GC-MS), Nuclear Magnetic Resonance Spectroscopy, liquid chromatography-linked mass spectrometry. See The Handbook of Plant Metabolomics, edited by Weckwerth and Kahl, (Wiley-Blackwell) (May 28, 2013).

As used herein, "reducing sugar(s)" are any sugar (monosaccharide or polysaccharide) that has a free or potentially free aldehyde or ketone group. Glucose and fructose act as nicotine buffers in cigarette smoke by reducing smoke pH and effectively reducing the amount of "free" unprotonated nicotine. Reducing sugars balances smoke flavor, for example, by modifying the sensory impact of nicotine and other tobacco alkaloids. An inverse relationship between sugar content and alkaloid content has been reported across tobacco varieties, within the same variety, and within the same plant line caused by planting conditions. Reducing sugar levels can be measured using a segmented-flow colorimetric method developed for analysis of tobacco samples as adapted by Skalar Instrument Co (West Chester, PA) and described by Davis, *Tobacco Science* 20:139-144 (1976). For example, a sample is dialyzed against a sodium carbonate solution. Copper neocuproin is added to the sample and the solution is heated. The copper neocuproin chelate is reduced in the presence of sugars resulting in a colored complex which is measured at 460 nm.

Tobacco Types

In an aspect, a tobacco plant provided is from a tobacco type selected from the group consisting of flue-cured tobacco, air-cured tobacco, dark air-cured tobacco, dark fire-cured tobacco, Galpão tobacco, and Oriental tobacco. In another aspect, a tobacco plant provided is from a tobacco type selected from the group consisting of Burley tobacco, Maryland tobacco, and dark tobacco.

In an aspect, a tobacco plant provided is in a flue-cured tobacco background or exhibits one or more flue-cured tobacco characteristic described here. Flue-cured tobaccos (also called "Virginia" or "bright" tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the United States of America. In one aspect, tobacco plants or seeds or modified tobacco plants or seeds provided herein are of a flue-cured tobacco variety selected from the group consisting of the varieties listed in Table 1, and any variety essentially derived from any one of the foregoing varieties. See WO 2004/041006 A1. In a further aspect, modified tobacco plants or seeds provided herein are in a flue-cured variety selected from the group consisting of K326, K346, and NC196.

TABLE 1

| Flue-cured Tobacco Varieties | | |
|---|---|---|
| 400 (TC 225) | K 346 | Reams 134 |
| 401 (TC 226) | K 346 (TC 569) | Reams 158 |
| 401 Cherry Red (TC 227) | K 358 | Reams 713 |
| 401 Cherry Red Free (TC 228) | K 394 (TC 321) | Reams 744 |
| Cash (TC 250) | K 399 | Reams M1 |
| Cash (TI 278) | K 399 (TC 322) | RG 11 (TC 600) |
| CC 101 | K 730 | RG 13 (TC 601) |
| CC 1063 | Lonibow (TI 1573) | RG 17 (TC 627) |
| CC 13 | Lonibow (TI 1613) | RG 22 (TC 584) |
| CC 143 | McNair 10 (TC 330) | RG 8 (TC 585) |
| CC 200 | McNair 135 (TC 337) | RG 81 (TC 618) |
| CC 27 | McNair 30 (TC 334) | RG H51 |
| CC 301 | McNair 373 (TC 338) | RG4H 217 |
| CC 33 | McNair 944 (TC 339) | RGH 12 |
| CC 35 | MK94 (TI 1512) | RGH 4 |

TABLE 1-continued

| Flue-cured Tobacco Varieties | | |
|---|---|---|
| CC 37 | MS K 326 | RGH 51 |
| CC 400 | MS NC 71 | RGH 61 |
| CC 500 | MS NC 72 | SC 58 (TC 400) |
| CC 600 | NC 100 | SC 72 (TC 403) |
| CC 65 | NC 102 | Sp. G-168 |
| CC 67 | NC 1071 (TC 364) | SPEIGHT 168 |
| CC 700 | NC 1125-2 | Speight 168 (TC 633) |
| CC 800 | NC 12 (TC 346) | Speight 172 (TC 634) |
| CC 900 | NC 1226 | Speight 178 |
| Coker 139 (TC 259) | NC 196 | Speight 179 |
| Coker 139 yb1, yb2 | NC 2326 (TC 365) | Speight 190 |
| Coker 140 (TC 260) | NC 27 NF (TC 349) | Speight 196 |
| Coker 176 (TC 262) | NC 291 | SPEIGHT 220 |
| Coker 187 (TC 263) | NC 297 | SPEIGHT 225 |
| Coker 187-Hicks (TC 265) | NC 299 | SPEIGHT 227 |
| Coker 209 (TC 267) | NC 37 NF (TC 350) | SPEIGHT 236 |
| Coker 258 (TC 270) | NC 471 | Speight G-10 (TC 416) |
| Coker 298 (TC 272) | NC 55 | Speight G-102 |
| Coker 316 (TC 273) | NC 567 (TC 362) | Speight G-108 |
| Coker 319 (TC 274) | NC 60 (TC 352) | Speight G-111 |
| Coker 347 (TC 275) | NC 606 | Speight G-117 |
| Coker 371-Gold (TC 276) | NC 6140 | Speight G-126 |
| Coker 411 (TC 277) | NC 71 | Speight G-15 (TC 418) |
| Coker 48 (TC 253) | NC 72 | Speight G-23 |
| Coker 51 (TC 254) | NC 729 (TC 557) | Speight G-28 (TC 420) |
| Coker 86 (TC 256) | NC 810 (TC 659) | Speight G-33 |
| CU 263 (TC 619) | NC 82 (TC 356) | Speight G-41 |
| CU 561 | NC 8640 | Speight G-5 |
| DH95-1562-1 | NC 89 (TC 359) | Speight G-52 |
| Dixie Bright 101 (TC 290) | NC 92 | Speight G-58 |
| Dixie Bright 102 (TC 291) | NC 925 | Speight G-70 |
| Dixie Bright 244 (TC 292) | NC 95 (TC 360) | Speight G-70 (TC 426) |
| Dixie Bright 27 (TC 288) | NC 98 (TC 361) | Speight G-80 (TC 427) |
| Dixie Bright 28 (TC 289) | NC EX 24 | Speight NF3 (TC 629) |
| GF 157 | NC PY 10 (TC 367) | STNCB |
| GF 318 | NC TG 61 | VA 182 |
| GL 26H | Oxford 1 (TC 369) | VA 45 (TC 559) |
| GL 338 | Oxford 1-181 (TC 370) | Vesta 30 (TC 439) |
| GL 350 | Oxford 2 (TC 371) | Vesta 33 (TC 440) |
| GL 368 | Oxford 207 (TC 632) | Vesta 5 (TC 438) |
| GL 395 | Oxford 26 (TC 373) | Vesta 62 (TC 441) |
| GL 600 | Oxford 3 (TC 372) | Virginia (TI 220) |
| GL 737 | Oxford 414 NF | Virginia (TI 273) |
| GL 939 | PD 611 (TC 387) | Virginia (TI 877) |
| GL 939 (TC 628) | PVH 03 | Virginia 115 (TC 444) |
| Hicks (TC 310) | PVH 09 | Virginia 21 (TC 443) |
| Hicks Broadleaf (TC 311) | PVH 1118 | Virginia Bright (TI 964) |
| K 149 (TC 568) | PVH 1452 | Virginia Bright Leaf (TC 446) |
| K 317 | PVH 1600 | Virginia Gold (TC 447) |
| K 326 | PVH 2110 | White Stem Orinoco (TC 451) |
| K 326 (TC 319) | PVH 2275 | |
| K 340 (TC 320) | R 83 (Line 256-1) (TI 1400) | |

In an aspect, a tobacco plant provided is in an air-cured tobacco background or exhibits one or more air-cured tobacco characteristic described here. Air-cured tobaccos include "Burley," "Maryland," and "dark" tobaccos. The common factor linking air-cured tobaccos is that curing occurs primarily without artificial sources of heat and humidity. Burley tobaccos are light to dark brown in color, high in oil, and low in sugar. Burley tobaccos are typically air-cured in barns. Major Burley growing countries include Argentina, Brazil, Italy, Malawi, and the United States of America.

Maryland tobaccos are extremely fluffy, have good burning properties, low nicotine and a neutral aroma. Major Maryland growing countries include the United States of America and Italy.

In one aspect, tobacco plants or seeds or modified tobacco plants or seeds provided herein are of a Burley tobacco variety selected from the group consisting of the tobacco varieties listed in Table 2, and any variety essentially derived from any one of the foregoing varieties. In a further aspect, modified tobacco plants or seeds provided herein are in a Burley variety selected from the group consisting of TN 90, KT 209, KT 206, KT212, and HB 4488.

TABLE 2

| Burley Tobacco Varieties | | |
|---|---|---|
| 4407 LC | HB 4108P | KY 54 (TC 71) |
| AA-37-1 | HB 4151P | KY 56 (TC 72) |
| Burley 21 (TC 7) | HB 4192P | KY 56 (TC 72) |
| Burley 49 (TC 10) | HB 4194P | KY 57 (TC 73) |
| Burley 64 (TC 11) | HB 4196 | KY 58 (TC 74) |
| Burley Mammoth KY 16 (TC 12) | HB 4488 | KY 8654 (TC 77) |
| Clay 402 | HB 4488P | KY 8959 |
| Clay 403 | HB04P | KY 9 (TC 54) |
| Clay 502 | HB 4488 LC | KY 907 LC |
| Clays 403 | HIB 21 | KY 908 (TC 630) |
| GR 10 (TC 19) | HPB 21 | NBH 98 (Screened) |
| GR 10 (TC 19) | HY 403 | NC 1206 |
| GR 10A (TC 20) | Hybrid 403 LC | NC 129 |
| GR 13 (TC 21) | Hybrid 404 LC | NC 2000 LC |
| GR 14 (TC 22) | Hybrid 501 LC | NC 2002 LC |
| GR 149 LC | KDH-959 (TC 576) | NC 3 LC |
| GR 153 | KDH-960 (TC 577) | NC 5 LC |
| GR 17 (TC 23) | KT 200 LC | NC 6 LC |
| GR 17B (TC 24) | KT 204 LC | NC 7 LC |
| GR 18 (TC 25) | KT 206 LC | NC BH 129 LC |
| GR 19 (TC 26) | KT 209 LC | NC03-42-2 |
| GR 2 (TC 15) | KT 210 LC | Newton 98 |
| GR 24 (TC 27) | KT 212 LC | R 610 LC |
| GR 36 (TC 28) | KT 215 LC | R 630 LC |
| GR 38 (TC 29) | KY 1 (TC 52) | R 7-11 |
| GR 38A (TC 30) | KY 10 (TC 55) | R 7-12 LC |
| GR 40 (TC 31) | KY 12 (TC 56) | RG 17 |
| GR 42 (TC 32) | KY 14 (TC 57) | TKF 1801 LC |
| GR 42C (TC 33) | KY 14 x L8 LC | TKF 2002 LC |
| GR 43 (TC 34) | KY 15 (TC 58) | TKF 4024 LC |
| GR 44 (TC 35) | KY 16 (TC 59) | TKF 4028 LC |
| GR 45 (TC 36) | KY 17 (TC 60) | TKF 6400 LC |
| GR 46 (TC 37) | KY 19 (TC 61) | TKF 7002 LC |
| GR 48 (TC 38) | KY 21 (TC 62) | TKS 2002 LC |
| GR 5 (TC 16) | KY 22 (TC 63) | TN 86 (TC 82) |
| GR 53 (TC 39) | KY 24 (TC 64) | TN 90 LC |
| GR 6 (TC 17) | KY 26 (TC 65) | TN 97 Hybrid LC |
| GR 9 (TC 18) | KY 33 (TC 66) | TN 97 LC |
| GR139 NS | KY 34 (TC 67) | VA 116 |
| GR139 S | KY 35 (TC 68) | VA 119 |
| HB 04P | KY 41A (TC 69) | Virgin A Mutante (TI 1406) |
| HB 04P LC | KY 5 (TC 53) | Virginia 509 (TC 84) |
| HB 3307P LC | KY 52 (TC 70) | |

In another aspect, tobacco plants or seeds or modified tobacco plants or seeds provided herein are of a Maryland tobacco variety selected from the group consisting of the tobacco varieties listed in Table 3, and any variety essentially derived from any one of the foregoing varieties.

TABLE 3

| Maryland Tobacco Varieties | |
|---|---|
| Maryland 10 (TC 498) | K326 |
| Maryland 14 D2 (TC 499) | K346 |
| Maryland 201 (TC 503) | K358 |
| Maryland 21 (TC 500) | K394 |
| Maryland 341 (TC 504) | K399 |
| Maryland 40 | K730 |
| Maryland 402 | NC196 |
| Maryland 59 (TC 501) | NC37NF |
| Maryland 601 | NC471 |
| Maryland 609 (TC 505) | NC55 |
| Maryland 64 (TC 502) | NC92 |
| Maryland 872 (TC 506) | NC2326 |
| Maryland Mammoth (TC 507) | NC95 |
| Banket A1 | NC925 |

In an aspect, a tobacco plant provided is in a dark air-cured tobacco background or exhibits one or more dark air-cured tobacco characteristic described here. Dark air-cured tobaccos are distinguished from other tobacco types primarily by its curing process, which gives dark air-cured tobacco its medium-brown to dark-brown color and a distinct aroma. Dark air-cured tobaccos are mainly used in the production of chewing tobacco and snuff. In one aspect, modified tobacco plants or seeds provided herein are of a dark air-cured tobacco variety selected from the group consisting of Sumatra, Jatim, Dominican Cubano, Besuki, One sucker, Green River, Virginia sun-cured, and Paraguayan Passado, and any variety essentially derived from any one of the foregoing varieties.

In an aspect, a tobacco plant provided is in a dark fire-cured tobacco background or exhibits one or more dark fire-cured tobacco characteristic described here. Dark fire-cured tobaccos are generally cured with low-burning wood fires on the floors of closed curing barns. Dark fire-cured tobaccos are typically used for making pipe blends, cigarettes, chewing tobacco, snuff, and strong-tasting cigars. Major growing regions for dark fire-cured tobaccos are Tennessee, Kentucky, and Virginia in the United States of America. In one aspect, tobacco plants or seeds or modified tobacco plants or seeds provided herein are of a dark fire-cured tobacco variety selected from the group consisting of the tobacco varieties listed in Table 4, and any variety essentially derived from any one of the foregoing varieties.

TABLE 4

| Dark Fire-Cured Tobacco Varieties | | |
|---|---|---|
| Black Mammoth (TC 461) | KY 171 (TC 475) | PD 7309 LC |
| Black Mammoth Small Stalk (TC 641) | KY 171 LC | PD 7312 LC |
| Certified Madole (TC 463) | KY 171 NS | PD 7318 LC |
| D-534-A-1 (TC 464) | KY 180 (TC 573) | PD 7319 LC |
| DAC ULT 302 | KY 190 (TC 574) | Petico M PG04 |
| DAC ULT 303 | Little Crittenden | PY KY 160 (TC 612) |
| DAC ULT 306 | Little Crittenden (TC 476) | PY KY 171 (TC 613) |
| DAC ULT 308 | Little Crittenden LC (certified) | Shirey |
| DAC ULT 312 | Little Crittenden PhPh | TI 1372 |
| DF 300 (TC 465) | Lizard Tail Turtle Foot | TN D94 |
| DF 485 (TC 466) | Madole (TC 478) | TN D94 (TC 621) |
| DF 516 (TC 467) | Madole (TC 479) | TN D950 |
| DF 911 (TC 468) | MS KY 171 | TN D950 (PhPh) |
| DT 508 | MS NL Madole LC | TN D950 |
| DT 518 (Screened) | MS TN D950 LC | TN D950 (TC 622) |
| DT 538 LC | Nance (TC 616) | TR Madole (TC 486) |

TABLE 4-continued

| Dark Fire-Cured Tobacco Varieties | | |
|---|---|---|
| DT 592 | Narrow Leaf Madole LC (certified) | VA 309 |
| Improved Madole (TC 471) | Neal Smith Madole (TC 646) | VA 309 (TC 560) |
| Jernigan's Madole (TC 472) | Newtons VH Madole | VA 309 LC (certified) |
| KT 14LC | NL Madole | VA 310 (TC 487) |
| KT D17LC | NL Madole (PhPh) | VA 331 (TC 592) |
| KT D4 LC | NL Madole (TC 484) | VA 355 (TC 638) |
| KT D6 LC | NL Madole LC | VA 359 |
| KT D8 LC | NL Madole LC (PhPh) | VA 359 (Screened) |
| KY 153 (TC 216) | NL Madole NS | VA 359 (TC 639) |
| KY 157 (TC 217) | One Sucker (TC 224) | VA 359 LC (certified) |
| KY 160 | OS 400 | VA 403 (TC 580) |
| KY 160 (TC 218) | PD 302H | VA 405 (TC 581) |
| KY 163 (TC 219) | PD 312H | VA 409 (TC 562) |
| KY 165 (TC 220) | PD 318H | VA 510 (TC 572) |
| KY 170 (TC 474) | PD 7302 LC | |
| KY 171 (PhPh) | PD 7305 | |

In an aspect, a tobacco plant provided is in an Oriental tobacco background or exhibits one or more Oriental tobacco characteristic described here. Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant size, small leaf size, and unique aroma properties of Oriental tobacco varieties are a result of their adaptation to the poor soil and stressful climatic conditions in which they have been developed. In one aspect, tobacco plants or seeds or modified tobacco plants or seeds provided herein are of an Oriental tobacco variety selected from the group consisting of the tobacco varieties listed in Table 5, and any variety essentially derived from any one of the foregoing varieties.

TABLE 5

| Oriental Tobacco Varieties | | |
|---|---|---|
| Bafra (TI 1641) | Edirne (TI 1671) | Samsun (TC 536) |
| Bahce (TI 1730) | Ege (TI 1642) | Samsun 959 (TI 1570) |
| Bahia (TI 1416) | Ege-64 (TI 1672) | Samsun Evkaf (TI 1723) |
| Bahia (TI 1455) | Izmir (Akhisar) (TI 1729) | Samsun Holmes NN (TC 540) |
| Baiano (TI 128) | Izmir (Gavurkoy) (TI 1727) | Samsun Maden (TI 1647) |
| Basma | Izmir Ege 64 | Samsun NO 15 (TC 541) |
| Basma (TI 1666) | Izmir-Incekara (TI 1674) | Samsun-BLK SHK Tol (TC 542) |
| Basma Drama | Izmir-Ozbas (TI 1675) | Samsun-Canik (TI 1678) |
| Basma Hybrid (PhPh) | Jaka Dzebel (TI 1326) | Samsun-Maden (TI 1679) |
| Basma Zihna I | Kaba-Kulak | Saribaptar 407 - Izmir Region |
| Bitlis (TI 1667) | Kagoshima Maruba (TI 158) | Smyrna (TC 543) |
| Bitlis (TI 1725) | Katerini | Smyrna No. 23 (TC 545) |
| Bubalovac (TI 1282) | Katerini S53 | Smyrna No. 9 (TC 544) |
| Bursa (TI 1650) | Krumovgrad 58 | Smyrna-Blk Shk Tol (TC 546) |
| Bursa (TI 1668) | MS Basma | Trabzon (TI 1649) |
| Canik (TI 1644) | MS Katerini S53 | Trabzon (TI 1682) |
| Djebel 174 (TI 1492) | Nevrokop 1146 | Trapezund 161 (TI 1407) |
| Djebel 359 (TI 1493) | Ozbas (TI 1645) | Turkish (TC 548) |
| Djebel 81 | Perustitza (TI 980) | Turkish Angshit (TI 90) |
| Dubec 566 (TI 1409) | Prilep (TI 1291) | Turkish Samsum (TI 92) |
| Dubec 7 (TI 1410) | Prilep (TI 1325) | Turkish Tropizoid (TI 93) |
| Dubek 566 (TI 1567) | Prilep 12-2/1 | Turkish Varotic (TI 89) |
| Duzce (TI 1670) | Prilep 23 | Xanthi (TI 1662) |

In an aspect, tobacco plants or seeds or modified tobacco plants or seeds provided herein are of a cigar tobacco variety selected from the group consisting of the tobacco varieties listed in Table 6, and any variety essentially derived from any one of the foregoing varieties.

TABLE 6

| Cigar Tobacco Varieties | | |
|---|---|---|
| Bahai (TI 62) | Castillo Negro, Blanco, Pina (TI 449) | Enshu (TI 1586) |
| Beinhart 1000 | Caujaro (TI 893) | Florida 301 |
| Beinhart 1000 (TI 1562) | Chocoa (TI 289) | Florida 301 (TC 195) |
| Beinhart 1000-1 (TI 1561) | Chocoa (TI 313) | PA Broadleaf (TC 119) |
| Bergerac C | Connecticut 15 (TC 183) | Pennsylvania Broadleaf |
| Bergerac C (TI 1529) | Connecticut Broadleaf | Pennsylvania Broadleaf (TC 119) |
| Big Cuban (TI 1565) | Connecticut Broadleaf (TC 186) | Petite Havana SR1 |
| Castillo Negro, Blanco, Pina (TI 448) | Connecticut Shade (TC 188) | Petite Havana SR1 (TC 105) |
| Castillo Negro, Blanco, Pina (TI 448A) | Criollo, Colorado (TI 1093) | |

In an aspect, tobacco plants or seeds or modified tobacco plants or seeds provided herein are of a tobacco variety selected from the group consisting of the tobacco varieties listed in Table 7, and any variety essentially derived from any one of the foregoing varieties.

TABLE 7

| Other Tobacco Varieties |
|---|
| Chocoa (TI 319) |
| Hoja Parada (TI 1089) |
| Hoja Parado (Galpoa) (TI 1068) |
| Perique (St. James Parrish) |
| Perique (TC 556) |
| Perique (TI 1374) |
| Sylvestris (TI 984) |
| TI 179 |

In an aspect, a modified tobacco plant, seed, or cell described here is from a variety selected from the group consisting of the tobacco varieties listed in Table 1, Table 2, Table 3, Table 4, Table 5, Table 6, and Table 7.

In an aspect, low-alkaloid or low-nicotine tobacco plants, seeds, hybrids, varieties, or lines are essentially derived from or in the genetic background of BU 64, CC 101, CC 200, CC 27, CC 301, CC 400, CC 500, CC 600, CC 700, CC 800, CC 900, Coker 176, Coker 319, Coker 371 Gold, Coker 48, CU 263, DF911, Galpao tobacco, GL 26H, GL 350, GL 600, GL 737, GL 939, GL 973, HB 04P, K 149, K 326, K 346, K 358, K394, K 399, K 730, KDH 959, KT 200, KT204LC, KY 10, KY 14, KY 160, KY 17, KY 171, KY 907, KY907LC, KTY14 x L8 LC, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, or VA359, Maryland 609, HB3307PLC, HB4488PLC, KT206LC, KT209LC, KT210LC, KT212LC, R610LC, PVH2310, NC196, KTD14LC, KTD6LC, KTD8LC, PD7302LC, PD7305LC, PD7309LC, PD7318LC, PD7319LC, PD7312LC, ShireyLC, or any commercial tobacco variety according to standard tobacco breeding techniques known in the art.

All foregoing mentioned specific varieties of dark air-cured, Burley, Maryland, dark fire-cured, or Oriental type are listed only for exemplary purposes. Any additional dark air-cured, Burley, Maryland, dark fire-cured, Oriental varieties are also contemplated in the present application.

Also provided are populations of tobacco plants described. In an aspect, a population of tobacco plants has a planting density of between about 5,000 and about 8,000, between about 5,000 and about 7,600, between about 5,000 and about 7,200, between about 5,000 and about 6,800, between about 5,000 and about 6,400, between about 5,000 and about 6,000, between about 5,000 and about 5,600, between about 5,000 and about 5,200, between about 5,200 and about 8,000, between about 5,600 and about 8,000, between about 6,000 and about 8,000, between about 6,400 and about 8,000, between about 6,800 and about 8,000, between about 7,200 and about 8,000, or between about 7,600 and about 8,000 plants per acre. In another aspect, a population of tobacco plants is in a soil type with low to medium fertility.

Also provided are containers of seeds from tobacco plants described. A container of tobacco seeds of the present disclosure may contain any number, weight, or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 50, 100, 200, 300, 400, 500, 600, 700, 800, 900, 1000, 1500, 2000, 2500, 3000, 3500, 4000 grams or more seeds. Containers of tobacco seeds may be any container available in the art. By way of non-limiting example, a container may be a box, a bag, a packet, a pouch, a tape roll, a tube, or a bottle.

Mutation Types

As used herein, a "genetic modification" refers to a change in the genetic makeup of a plant or plant genome. A genetic modification can be introduced by methods including, but not limited to, mutagenesis, genome editing, genetic transformation, or a combination thereof. A genetic modification includes, for example, a mutation (e.g., a non-natural mutation) in a gene or a transgene targeting a gene (e.g., an arginine decarboxylase (ADC) transgene targets an ADC gene). As used here, "targeting" refers to either directly upregulating or directly downregulating the expression or activity of a gene. As used here, "directly", in the context of a transgene impacting the expression or activity of a gene, refers to the impact being exerted over the gene via a physical contact or chemical interaction between the gene (e.g., a promoter region or a UTR region) or a product encoded therein (e.g., a mRNA molecule or a polypeptide) and a product encoded by the transgene (e.g., a small non-coding RNA molecule or a protein such as a transcription factor or a dominant negative polypeptide variant). In an aspect, a transgene impacts the expression or activity of a target gene without involving a transcription factor (e.g., the transgene does not encode a transcription factor and/or does not suppress the expression or activity of a transcription factor that in turn regulates the target gene).

As used herein, a "mutation" refers to an inheritable genetic modification introduced into a gene to alter the expression or activity of a product encoded by a reference sequence of the gene. A mutation in a certain gene, e.g., an arginine decarboxylase (ADC) is referred to as an ADC mutant. Such a modification can be in any sequence region of a gene, for example, in a promoter, 5' UTR, exon, intron, 3' UTR, or terminator region. In an aspect, a mutation reduces, inhibits, or eliminates the expression or activity of a gene product. In another aspect, a mutation increases, elevates, strengthens, or augments the expression or activity of a gene product. In an aspect, mutations are not natural polymorphisms that exist in a particular tobacco variety or cultivar. It will be appreciated that, when identifying a mutation, the reference sequence should be from the same tobacco variety or background. For example, if a modified tobacco plant comprising a mutation is from the variety TN90, then the corresponding reference sequence should be the endogenous TN90 sequence, not a homologous sequence from a different tobacco variety (e.g., K326). In an aspect, a mutation is a "non-natural" or "non-naturally occurring" mutation. As used herein, a "non-natural" or "non-naturally occurring" mutation refers to a mutation that is not, and does not correspond to, a spontaneous mutation generated without human intervention. Non-limiting examples of human intervention include mutagenesis (e.g., chemical mutagenesis, ionizing radiation mutagenesis) and targeted genetic modifications (e.g., CRISPR-based methods, TALEN-based methods, zinc finger-based methods). Non-natural mutations and non-naturally occurring mutations do not include spontaneous mutations that arise naturally (e.g., via aberrant DNA replication in a germ line of a plant.

In an aspect, the present disclosure provides a tobacco plant, or part thereof, comprising a non-natural mutation in an enhanced NUE locus. In an aspect, a non-natural mutation comprises one or more mutation types selected from the group consisting of a nonsense mutation, a missense mutation, a frameshift mutation, a splice-site mutation, and any combinations thereof. As used herein, a "nonsense mutation" refers to a mutation to a nucleic acid sequence that introduces a premature stop codon to an amino acid sequence by the nucleic acid sequence. As used herein, a "missense mutation" refers to a mutation to a nucleic acid sequence that causes a substitution within the amino acid sequence encoded by the nucleic acid sequence. As used herein, a "frameshift mutation" refers to an insertion or deletion to a nucleic acid sequence that shifts the frame for translating the nucleic acid sequence to an amino acid sequence. A "splice-site mutation" refers to a mutation in a nucleic acid sequence that causes an intron to be retained for protein translation, or, alternatively, for an exon to be excluded from protein translation. Splice-site mutations can cause nonsense, missense, or frameshift mutations.

Mutations in coding regions of genes (e.g., exonic mutations) can result in a truncated protein or polypeptide when a mutated messenger RNA (mRNA) is translated into a protein or polypeptide. In an aspect, this disclosure provides a mutation that results in the truncation of a protein or polypeptide. As used herein, a "truncated" protein or polypeptide comprises at least one fewer amino acid as compared to an endogenous control protein or polypeptide. For example, if endogenous Protein A comprises 100 amino acids, a truncated version of Protein A can comprise between 1 and 99 amino acids.

Without being limited by any scientific theory, one way to cause a protein or polypeptide truncation is by the introduction of a premature stop codon in an mRNA transcript of an endogenous gene. In an aspect, this disclosure provides a mutation that results in a premature stop codon in an mRNA transcript of an endogenous gene. As used herein, a "stop codon" refers to a nucleotide triplet within an mRNA transcript that signals a termination of protein translation. A "premature stop codon" refers to a stop codon positioned earlier (e.g., on the 5'-side) than the normal stop codon position in an endogenous mRNA transcript. Without being limiting, several stop codons are known in the art, including "UAG," "UAA," "UGA," "TAG," "TAA," and "TGA."

In an aspect, a mutation provided herein comprises a null mutation. As used herein, a "null mutation" refers to a mutation that confers a complete loss-of-function for a protein encoded by a gene comprising the mutation, or, alternatively, a mutation that confers a complete loss-of-function for a small RNA encoded by a genomic locus. A null mutation can cause lack of mRNA transcript production, a lack of small RNA transcript production, a lack of protein function, or a combination thereof.

A mutation provided herein can be positioned in any part of an endogenous gene. In an aspect, a mutation provided herein is positioned within an exon of an endogenous gene. In another aspect, a mutation provided herein is positioned within an intron of an endogenous gene. In a further aspect, a mutation provided herein is positioned within a 5'-untranslated region (UTR) of an endogenous gene. In still another aspect, a mutation provided herein is positioned within a 3'-UTR of an endogenous gene. In yet another aspect, a mutation provided herein is positioned within a promoter of an endogenous gene. In yet another aspect, a mutation provided herein is positioned within a terminator of an endogenous gene.

In an aspect, a mutation in an endogenous gene results in a reduced level of expression as compared to the endogenous gene lacking the mutation. In another aspect, a mutation in an endogenous gene results in an increased level of expression as compared to the endogenous gene lacking the mutation.

In an aspect, a non-natural mutation results in a reduced level of expression as compared to expression of the gene in a control tobacco plant. In an aspect, a non-natural mutation results in an increased level of expression as compared to expression of the gene in a control tobacco plant.

In a further aspect, a mutation in an endogenous gene results in a reduced level of activity by a protein or polypeptide encoded by the endogenous gene having the mutation as compared to a protein or polypeptide encoded by the endogenous gene lacking the mutation. In a further aspect, a mutation in an endogenous gene results in an increased level of activity by a protein or polypeptide encoded by the endogenous gene having the mutation as compared to a protein or polypeptide encoded by the endogenous gene lacking the mutation.

In an aspect, a non-natural mutation results in a reduced level of activity by a protein or polypeptide encoded by the polynucleotide comprising the non-natural mutation as compared to a protein or polypeptide encoded by the polynucleotide lacking the non-natural mutation. In another aspect, a non-natural mutation results in an increased level of activity by a protein or polypeptide encoded by the polynucleotide comprising the non-natural mutation as compared to a protein or polypeptide encoded by the polynucleotide lacking the non-natural mutation.

In an aspect, a mutation provided here provides a dominant mutant that activates the expression or elevates the activity of a gene of interest, e.g., one or more enhanced NUE loci.

Levels of gene expression are routinely investigated in the art. As non-limiting examples, gene expression can be measured using quantitative reverse transcriptase PCR (qRT-PCR), RNA sequencing, or Northern blots. In an aspect, gene expression is measured using qRT-PCR. In another aspect, gene expression is measured using a Northern blot. In another aspect, gene expression is measured using RNA sequencing.

Enhanced NUE tobacco plants can be made by any method known in the art including random or targeted mutagenesis approaches. Such mutagenesis methods include, without limitation, treatment of seeds with ethyl methylsulfate (EMS) (Hildering and Verkerk, In, The use of induced mutations in plant breeding. Pergamon press, pp 317-320, 1965) or UV-irradiation, X-rays, and fast neutron irradiation (see, for example, Verkerk, *Neth. J. Agric. Sci.* 19:197-203, 1971; and Poehlman, Breeding Field Crops, Van Nostrand Reinhold, New York (3.sup.rd ed), 1987), transposon tagging (Fedoroff et al., 1984; U.S. Pat. Nos. 4,732,856 and 5,013,658), as well as T-DNA insertion methodologies (Hoekema et al., 1983; U.S. Pat. No. 5,149,645). EMS-induced mutagenesis consists of chemically inducing random point mutations over the length of the genome. Fast neutron mutagenesis consists of exposing seeds to neutron bombardment which causes large deletions through double stranded DNA breakage. Transposon tagging comprises inserting a transposon within an endogenous gene to reduce or eliminate expression of the gene. The types of mutations that may be present in a tobacco gene include, for example, point mutations, deletions, insertions, duplications, and inversions. Such mutations desirably are present in the coding region of a tobacco gene; however, mutations in the promoter region, and intron, or an untranslated region of a tobacco gene may also be desirable.

In addition, a fast and automatable method for screening for chemically induced mutations, TILLING (Targeting Induced Local Lesions In Genomes), using denaturing HPLC or selective endonuclease digestion of selected PCR products is also applicable to the present disclosure. See, McCallum et al. (2000) *Nat. Biotechnol.* 18:455-457. Mutations that impact gene expression or that interfere with the function of genes can be determined using methods that are well known in the art. Insertional mutations in gene exons usually result in null-mutants. Mutations in conserved residues can be particularly effective in inhibiting the function of a protein. In an aspect, tobacco plants comprise a nonsense (e.g., stop codon) mutation in one or more NCG genes described in U.S. Provisional Application Nos. 62/616,959 and 62/625,878, both of which are incorporated by reference in their entirety.

In an aspect, the present disclosure also provides tobacco lines with enhanced NUE while maintaining commercially acceptable leaf quality. In an aspect, such a line can be produced by introducing mutations into one or more enhanced NUE loci via precise genome engineering technologies, for example, Transcription activator-like effector nucleases (TALENs), meganuclease, zinc finger nuclease, and a clustered regularly-interspaced short palindromic repeats (CRISPR)/Cas9 system, a CRISPR/Cpf1 system, a CRISPR/Csm1 system, and a combination thereof (see, for example, U.S. Patent Application publication 2017/0233756). See, e.g., Gaj et al., *Trends in Biotechnology,* 31 (7): 397-405 (2013). The prime editing methodology, which uses a reverse transcriptase fused to an RNA-programmable nickase (e.g., a modified Cas9), described by Anzalone et al. ("Search-and-replace genome editing without double-stranded breaks or donor DNA," *Nature,* 21 Oct. 2019 (doi[dot]org/10.1038/s41586-019-1711-4)), can also be used to introduce mutations into one or more enhanced NUE loci.

The screening and selection of mutagenized tobacco plants can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454), enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

In an aspect, a tobacco plant or plant genome provided herein is mutated or edited by a genome editing technique, e.g., by a nuclease selected from the group consisting of a meganuclease, a zinc-finger nuclease (ZFN), a transcription activator-like effector nuclease (TALEN), a CRISPR/Cas9 nuclease, a CRISPR/Cpf1 nuclease, or a CRISPR/Csm1 nuclease.

As used herein, "editing" or "genome editing" refers to targeted mutagenesis of at least 1, at least 2, at least 3, at least 4, at least 5, at least 6, at least 7, at least 8, at least 9, or at least 10 nucleotides of an endogenous plant genome nucleic acid sequence, or removal or replacement of an endogenous plant genome nucleic acid sequence. In an aspect, an edited nucleic acid sequence provided has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with an endogenous nucleic acid sequence. In an aspect, an edited nucleic acid sequence provided has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with SEQ ID NOs: 1-8 or 25-40, and fragments thereof.

Meganucleases, ZFNs, TALENs, CRISPR/Cas9, CRISPR/Csm1 and CRISPR/Cpf1 induce a double-strand DNA break at a target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of donor nucleic acid sequences by HR. In an aspect, a method provided comprises editing a plant genome with a nuclease provided to mutate at least 1, at least 2, at least 3, at least 4, at least 5, at least 6, at least 7, at least 8, at least 9, at least 10, or more than 10 nucleotides in the plant genome via HR with a donor polynucleotide. In an aspect, a mutation provided is caused by genome editing using a nuclease. In another aspect, a mutation provided is caused by non-homologous end-joining or homologous recombination.

Meganucleases, which are commonly identified in microbes, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). The engineering of meganucleases can be more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

ZFNs are synthetic proteins consisting of an engineered zinc finger DNA-binding domain fused to the cleavage domain of the FokI restriction endonuclease. ZFNs can be designed to cleave almost any long stretch of double-stranded DNA for modification of the zinc finger DNA-binding domain. ZFNs form dimers from monomers composed of a non-specific DNA cleavage domain of FokI endonuclease fused to a zinc finger array engineered to bind a target DNA sequence.

The DNA-binding domain of a ZFN is typically composed of 3-4 zinc-finger arrays. The amino acids at positions-1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

The FokI nuclease domain requires dimerization to cleave DNA and therefore two ZFNs with their C-terminal regions are needed to bind opposite DNA strands of the cleavage site (separated by 5-7 bp). The ZFN monomer can cute the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The *Xanthomonas* pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

A relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122; Cermak et al., *Nucleic Acids Research* (2011). 39: e82; and tale-nt.cac.cornell.edu/about.

A CRISPR/Cas9 system, CRISPR/Csm1, CRISPR/Cpf1 system, or a prime editing system (see Anzalone et al.) are alternatives to the FokI-based methods ZFN and TALEN. The CRISPR systems are based on RNA-guided engineered nucleases that use complementary base pairing to recognize DNA sequences at target sites.

CRISPR/Cas9, CRISPR/Csm1, and a CRISPR/Cpf1 systems are part of the adaptive immune system of bacteria and archaea, protecting them against invading nucleic acids such as viruses by cleaving the foreign DNA in a sequence-dependent manner. The immunity is acquired by the integration of short fragments of the invading DNA known as spacers between two adjacent repeats at the proximal end of a CRISPR locus. The CRISPR arrays, including the spacers, are transcribed during subsequent encounters with invasive DNA and are processed into small interfering CRISPR RNAs (crRNAs) approximately 40 nt in length, which combine with the trans-activating CRISPR RNA (tracrRNA) to activate and guide the Cas9 nuclease. This cleaves homologous double-stranded DNA sequences known as protospacers in the invading DNA. A prerequisite for cleavage is the presence of a conserved protospacer-adjacent motif (PAM) downstream of the target DNA, which usually has the sequence 5-NGG-3 but less frequently NAG. Specificity is provided by the so-called "seed sequence" approximately 12 bases upstream of the PAM, which must match between the RNA and target DNA. Cpf1 and Csm1 act in a similar manner to Cas9, but Cpf1 and Csm1 do not require a tracrRNA.

The prime editing system described by Anzalone et al. uses a reverse transcriptase fused to an RNA-programmable nickase with a prime editing extended guide RNA (pegRNA) to directly copy genetic information from the pegRNA into the targeted genomic locus.

As used herein, "modified" refers to plants, seeds, plant components, plant cells, and plant genomes that have been subjected to mutagenesis, genome editing, genetic transformation, or a combination thereof.

As used herein, "cisgenesis" or "cisgenic" refers to genetic modification of a plant, plant cell, or plant genome in which all components (e.g., promoter, donor nucleic acid, selection gene) have only plant origins (e.g., no non-plant origin components are used). In one aspect, a modified plant, plant cell, or plant genome provided herein is cisgenic. Cisgenic plants, plant cells, and plant genomes provided herein can lead to ready-to-use tobacco lines. In another aspect, a modified tobacco plant provided herein comprises no non-tobacco genetic material or sequences.

As used herein, a "functional fragment" or "functional fragment thereof" refers to a nucleotide or amino acid sequence of any size that retains the function of the full-length sequence to which it refers. In an aspect, a functional fragment can be at least 5, at least 10, at least 25, at least 50, at least 75, at least 100, at least 150, at least 200, at least 250, at least 300, at least 400, at least 500, at least 600, at least 700, at least 800, at least 900, at least 1000, at least 2000, at least 3000, at least 4000, at least 5000, or more than 5000 nucleotides in length. In an aspect, a functional fragment can be at least 5, at least 10, at least 25, at least 50, at least 75, at least 100, at least 150, at least 200, at least 250, at least 300, at least 400, at least 500, at least 600, at least 700, at least 800, at least 900, at least 1000, at least 2000, or more than 2000 amino acids in length. In an aspect, a functional fragment can be between 5 and 5000 nucleotides, between 10 and 4000 nucleotides, between 25 and 3000 nucleotides, between 50 and 2000 nucleotides, between 75 and 1000 nucleotides, between 100 and 900 nucleotides, between 150 and 800 nucleotides, between 200 and 700 nucleotides, between 250 and 600 nucleotides, or between 300 and 500 nucleotides in length. In an aspect, a functional fragment can be between 5 and 2000 amino acids, between 10 and 1000 amino acids, between 25 and 900 amino acids, between 50 and 800 amino acids, between 50 and 800 amino acids, between 75 and 700 amino acids, between 100 and 600 amino acids, between 150 and 500 amino acids, between 200 and 400 amino acids, or between 250 and 300 amino acids in length. In a further aspect, the polynucleotides described herein are envisioned in their entirety and as any functional fragments thereof. In a further aspect, the polypeptides described herein are envisioned in their entirety and as any functional fragments thereof. In a further aspect, the polynucleotides having the sequence of SEQ ID NOs: 9 to 24 and 41 to 56 are envisioned in their entirety and as any functional fragments thereof. In a further aspect, the polypeptides having the sequence of SEQ ID NOs: 1 to 8 and 25 to 40 are envisioned in their entirety and as any functional fragments thereof.

In one aspect, inhibition of the expression of one or more polypeptides provided herein may be obtained by RNA interference (RNAi) by expression of a polynucleotide provided herein. In one aspect, RNAi comprises expressing a non-coding RNA. As used herein, a "non-coding RNA" is selected from the group consisting of a microRNA (miRNA), a small interfering RNA (siRNA), a trans-acting siRNA (ta-siRNA), a transfer RNA (tRNA), a ribosomal RNA (rRNA), an intron, a hairpin RNA (hpRNA), an intron-containing hairpin RNA (ihpRNA), and guide RNA. In one aspect, a single non-coding RNA provided herein inhibits the expression of at least 1, at least 2, at least 3, at least 4, at least 5, at least 6, at least 7, at least 8, at least 9, at least 10, or more than 10 polypeptides. In one aspect, a non-coding RNA provided herein is stably transformed into a plant genome. In another aspect, a non-coding RNA provided herein is transiently transformed into a plant genome.

As used herein, the terms "down-regulate," "suppress," "inhibit," "inhibition," and "inhibiting" are defined as any method known in the art or described herein that decreases the expression or function of a gene product of interest (e.g., an mRNA, a protein, a non-coding RNA). "Inhibition" can be in the context of a comparison between two plants, for example, a modified plant versus a control plant. Alternatively, inhibition of expression or function of a target gene product can be in the context of a comparison between plant cells, organelles, organs, tissues, or plant components within the same plant or between different plants, and includes comparisons between developmental or temporal stages within the same plant or plant component or between plants or plant components. "Inhibition" includes any relative decrement of function or production of a gene product of interest, up to and including complete elimination of function or production of that gene product. The term "inhibition" encompasses any method or composition that down-regulates translation and/or transcription of the target gene product or functional activity of the target gene product.

The term "inhibitory sequence" encompasses any polynucleotide or polypeptide sequence capable of inhibiting the expression or function of a gene in a plant, such as full-length polynucleotide or polypeptide sequences, truncated polynucleotide or polypeptide sequences, fragments of polynucleotide or polypeptide sequences, variants of polynucleotide or polypeptide sequences, sense-oriented nucleotide sequences, antisense-oriented nucleotide sequences, the complement of a sense- or antisense-oriented nucleotide sequence, inverted regions of nucleotide sequences, hairpins of nucleotide sequences, double-stranded nucleotide sequences, single-stranded nucleotide sequences, combinations thereof, and the like. The term "polynucleotide sequence" includes sequences of RNA, DNA, chemically modified nucleic acids, nucleic acid analogs, combinations thereof, and the like.

When the phrase "capable of inhibiting" is used in the context of a polynucleotide inhibitory sequence, it is intended to mean that the inhibitory sequence itself exerts the inhibitory effect; or, where the inhibitory sequence encodes an inhibitory nucleotide molecule (for example, hairpin RNA, miRNA, or double-stranded RNA polynucleotides), or encodes an inhibitory polypeptide (e.g., a polypeptide that inhibits expression or function of the target gene product), following its transcription (for example, in the case of an inhibitory sequence encoding a hairpin RNA, miRNA, or double-stranded RNA polynucleotide) or its transcription and translation (in the case of an inhibitory sequence encoding an inhibitory polypeptide), the transcribed or translated product, respectively, exerts the inhibitory effect on the target gene product (e.g., inhibits expression or function of the target gene product).

An inhibitory sequence provided herein can be a sequence triggering gene silencing via any silencing pathway or mechanism known in the art, including, but not limited to, sense suppression/co-suppression, antisense suppression, double-stranded RNA (dsRNA) interference, hairpin RNA interference and intron-containing hairpin RNA interference, amplicon-mediated interference, ribozymes, small interfering RNA, artificial or synthetic microRNA, and artificial trans-acting siRNA. An inhibitory sequence may range from at least 20 nucleotides, at least 50 nucleotides, at least 70 nucleotides, at least 100 nucleotides, at least 150 nucleotides, at least 200 nucleotides, at least 250 nucleotides, at least 300 nucleotides, at least 350 nucleotides, at least 400 nucleotides, and up to the full-length polynucleotide encoding the proteins of the present disclosure, depending upon the desired outcome. In one aspect, an inhibitory sequence can be a fragment of between 50 and 400 nucleotides, between 70 and 350 nucleotides, between 90 and 325 nucleotides, between 90 and 300 nucleotides, between 90 and 275 nucleotides, between 100 and 400 nucleotides, between 100 and 350 nucleotides, between 100 and 325 nucleotides, between 100 and 300 nucleotides, between 125 and 300 nucleotides, or between 125 and 275 nucleotides in length.

MicroRNAs (miRNAs) are non-protein coding RNAs, generally of between 19 to 25 nucleotides (commonly 20 to 24 nucleotides in plants), that guide cleavage in trans of target transcripts, negatively regulating the expression of genes involved in various regulation and development pathways (Bartel (2004) Cell, 116:281-297). In some cases, miRNAs serve to guide in-phase processing of siRNA primary transcripts (see Allen et al. (2005) Cell, 121:207-221).

Many microRNA genes (MIR genes) have been identified and made publicly available in a database ("miRBase", available online at microrna.sanger.ac.uk/sequences; also see Griffiths-Jones et al. (2003) Nucleic Acids Res., 31:439-441). MIR genes have been reported to occur in intergenic regions, both isolated and in clusters in the genome, but can also be located entirely or partially within introns of other genes (both protein-coding and non-protein-coding). Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (fold-back structures containing a stem-loop arrangement that is processed to the mature miRNA) as well as the usual 5' "cap" and polyadenylated tail of an mRNA.

Maturation of a mature miRNA from its corresponding precursors (pri-miRNAs and pre-miRNAs) differs significantly between animals and plants. For example, in plant cells, microRNA precursor molecules are believed to be largely processed to the mature miRNA entirely in the nucleus, whereas in animal cells, the pri-miRNA transcript is processed in the nucleus by the animal-specific enzyme Drosha, followed by export of the pre-miRNA to the cytoplasm where it is further processed to the mature miRNA. Mature miRNAs in plants are typically 21 nucleotides in length.

Transgenic expression of miRNAs (whether a naturally occurring sequence or an artificial sequence) can be employed to regulate expression of the miRNA's target gene or genes. Inclusion of a miRNA recognition site in a transgenically expressed transcript is also useful in regulating expression of the transcript; see, for example, Parizotto et al. (2004) Genes Dev., 18:2237-2242. Recognition sites of miRNAs have been validated in all regions of an mRNA, including the 5' untranslated region, coding region, and 3' untranslated region, indicating that the position of the miRNA target site relative to the coding sequence may not necessarily affect suppression. Because miRNAs are important regulatory elements in eukaryotes, transgenic suppression of miRNAs is useful for manipulating biological pathways and responses. Finally, promoters of MIR genes can have very specific expression patterns (e.g., cell-specific, tissue-specific, temporally specific, or inducible), and thus are useful in recombinant constructs to induce such specific transcription of a DNA sequence to which they are operably linked. Various utilities of miRNAs, their precursors, their recognition sites, and their promoters are known. Non-limiting examples of these utilities include: (1) the expression of a native miRNA or miRNA precursor sequence to suppress a target gene; (2) the expression of an artificial miRNA or miRNA precursor sequence to suppress a target gene; (3) expression of a transgene with a miRNA recognition site, where the transgene is suppressed when the mature miRNA is expressed; (4) expression of a transgene driven by a miRNA promoter.

Designing an artificial miRNA sequence can be as simple as substituting sequence that is complementary to the intended target for nucleotides in the miRNA stem region of the miRNA precursor. One non-limiting example of a general method for determining nucleotide changes in the native miRNA sequence to produce the engineered miRNA precursor includes the following steps: (a) Selecting a unique target sequence of at least 18 nucleotides specific to the target gene, e.g., by using sequence alignment tools such as BLAST® (see, for example, Altschul et al. (1990) J. Mol. Biol., 215:403-410; Altschul et al. (1997) Nucleic Acids Res., 25:3389-3402), for example, of both tobacco cDNA and genomic DNA databases, to identify target transcript orthologues and any potential matches to unrelated genes, thereby avoiding unintentional silencing of non-target sequences; (b) Analyzing the target gene for undesirable sequences (e.g., matches to sequences from non-target species), and score each potential 19-mer segment for GC content, Reynolds score (see Reynolds et al. (2004) Nature Biotechnol., 22:326-330), and functional asymmetry characterized by a negative difference in free energy (".DELTA..DELTA.G" or "ΔΔG"). Preferably 19-mers are selected that have all or most of the following characteristics: (1) a Reynolds score>4, (2) a GC content between 40% to 60%, (3) a negative ΔΔG, (4) a terminal adenosine, (5) lack of a consecutive run of 4 or more of the same nucleotide; (6) a location near the 3' terminus of the target gene; (7) minimal differences from the miRNA precursor transcript. Positions at every third nucleotide in an siRNA have been reported to be especially important in influencing RNAi efficacy and an algorithm, "siExplorer" is publicly available at rna.chem.t.u-tokyo.ac.jp/siexplorer.htm; (c) Determining the reverse complement of the selected 19-mers to use in making a modified mature miRNA. The additional nucleotide at position 20 is preferably matched to the selected target sequence, and the nucleotide at position 21 is preferably chosen to either be unpaired to prevent spreading of silencing on the target transcript or paired to the target sequence to promote spreading of silencing on the target transcript; and (d) transforming the artificial miRNA into a plant.

In one aspect, an artificial miRNA provided herein reduces or eliminates RNA transcription or protein translation of a target gene.

In one aspect, a miRNA or an artificial miRNA provided herein is under the control of a tissue specific promoter. In a further aspect, a miRNA or an artificial miRNA provided herein is under the control of a tissue-preferred promoter. In a further aspect, a miRNA or an artificial miRNA provided herein is under the control of a constitutive promoter.

Transgenes

The present disclosure also provides compositions and methods for activating or inhibiting the expression or function of one or more enhanced NUE loci, YB1, or YB2 in a plant, particularly plants of the *Nicotiana* genus, including tobacco plants of the various commercial varieties.

As used herein, the terms "inhibit," "inhibition," and "inhibiting" are defined as any method known in the art or described herein that decreases the expression or function of a gene product of interest (e.g., a target gene product). "Inhibition" can be in the context of a comparison between two plants, for example, a genetically altered plant versus a wild-type plant. Alternatively, inhibition of expression or function of a target gene product can be in the context of a comparison between plant cells, organelles, organs, tissues, or plant parts within the same plant or between different plants, and includes comparisons between developmental or temporal stages within the same plant or plant part or between plants or plant parts. "Inhibition" includes any relative decrement of function or production of a gene product of interest, up to and including complete elimination of function or production of that gene product. The term "inhibition" encompasses any method or composition that down-regulates translation and/or transcription of the target gene product or functional activity of the target gene product. In an aspect, the mRNA or protein level of one or more genes in a modified plant is less than 95%, less than 90%, less than 80%, less than 70%, less than 60%, less than 50%, less than 40%, less than 30%, less than 20%, less than 10%, less than 5%, less than 4%, less than 3%, less than 2%, or less than 1% of the mRNA or protein level of the same gene in a plant that is not a mutant or that has not been genetically modified to inhibit the expression of that gene.

The use of the term "polynucleotide" is not intended to limit the present disclosure to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous.

As used herein and when used in reference to a sequence, "heterologous" refers to a sequence that originates from a foreign species, or, if from the same species, is substantially modified from its native form in composition and/or genomic location by deliberate human intervention. The term also is applicable to nucleic acid constructs, also referred to herein as "polynucleotide constructs" or "nucleotide constructs." In this manner, a "heterologous" nucleic acid construct is intended to mean a construct that originates from a foreign species, or, if from the same species, is substantially modified from its native form in composition and/or genomic location by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest. In an aspect, a promoter used is heterologous to the sequence driven by the promoter. In another aspect, a promoter used is heterologous to tobacco. In a further aspect, a promoter used is native to tobacco.

As used herein, "gene expression" refers to the biosynthesis or production of a gene product, including the transcription and/or translation of the gene product.

In an aspect, recombinant DNA constructs or expression cassettes can also comprise a selectable marker gene for the selection of transgenic cells. Selectable marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP).

In an aspect, a tobacco plant provided further comprises increased or reduced expression of activity of genes involved in nicotine biosynthesis or transport. Genes involved in nicotine biosynthesis include, but are not limited to, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), and S-adenosyl-methionine synthetase (SAMS). Nicotine Synthase, which catalyzes the condensation step between a nicotinic acid derivative and methylpyrrolinium cation, has not been elucidated although two candidate genes (A622 and NBB1) have been proposed. See US 2007/0240728 A1 and US 2008/0120737A1. A622 encodes an isoflavone reductase-like protein. In addition, several transporters may be involved in the translocation of nicotine. A transporter gene, named MATE, has been cloned and characterized (Morita et al., *PNAS* 106:2447-52 (2009)).

In an aspect, a tobacco plant provided further comprises an increased or reduced level of mRNA, protein, or both of one or more genes encoding a product selected from the group consisting of PMT, MPO, QPT, ADC, ODC, PRAI, SAMS, BBL, MATE, A622, and NBB1, compared to a control tobacco plant. In another aspect, a tobacco plants provided further comprises a transgene directly suppressing the expression of one or more genes encoding a product selected from the group consisting of PMT, MPO, QPT, ADC, ODC, PRAI, SAMS, BBL, MATE, A622, and NBB1. In another aspect, a tobacco plant provided further comprises a transgene or mutation suppressing the expression or activity of one or more genes encoding a product selected from the group consisting of PMT, MPO, QPT, ADC, ODC, PRAI, SAMS, BBL, MATE, A622, and NBB1. In another aspect, a tobacco plant provided further comprises a transgene overexpressing one or more genes encoding a product selected from the group consisting of PMT, MPO, QPT, ADC, ODC, PRAI, SAMS, BBL, MATE, A622, and NBB1.

Also disclosed are the transformation of tobacco plants with recombinant constructs or expression cassettes described using any suitable transformation methods known in the art. Methods for introducing polynucleotide sequences into tobacco plants are known in the art and include, but are not limited to, stable transformation methods, transient transformation methods, and virus-mediated methods. "Stable transformation" refers to transformation where the nucleotide construct of interest introduced into a plant integrates into the genome of the plant and is capable of being inherited by the progeny thereof. "Transient transformation" is intended to mean that a sequence is introduced into the plant and is only temporally expressed or is only transiently present in the plant.

Suitable methods of introducing polynucleotides into plant cells of the present disclosure include microinjection (Crossway et al. (1986) *Biotechniques* 4:320-334), electroporation (Shillito et al. (1987) *Meth. Enzymol.* 153:313-336; Riggs et al. (1986) *Proc. Natl. Acad. Sci. USA* 83:5602-5606), *Agrobacterium*-mediated transformation (U.S. Pat. Nos. 5,104,310, 5,149,645, 5,177,010, 5,231,019, 5,463,174, 5,464,763, 5,469,976, 4,762,785, 5,004,863, 5,159,135, 5,563,055, and 5,981,840), direct gene transfer (Paszkowski et al. (1984) *EMBO J.* 3:2717-2722), and ballistic particle acceleration (see, for example, U.S. Pat. Nos. 4,945,050, 5,141,131, 5,886,244, 5,879,918, and 5,932,782; Tomes et al. (1995) in *Plant Cell, Tissue, and Organ Culture Fundamental Methods*, ed. Gamborg and Phillips (Springer-Verlag, Berlin); McCabe et al. (1988) *Biotechnology* 6:923-926). Also see Weissinger et al. (1988) *Ann. Rev. Genet.* 22:421-477; Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation).

In another aspect, recombinant constructs or expression cassettes may be introduced into plants by contacting plants with a virus or viral nucleic acids. Generally, such methods involve incorporating an expression cassette of the present disclosure within a viral DNA or RNA molecule. It is recognized that promoters for use in expression cassettes also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221.

Any plant tissue that can be subsequently propagated using clonal methods, whether by organogenesis or embryogenesis, may be transformed with a recombinant construct or an expression cassette. By "organogenesis" in intended the process by which shoots and roots are developed sequentially from meristematic centers. By "embryogenesis" is intended the process by which shoots and roots develop together in a concerted fashion (not sequentially), whether from somatic cells or gametes. Exemplary tissues that are suitable for various transformation protocols described include, but are not limited to, callus tissue, existing meristematic tissue (e.g., apical meristems, axillary buds, and root meristems) and induced meristem tissue (e.g., cotyledon meristem and hypocotyl meristem), hypocotyls, cotyledons, leaf disks, pollen, embryos, and the like.

Embodiments

The following are exemplary embodiments of the subject matter disclosed herein:

Embodiment 1 A tobacco plant, or part thereof, comprising enhanced nitrogen use efficiency (NUE), wherein said tobacco plant comprises at least one functional allele of a Yellow Burley 1 (YB1) locus and further comprises at least one allele associated with enhanced NUE at one or more molecular markers selected from the group consisting of SEQ ID NOs: 57, 58, 59, 60, 61, 62, 63, and 64, wherein said enhanced NUE is relative to a control tobacco plant without said at least one functional allele of a YB1 locus.

Embodiment 2 A tobacco plant, or part thereof, comprising enhanced NUE, wherein said tobacco plant comprises at least one functional allele of a YB1 locus, and further comprises at least one allele associated with enhanced NUE at one or more molecular markers located within 20 cM of a sequence selected from the group consisting of SEQ ID NOs: 57, 58, 59, 60, 61, 62, 63, and 64.

Embodiment 3 A tobacco plant, or part thereof, comprising enhanced NUE, wherein said tobacco plant comprises at least one functional allele of a YB1 locus, and further comprises at least one allele associated with enhanced NUE at one or more molecular markers located within 5,000,000 nucleotides of a sequence selected from the group consisting of SEQ ID NOs: 57, 58, 59, 60, 61, 62, 63, and 64

Embodiment 4 The tobacco plant, or part thereof, of any one of Embodiments 1 to 3, wherein said tobacco plant is a Burley tobacco variety.

Embodiment 5 The tobacco plant, or part thereof, of any one of Embodiments 1 to 3, wherein said plant is homozygous for said functional allele at a YB1 locus.

Embodiment 6 The tobacco plant, or part thereof, of any one of Embodiments 1 to 3, wherein said plant is homozygous for said allele associated with enhanced NUE.

Embodiment 7 The tobacco plant, or part thereof, of any one of Embodiments 1 to 3, wherein said allele associated with enhanced NUE is present in a Maryland tobacco variety.

Embodiment 8 The tobacco plant, or part thereof, of Embodiment 7, wherein said Maryland tobacco variety is selected from the group consisting of Md 10, Md 14D2, Md 21, Md 40, Md 59, Md 64, Md 201, Md 341, Md 402, Md 601, Md 609, Md 872, Md Mammoth, Banket A1, K326, K346, K358, K394, K399, K730, NC196, NC37NF, NC471, NC55, NC92, NC2326, NC95, and NC925.

Embodiment 9 The tobacco plant, or part thereof, of any one of Embodiments 2 to 3, wherein said tobacco plant is a Burley tobacco plant.

Embodiment 10 The tobacco plant, or part thereof, of Embodiment 9, wherein said Burley tobacco plant is selected from the group consisting of TN86, TN86LC, TN90, TN90LC, TN97, and TN97LC.

Embodiment 11 The tobacco plant, or part thereof, of any one of Embodiments 1 to 3, wherein said plant is a double haploid plant.

Embodiment 12 The tobacco plant, or part thereof, of any one of Embodiments 2 to 3, wherein said molecular marker is a single nucleotide polymorphism (SNP) or a mutation.

Embodiment 13 The tobacco plant, or part thereof, of Embodiment 12, wherein said mutation is selected from the group consisting of substitutions, deletions, insertions, duplications, inversions, silent mutations, non-silent mutations, and null mutations.

Embodiment 14 The tobacco plant, or part thereof, of any one of Embodiments 2 to 3, wherein said molecular marker is selected from the group consisting of SEQ ID NOs: 57, 58, 59, 60, 61, 62, 63, and 64.

Embodiment 15 The tobacco plant, or part thereof, of Embodiment 14, wherein said molecular marker comprises a G nucleotide at position 57 of SEQ ID NO:58.

Embodiment 16 The tobacco plant, or part thereof, of Embodiment 14, wherein said molecular marker comprises a C nucleotide at position 117 of SEQ ID NO:58.

Embodiment 17 The tobacco plant, or part thereof, of Embodiment 14, wherein said molecular marker comprises a G nucleotide at position 57 and a C nucleotide at position 117 of SEQ ID NO:58.

Embodiment 18 The tobacco plant, or part thereof, of Embodiment 14, wherein said molecular marker comprises a T nucleotide at position 147 of SEQ ID NO:57.

Embodiment 19 The tobacco plant, or part thereof, of Embodiment 14, wherein said molecular marker comprises a G nucleotide at position 162 of SEQ ID NO:59.

Embodiment 20 The tobacco plant, or part thereof, of Embodiment 14, wherein said molecular marker comprises a C nucleotide at position 36 of SEQ ID NO:60.

Embodiment 21 The tobacco plant, or part thereof, of Embodiment 14, wherein said molecular marker comprises a T nucleotide at position 36 of SEQ ID NO:61.

Embodiment 22 The tobacco plant, or part thereof, of Embodiment 14, wherein said molecular marker comprises a T nucleotide at position 36 of SEQ ID NO:62.

Embodiment 23 The tobacco plant, or part thereof, of Embodiment 14, wherein said molecular marker comprises a G nucleotide at position 36 of SEQ ID NO:63.

Embodiment 24 The tobacco plant, or part thereof, of Embodiment 14, wherein said molecular marker comprises a T nucleotide at position 36 of SEQ ID NO:64.

Embodiment 25 The tobacco plant, or part thereof, of Embodiment 2, wherein said one or more molecular markers are within 10 cM of a sequence selected from the group consisting of SEQ ID NOs: 57-64.

Embodiment 26 The tobacco plant, or part thereof, of Embodiment 2, wherein said one or more molecular markers are within 5 CM of a sequence selected from the group consisting of SEQ ID NOs: 57-64.

Embodiment 27 The tobacco plant, or part thereof, of Embodiment 2, wherein said one or more molecular markers are within 1 cM of a sequence selected from the group consisting of SEQ ID NOs: 57-64.

Embodiment 28 The tobacco plant, or part thereof, of Embodiment 3, wherein said one or more molecular markers are within 2,500,000 nucleotides of a sequence selected from the group consisting of SEQ ID NOs: 57-64.

Embodiment 29 The tobacco plant, or part thereof, of Embodiment 3, wherein said one or more molecular markers are within 1,250,000 nucleotides of a sequence selected from the group consisting of SEQ ID NOs: 57-64.

Embodiment 30 The tobacco plant, or part thereof, of Embodiment 3, wherein said one or more molecular markers are within 500,000 nucleotides of a sequence selected from the group consisting of SEQ ID NOs: 57-64.

Embodiment 31 The tobacco plant, or part thereof, of Embodiment 3, wherein said one or more molecular markers are within 150,000 nucleotides of a sequence selected from the group consisting of SEQ ID NOs: 57-64.

Embodiment 32 The tobacco plant, or part thereof, of any one of Embodiments 1 to 31, wherein said part thereof is a seed.

Embodiment 33 The seed of Embodiment 32, wherein a representative sample of said seed of said tobacco plant of any one of Embodiments 1 to 3 has been deposited under ATCC Accession Nos. PTA-126901 or PTA-126902.

Embodiment 34 The tobacco plant, or part thereof, of any one of Embodiments 1 to 3, wherein said enhanced NUE is an enhanced NUE trait selected from the group consisting of an increased partial factor productivity (PFP), an increased agronomic efficiency (AE), an increased recovery efficiency (RE), an increased physiological efficiency (PE), and an increased internal efficiency (IE), when compared to a tobacco plant lacking said enhanced NUE trait when grown in the same conditions.

Embodiment 35 The tobacco plant, or part thereof, of any one of Embodiments 1 to 3, wherein said tobacco plant comprises a yield that is increased compared to a wild-type Burley plant when grown in the same conditions.

Embodiment 36 The tobacco plant, or part thereof, of any one of Embodiments 1 to 3, wherein said tobacco plant comprises a yield that is not significantly less compared to a wild-type Burley plant when grown in the same conditions.

Embodiment 37 The tobacco plant, or part thereof, of any one of Embodiments 1 to 3, wherein said tobacco plant comprises a yield that is increased by at least 25%, 35%, 45%, 55%, 65%, 75%, 85%, 95%, 105%, or 115% compared to a wild-type Burley plant when grown in the same conditions.

Embodiment 38 The tobacco plant, or part thereof, of any one of Embodiments 35 to 37, wherein said yield comprises a range of between 1500 to 3500 pounds per acre (lbs/ac).

Embodiment 39 The tobacco plant, or part thereof, of any one of Embodiments 35 to 37, wherein said wild-type Burley plant is a TN90 plant.

Embodiment 40 The tobacco plant, or part thereof, of any one of the preceding Embodiments, wherein the tobacco plant is grown at a fertilization rate of 75 to 95 lbs nitrogen per acre.

Embodiment 41 The tobacco plant, or part thereof, of any one of the preceding Embodiments, wherein the tobacco plant comprises, relative to a control plant, one of more, two or more, three or more, or four or more traits selected from the group consisting of (i) exhibiting more consistent leaf grade from top to bottom of the plant when grown at recommended Burley fertilization rates of 180 lbs nitrogen per acre, (ii) increased leaf grade index in leaves from the lower half of the plant, (iii) increased nitrogen use efficiency, (iv) decreased leaf nitrate nitrogen (NO3-N), (v) reduced TSNA levels, and (vi) a lack of chlorophyll-deficient phenotype.

Embodiment 42 Cured tobacco material from the tobacco plant of any one of Embodiments 1 to 41.

Embodiment 43 The cured tobacco material of Embodiment 42, wherein said cured tobacco material is made by a curing process selected from the group consisting of flue curing, air curing, fire curing, and sun curing.

Embodiment 44 A tobacco blend comprising said cured tobacco material of Embodiment 42.

Embodiment 45 The tobacco blend of Embodiment 44, wherein said cured tobacco material constitutes at least 10% of cured tobacco in said tobacco blend by weight.

Embodiment 46 The tobacco blend of Embodiment 44, wherein said cured tobacco material constitutes at least 10% of cured tobacco in said tobacco blend by volume.

Embodiment 47 A tobacco product comprising said cured tobacco material of Embodiment 42.

Embodiment 48 The tobacco product of Embodiment 47, wherein said tobacco product is selected from the group consisting of a cigarette, a cigarillo, a non-ventilated recess filter cigarette, a vented recess filter cigarette, a cigar, snuff, pipe tobacco, cigar tobacco, cigarette tobacco, chewing tobacco, leaf tobacco, shredded tobacco, and cut tobacco.

Embodiment 49 The tobacco product of Embodiment 47, wherein said tobacco product is a smokeless tobacco product or a heated tobacco product.

Embodiment 50 The smokeless tobacco product of Embodiment 49, wherein said smokeless tobacco product is selected from the group consisting of loose leaf chewing tobacco, plug chewing tobacco, moist snuff, and nasal snuff.

Embodiment 51 A reconstituted tobacco comprising the cured tobacco material of Embodiment 42.

Embodiment 52 A method of creating a tobacco plant or a population of tobacco plants comprising enhanced nitrogen use efficiency (NUE), said method comprising:

a. providing a first population of tobacco plants comprising at least one enhanced NUE trait and second population of tobacco plants;
b. genotyping said first population of tobacco plants for the presence of one or more molecular markers within 20 cM of an allele associated with enhanced NUE comprising a sequence selected from the group consisting of SEQ ID NOs: 57, 58, 59, 60, 61, 62, 63, and 64;

c. selecting one or more tobacco plants of a first population of tobacco plants genotyped in step (b) that comprise said one or more molecular markers;

d. genotyping a second population of tobacco plants comprising at least one functional allele of a Yellow Burley 1 (YB1) locus;

e. selecting one or more tobacco plants of a second population of tobacco plants genotyped in step (d) that comprise said at least one functional allele;

f. crossing said at least one plant of said first population selected in step (c) with at least one plant of said second population selected in step (e) to produce progeny tobacco plants or tobacco seeds; and g. obtaining progeny plants or progeny seeds from step (f) that comprise said enhanced NUE trait, said one or more molecular markers associated with enhanced NUE, and at least one functional allele of a YB1 locus.

Embodiment 53 A method of creating a tobacco plant or a population of tobacco plants comprising enhanced nitrogen use efficiency (NUE), said method comprising:

a. providing a first population of tobacco plants comprising enhanced NUE;

b. genotyping said first population of tobacco plants for the presence of one or more molecular markers within 5,000,000 nucleotides of an allele associated with enhanced NUE comprising a sequence selected from the group consisting of SEQ ID NOs: 57, 58, 59, 60, 61, 62, 63, and 64;

c. selecting one or more tobacco plants of a first population of tobacco plants genotyped in step (b) that comprise said one or more molecular markers;

d. genotyping a second population of tobacco plants comprising at least one functional allele of a Yellow Burley 1 (YB1) locus;

e. selecting one or more tobacco plants of a second population of tobacco plants genotyped in step (d) that comprise said at least one functional allele;

f. crossing said at least one plant of said first population selected in step (c) with at least one plant of said second population selected in step (e) to produce progeny tobacco plants or tobacco seeds; and g. obtaining progeny plants or progeny seeds from step (f) that comprise said enhanced NUE trait, said one or more molecular markers associated with enhanced NUE, and said at least one functional allele of a YB1 locus.

Embodiment 54 A method of creating a tobacco plant or a population of tobacco plants comprising enhanced nitrogen use efficiency (NUE), said method comprising:

a. providing a first population of tobacco plants comprising at least one enhanced NUE trait and second population of tobacco plants lacking said at least one enhanced NUE trait;

b. genotyping said first population of tobacco plants for the presence of one or more molecular markers within 20 cM of an allele associated with enhanced NUE at a sequence selected from the group consisting of SEQ ID NOs: 57, 58, 59, 60, 61, 62, 63, and 64;

c. selecting one or more tobacco plants of a first population of tobacco plants genotyped in step (b) that comprise said one or more molecular markers;

d. crossing said at least one plant of said first population selected in step (c) with at least one plant of said second population that does not comprise said at least one enhanced NUE trait; and e. obtaining progeny plants or progeny seeds from step (d) that comprise said enhanced NUE trait, said allele associated with enhanced NUE, and at least one functional allele of a Yellow Burley 1 locus.

Embodiment 55 A method of creating a tobacco plant or a population of tobacco plants comprising enhanced nitrogen use efficiency (NUE), said method comprising:

a. providing a first population of tobacco plants comprising enhanced NUE;

b. genotyping said first population of tobacco plants for the presence of one or more molecular markers within 5,000,000 nucleotides of an allele associated with enhanced NUE comprising a sequence selected from the group consisting of SEQ ID NOs: 57, 58, 59, 60, 61, 62, 63, and 64;

c. selecting one or more tobacco plants of a first population of tobacco plants genotyped in step (b) that comprise said one or more molecular markers;

d. crossing said at least one plant of said first population selected in step (c) with at least one plant of said second population that does not comprise said at least one enhanced NUE trait; and e. obtaining progeny plants or progeny seeds from step (d) that comprise said enhanced NUE trait, said one or more molecular markers associated with enhanced NUE, and at least one functional allele of a Yellow Burley 1 locus.

Embodiment 56 A method of selecting a tobacco plant comprising an enhanced nitrogen use efficiency (NUE) trait comprising:

a. isolating nucleic acids from at least one tobacco plant;

b. assaying said nucleic acids for one or more molecular markers located within 20 cM of one or more alleles associated with enhanced NUE selected from the group consisting of SEQ ID NOs: 57, 58, 59, 60, 61, 62, 63, and 64;

c. assaying said nucleic acids for at least one functional allele of a Yellow Burley 1 (YB1) locus; and d. selecting said tobacco plant comprising said enhanced NUE trait, said one or more alleles associated with enhanced NUE, and said at least one functional allele of a YB1 locus.

Embodiment 57 A method of selecting a tobacco plant comprising an enhanced nitrogen use efficiency (NUE) trait comprising:

a. isolating nucleic acids from at least one tobacco plant;

b. assaying said nucleic acids for one or more molecular markers located within 5,000,000 nucleotides of one or more molecular markers selected from the group consisting of SEQ ID NOs: 57 to 64;

c. assaying said nucleic acids for at least one functional allele of a Yellow Burley 1 (YB1) locus; and d. selecting said tobacco plant comprising said enhanced NUE trait, said one or more alleles associated with enhanced NUE selected from the group consisting of SEQ ID NOs: 57, 58, 59, 60, 61, 62, 63, and 64, and said at least one functional allele of a YB1 locus.

Embodiment 58 The method of any one of Embodiments 56 to 57, wherein said method further comprises:

e. crossing said tobacco plant selected in step (d) with a second tobacco plant that does not comprise an enhanced NUE trait; and f. obtaining progeny plants or progeny seeds from the cross of step (e).

Embodiment 59 The method of any one of Embodiments 52 to 57, wherein said molecular marker is selected from the group consisting of SEQ ID NOs: 57, 58, 59, 60, 61, 62, 63, and 64.

Embodiment 60 The method of Embodiment 59, wherein said molecular marker comprises a G nucleotide at position 57 of SEQ ID NO:58.

Embodiment 61 The method of Embodiment 59, wherein said molecular marker comprises a C nucleotide at position 117 of SEQ ID NO:58.

Embodiment 62 The method of Embodiment 59, wherein said molecular marker comprises a G nucleotide at position 57 and a C nucleotide at position 117 of SEQ ID NO:58.

Embodiment 63 The method of Embodiment 59, wherein said molecular marker comprises a T nucleotide at position 147 of SEQ ID NO:57.

Embodiment 64 The method of Embodiment 59, wherein said molecular marker comprises a G nucleotide at position 162 of SEQ ID NO:59.

Embodiment 65 The method of Embodiment 59, wherein said molecular marker comprises a C nucleotide at position 36 of SEQ ID NO:60.

Embodiment 66 The method of Embodiment 59, wherein said molecular marker comprises a T nucleotide at position 36 of SEQ ID NO:61.

Embodiment 67 The method of Embodiment 59, wherein said molecular marker comprises a T nucleotide at position 36 of SEQ ID NO:62.

Embodiment 68 The method of Embodiment 59, wherein said molecular marker comprises a G nucleotide at position 36 of SEQ ID NO:63.

Embodiment 69 The method of Embodiment 59, wherein said molecular marker comprises a T nucleotide at position 36 of SEQ ID NO:64.

Embodiment 70 The method of any one of Embodiments 52 to 58, wherein a double haploid plant or double haploid seed is produced from said progeny seed.

Embodiment 71 The method of any one of Embodiments 52 to 53, wherein said second population of plants is homozygous for a functional allele at a YB1 locus.

Embodiment 72 The method of any one of Embodiments 52 to 57, wherein said tobacco plant is heterozygous for said allele associated with enhanced NUE.

Embodiment 73 The method of any one of Embodiments 52 to 57, wherein said tobacco plant is homozygous for said allele associated with enhanced NUE.

Embodiment 74 The tobacco plant of any one of Embodiments 52 to 57, wherein said molecular marker is a single nucleotide polymorphism (SNP) or a mutation.

Embodiment 75 The mutation of Embodiment 74, wherein said mutation is selected from the group consisting of substitutions, deletions, insertions, duplications, inversions, silent mutations, non-silent mutations, and null mutations.

Embodiment 76 The method of any one of Embodiments 53, 55, and 57, wherein said one or more molecular markers are within 2,500,000 nucleotides of a sequence selected from the group consisting of SEQ ID NOs: 57-64.

Embodiment 77 The method of any one of Embodiments 53, 55, and 57, wherein said one or more molecular markers are within 1,250,000 nucleotides of a sequence selected from the group consisting of SEQ ID NOs: 57-64.

Embodiment 78 The method of any one of Embodiments 53, 55, and 57, wherein said one or more molecular markers are within 500,000 nucleotides of a sequence selected from the group consisting of SEQ ID NOs: 57-64.

Embodiment 79 The method of any one of Embodiments 53, 55, and 57, wherein said one or more molecular markers are within 150,000 nucleotides of a sequence selected from the group consisting of SEQ ID NOs: 57-64.

Embodiment 80 The method of any one of Embodiments 52, 54, and 56, wherein said one or more molecular markers are within 10 cM of a sequence selected from the group consisting of SEQ ID NOs: 57-64.

Embodiment 81 The method of any one of Embodiments 52, 54, and 56, wherein said one or more molecular markers are within 5 CM of a sequence selected from the group consisting of SEQ ID NOs: 57-64.

Embodiment 82 The method of any one of Embodiments 52, 54, and 56, wherein said one or more molecular markers are within 1 cM of a sequence selected from the group consisting of SEQ ID NOs: 57-64.

Embodiment 83 The method of any one of Embodiments 52 to 58, wherein said enhanced NUE trait is selected from the group consisting of an increased partial factor productivity (PFP), an increased agronomic efficiency (AE), an increased recovery efficiency (RE), an increased physiological efficiency (PE), and an increased internal efficiency (IE), when compared to a tobacco plant lacking said enhanced NUE trait when grown in the same conditions.

Embodiment 84 The method of any one of Embodiments 52 to 57, wherein said enhanced NUE comprises a yield that is increased compared to a wild-type Burley plant when grown in the same conditions.

Embodiment 85 The method of any one of Embodiments 52 to 57, wherein said enhanced NUE comprises a yield that is not significantly less compared to a wild-type Burley plant when grown in the same conditions.

Embodiment 86 The method of any one of Embodiments 52 to 57, wherein said enhanced NUE comprises a yield that is increased by at least 25% compared to a wild-type Burley plant when grown in the same conditions.

Embodiment 87 The method of any one of Embodiments 84 to 86, wherein said yield comprises a range of between 1500 to 3500 pounds per acre (lbs/ac).

Embodiment 88 The method of any one of Embodiments 84 to 86 wherein said wild-type Burley plant is a TN90 plant.

Embodiment 89 The method of any one of Embodiments 52 to 55, wherein said first population of tobacco plants is of a Maryland tobacco variety.

Embodiment 90 The method of Embodiment 89, wherein said Maryland tobacco variety is selected from the group consisting of Md 10, Md 14D2, Md 21, Md 40, Md 59, Md 64, Md 201, Md 341, Md 402, Md 601, Md 609, Md 872, Md Mammoth, Banket A1, K326, K346, K358, K394, K399, K730, NC196, NC37NF, NC471, NC55, NC92, NC2326, NC95, and NC925.

Embodiment 91 The method of any one of Embodiments 54, 55, and 58, wherein said second population of tobacco plants is of a Burley tobacco variety.

Embodiment 92 The method of Embodiment 91, wherein said Burley tobacco variety is selected from the group consisting of TN86, TN86LC, TN90, TN90LC, TN97, and TN97LC.

Embodiment 93 The method of any one of the preceding Embodiments, wherein the created or selected tobacco plant or population is grown at a fertilization rate of 75 to 95 lbs nitrogen per acre.

Embodiment 94 The method of any one of the preceding Embodiments, wherein the created or selected tobacco plant or population comprises, relative to a control plant or population, one of more, two or more, three or more, or four or more traits selected from the group consisting of (i) exhibiting more consistent leaf grade from top to bottom of the plant when grown at recommended Burley fertilization rates of 180 lbs nitrogen per acre, (ii) increased leaf grade index in leaves from the lower half of the plant, (iii) increased nitrogen use efficiency, (iv) decreased leaf nitrate nitrogen (NO3-N), (v) reduced TSNA levels, and (vi) a lack of chlorophyll-deficient phenotype.

Embodiment 95 The method of any one of Embodiments 52 to 54, wherein said first population of tobacco plants is grown from seed, a representative sample of said seed of said first population of tobacco plant having been deposited under ATCC Accession Nos. PTA-126901 or PTA-126902.

EXAMPLES

Example 1. Field Production Practices

Field grown tobacco plants are generated using standard field production practices. Each test plot comprises up to 40 rows of transplanted seedlings. Seedlings are germinated in a greenhouse before transplantation. For testing NUE traits, a test plot receives a nitrogen rate of 60 pounds of nitrogen per acre. Plants are topped using standard procedures when 50% of the plants in a test plot reach the elongated button stage. Pesticide application follows standard protocols. Leaves are harvested at maturity and sorted into 3 sticks per plot with 5 plants per stick for curing. After curing, plants are stripped into 4 equal leaf positions from top to bottom and the resulting yields are calculated by the aggregate weight of each leaf position. Each individual leaf position is graded by a USDA grader which includes a quality rating as well as a predicted stalk position related to the characteristics of the leaf that would normally be present at that stalk position. Analytical analysis of alkaloids, TSNA and NO3 are conducted using routine methods known in the art.

For evaluation of DH lines, sixty three double haploid populations and two controls (Maryland 609 and TN90) were grown using 60 lbs of nitrogen fertilizer per acre and grown with standard tobacco management conditions. The field was set with 4 replications for each line.

Example 2. Identification of Metabolites Associated with Enhanced Nitrogen Use Efficiency Maryland tobacco varieties require approximately 25% less nitrogen fertilizer input as compared to Burley tobacco varieties. In order to identify metabolites associated with high nitrogen efficiency (Maryland) and low nitrogen efficiency (Burley) tobacco varieties, differences in metabolite levels were examined in the Maryland tobacco variety MD609 and the Burley tobacco variety TN90.

MD609 and TN90 seedlings were germinated from seed and grown without the addition of nitrogen for six weeks. After six weeks, the seedlings from each variety were split into two groups: Group A comprised plants that were provided with 100 parts per million nitrogen or the normal greenhouse fertilization; and Group B comprised plants that were provided with 25 ppm or 25% of the normal greenhouse fertilization rate. Metabolites were extracted using methanol from root leaf tissue at 10 and 14 weeks after seeding.

The isolated metabolites were analyzed using three different LC/MS approaches (UHPLC-MS/MS (+ESI), UHPLC-MS/MS (−ESI), and GC-MS (+EI)) to separate and identify individual metabolites. Metabolites were identified by comparing the obtained mass spectra to standard spectral databases (Metabolon Inc, Morrisville, NC). Peaks were quantified using area-under-the-curve. Each compound was scaled by registering the medians to equal one (1.00) and normalizing each data point proportionately (termed the "block correction"). The molecular mass of unknown metabolites is provided in Table 8. Discriminant metabolites are shown below in Tables 9 to 12, along with scaled measured values for each sample. Discriminant metabolites were determined by Student's t-test comparisons between TN90 and MD609 considering all time points. Metabolites with a p-value less than 0.01 were included in the analysis.

TABLE 8

Molecular mass in kilodaltons for unknown metabolite compounds

| Metabolite | Mass |
|---|---|
| X - 21756 | 247.0918 |
| X - 21796 | 138.0566 |
| X - 23319 | 299.0771 |
| X - 23330 | 251.1136 |
| X - 23366 | 189.1023 |
| X - 23389 | 157.0762 |
| X - 23453 | 161.0818 |
| X - 23454 | 319.0933 |
| X - 23576 | 267.1237 |
| X - 23580 | 311.1136 |
| X - 23852 | 374.144 |
| X - 23916 | 395.0291 |
| X - 23937 | 161.0819 |

TABLE 9

Metabolites negatively correlated with enhanced nitrogen efficiency identified in root tissue when comparing MD609 and TN90 tobacco lines at week 10 and week 14 after seeding

| | TN90 | | | | MD609 | | | |
|---|---|---|---|---|---|---|---|---|
| | 25% Nitrogen | | 100% Nitrogen | | 25% Nitrogen | | 100% Nitrogen | |
| Metabolite | W10 | W14 | W10 | W14 | W10 | W14 | W10 | W14 |
| X-23576 | 4.6 | 3.6 | 1.2 | 8.4 | 2.5 | 1.2 | 1 | 2.3 |
| N-acetylmuramate | 0.3 | 0.4 | 2.5 | 4 | 0.1 | 0.2 | 0.3 | 0.6 |
| X-23319 | 0.5 | 0.5 | 3.2 | 2.9 | 0.3 | 0.3 | 0.4 | 1.2 |
| X-23852 | 0.8 | 1.0 | 2.2 | 3.1 | 0.1 | 1.0 | 0.9 | 0.4 |
| X-23330 | 0.7 | 0.5 | 3.5 | 2.4 | 0.4 | 0.6 | 0.9 | 1.0 |
| Alpha-ketoglutarate | 2.1 | 1.5 | 1.5 | 0.9 | 0.8 | 0.6 | 0.8 | 0.5 |
| X-21756 | 0.6 | 0.4 | 1.9 | 1.3 | 0.2 | 0.3 | 1.0 | 0.5 |
| 4-hydroxy-2-oxoglutaric acid | 0.9 | 0.4 | 1.1 | 1.2 | 0.5 | 0.4 | 0.5 | 0.6 |
| X-23937 | 0.2 | 0.2 | 0.7 | 1.1 | 0.1 | 0.2 | 0.1 | 0.4 |
| X-23916 | 0.6 | 0.6 | 0.5 | 1.0 | 0.3 | 0.3 | 0.2 | 0.3 |
| 1-methyladenine | 1.2 | 0.9 | 1.2 | 1.1 | 1.0 | 0.8 | 0.8 | 0.7 |

TABLE 10

Metabolites positively correlated with enhanced nitrogen efficiency identified in root tissue when comparing MD609 and TN90 tobacco lines

| | TN90 | | | | MD609 | | | |
|---|---|---|---|---|---|---|---|---|
| | 25% Nitrogen | | 100% Nitrogen | | 25% Nitrogen | | 100% Nitrogen | |
| Metabolite | W10 | W14 | W10 | W14 | W10 | W14 | W10 | W14 |
| 4-guanidino-butanoate | 0.7 | 0.7 | 0.7 | 0.6 | 1.0 | 1.1 | 0.8 | 0.7 |
| Syringaldehyde | 0.5 | 0.6 | 0.4 | 0.3 | 0.9 | 1.0 | 0.6 | 0.4 |
| Thiamin | 0.2 | 0.1 | 0.7 | 0.7 | 0.7 | 1.1 | 0.7 | 1.1 |
| p-hydroxy benzaldehyde | 0.4 | 1.0 | 0.8 | 0.9 | 0.6 | 1.6 | 1.4 | 1.5 |

TABLE 11

Metabolites negatively correlated with enhanced nitrogen efficiency identified in leaf tissue when comparing MD609 and TN90 tobacco lines

| | TN90 | | | | MD609 | | | |
|---|---|---|---|---|---|---|---|---|
| | 25% Nitrogen | | 100% Nitrogen | | 25% Nitrogen | | 100% Nitrogen | |
| Metabolite | W10 | W14 | W10 | W14 | W10 | W14 | W10 | W14 |
| X-23453 | 1.2 | 4.9 | 2.2 | 3.9 | 0.9 | 1.3 | 1.3 | 1.9 |
| X-21756 | 1.6 | 0.8 | 2.3 | 2.5 | 0.8 | 0.3 | 1.0 | 0.8 |
| X-11429 | 1.3 | 0.6 | 2.7 | 2.4 | 0.7 | 0.2 | 1.0 | 1.0 |
| X-21796 | 0.7 | 2.0 | 0.7 | 2.0 | 0.2 | 0.6 | 0.2 | 0.5 |
| N'-methyl-nicotinamide | 0.7 | 1.0 | 1.9 | 1.1 | 0.9 | 0.1 | 0.1 | 0.2 |
| Cotinine | 0.5 | 1.4 | 0.3 | 1.7 | 0.4 | 0.4 | 0.1 | 0.3 |
| X-23389 | 0.9 | 1.2 | 0.4 | 1.2 | 0.5 | 0.3 | 0.1 | 0.2 |
| N-acetylarginine | 1.0 | 0.7 | 0.8 | 1.9 | 0.6 | 0.3 | 0.7 | 0.8 |
| X-23366 | 0.6 | 0.9 | 0.1 | 0.8 | 0.3 | 0.2 | 0.1 | 0.1 |
| N-acetylphenyl-alanine | 1.0 | 1.0 | 1.2 | 1.0 | 0.9 | 0.4 | 0.7 | 0.5 |
| Naringenin | 0.4 | 0.8 | 0.3 | 0.8 | 0.2 | 0.2 | 0.1 | 0.4 |

TABLE 12

Metabolites positively correlated with enhanced nitrogen efficiency identified in leaf tissue when comparing MD609 and TN90 tobacco lines

| | TN90 | | | | MD609 | | | |
|---|---|---|---|---|---|---|---|---|
| | 25% Nitrogen | | 100% Nitrogen | | 25% Nitrogen | | 100% Nitrogen | |
| Metabolite | W10 | W14 | W10 | W14 | W10 | W14 | W10 | W14 |
| 4-guanidino-butanoate | 0.6 | 0.8 | 1.0 | 1.1 | 1.3 | 0.9 | 1.6 | 1.6 |
| X-23454 | 0.1 | 0.1 | 0.5 | 0.1 | 0.8 | 0.1 | 1.5 | 1.5 |
| X-23580 | 1.1 | 3.6 | 1.8 | 1.5 | 4.9 | 6.0 | 3.5 | 5.3 |
| X-23852 | 0.9 | 7.7 | 3.6 | 2.1 | 9.8 | 13.2 | 7.6 | 11.0 |

Example 3. Identification of Gene Expression Associated with Enhanced Nitrogen Use Efficiency The same plants used in Example 2 are also subjected to RNA extraction to be used for RNAseq. RNA is extracted from leaf and root tissue at 10 weeks and 14 weeks after seeding and used for Illumina sequencing. The RNAseq data were analyzed according to methods standard in the art. Candidate genes are subsequently verified.

Seventeen genes (Tables 13 and 14) were found to negatively correlate with the enhanced nitrogen use efficiency phenotype of MD609, and seven genes (Tables 15 and 16) were found to positively correlate with the enhanced nitrogen use efficiency phenotype of MD609. The negatively correlated genes are candidates for down-regulation in Burley tobacco varieties (via mutagenesis, cisgenic transformation, or transgenic transformation), and the positively correlated genes are candidates for over-expression in Burley tobacco varieties to improve nitrogen use efficiency. Single nucleotide polymorphism (SNP) markers associated are provided for tracking each candidate gene (Tables 13 to 17). The polymorphism associated with the MD609 alleles, and therefore favorable for enhanced NUE is provided (Table 17).

Figure 2:
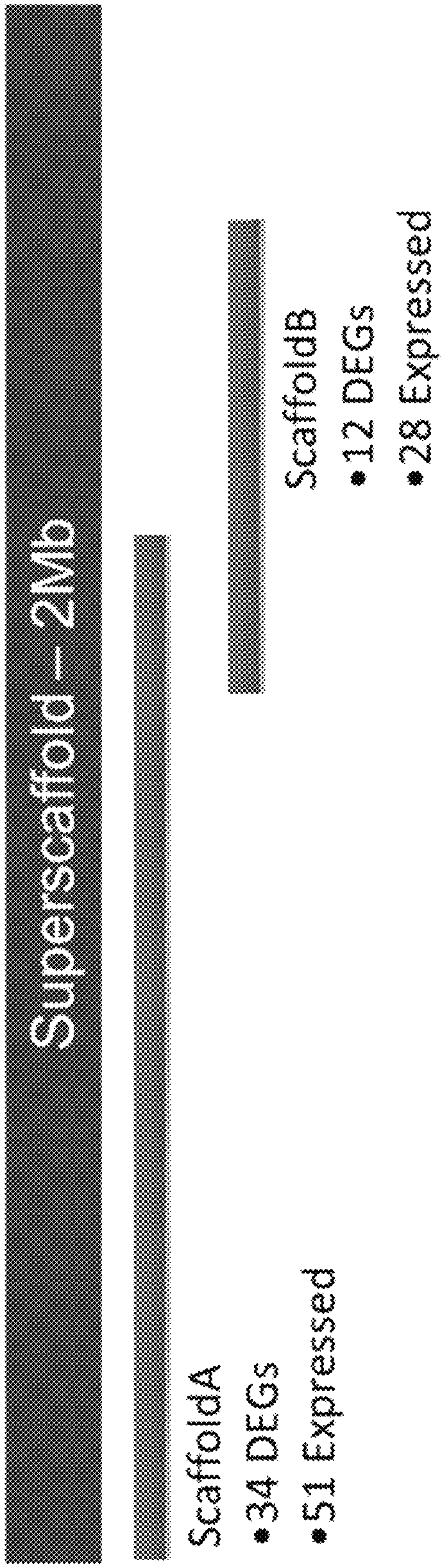
FIG. 2 depicts a 2 megabase region of tobacco chromosome 11 that is covered by superscaffold 1. Superscaffold1 is a contig of scaffolds A and B. Of the 79 expressed genes located in this region, 56 genes are differentially expressed.

Identification of the genomic location for each of the correlated genes identifies four clusters of genes associated with enhanced NUE in the tobacco genome (FIG. 1). Seven genes are similarly located on chromosome 1, four genes are similarly located on chromosome 11, three genes are similarly located on chromosome 14, and five genes are similarly located on chromosome 20 (FIG. 1). These four locations are also hotspots for genes differentially expressed between low and normal nitrogen conditions (FIG. 1). SNP markers are created to identify MD609 specific and therefore enhanced NUE polymorphisms for each of these locations (Tables 13 to 17). The area on chromosome 11 is further characterized and contains 79 total expressed genes and 46 of these genes are differentially expressed genes under low nitrogen conditions (FIG. 2).

TABLE 13

Genes identified as negatively correlated with enhanced nitrogen use efficiency in root tissue.

| Gene Identifier | SEQ ID NO | Gene Description | SNP marker SEQ ID NO: |
|---|---|---|---|
| G38453 | 25 | Putative vacuolar proton ATPase subunit E | 57 |
| G64360 | 26 | Clathrin interactor epsin 1-like | 63 |
| G26157 | 27 | Serine/threonine-protein kinase PBS1 | 59 |
| G54692 | 28 | ATPase family AAA domain-containing protein 1-a-like | 57 |
| G32111 | 29 | Uncharacterized protein | 57 |
| G49619 | 30 | Coatomer subunit gamma | 61 |
| G19982 | 31 | Uncharacterized protein | 60 |
| G39737 | 32 | Uncharacterized protein | 58 |
| G28894 | 33 | Putative quinolinate phosphoribosyltransferase | 60 |
| G30288 | 38 | Probable acyl-activating enzyme chloroplastic-like | 59 |
| G39762 | 39 | Alpha-1-fucosidase | 58 |
| G39442 | 40 | Uncharacterized protein | 57 |

TABLE 14

Genes identified as negatively correlated with enhanced nitrogen use efficiency in leaf tissue.

| Gene Identifier | SEQ ID NO | Gene Description | SNP Marker SEQ ID NO: |
|---|---|---|---|
| G41803 | 34 | ABC transporter F-family member 3-like | 57 |
| G46356 | 35 | Uncharacterized protein | 57 |
| G56420 | 36 | WD repeat-containing protein 26-like | 58 |
| G59801 | 37 | Protein phosphatase 2A | 60 |
| G30288 | 38 | Probable acyl-activating enzyme chloroplastic-like | 59 |

TABLE 14-continued

| Genes identified as negatively correlated with enhanced nitrogen use efficiency in leaf tissue. | | | |
|---|---|---|---|
| Gene Identifier | SEQ ID NO | Gene Description | SNP Marker SEQ ID NO: |
| G39762 | 39 | Alpha-1-fucosidase | 58 |
| G39442 | 40 | Uncharacterized protein | 57 |

TABLE 15

| Genes identified as positively correlated with enhanced nitrogen use efficiency in root tissue. | | | |
|---|---|---|---|
| Gene Identifier | SEQ ID NO | Gene Description | SNP Marker SEQ ID NO: |
| G59318 | 1 | PR-10 type pathogenesis-related protein | 57 |
| G20580 | 2 | Uncharacterized amino acid permease | 60 |
| G30999 | 3 | TBZ17 | 62 |
| G29260 | 4 | BTB/POZ domain-containing protein (AT5G48800-like) | 64 |
| G41446 | 8 | 3-isopropylmalate dehydratase small subunit | 57 |

TABLE 16

| Genes identified as positively correlated with enhanced nitrogen use efficiency in leaf tissue. | | | |
|---|---|---|---|
| Gene Identifier | SEQ ID NO | Gene Description | SNP Marker SEQ ID NO: |
| G41343 | 5 | Glucose-6-phosphate 1-epimerase-like | 57 |
| G53261 | 6 | Probable nitrite transporter (AT1G68570-like) | 60 |
| G42290 | 7 | Phospho-2-dehydro-3-deoxyheptonate aldolase | 58 |
| G41446 | 8 | 3-isopropylmalate dehydratase small subunit | 61 |

TABLE 17

| SNP markers comprising polymorphisms associated with enhanced NUE. | | |
|---|---|---|
| SNP marker SEQ ID NO | Position of polymorphism | Allele associated with NUE |
| 57 | 147 | T |
| 58 | 57 | G |
| | 117 | C |
| 59 | 162 | G |
| 60 | 36 | C |
| 61 | 36 | T |
| 62 | 36 | T |
| 63 | 36 | G |
| 64 | 36 | T |

Example 4. Identifying Tobacco Leaf- and Root-Preferred Promoters

RNA samples from 4 week old TN90 tobacco plants are obtained from 10 tissue types (axillary buds before topping; axillary buds 2 hours after topping; axillary buds 6 hours after topping; axillary buds 24 hours after topping; axillary buds 72 hours after topping; roots before topping; roots 24 hours after topping; roots 72 hours after topping; young leaf at the time of topping; and shoot apical meristem). The resulting RNA samples (three independently collected samples for each tissue type) are used as starting material for Illumina 1×100 bp sequencing.

Illumina reads are mapped and used to identify a list of candidate genes exhibiting high root or leaf expression. Tables 18 and 19 provide RPKM expression values for genes identified as having leaf-preferred or root-preferred expression. These genes are candidates for possessing leaf-preferred promoters or root-preferred promoters, respectively.

TABLE 18

| Genes with leaf-preferred expression | | | | | | | | | | | | |
|---|---|---|---|---|---|---|---|---|---|---|---|---|
| | | SEQ | Axillary Bud | | | | | Root | | | | |
| Promoter | Gene Description | ID NO: | 0 hr. | 2 hr. | 6 hr. | 24 hr. | 72 hr. | 0 hr. | 24 hr. | 72 hr. | SAM | Leaf |
| P16098 | Carbonic anhydrase | 17 | 4.88 | 5.94 | 7.49 | 4.67 | 16.12 | 0.45 | 0.41 | 0.52 | 2.89 | 1002.14 |
| P42207 | CP12 | 18 | 0.41 | 0.99 | 1.24 | 0.52 | 1.83 | 0.05 | 0.02 | 0.07 | 0.13 | 34.34 |
| P47582 | Chloroplast sedoheptulose-1,7-bisphosphatase | 19 | 0.32 | 0.68 | 0.91 | 0.68 | 1.96 | 0.03 | 0.03 | 0.06 | 0.06 | 96.69 |

TABLE 19

Genes with root-preferred expression

| Promoter | Gene Description | SEQ ID NO: | Axillary Bud 0 hr. | Axillary Bud 2 hr. | Axillary Bud 6 hr. | Axillary Bud 24 hr. | Axillary Bud 72 hr. | Root 0 hr. | Root 24 hr. | Root 72 hr. | SAM | Leaf |
|---|---|---|---|---|---|---|---|---|---|---|---|---|
| P2862 | Putative PLA2 | 20 | 0.65 | 0.78 | 0.58 | 0.38 | 0.38 | 336.69 | 391.95 | 511.86 | 0.36 | 0.43 |
| P57190 | Uncharacterized protein | 21 | 0.38 | 0.45 | 0.29 | 0.39 | 0.35 | 198.00 | 416.84 | 384.52 | 0.47 | 0.26 |
| P49330 | Glutathione S-transferase parC | 22 | 0.35 | 0.35 | 0.27 | 0.75 | 0.38 | 196.29 | 269.39 | 417.71 | 0.23 | 0.22 |
| P3788 | PR-10 type pathogenesis-related protein | 23 | 0.29 | 0.36 | 0.45 | 0.15 | 0.23 | 192.16 | 88.51 | 193.35 | 0.26 | 0.16 |
| P77628 | Cytochrome P450 | 24 | 0.39 | 0.71 | 0.53 | 0.39 | 0.44 | 144.99 | 333.54 | 386.32 | 0.52 | 0.50 |

Example 5. Development of Modified Plants

An expression vector, p45-2-7 (SEQ ID NO: 65), is used as a backbone to generate multiple transformation vectors (See Examples X-Y). p45-2-7 contains a CsVMV promoter, a NOS terminator, and a cassette comprising a kanamycin selection marker (NPT II) operably linked to an Actin2 promoter and a NOS terminator. Nucleic acid vectors comprising transgenes of interest are introduced into tobacco leaf discs via *Agrobacterium* transformation. See, for example, Mayo et al., 2006, *Nat Protoc.* 1:1105-11 and Horsch et al., 1985, *Science* 227:1229-1231.

TN90 tobacco plants are grown in Magenta™ GA-7 boxes and leaf discs are cut and placed into Petri plates. *Agrobacterium tumefaciens* cells comprising a transformation vector are collected by centrifuging a 20 mL cell suspension in a 50 mL centrifuge tube at 3500 RPM for 10 minutes. The supernatant is removed and the *Agrobacterium tumefaciens* cell pellet is resuspended in 40 mL liquid re-suspension medium. Tobacco leaves, avoiding the midrib, are cut into eight 0.6 cm discs with a #15 razor blade and placed upside down in a Petri plate. A thin layer of Murashige & Skoog with B5 vitamins liquid re-suspension medium is added to the Petri plate and the leaf discs are poked uniformly with a fine point needle. Approximately 25 mL of the *Agrobacterium tumefaciens* suspension is added to the Petri plate and the leaf discs are incubated in the suspension for 10 minutes.

Leaf discs are transferred to co-cultivation Petri plates (1/2 MS medium) and discs are placed upside down in contact with filter paper overlaid on the co-cultivation TOM medium (MS medium with 20 g/L sucrose; 1 mg/L indole-3-acetic acid; and 2.5 mg/L 6-benzyl aminopurine (BAP)). The Petri plate is sealed with parafilm prior to incubation in dim light (60-80 mE/ms) with 18 hours on, 6 hours off photoperiods at 24 degrees Celsius for three days. After incubation, leaf discs are transferred to regeneration/selection TOM K medium Petri plates (TOM medium plus 300 mg/L kanamycin). Leaf discs are sub-cultured bi-weekly to fresh TOM K medium in dim light with 18 hours on, 6 hours off photoperiods at 24 degrees Celsius until shoots become excisable. Shoots from leaves are removed with forceps and inserted in MS basal medium with 100 mg/L kanamycin. Shoots on MS basal medium with 100 mg/L kanamycin are incubated at 24 degrees Celsius with 18 hours on, 6 hours off photoperiods with high intensity lighting (6080 mE/ms) to induce rooting.

When plantlets containing both shoots and roots grow large enough (e.g., reach approximately half the height of a Magenta™ GA-7 box), they are transferred to soil. Established seedlings are transferred to a greenhouse for further analysis and to set seed. Evaluation of enhanced nitrogen use efficiency phenotypes is conducted by growing modified plants ($T_0$, $T_1$, $T_2$, or later generations) and control plants. Control plants are either NLM plants that have not been transformed or NLM plants that have been transformed with an empty p45-2-7 vector.

Phenotypic screening for enhanced nitrogen use efficiency is conducted in a greenhouse using zero parts per million (ppm) nitrogen (no nitrogen), 25 ppm nitrogen (low nitrogen), and 100 ppm nitrogen (normal nitrogen). Initial screening is undertaken in the greenhouse with $T_1$ plants. Homozygous $T_2$ populations are then evaluated in the field using 60 pounds per acre fertilizer (~25% of the recommended rate for Burley tobacco. Seedling growth, chlorophyll loss, and final yield are measured and compared to control plants grown at normal nitrogen levels.

Figure 5:
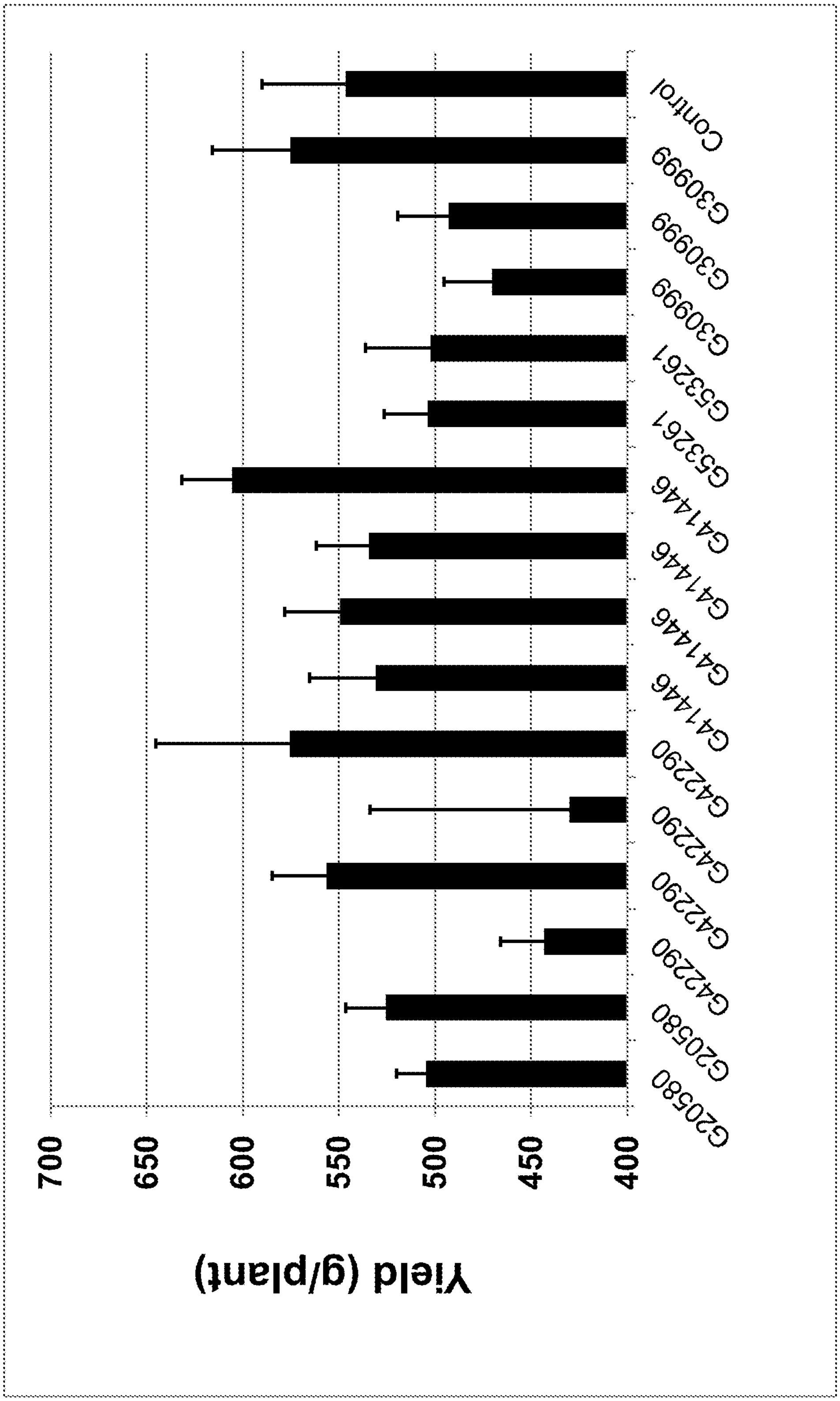
FIG. 5 depicts yield in grams fresh weight per plant of greenhouse grown $T_1$ plants overexpressing genes positively correlated with increased yield under nitrogen stress. The mean and standard deviation based on 9 plants per sample is displayed.

In the Ti generation, plants overexpressing G20580 (2 independent transformants), G42290 (4 independent transformants), G41446 (4 independent transformants), G53261 (2 independent transformants), and G30999 (3 independent transformants) are grown in the greenhouse along with controls under nitrogen limiting conditions equivalent to 60 pounds of Nitrogen per acre. Nine plants per transformant are sampled and one of the lines overexpressing G41446 show a statistically significant increase in yield (grams fresh weight per plant) compared to the control (See FIG. 5).

Example 6. Creating a Cisgenic Tobacco Plant with Enhanced Nitrogen Use Efficiency Nitrogen use efficiency can be improved by modifying the expression of genes involving the genes that were identified as differentially expressed in Example 2. Similarly, genes involved in the biosynthesis or degradation of the metabolites identified in Example 1 can be modulated to improve nitrogen use efficiency. Genes that are positively associated with enhanced nitrogen use efficiency can be over-expressed using a general over-expression promoter or a tissue-preferred promoter to over-express the gene in desired tissues.

Transformation vectors are created to overexpress proteins that are positively associated with enhanced nitrogen use efficiency. Separate transformation vectors comprising one of SEQ ID NOs: 9 to 16 are incorporated into p45-2-7 transformation vectors. Additionally, transformation vectors are created comprising one of SEQ ID NOs: 9 to 16.

Modified tobacco plants are generated using these transformation vectors according to Example 4. Modified tobacco plants ($T_1$ generation) and control tobacco plants are then phenotypically evaluated as described in Example 4. The modified tobacco plants exhibit enhanced nitrogen use efficiency as compared to control tobacco plants grown under the same conditions.

Example 7. Creating a Transgenic Tobacco Plant with Enhanced Nitrogen Use Efficiency Nitrogen use efficiency can also be enhanced by down-regulating the expression of genes identified as being negatively associated with nitrogen use efficiency in Example 2.

Transformation vectors comprising RNAi constructs are designed to inhibit tobacco genes whose expression is negatively associated with nitrogen use efficiency in Example 2. Separate transformation vectors comprise one of SEQ ID NOs: 41 to 56, which are incorporated into p45-2-7 transformation vectors. Additional transformation vectors are created comprising one of SEQ ID NOs: 41 to 56.

Modified tobacco plants are generated using these transformation vectors according to Example 4. Modified tobacco plants ($T_1$ generation) and control tobacco plants are then phenotypically evaluated as described in Example 4. The modified tobacco plants exhibit enhanced nitrogen use efficiency as compared to control tobacco plants grown under the same conditions.

Example 8. Additional Methods of Improving Nitrogen Use Efficiency Using Gene Editing Technologies Gene editing technologies such as CRISPR/Cas9, CRISPR/Cpf1, CRISPR/CasX, CRISPR/CasY, CRISPR/Csm1, zinc-finger nucleases (ZFN), and transcription activator-like effector nucleases (TALENs) are used to modify the coding region of a gene negatively associated with enhanced nitrogen use efficiency so that the gene encodes a non-functional protein or a lower-functioning protein. These gene editing technologies are also used to edit or replace an endogenous promoter sequence to drive its cognate protein expression in either leaf or root tissue to improve nitrogen use efficiency. For example, an endogenous G64360 is edited or replaced so the gene is only expressed in leaf tissue, where it can function to improve nitrogen use efficiency of the plant. Separate CRISPR/Cas9 or CRISPR/Cpf1 guide RNAs are constructed to recognize and hybridize to the promoter sequence of each one of SEQ ID NOs: 9 to 40. The engineered guide RNA and a donor polynucleotide comprising a promoter selected from the group consisting of SEQ ID NOs: 17 to 24 are provided to a tobacco plant, allowing the selected promoter to replace the endogenous promoter of the selected genes and restrict expression of endogenous to either leaf or root tissue as desired. The edited tobacco plants exhibit enhanced nitrogen use efficiency compared to control tobacco plants grown under similar conditions.

Example 9. Development of Novel Mutations to Improve Nitrogen Use Efficiency Via Random Mutagenesis Random mutagenesis of tobacco plants is performed using ethyl methanesulfonate (EMS) mutagenesis or fast neutron bombardment. EMS mutagenesis consists of chemically inducing random point mutations. Fast neutron mutagenesis consists of exposing seeds to neutron bombardment which causes large deletions through double stranded DNA breakage.

For EMS mutagenesis, one gram (approximately 10,000 seeds) of the Burley tobacco variety TN90 seeds are washed in 0.1% Tween for fifteen minutes and then soaked in 30 mL of $ddH_2O$ for two hours. One hundred fifty (150) μL of 0.5% EMS (Sigma, Catalogue No. M-0880) is then mixed into the seed/$ddH_2O$ solution and incubated for 8-12 hours (rotating at 30 R.P.M.) under a hood at room temperature (RT; approximately 20° C.). The liquid then is removed from the seeds and mixed into 1 M NaOH overnight for decontamination and disposal. The seeds are then washed twice with 100 mL $ddH_2O$ for 2-4 hours. The washed seeds are then suspended in 0.1% agar solution.

The EMS-treated seeds in the agar solution are evenly spread onto water-soaked Carolina's Choice Tobacco Mix (Carolina Soil Company, Kinston, NC) in flats at ~2000 seeds/flat. The flats are then covered with plastic wrap and placed in a growth chamber. Once the seedlings emerge from the soil, the plastic wrap is punctured to allow humidity to decline gradually. The plastic wrap is completely removed after two weeks. Flats are moved to a greenhouse and fertilized with NPK fertilizer. The seedlings are replugged into a float tray and grown until transplanting size. The plants are subsequently transplanted into a field. During growth, the plants self-pollinate to form M1 seeds. At the mature stage, five capsules are harvested from each plant and individual designations are given to the set of seeds from each plant. This forms the M1 population. A composite of M1 seed from each M0 plant are grown, and plants are phenotypically evaluated for enhanced nitrogen efficiency as described in Example 4. M1 plants exhibiting enhanced nitrogen efficiency are selected and screened for mutations using DNA sequencing and gene mapping techniques known in the art.

Example 10. Using Breeding to Create a Tobacco Plant with Enhanced Nitrogen Use Efficiency Traditional breeding techniques can be used to introduce NUE favorable alleles provided herein into any tobacco variety to enhance NUE. A population of tobacco plants can be created by crossing a tobacco plant with at least one favorable NUE allele (See Table 10) to a tobacco plant lacking that favorable allele. Marker assisted selection, or other techniques known in the art (e.g. direct sequencing) can be used to track introgression of a favorable allele in the $F_1$ generation and can be used to determine heterozygosity or homozygosity in subsequent generations. Enhanced NUE of progeny plants can be determined using methods known in the art or described above. Multiple different NUE favorable alleles can be combined into a single line. A molecular phenotype as determined by metabolite signature can be used to track enhanced NUE during breeding. The metabolite signatures of progeny plants can be determined using methods described above. Progeny plants with metabolite signatures of parental plants with enhanced NUE are crossed to create subsequent populations of tobacco plants with enhanced NUE.

Figure 3:
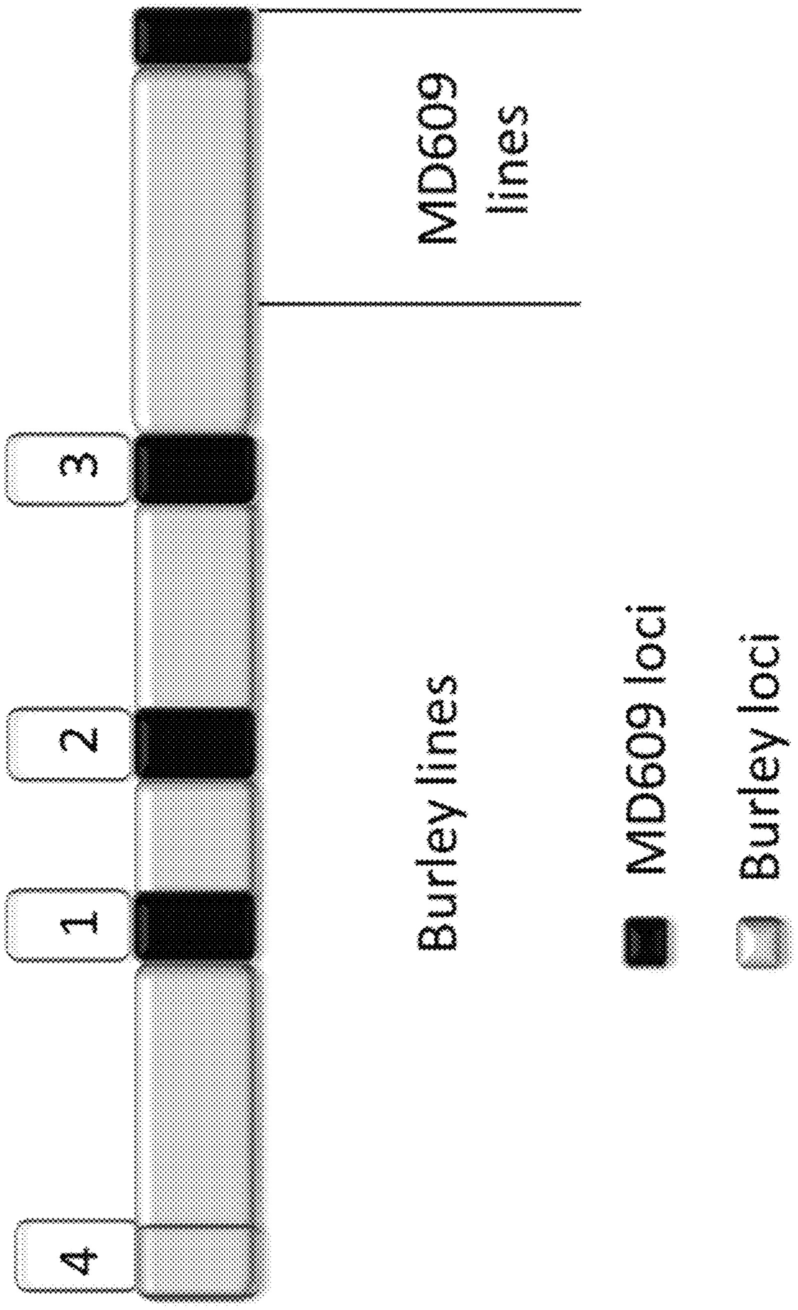
FIG. 3 depicts the allelic constitution for 23 Burley and 6 Maryland varieties at a genetic locus correlated with NUE on tobacco chromosome 11. Lines 1, 2, and 3 are Burley lines that contain a favorable Maryland allele at SEQ ID NO:58, and line 4 is a standard Burley line that contains an unfavorable Burley allele at SEQ ID NO:58.
Figure 4:
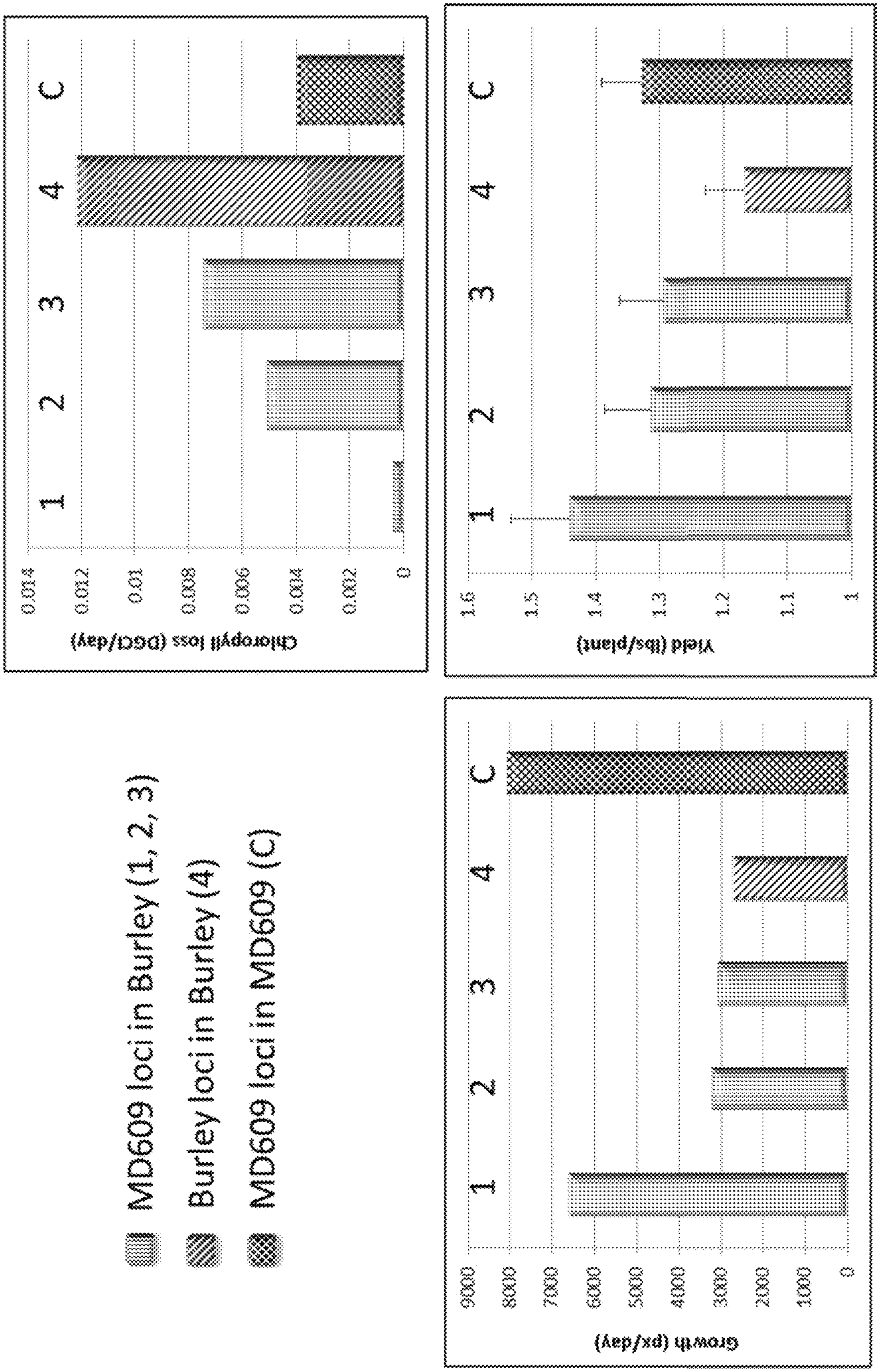
FIG. 4 depicts chlorophyll loss, growth, and yield for Lines 1 to 4 as described in FIG. 3 and a MD609 control (C). Lines 1, 2, and 3 are Burley lines that contain a favorable Maryland allele at SEQ ID NO:58 and line 4 is a standard Burley line that contains an unfavorable Burley allele at SEQ ID NO:58.

Introduction of Maryland 609 loci into commercially available Burley varieties can be performed as described to develop Burley lines with enhanced NUE. Screening of 23 Burley and 6 MD609 lines identified 3 Burley lines containing the MD609 allele at SNP marker S451 (SEQ ID NO:58) (FIG. 3). The three Burley lines with the MD609 allele were tested for chlorophyll loss, growth, and yield under nitrogen limiting conditions and compared to a control TN90 Burley line and a control MD609 line (MD609 with the MD609 allele at SNP marker S451) (FIG. 4). The Burley lines with the MD609 allele exhibit chlorophyll lose, growth, and yield more similar to the Maryland control (FIG. 4). The TN90 Burley control exhibits increased chlorophyll lose, decreased growth, and decreased yield compared to the MD609 control (FIG. 4). These results indicate that introduction of the MD609 allele at SNP marker S451 can enhance NUE.

Figure 6:
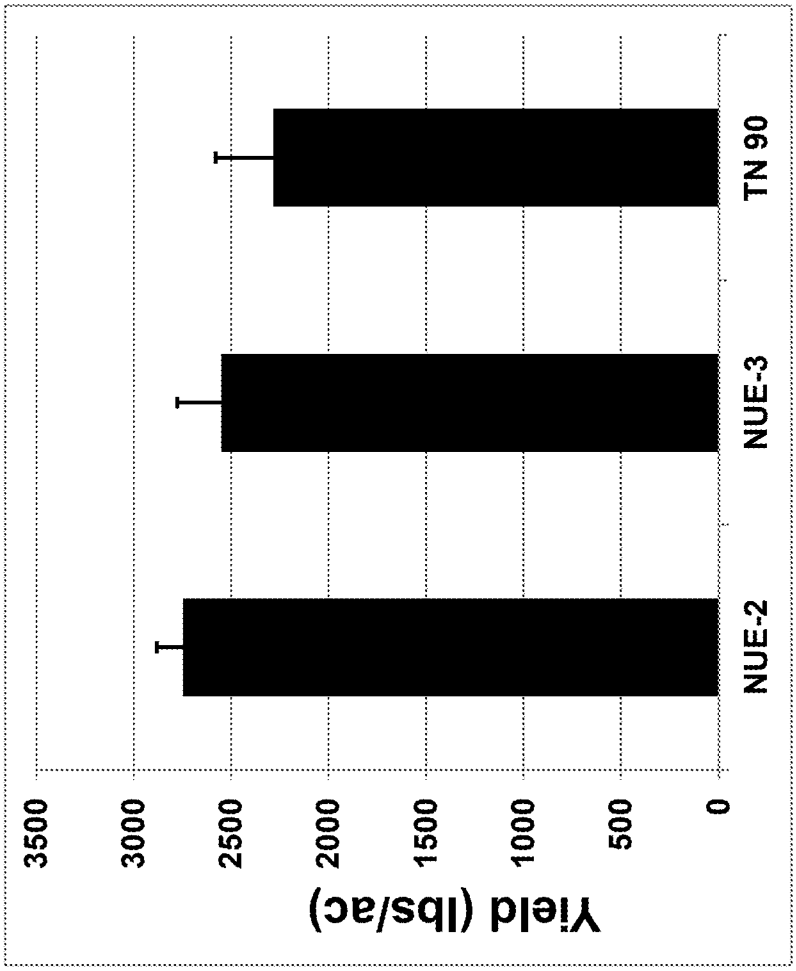
FIG. 6 depicts yield in pounds per acre after harvest for two independent field grown $F_4$ lines, NUE-2 and NUE-3. The test lines are generated from crosses of MD609 to Burley TN90 as described. The mean and standard deviation is provided in comparison to control TN90 Burley tobacco.

In order to introduce MD609 alleles into Burley, MD609 was crossed with Burley. $F_1$ progeny from this cross were selected and subsequently selfed to produce $F_2$ seed. $F_2$ and $F_3$ plants were grown and selfed to generate $F_4$ seed. Bulked $F_4$ seed from two independent crossing schemes, identified as the NUE-2 and NUE-3 lines, are grown and harvested in the field. The genotypes of the SNP markers S451, S317, S12385, S238, S3894, and S2237 are determined for $F_4$ seed of both NUE-2 and NUE-3 lines (See Table 20). $F_4$ plants are grown using reduced nitrogen production practices described in Example 1. Both NUE-2 and NUE-3 lines demonstrate an increased yield in pounds per acre compared to the Burley control TN90 (See FIG. 6).

Alternatively, a modified tobacco plant comprising an enhanced NUE phenotype can be created using the methods described herein and crossed to an unmodified tobacco plant to propagate the modification in subsequent generations. Selection for the genetic modification can be tracked using appropriate techniques known in the art. Enhanced NUE of progeny plants can be determined using methods known in the art or described above.

TABLE 20

Genotypes of field grown plants from F4 NUE-2 and NUE-3 lines and TN90. MD represents a MD609 allele, Burley represents a Burley allele, and HET represents a heterozygous MD609/Burley.

| | S451 | S317 | S12835 | S238 | S3894 | S2237 |
|---|---|---|---|---|---|---|
| NUE-2 | MD | HET | MD | Burley | Burley | MD |
| NUE-3 | MD | HET | MD | Burley | Burley | MD |
| TN90 | Burley | Burley | Burley | Burley | Burley | Burley |

Example 11. Breeding of Plants Double Haploid Production

In order to introduce MD609 alleles into Burley, MD609 is crossed with Burley TN90. $F_1$ progeny from this cross are selected and subsequently selfed to produce $F_2$ seed. A population of $F_2$ plants is screened in field plots as described in Example 1. Selected plants are selfed to produce $F_3$ seed. $F_3$ plants are grown and screened using both marker analysis as described in examples 3 and 10 and a greenhouse standard nitrogen depletion protocol that mimics field conditions.

The nitrogen depletion protocol is as follows. Seedlings are plugged into 21 cell trays and placed on 0 ppm nitrogen. Trays are imaged at 1, 2, and 3 weeks after plugging using an enclosed RGB camera system. Images are analyzed using Phenosuite software (Keygene) which determines the color in Red/Green/Blue and number of individual pixels of each color. The yellowness of the plant is calculated from a ratio of red to green pixels (red/green ratio). The loss of chlorophyll over time is calculated by the increase in red/green ratio over the three weeks. Plant growth is calculated by the increase in total plant area as calculated by the number of non-black pixels within each cell. The soil registers as black.

Plants are repotted in 6 inch pots when they are deemed to be ready and placed on standard Oct. 10, 2010 fertilizer blend that results in 100 ppm of nitrogen being applied. In two weeks, they are repotted in 10 inch pots and fertilizer application is reduced using the following schedule:

a. 2 weeks 75 ppm
b. 1 week 50 ppm
c. 1 week 35 ppm

For the remainder of time until harvest, 25 ppm application is conducted with Oct. 30, 2020 fertilizer mixed at half strength. Fertilizer application is modified based on plant health.

Plants are topped according to normal agronomic practices and yield is determined 4 weeks after topping by weighing the leaves from individual plants.

Populations are also tested under the nitrogen depletion protocol in the field plots as well, as described above. A standard backcrossing protocol (BC) is initiated by selecting F3 plants and crossing these with standard burley tobacco (TN90) generating BC1F1 seed. The BC1F1 seed is grown and plants are screened using the methods outlined above in example 10. Selected plants are crossed with TN90 to generate BC2F1 seed and the resulting progeny is screened again using a nitrogen depletion protocol. A third backcross is preformed using the selected plants to generate BC3F1 seed. The progeny of this cross (BC3) is screened using methods outlined above and the selected plants are used as donor plants to develop doubled haploid populations.

Example 12. Production of Double Haploid Populations

Figure 11:
FIG. 11 depicts representative images from two double haploid lines, Ds1532 and Ds1563, in comparison to Burley TN90 and MD609. The double haploid lines are generated from crosses of MD609 to Burley TN90 as described. Exemplary double haploid plants phenotypically resemble Burley tobacco and have smoking characteristics that are closer to burley tobacco than Maryland tobacco.

Donor plants, described in example 11, are grown in a greenhouse under standard greenhouse conditions. Flower buds are harvested when they are 12-16 mm in length. Anthers are removed and either placed directly on solid Nitsch medium with activated charcoal and 1% sucrose (bioWORLD, Mfr. No. 30630095, Dublin, OH, USA) in petri dishes for anther culture, or microspores are induced by heat for microspore culture. For anther culture, anthers are left on Nitsch medium until plantlets begin to grow. For microspore culture, anthers are macerated (B medium) with a glass pestle, filtered using a 60 micron filter (Millipore Sigma, SCNY00060, Burlington, MA) and centrifuged at 250 g for 2 minutes. The pellet is resuspended in 2-4 mL of B medium. To collect the formed embryogenic microspore, the suspension is centrifuged at 250 g for 5 min. The pellet is resuspended in 2 mL of AT3 medium and plated on a Petri Dish (35 mm) at a density of $5\times10^5$ microspores per mL. Plates are wrapped in parafilm and aluminum foil and incubated for 4 to 6 weeks at 25° C. For both protocols, developing plantlets are moved to agar solidified half strength MS medium and incubated in the light. The seedlings are treated with a 0.2% colchicine solution in moderated agitation for 7 hours (Sigma Aldrich, C3915) for chromosome doubling and subsequently transferred to the greenhouse for seed collection. The seed collected from these plants constitutes the first generation double haploid seed (DH0 seed) with the progeny from each individual plant being a DH1 population of identical genotypic individuals. Exemplary DH plants generated from the BC3 generation are Ds1532 and Ds1563 which are genotypically 89% Burley at the genomic level phenotypically resembling Burley tobacco and having smoking characteristics that are closer to burley tobacco than Maryland tobacco (See FIG. 11).

Example 13. Evaluation of Double Haploid Populations

Sixty three double haploid populations and two controls (Maryland 609 and TN90) are grown using 60 lbs of nitrogen fertilizer per acre and grown with standard tobacco management conditions (as described in Example 1). The field is set with 4 replications for each line. Yield and quality determination are done essentially as described in Example 1. As part of a screen of 173,000 SNP, plants homozygous or heterozygous for a mutant allele at the Yellow Burley 1 locus (YB1), homozygous mutant at the Yellow Burley 2 locus (YB2) and comprising SNP markers corresponding to MD609 at chromosome 11 (referenced herein as a “M11” locus with a Maryland allele as “M11” and a Burley allele as “B11”; e.g., via genotyping by SEQ ID NO. 58) are determined.

Figure 7:
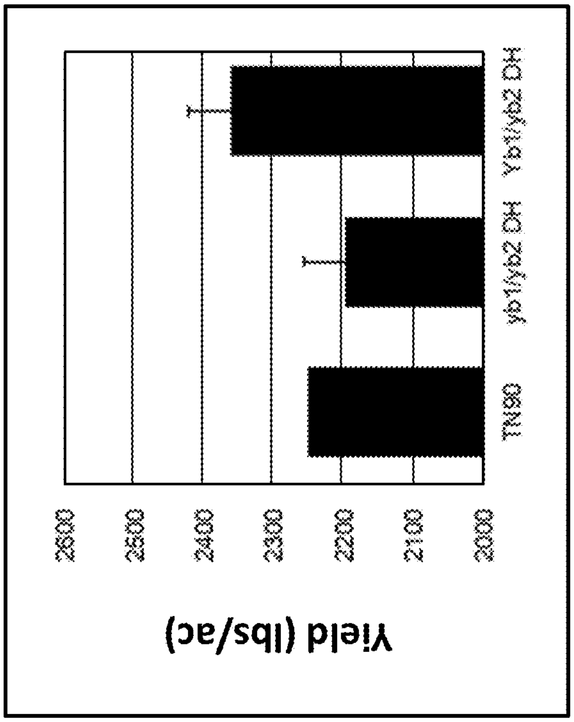
FIG. 7 depicts yield in pounds per acre after harvest for two independent field grown double haploid lines, yb1/yb2 and Yb1/yb2 with application of 60 pounds per acre (lbs/ac) Nitrogen. The double haploid lines are generated from crosses of MD609 to Burley TN90 as described. The mean and standard deviation is provided in comparison to control TN90 Burley tobacco.
Figure 8:
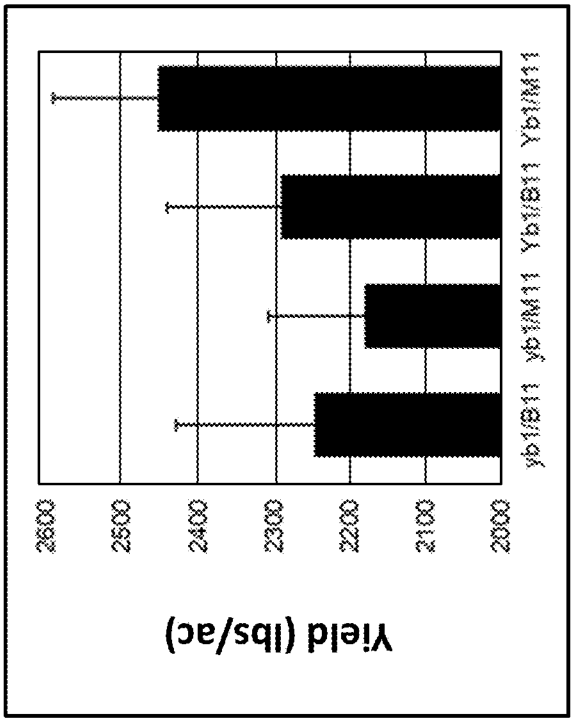
FIG. 8 depicts yield in pounds per acre after harvest of four independent double haploid lines, yb1/B11, yb1/M11, Yb1/B11 and Yb1/M11 with application of 60 lbs/ac Nitrogen. The double haploid lines are generated from crosses of MD609 to Burley TN90 as described.

Plants comprising a heterozygous mutant allele at YB1 (Yb1/yb2 DH) demonstrate a 7% increase in yield compared to plants homozygous mutant at YB1 (yb1/yb2 DH) (See Table 21 and FIG. 7). Unexpectedly, the Yb1 locus and the M11 locus appear to exert a synergistic effect over NUE which is reflected by a further increase of tobacco yield in Yb1 M11 double haploid plants compared to double haploid plants having Yb1 or M11 alone (See Table 22 and FIG. 8, comparing Yb1/M11 with yb1/M11 or Yb1/B11).

TABLE 21

Yield of double haploid (DH) lines compared to TN90 Burley. Yield is shown in pounds per acre. Yb1-wild type, yb1-mutant. See also, FIG. 7.

| | Yield (lbs/ac) | Std. Dev. |
|---|---|---|
| TN90 | 2252 | N/A |
| yb1/yb2 DH | 2200 | 58.6 |
| Yb1/yb2 DH | 2363 | 61.34 |

TABLE 22

Genotype of Chromosome 11 markers influences yield in double haploid lines. Yield in pounds per acre is shown for each indicated genotype. Yb1-wild type or functional allele, yb1-mutant allele, B11-Burley at a Chromosome 11 marker, M11-MD609 at a Chromosome 11 marker. See also, FIGS. 8 and 11.

| Genotype | Yield (lbs/ac) | Std. Dev. |
|---|---|---|
| yb1/B11 | 2248 | 182.6 |
| yb1/M11 | 2182 | 125.9 |
| Yb1/B11 | 2291 | 150.1 |
| Yb1/M11 | 2454 | 138.9 |

Example 14: Generation of Hybrid Tobacco Plants with Enhanced NUE

Figure 10:
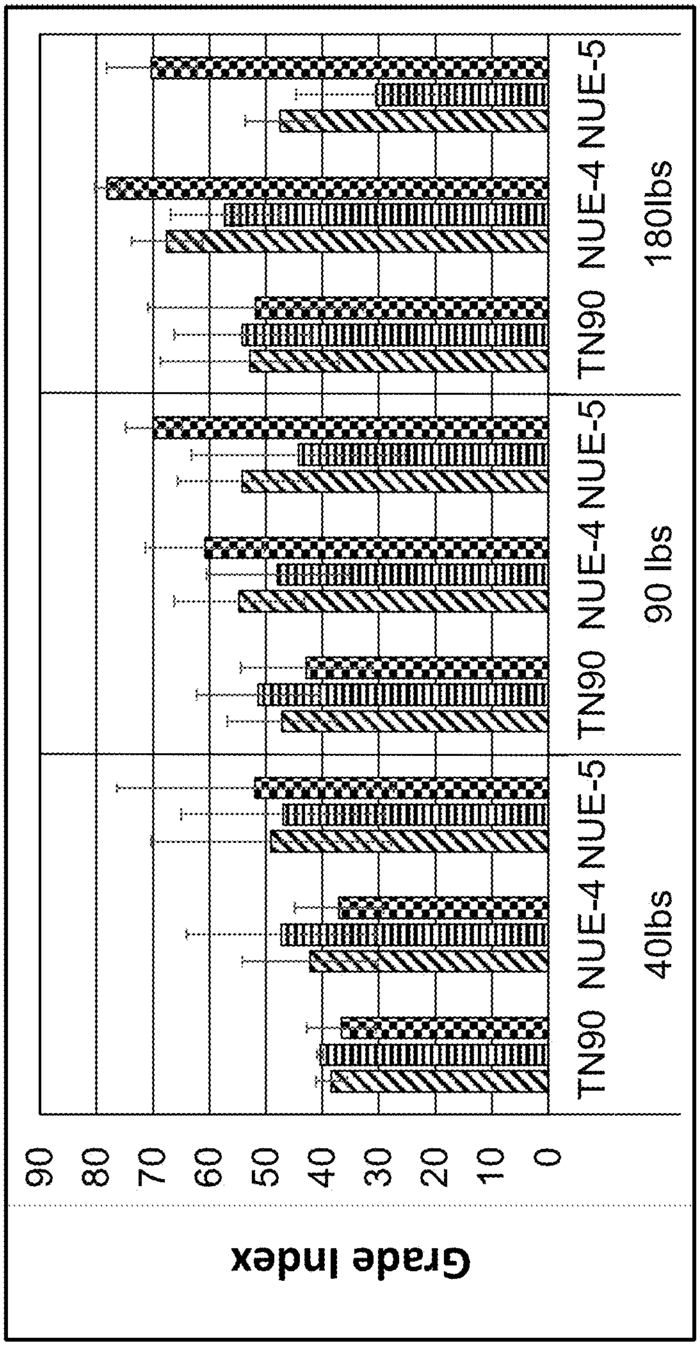
FIG. 10 depicts mean grade index (GI) for total stalk, and upper and lower stalk portions for yield in pounds per acre after harvest for two independent field grown $F_4$ lines, NUE-4 and NUE-5 grown with application of 40, 90, or 180 lbs/ac Nitrogen, in comparison to Burley TN90. The test lines are generated from crosses of MD609 to Burley TN90 as described. For each group of three bars, the left bar is total stalk (diagonal pattern), the middle bar is lower stalk (horizontal pattern), and the right bar is upper stalk (checker pattern). Error bars represent the 95% confidence interval.

Hybrid plants are produced essentially as described in example 10. From these hybrids two additional enhanced NUE lines, NUE-4 and NUE-5, are identified that are heterozygous at the YB1 locus (See Table 23). Both are homozygous mutant at the YB2 locus while NUE-4 comprises enhanced NUE alleles at the M11 locus and NUE-5 is heterozygous at the M11 locus (See Table 23). The female parents for both NUE-4 and NUE-5 are the $F_4$ breeding line from an initial cross between MD609 and TN90 (See Table 24, see also, Example 10). The Male parent for NUE-4 is Banket A1 and the male parent for NUE-5 is Burley L8 (See Table 24). To compare the yield of NUE-4 and NUE-5 under reduced nitrogen (90 lbs per acre compared to 180 lbs per acre), plants are grown and compared to TN90 (See FIG. 9). Both NUE-4 and NUE-5 demonstrate a yield increase when compared to TN90 grown at 90 lbs nitrogen per acre (See Table 25, see also, FIG. 9). NUE-5 also demonstrates a small yield increase when grown at 90 lbs nitrogen per acre compared to TN90 grown at 180 lbs nitrogen per acre (See Table 25, see also, FIG. 9). Importantly, NUE-4 and NUE-5 maintain the yield increase at 90 lbs nitrogen per acre with no decline in grade index at both upper stalk positions and lower stalk positions (See Table 26 and, see also, FIG. 10). It is found that when NUE-5 is grown at 180 lbs nitrogen per acre (a typical nitrogen level used for Burley), its lower stalk positions show a sizable decrease in average grade index, which decrease also leads to a decrease in overall grade index average for the entire plant. (See FIG. 10). As such, a recommended nitrogen range for hybrid plants like NUE-4 and NUE05 is around 75-90 lbs/ac.

In summary, allelic combinations in the YB1 and M11 loci are identified to produce hybrid tobacco plants with essentially Burley characteristics which, when grown at 50% of recommended burley fertilization rates, can still obtain leaf yields similar to or slightly better than Burley control plants grown under standard burley fertilization rates. Overfertilization of some hybrid plants (e.g., NUE-5 which has a genotype of Yb1/yb1, M11/B11) can lead to leaf quality loss in lower stalk leaves. The M11 locus works with dominant Yb1 wild-type allele(s) to maximize nitrogen efficiency and functions in a dominant manner.

TABLE 23

NUE-4 and NUE-5 hybrids and their genotype at Yb1, Yb2 and Chromosome 11 markers. “Het” represents heterozygous while the indicated alleles represent homozygous state.

| | Hybrids | |
|---|---|---|
| Marker Locus | NUE-4 | NUE-5 |
| YB1 | Het | Het |
| YB2 | yb2 | yb2 |
| Chr11 | Maryland | Het |

TABLE 24

The genotype of parental lines of NUE-4 and NUE-5

| | | Male | |
|---|---|---|---|
| Marker Locus | Female | NUE-4 | NUE-5 |
| | Breeding line ($F_4$) | Banket A1 | L8 |
| YB1 | Yb1 | yb1 | yb1 |
| YB2 | yb2 | yb2 | yb2 |
| Chr11 | Maryland | Maryland | Burley |

TABLE 25

Yield of NUE-4 and NUE-5 when grown with 90 lbs nitrogen fertilizer per acre compared to TN90.

| | Plant | Yield |
|---|---|---|
| 180 lbs N per acre | TN90 | 2302.63 |
| 90 lbs N per acre | TN90 | 1922.69 |
| | NUE-4 | 2193.73 |
| | NUE-5 | 2372.81 |

TABLE 26

Average yield and grade index (GI) of control and hybrid NUE-4 and NUE-5 populations grown using 40, 90, and 180 lbs of nitrogen fertilizer per acre from F4 NUE-1 and NUE-2 lines and TN90. The 95% Confidence Interval is also shown. See also, FIG. 10.

| | | Average | | | | 95% Confidence Interval | | | |
|---|---|---|---|---|---|---|---|---|---|
| | | Yield | Lower GI | Upper GI | GI | Yield | Lower GI | Upper GI | GI |
| 40 lbs N per acre | TN90 | 1,713 | 40 | 37 | 38 | 166 | 1 | 6 | 3 |
| | NUE-4 | 1,880 | 47 | 37 | 42 | 174 | 17 | 8 | 12 |
| | NUE-5 | 1,872 | 47 | 52 | 49 | 514 | 18 | 25 | 21 |
| 90 lbs N per acre | TN90 | 1,923 | 51 | 43 | 47 | 145 | 11 | 12 | 10 |
| | NUE-4 | 2,194 | 48 | 61 | 55 | 366 | 13 | 11 | 12 |
| | NUE-5 | 2,373 | 44 | 70 | 54 | 305 | 19 | 5 | 12 |

TABLE 26-continued

Average yield and grade index (GI) of control and hybrid NUE-4 and NUE-5 populations grown using 40, 90, and 180 lbs of nitrogen fertilizer per acre from F4 NUE-1 and NUE-2 lines and TN90. The 95% Confidence Interval is also shown. See also, FIG. 10.

| | | Average | | | | 95% Confidence Interval | | | |
|---|---|---|---|---|---|---|---|---|---|
| | | Yield | Lower GI | Upper GI | GI | Yield | Lower GI | Upper GI | GI |
| 180 lbs N per acre | TN90 | 2,303 | 54 | 52 | 53 | 171 | 12 | 19 | 16 |
| | NUE-4 | 2,669 | 57 | 78 | 68 | 203 | 10 | 2 | 6 |
| | NUE-5 | 2,906 | 30 | 70 | 47 | 265 | 14 | 8 | 6 |

DEPOSIT INFORMATION

A deposit of the proprietary inbred plant lines disclosed above and recited in the appended claims have been made with American Type Culture Collection (ATCC), 10801 University Boulevard, Manassas, VA 20110. The date of deposit for double haploid lines dS1532 and dS1563 was Dec. 18, 2020. The deposits of 2500 seeds for each variety was taken from the same deposits maintained since prior to the filing date of this application. Upon issuance of a patent, all restrictions upon the deposits will be irrevocably removed, and the deposits are intended by Applicant to meet all requirements of 37 C.F.R. § 1.801-1.809. The ATCC has issued the following accession numbers: ATCC Accession No. PTA-126901 for dS1532 and ATCC Accession No. PTA-126902 for dS1563. These deposits will be maintained in the depository for a period of 30 years, or 5 years after the last request, or for the effective life of the patent, whichever is longer, and will be replaced as necessary during that period. Applicants do not waive any infringement of their rights granted under this patent or under the Plant Variety Protection Act (7 U.S.C. 2321 et seq.).

What is claimed is:

1. A tobacco plant, or part thereof; a representative seed sample of the tobacco plant having been deposited under ATCC Accession Nos. PTA-126901 or PTA-126902.

2. The tobacco part thereof of claim 1, wherein the part thereof is a seed.

3. Cured tobacco material from the tobacco plant of claim 1.

4. A tobacco product comprising the cured tobacco material of claim 3.

5. A method comprising the steps of:

a) crossing at least one tobacco plant grown from a seed, a representative sample of said seed having been deposited under ATCC Accession Nos. PTA-126901 or PTA-126902, with a second tobacco plant; and b) obtaining at least one progeny seed from the crossing of step a).

6. The method of claim 5, the method further comprising growing the at least one progeny seed into a tobacco plant.

7. Cured tobacco material from the tobacco plant of claim 6.

8. A tobacco product comprising the cured tobacco material of claim 7.

* * * * *